United States Patent
Crosignani

(10) Patent No.: US 11,427,594 B2
(45) Date of Patent: Aug. 30, 2022

(54) NON BRAIN PENETRANT A2A INHIBITORS AND METHODS FOR USE IN THE TREATMENT OF CANCERS

(71) Applicant: iTeos Belgium SA, Gosselies (BE)

(72) Inventor: Stefano Crosignani, Nivelles (BE)

(73) Assignee: ITEOS BELGIUM SA, Gosselies (BE)

( * ) Notice: Subject to any disclaimer, the term of this patent is extended or adjusted under 35 U.S.C. 154(b) by 0 days.

(21) Appl. No.: 16/584,596

(22) Filed: Sep. 26, 2019

(65) Prior Publication Data

US 2020/0102319 A1   Apr. 2, 2020

Related U.S. Application Data

(60) Provisional application No. 62/737,695, filed on Sep. 27, 2018.

(51) Int. Cl.
*C07D 487/04* (2006.01)
*C07D 487/14* (2006.01)

(52) U.S. Cl.
CPC ......... *C07D 487/14* (2013.01); *C07D 487/04* (2013.01)

(58) Field of Classification Search
CPC ............................ C07D 487/04; C07D 487/14
See application file for complete search history.

(56) References Cited

U.S. PATENT DOCUMENTS

| 2005/0239795 A1 | 10/2005 | Neustad et al. |
| 2019/0276473 A1 | 9/2019 | Crosignani et al. |

FOREIGN PATENT DOCUMENTS

| WO | WO-2004/092171 A2 | 10/2004 |
| WO | WO-2012/135084 A1 | 10/2012 |
| WO | WO-2018/178338 A1 | 10/2018 |

OTHER PUBLICATIONS

Segala, et al., Controlling the Dissociation of Ligands from the Adenosine A2A Receptor through Modulation of Salt Bridge Strength, J. of Med. Chem. 59(13), 6470-6479 (2016). (Year: 2016).*

Munoz-Gutierrez, et al., HQSAR and molecular docking studies of furanyl derivatives as adenosine A2A receptor antagonists, Med. Chem. Res., 25:1316-1328 (2016). (Year: 2016).*

Guo, et al., Binding Kinetics of ZM241385 Derivatives at the Human Adenosine A2A Receptor, ChemMedChem 9, 752-761 (2014). (Year: 2014).*

Allard, B., et al., "Immunosuppressive activities of adenosine in cancer.", Curr. Opin. Pharmacol., Aug. 2016, vol. 29: pp. 7-16.

Hauser, R.A., et al., "Preladenant as an Adjunctive Therapy With Levodopa in Parkinson Disease: Two Randomized Clinical Trials and Lessons Learned", JAMA Neurol., Dec. 2015, vol. 72, Issue 12 pp. 1491-1500.

Hodgson, R. A., et al., "Characterization of the Potent and Highly Selective A2A Receptor Antagonists Preladenant and SCH 412348 [7-[2-[4-2,4-Difluorophenyl]-1-piperazinyl]ethyl]-2-(2-furanyl)-7H-pyrazolo[4,3-e][1,2,4]triazolo[1,5-c]pyrimidin-5-amine] in Rodent Models of Movement Disorders and Depression", The Journal of Pharmacology and Experimental Therapeutics, Jul. 2009, vol. 330, Issue 1: pp. 294-303.

Ohta, A., "A Metabolic Immune Checkpoint: Adenosine in Tumor Microenvironment", Frontiers in Immunology, Mar. 29, 2016, vol. 7, Article 109: pp. 1-11.

PCT International Search Report and Written Opinion, PCT Application No. PCT/EP2018/058301, dated Apr. 10, 2018, 10 pages.

Pinna, A., "Adenosine A2A Receptor Antagonists in Parkinson's Disease: Progress in Clinical Trials from the Newly Approved Istradefylline to Drugs in Early Development and Those Already Discontinued", CNS Drugs, May 2014, vol. 28, Issue 5: pp. 455-474.

West, Anthony R., Solid State Chemistry and Its Applications, Wiley, New York, 1988, 358. (Year: 1988).

* cited by examiner

*Primary Examiner* — Erich A Leeser

(74) *Attorney, Agent, or Firm* — Goodwin Procter LLP

(57) ABSTRACT

The present invention relates to compounds of Formula (I)

(I)

or pharmaceutically acceptable salts thereof. The invention further relates to the use of the compounds of Formula (I) as A2A inhibitors. The invention also relates to the use of the compounds of Formula (I) for the treatment and/or prevention of proliferative disorders, including cancers.

2 Claims, No Drawings

NON BRAIN PENETRANT A2A INHIBITORS AND METHODS FOR USE IN THE TREATMENT OF CANCERS

RELATED APPLICATIONS

This application claims the benefit of U.S. provisional application No. 62/737,695 filed Sep. 27, 2018, the contents of which are incorporated in their entirety for all purposes.

FIELD OF INVENTION

The present invention relates to novel non-brain penetrant inhibitors of adenosine A2A receptor. The compounds of the invention are useful as therapeutic compounds, particularly in the treatment and/or prevention of proliferative disorders, including cancers.

BACKGROUND OF INVENTION

Many of the immunosuppressive mechanisms in tumors are common to physiological immunoregulation in normal tissues. Such immunoregulation is very important in keeping the immune system under control in order to block a self-reactive immune response and to prevent an ongoing immune response from causing critical tissue damage. The lack of physiological immunoregulation often results in overwhelming immune activation that accompanies autoimmunity. For example, CTLA-4 is a physiological mechanism that negatively regulates T cell activity by blocking a costimulatory signal through CD28-B7 interaction. The lack of CTLA4 causes non-specific T cell activation, and CTLA-4-deficient mice die in several weeks with massive lymphocytic tissue infiltration. PD-1 also provides a T cell inhibitory signal upon interaction with its ligands, PD-L1 and PD-L2. Deficiency of PD-1 in mice is known to cause various types of autoimmune disorders depending on the genetic strains.

Besides cell surface transducers of immunosuppressive signal, e.g., CTLA-4 and PD-1, immunosuppression in the tumor microenvironment involves anti-inflammatory cytokines (IL-10, TGF-β), enzymes (indoleamine-2,3-dioxygenase), and professional immunoregulatory cells (regulatory T cells, myeloid-derived suppressor cells MDSCs). These immunosuppressive mechanisms play an important role in controlling immune response in normal tissues. Since tumors take advantage of such physiological immunoregulatory mechanisms to protect their tissue from immune attack, these mechanisms intended to prevent inflammatory complication, now turn out to be major obstacles hampering spontaneous cancer regression and immunological cancer treatment. The identification of immunosuppressive mechanisms in tumors pointed out molecular targets to restore the antitumor immune response. Thus, these negative immunoregulatory mechanisms, so-called immune checkpoints, became a focus in drug discovery. Antibodies against PD1, PDL1 or CTLA4 have been approved as anticancer therapies on a large number of indications, such as Metastatic Melanoma, Non-Small Cell Lung Cancer, Renal Cell Carcinoma, Hodgkin's Lymphoma, Head and Neck Cancer, Urothelial Carcinoma, Hepatocellular Carcinoma, as well as treatment of for patients with solid tumors that have one of two specific genetic features known as mismatch repair deficiency and high microsatellite instability (irrespective of cancer type).

Extracellular adenosine has been known as an inhibitor of immune functions. While intracellular adenosine is involved in energy metabolism, nucleic acid metabolism, and the methionine cycle, extracellular adenosine plays an important role in intercellular signaling. Its signal is transmitted by G protein-coupled adenosine receptors on the cell surface, and it affects diverse physiological functions including neurological, cardiovascular, and immunological systems.

Tumors contain high levels of extracellular adenosine, suggesting that tumor cells may benefit from its immunosuppressive effect and catabolic energy production (Allard et al., Curr. Opin. Pharmacol., 2016, 29, 7-16; Otta A., Frontiers in Immunology, 2016, 7: 109). This high level of extracellular adenosine is probably due to overexpression of the enzyme CD73, which is responsible for production of extracellular adenosine. CD73 is overexpressed by a large number of tumors, with all the following tumors expressing medium or high levels of CD73 in ≥50% of tumor surface by immunohistochemistry (www.proteinatlas.org): Breast, Carcinoid, Cervical, Colorectal, Endometrial, Glioma, Head and Neck, Liver, Lung, Melanoma, Ovarian, Pancreatic, Prostate, Renal, Gastric, Thyroid, Urothelial.

Of the four known types of adenosine receptors, A2A adenosine receptor (A2AR) is the predominantly expressed subtype in most immune cells. Stimulation of A2AR generally provides an immunosuppressive signal that inhibits activities of T cells (proliferation, cytokine production, cytotoxicity), NK cells (cytotoxicity), NKT cells (cytokine production, CD40L upregulation), macrophages/dendritic cells (antigen presentation, cytokine production), and neutrophils (oxidative burst). The presence of high levels of extracellular adenosine in tumors was found to play a significant role in the evasion of antitumor immune response. Especially, it was shown that A2AR-deficient mice could spontaneously regress the inoculated tumor, whereas no wild-type mice showed similar tumor regression. A2AR antagonists were also beneficial in tumor-bearing wild-type animals. Importantly, depletion of T cells and NK cells impaired the retardation of tumor growth by A2AR antagonists, suggesting improvement of antitumor cellular immune response. Effector functions of T cells and NK cells are susceptible to A2AR stimulation. In addition, when activated in the presence of A2AR agonist, the effector function of T cells is persistently impaired even after removal of A2AR agonist. This result suggests that the adenosine-rich environment in tumors may induce T cells that are anergic to the tumor cells.

Therefore, given that A2A receptor is expressed in most immune cells and particularly effector immune cells such as T cells and NK cells and given that A2A receptor is engaged in tissues where adenosine is produced, it is thought that A2A inhibitors can be helpful in all the cancer indications.

Consequently, there is a need for A2A inhibitors able to restore immune functions in tumors environment.

Adenosine is known to be an endogenous modulator of a number of other physiological functions. For example, at the central nervous system (CNS) level, adenosine in known to induce sedative, anxiolytic and antiepileptic effects level.

Thus, A2A inhibitors were previously developed for the treatment of depression and neurodegenerative diseases such as Parkinson's disease or Alzheimer's disease (Pinna A., CNS Drugs, 2014, 28, 455). One of the most advanced A2A inhibitors developed for the treatment of CNS diseases is Preladenant (Hodgson R A et al., J. Pharmacol. Exp. Ther., 2009, 330(1), 294-303; Hauser R A et al., JAMA Neurol., 2015, 72(12), 1491-500).

However, such previously developed A2A inhibitors were designed to cross the blood brain barrier, i.e. to be brain penetrant, in order to target A2A receptor in the CNS.

Given the higher level of adenosine in tumors when compared to the brain, much higher amounts of compounds will be needed to achieve the desired effect on immune functions restoration for treating cancers. Thus, in order to avoid deleterious side effects, one should provide A2A inhibitors which have a limited, if any, CNS penetrance, contrary to all previously developed A2A inhibitors.

The Applicant provided a first series of non-brain penetrant A2A inhibitors in international patent application PCT/EP2018/058301.

As evidenced in the experimental part below, the Applicant hereby provides further new A2A inhibitors which do not have any significant CNS penetrance, and which also find utility in the treatment of proliferative disorders, including cancers.

SUMMARY

The present invention thus relates to a compound of Formula (I)

(I)

or a pharmaceutically acceptable salt or solvate thereof, wherein X, Y, $R^A$, $R^1$, $R^2$, $R^3$, $R^4$, $R^5$ and $R^6$ are as defined below.

The invention also relates to a pharmaceutical composition comprising a compound according to the invention or a pharmaceutically acceptable salt or solvate thereof, and at least one pharmaceutically acceptable carrier.

The invention further relates to a compound according to the invention or a pharmaceutically acceptable salt or solvate thereof for use as medicament.

The invention also provides a compound according to the invention or a pharmaceutically acceptable salt or solvate thereof for use in the treatment and/or prevention of cancer.

The invention also provides a compound according to the invention or a pharmaceutically acceptable salt or solvate thereof for use as A2A inhibitor.

There is also provided processes for manufacturing a compound according the invention.

Definitions

In the present invention, the following terms have the following meanings:

The term "aldehyde" refers to a group —CHO.

The term "alkenyl" refers to unsaturated hydrocarbyl group, which may be linear or branched, comprising one or more carbon-carbon double bonds. Suitable alkenyl groups comprise between 2 and 6 carbon atoms, preferably between 2 and 4 carbon atoms, still more preferably between 2 and 3 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

The term "alkenylcarbonyl" refers to a group —(C=O)-alkenyl wherein alkenyl is as herein defined.

The term "alkenylcarbonylamino" refers to a group —NH—(C=O)-alkenyl wherein alkenyl is as herein defined.

The term "alkoxy" refers to a group —O-alkyl wherein alkyl is as herein defined.

The term "alkyl" refers to a hydrocarbyl radical of formula CnH2n+1 wherein n is a number greater than or equal to 1. Generally, alkyl groups of this invention comprise from 1 to 8 carbon atoms, more preferably, alkyl groups of this invention comprise from 1 to 6 carbon atoms. Alkyl groups may be linear or branched. Suitable alkyl groups include methyl, ethyl, propyl, butyl, pentyl, hexyl, heptyl and octyl.

The term "alkylaminoalkyl" refers to a group -alkyl-NH-alkyl wherein alkyl is as herein defined.

The term "alkylaminoalkylaminocarbonyl" refers to a group —(C=O)—NH-alkyl-NH-alkyl wherein alkyl is as herein defined.

The term "alkylaminoalkylcarbonyl" refers to a group —(C=O)-alkyl-NH-alkyl wherein alkyl is as herein defined.

The term "alkylcarbonyl" refers to a group —(C=O)-alkyl wherein alkyl is as herein defined.

The term "alkylheteroaryl" refers to any heteroaryl substituted by an alkyl group wherein alkyl is as herein defined.

The term "alkyloxycarbonyl" refers to a group —(C=O)—O-alkyl wherein alkyl is as herein defined.

The term "alkylsulfonyl" refers to a group —SO2-alkyl wherein alkyl is as herein defined.

The term "alkylsulfonealkyl" refers to a group -alkyl-SO2-alkyl wherein alkyl is as herein defined.

The term "alkylsulfonimidoyl" refers to a group —S(=O)(=NH)-alkyl wherein alkyl is as herein defined.

The term "alkylsulfoxide" refers to a group —(S=O)-alkyl wherein alkyl is as herein defined.

The term "alkylsulfoxidealkyl" refers to a group -alkyl-SO-alkyl wherein alkyl is as herein defined.

The term "alkyne" refers to a class of monovalent unsaturated hydrocarbyl groups, wherein the unsaturation arises from the presence of one or more carbon-carbon triple bonds. Alkynyl groups typically, and preferably, have the same number of carbon atoms as described above in relation to alkyl groups. Non-limiting examples of alkynyl groups are ethynyl, 2-propynyl, 2-butynyl, 3-butynyl, 2-pentynyl and its isomers, 2-hexynyl and its isomers—and the like.

The term "alkynealkyl" refers to a group -alkyl-alkyne wherein alkyl and alkyne are as herein defined.

The term "amino" refers to a group —NH2.

The term "aminoalkyl" refers to a group -alkyl-NH2 wherein alkyl is as herein defined.

The term "aminoalkylaminocarbonyl" refers to a group —(C=O)—NH-alkyl-NH2 wherein alkyl is as herein defined.

The term "aminoalkylcarbonylamino" refers to a group —NH—(C=O)-alkyl-NH2 wherein alkyl is as herein defined.

The term "aminocarbonyl" refers to a group —(C=O)—NH2.

The term "(aminocarbonylalkyl)(alkyl)amino" refers to a group —NR1R2 wherein R1 is an alkyl group and R2 is a -alkyl-(C=O)—NH2 group, wherein alkyl is as herein defined.

The term "aminocarbonylalkylamino" refers to a group —NH-alkyl-(C=O)—NH2 wherein alkyl is as herein defined.

The term "aminosulfonyl" refers to a group —SO2-NH2.

The term "aryl" refers to a polyunsaturated, aromatic hydrocarbyl group having a single ring (i.e. phenyl) or multiple aromatic rings fused together (e.g. naphtyl), typically containing 5 to 12 atoms; preferably 5 to 10; more preferably the aryl is a 5- or 6-membered aryl. Non-limiting examples of aryl comprise phenyl, naphthalenyl.

The term "carbonyl" refers to a group —(C═O)—.

The term "carbonylamino" refers to a group —NH—(C═O)—.

The term "cycloalkyl" refers to a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms; still more preferably more preferably the cycloalkyl is a 5- or 6-membered cycloalkyl. Examples of cycloalkyl groups include but are not limited to cyclopropyl, cyclobutyl, cyclopentyl, cyclohexyl.

The term "cycloalkyloxy" refers to a group —O-cycloalkyl wherein cycloalkyl is as herein defined.

The term "dialkylamino" refers to a group —NR1R2 wherein R1 and R2 are both independently alkyl group as herein defined.

The term "dialkylaminoalkyl" refers to a group -alkyl-NR1R2 wherein R1 and R2 are both independently alkyl group, as herein defined.

The term "dialkylaminoalkylaminocarbonyl" refers to a group —(C═O)—NH-alkyl-NR1R2 wherein R1 and R2 are both alkyl group, as herein defined.

The term "dialkylaminoalkylcarbonyl" refers to a group —(C═O)-alkyl-NR1R2 wherein R1 and R2 are both alkyl group, as herein defined.

The term "dihydroxyalkyl" refers to a group alkyl is as herein defined substituted by two hydroxyl (—OH) groups.

The term "halo" or "halogen" refers to fluoro, chloro, bromo, or iodo.

The term "heteroaryl" refers to an aryl group as herein defined wherein at least one carbon atom is replaced with a heteroatom. In other words, it refers to 5 to 12 carbon-atom aromatic single rings or ring systems containing 2 rings which are fused together, typically containing 5 to 6 atoms; in which one or more carbon atoms is replaced by oxygen, nitrogen and/or sulfur atoms where the nitrogen and sulfur heteroatoms may optionally be oxidized and the nitrogen heteroatoms may optionally be quaternized. Non-limiting examples of such heteroaryl, include: oxazolyl, thiazolyl, imidazolyl, furanyl and pyrrolyl. Preferably the heteroaryl is a 5- or 6-membered heteroaryl, more preferably the 5- or 6-membered heteroaryl is a furyl.

The term "heterocyclyl" refers to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Preferably the heterocyclyl is a 5- or 6-membered heterocyclyl. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include aziridinyl, oxiranyl, thiiranyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, succinimidyl, 3H-indolyl, indolinyl, isoindolinyl, 2H-pyrrolyl, 1-pyrrolinyl, 2-pyrrolinyl, 3-pyrrolinyl, pyrrolidinyl, 4H-quinolizinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, oxetanyl, thietanyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydrothiophenyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, 1-oxido-1-thiomorpholin-4-yl, 1-dioxido-1-thiomorpholin-4-yl, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, and morpholin-4-yl.

The term "heterocyclylalkylaminocarbonyl" refers to a group —(C═O)—NH-alkyl-heterocyclyl, wherein alkyl and heterocyclyl are as herein defined.

The term "(heterocyclyl)(alkyl)aminoalkyl" refers to a group -alkyl-NR1R2 wherein R1 is an alkyl group and R2 is an heterocyclyl group, wherein alkyl and heterocyclyl are as herein defined.

The term "heterocyclylcarbonyl" refers to a group —(C═O)-heterocyclyl wherein heterocyclyl is as herein defined.

The term "heterocyclylalkyl" refers to a group -alkyl-heterocyclyl wherein alkyl and heterocyclyl are as herein defined.

The term "heterocyclyloxy" to a group —O-heterocyclyl wherein heterocyclyl is as herein defined.

The term "heterocyclylsulfonyl" refers to a group —SO2-heterocyclyl wherein heterocyclyl is as herein defined.

The term "hydroxyalkyl" refers to a group -alkyl-OH wherein alkyl is as herein defined.

The term "hydroxyalkylaminoalkyl" refers to a group -alkyl-NH-alkyl-OH wherein alkyl is as herein defined.

The term "hydroxycarbonyl" refers to a group —C(═O)—OH wherein carbonyl is as herein defined. In other words, "hydroxycarbonyl" corresponds to a carboxylic acid group.

The term "oxo" refers to a ═O substituent.

The term "sulfonylamino" refers to a group —NH—SO2.

The term "about", preceding a figure, means plus or less 10% of the value of said figure.

The term "administration", or a variant thereof (e.g. "administering"), means providing the active agent or active ingredient (e.g. an A2A inhibitor), alone or as part of a pharmaceutically acceptable composition, to the patient in whom/which the condition, symptom, or disease is to be treated or prevented.

The terms "IC50" or "half maximal inhibitory concentration" represent the concentration of an inhibitor that is required for 50% inhibition in vitro.

The term "inhibitor" refers to a natural or synthetic compound that has a biological effect to inhibit or significantly reduce or down-regulate the expression of a gene and/or a protein or that has a biological effect to inhibit or significantly reduce the biological activity of a protein. Consequently, an "A2A inhibitor" refers to a compound that has a biological effect to inhibit or significantly reduce or down-regulate the biological activity of A2A receptor.

The term "human" refers to a subject of both genders and at any stage of development (i.e. neonate, infant, juvenile, adolescent, adult).

The term "patient" refers to a warm-blooded animal, more preferably a human, who/which is awaiting the receipt of, or is receiving medical care or is/will be the object of a medical procedure.

The expression "pharmaceutically acceptable" refers to the ingredients of a pharmaceutical composition are compatible with each other and not deleterious to the subject to which it is administered.

The expression "pharmaceutically acceptable carrier" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, e.g., FDA Office or EMA.

The term "predrug", as used herein, means any compound that will be modified to form a drug species, wherein the modification may take place either inside or outside of the body, and either before or after the predrug reaches the area of the body where administration of the drug is indicated.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "prodrug" as used herein means the pharmacologically acceptable derivatives of compounds of Formula (I), such as for example esters or amides, whose in vivo biotransformation product generates the biologically active drug. Prodrugs are generally characterized by increased bio-availability and are readily metabolized into biologically active compounds in vivo.

The terms "treating" or "treatment" refer to therapeutic treatment; wherein the object is to prevent or slow down the targeted pathologic condition or disease. A subject or mammal is successfully "treated" for a disease or affection or condition if, after receiving the treatment according to the present invention, the subject or mammal shows observable and/or measurable reduction in or absence of one or more of the following: reduction of the number of cancer cells; and/or relief to some extent, for one or more of the symptoms associated with the specific disease or condition; reduced morbidity and mortality, and improvement in quality of life issues. The above parameters for assessing successful treatment and improvement in the disease are readily measurable by routine procedures familiar to a physician.

The term "volunteer" or "subject" refers to an animal, including a human. In the sense of the present invention, a subject may be a patient, i.e., a person receiving medical attention, undergoing or having underwent a medical treatment, or monitored for the development of a disease. In one embodiment, the subject is a male. In another embodiment, the subject is a female.

DETAILED DESCRIPTION

Compounds

This invention relates to compounds of Formula (I)

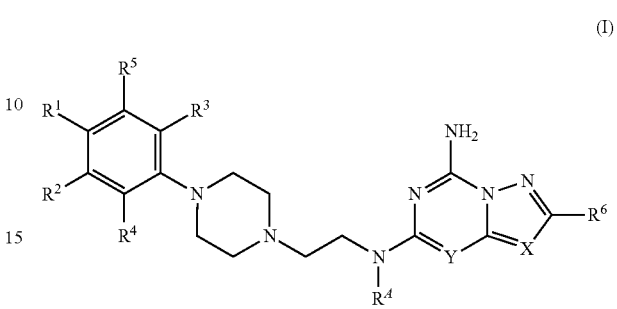

(I)

or a pharmaceutically acceptable salt or solvate thereof, wherein:

X represents N or CH;

Y represents N or C—$R^B$ wherein $R^B$ is linked to $R^A$;

$R^A$ represents H, $CH_3$ or $R^A$ is linked to $R^B$ so that —$R^A$—$R^B$— represents —C(=O)—N($CH_3$)—, —C(=O)—S—, —CH=N— or —N=CH—;

$R^1$ represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino or alkylsulfonealkyl;

said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl) amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

$R^2$ represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino, or alkylsulfonealkyl;

said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl) amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

or $R^1$ and $R^2$ form together with the atoms to which they are attached a 5- or 6-membered aryl ring, a 5- or 6-membered heteroaryl ring, a 5- or 6-membered cycloalkyl ring or a 5- or 6-membered heterocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

$R^3$ represents H or halo, preferably H or F;
$R^4$ represents H or halo, preferably H or F;
$R^5$ represents H or halo, preferably H or F; and
$R^6$ represents 5- or 6-membered heteroaryl or 5- or 6-membered aryl, wherein heteroaryl or aryl groups are optionally substituted by one or more substituent selected from C1-C6 alkyl (preferably methyl) and halo (preferably fluoro or chloro); preferably $R^1$ represents 5-membered heteroaryl; more preferably $R^1$ represents furyl;

provided that when Y represents C—$R^B$ wherein $R^B$ is linked to $R^A$ so that —$R^A$—$R^B$— represents —C(=O)—S—, then X is not N.

In one specific embodiment, $R^1$ represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino or alkylsulfonealkyl; said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In a preferred embodiment, R1 substituents are optionally substituted by one or more substituent selected from halo, hydroxy, alkyl, heterocyclylalkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkoxy, amino, dialkylamino, aminoalkylcarbonylamino, aminocarbonylalkylamino, heterocyclylalkylaminocarbonyl, (aminocarbonylalkyl)(alkyl)amino, hydroxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, heterocyclylcarbonyl, alkylsulfoxide and alkylsulfonealkyl.

In one specific embodiment of the invention, R2 represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino, or alkylsulfonealkyl; said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In a preferred embodiment, R2 substituents are optionally substituted by one or more substituent selected from oxo, halo, hydroxy, cyano, alkyl, heterocyclylalkyl, dihydroxyalkyl, dialkylaminoalkyl, heteroaryl, alkylheteroaryl, hydroxycarbonyl, alkyloxycarbonyl, aminocarbonyl, heterocyclylalkylaminocarbonyl, alkylaminoalkylcarbonyl, dialkylaminoalkylcarbonyl, alkylsulfoxide, alkylsulfonealkyl.

In another specific embodiment of the invention, R1 and R2 form together with the atoms to which they are attached a 5- or 6-membered aryl ring, a 5- or 6-membered heteroaryl ring, a 5- or 6-membered cycloalkyl ring or a 5- or 6-membered heterocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In one specific embodiment of the invention, R3 represents H or halo, preferably H or F.

In one specific embodiment of the invention, R4 represents H or halo, preferably H or F.

In one specific embodiment of the invention, R5 represents H or halo, preferably H or F.

In one specific embodiment of the invention, R6 represents 5- or 6-membered heteroaryl or 5- or 6-membered aryl, wherein heteroaryl or aryl groups are optionally substituted by one or more substituent selected from C1-C6 alkyl (preferably methyl) and halo (preferably fluoro or chloro). In a preferred embodiment, R6 represents a 5-membered heteroaryl; more preferably R6 represents furyl.

In one specific embodiment of the invention, X represents N. In an alternative embodiment, X represents CH.

In one specific embodiment of the invention, Y represents N. In an alternative embodiment, Y represents C—RB wherein RB is linked to RA In one specific embodiment of the invention, RA represents H or CH3 and therefore in this case, Y necessarily represents N. In an alternative embodiment, RA is linked to RB so that —RA-RB- represent —C(=O)—N(CH3)-, —C(=O)—S—, —CH=N— or —N=CH— and therefore in this care, Y necessarily represent C—RB.

In one specific embodiment of the invention, X represents N; Y represents N and RA represents H or CH3. In another specific embodiment, X represents CH; Y represents N and RA represents H or CH3.

In another specific embodiment, X represents N; Y represents C—RB wherein RB is linked to RA so that —RA-RB- represent —C(=O)—N(CH3)-, —CH=N— or —N=CH—. In another specific embodiment, X represents CH; Y represents C—RB wherein RB is linked to RA so that —RA-RB- represent —C(=O)—N(CH3)-, —C(=O)—S—, —CH=N— or —N=CH—.

In one embodiment, preferred compounds of Formula (I) are those of Formula (I'):

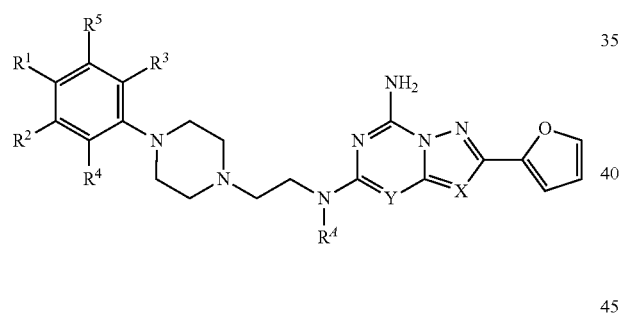

(I')

or a pharmaceutically acceptable salt or solvate thereof, wherein X, Y, $R^A$, $R^1$, $R^2$, $R^3$, $R^4$ and $R^5$ are as defined above.

According to one embodiment, the fused heteroaryl part of the compounds of Formula (I) or (I') is selected among the groups (1) to (11) below:

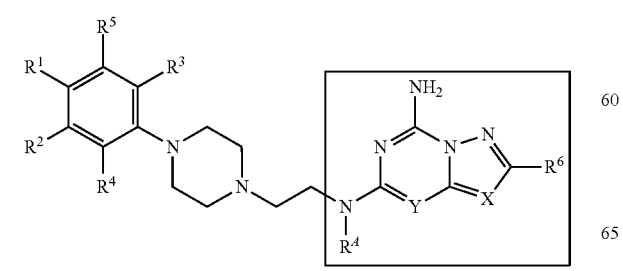

(I)

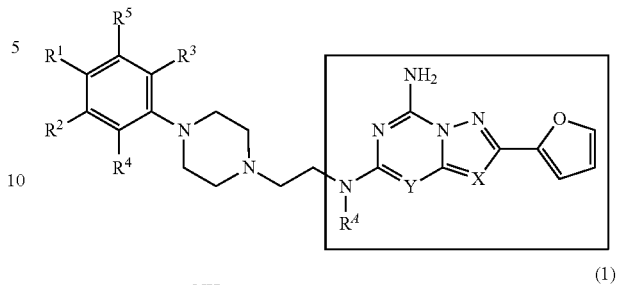

(I')

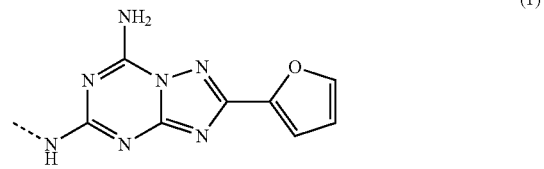

(1)

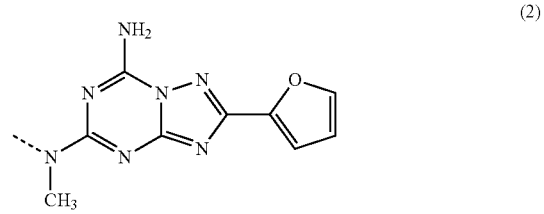

(2)

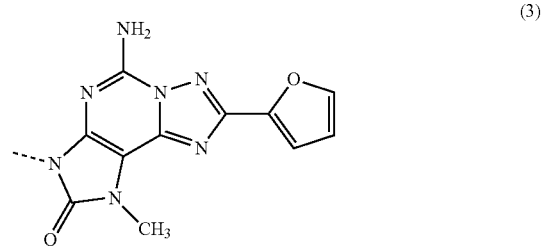

(3)

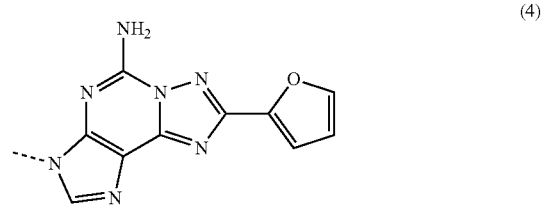

(4)

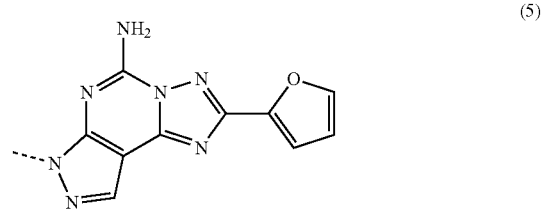

(5)

(6)

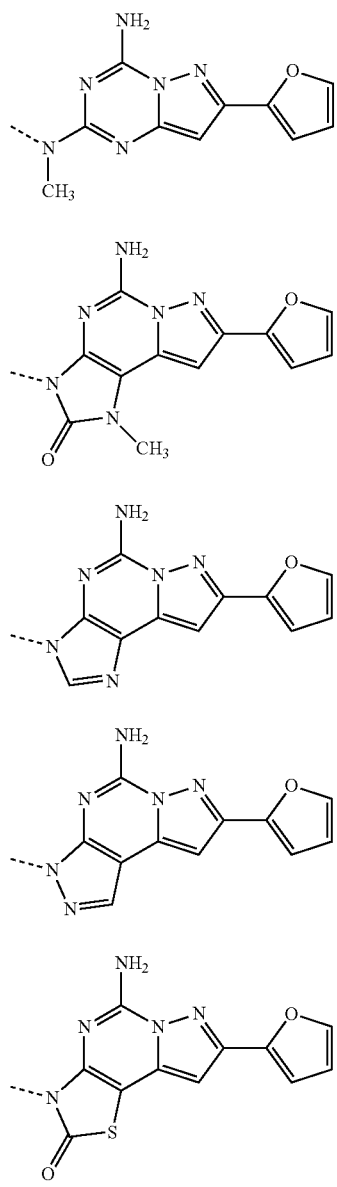
In one embodiment, preferred compounds of Formula (I) are of Formula (I-1), (I-2), (I-3), (I-4), (I-5), (I-6), (I-7), (I-8), (I-9), (I-10), (I-11) corresponding to the combination of Formula (I) with moieties (1) to (11) described above, and as detailed below:
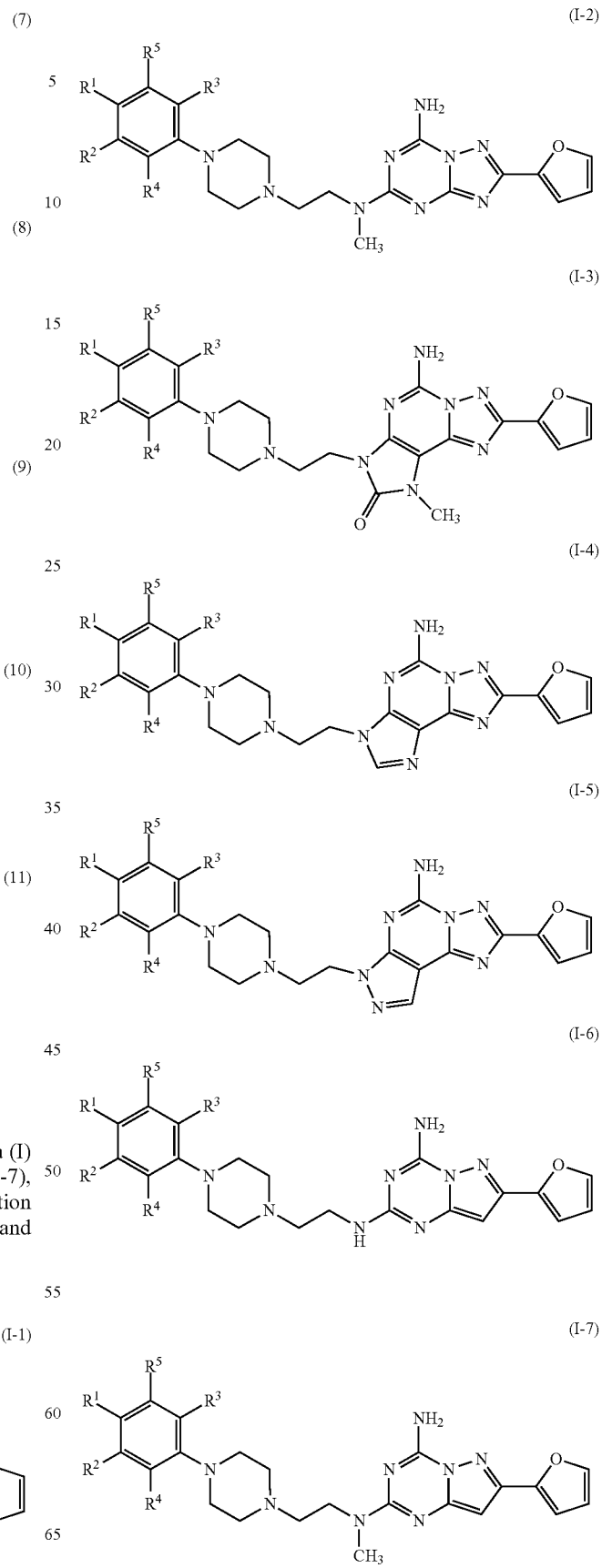

-continued

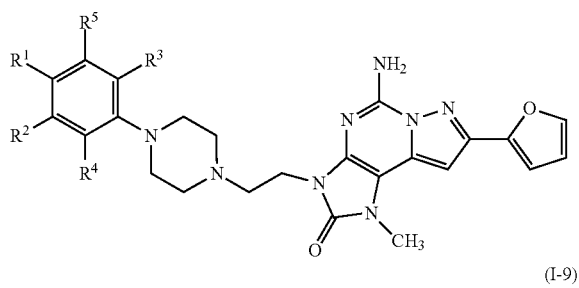
(I-8)

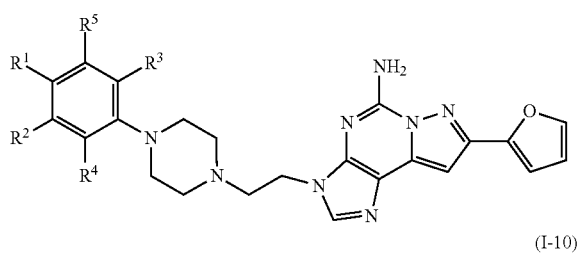
(I-9)

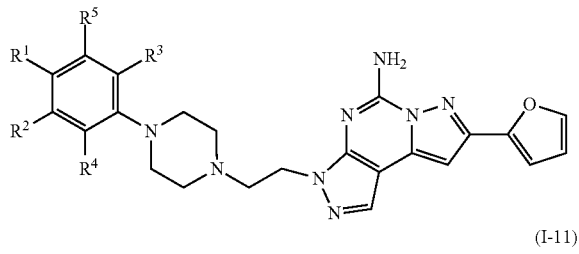
(I-10)

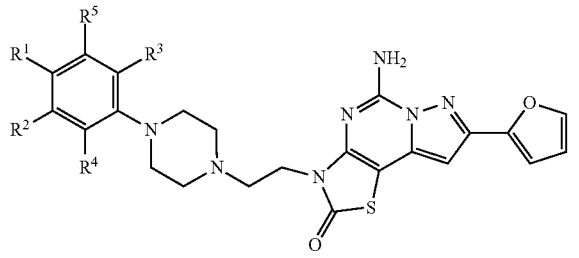
(I-11)

In one embodiment, preferred compounds of Formula (I) are those of Formula (I-a):

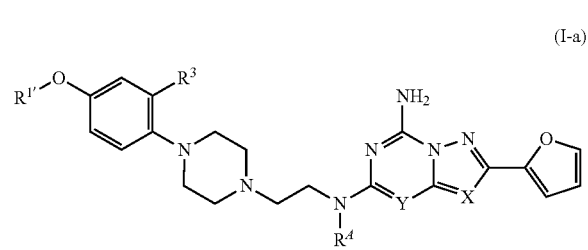
(I-a)

or a pharmaceutically acceptable salt or solvate thereof, wherein:

X, Y, $R^4$ and $R^3$ are as defined above; and $R^{1'}$ represents an alkyl or heterocyclyl group substituted by one or more group selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In one specific embodiment of the invention, R1' represents an alkyl or heterocyclyl group substituted by one or more group selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In one embodiment, preferred compounds of Formula (I) are of Formula (I-a-1), (I-a-2), (I-a-3), (I-a-4), (I-a-5), (I-a-6), (I-a-7), (I-a-8), (I-a-9), (I-a-10), (I-a-11) corresponding to the combination of Formula (I-a) with moieties (1) to (11), as respectively defined above.

In one embodiment, preferred compounds of Formula (I) are those of Formula (I-b):

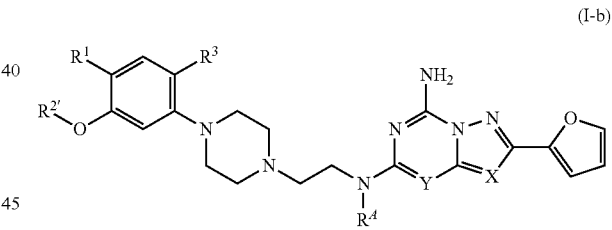
(I-b)

or a pharmaceutically acceptable salt or solvate thereof, wherein:

X, Y, $R^4$ and $R^3$ are as defined above;

$R^1$ represents H or halo, preferably H or F; and $R^{2'}$ represents an alkyl or heterocyclyl group substituted by one or more group selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In one specific embodiment of the invention, R1 represents H or halo, preferably H or F.

In one specific embodiment of the invention, R2' represents an alkyl or heterocyclyl group substituted by one or more group selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In one embodiment, preferred compounds of Formula (I) are of Formula (I-b-1), (I-b-2), (I-b-3), (I-b-4), (I-b-5), (I-b-6), (I-b-7), (I-b-8), (I-b-9), (I-b-10), (I-b-11) corresponding to the combination of Formula (I-b) with moieties (1) to (11), as respectively defined above.

In one embodiment, preferred compounds of Formula (I) are those of Formula (I-c) or (I-d):

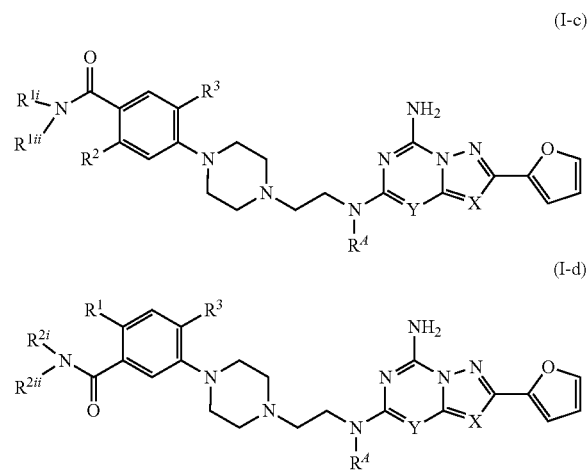

or a pharmaceutically acceptable salt or solvate thereof, wherein:

X, Y, $R^4$ and $R^3$ are as defined above;
$R^1$ represents H or halo, preferably H or F;
$R^2$ represents H or halo, preferably H or F;
$R^{1i}$ and $R^{1ii}$ represent each independently hydrogen, hydroxy, alkyl, alkenyl, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxidealkyl or alkylsulfonealkyl; and $R^{2i}$ and $R^{2ii}$ represent each independently hydrogen, hydroxy, alkyl, alkenyl, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxidealkyl or alkylsulfonealkyl.

In one specific embodiment of the invention, R1 represents H or halo, preferably H or F.

In one specific embodiment of the invention, R2 represents H or halo, preferably H or F.

In one specific embodiment of the invention, R1i and R1ii represent each independently hydrogen, hydroxy, alkyl, alkenyl, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxidealkyl or alkylsulfonealkyl. In a preferred embodiment, R1i and R1ii represent each independently hydrogen, alkyl, heterocyclylalkyl, hydroxyalkyl, hydroxyalkylaminoalkyl, aminoalkyl, alkylaminoalkyl, dialkylaminoalkyl, (heterocyclyl)(alkyl)aminoalkyl or heterocyclylalkylaminocarbonyl.

In one specific embodiment of the invention, R2i and R2ii represent each independently hydrogen, hydroxy, alkyl, alkenyl, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxidealkyl or alkylsulfonealkyl. In a preferred embodiment, R2i and R2ii represent each independently hydrogen, alkyl, heterocyclylalkyl, dihydroxyalkyl, dialkylaminoalkyl or heterocyclylalkylaminocarbonyl. In a preferred embodiment, R2i and R2ii represent each independently hydrogen, alkyl or dialkylaminoalkyl.

In one embodiment, preferred compounds of Formula (I) are of Formula (I-c-1), (I-c-2), (I-c-3), (I-c-4), (I-c-5), (I-c-6), (I-c-7), (I-c-8), (I-c-9), (I-c-10), (I-c-11), (I-d-1), (I-d-2), (I-d-3), (I-d-4), (I-d-5), (I-d-6), (I-d-7), (I-d-8), (I-d-9), (I-d-

10), (I-d-11) corresponding to the combination of Formula (I-c) or (I-d) with moieties (1) to (11), as respectively defined above.

Particularly preferred compounds of Formula (I) of the invention are those listed hereafter:

Heteroaryl Scaffold (1)

2-(4-(4-(2-((7-amino-2-(furan-2-yl)-[1,2,4]triazolo[1,5-a][1,3,5]triazin-5-yl)amino)ethyl)piperazin-1-yl)phenoxy)ethanol 2-(4-(4-(2-((7-amino-2-(furan-2-yl)-[1,2,4]triazolo[1,5-a][1,3,5]triazin-5-yl)amino)ethyl)piperazin-1-yl)phenoxy)acetic acid 2-(4-(4-(2-((7-amino-2-(furan-2-yl)-[1,2,4]triazolo[1,5-a][1,3,5]triazin-5-yl)amino)ethyl)piperazin-1-yl)phenoxy)acetamide 3-(4-(4-(2-((7-amino-2-(furan-2-yl)-[1,2,4]triazolo[1,5-a][1,3,5]triazin-5-yl)amino)ethyl)piperazin-1-yl)phenoxy)propane-1,2-diol N5-(2-(4-(4-(2-aminoethoxy)phenyl)piperazin-1-yl)ethyl)-2-(furan-2-yl)-[1,2,4]triazolo[1,5-a][1,3,5]triazine-5,7-diamine 4-(4-(2-((7-amino-2-(furan-2-yl)-[1,2,4]triazolo[1,5-a][1,3,5]triazin-5-yl)amino)ethyl)piperazin-1-yl)benzamide 4-(4-(2-((7-amino-2-(furan-2-yl)-[1,2,4]triazolo[1,5-a][1,3,5]triazin-5-yl)amino)ethyl)piperazin-1-yl)-N-methylbenzamide 2-(furan-2-yl)-N5-(2-(4-(4-(2-morpholinoethoxy)phenyl)piperazin-1-yl)ethyl)-[1,2,4]triazolo[1,5-a][1,3,5]triazine-5,7-diamine N5-(2-(4-(4-(2-(dimethylamino)ethoxy)phenyl)piperazin-1-yl)ethyl)-2-(furan-2-yl)-[1,2,4]triazolo[1,5-a][1,3,5]triazine-5,7-diamine 4-(4-(2-((7-amino-2-(furan-2-yl)-[1,2,4]triazolo[1,5-a][1,3,5]triazin-5-yl)amino)ethyl)piperazin-1-yl)benzenesulfonamide 4-(4-(2-((7-amino-2-(furan-2-yl)-[1,2,4]triazolo[1,5-a][1,3,5]triazin-5-yl)amino)ethyl)piperazin-1-yl)-N-methylbenzenesulfonamide 2-(furan-2-yl)-N5-(2-(4-(4-(methylsulfonyl)phenyl)piperazin-1-yl)ethyl)-[1,2,4]triazolo[1,5-a][1,3,5]triazine-5,7-diamine 2-(furan-2-yl)-N5-(2-(4-(4-(methylsulfinyl)phenyl)piperazin-1-yl)ethyl)-[1,2,4]triazolo[1,5-a][1,3,5]triazine-5,7-diamine 3-(4-(2-((7-amino-2-(furan-2-yl)-[1,2,4]triazolo[1,5-a][1,3,5]triazin-5-yl)amino)ethyl)piperazin-1-yl)benzamide 2-(3-(4-(2-((7-amino-2-(furan-2-yl)-[1,2,4]triazolo[1,5-a][1,3,5]triazin-5-yl)amino)ethyl)piperazin-1-yl)phenoxy)ethanol N5-(2-(4-(4-(azetidin-3-yloxy)phenyl)piperazin-1-yl)ethyl)-2-(furan-2-yl)-[1,2,4]triazolo[1,5-a][1,3,5]triazine-5,7-diamine N5-(2-(4-(4-((2H-1,2,3-triazol-4-yl)methoxy)-2-fluorophenyl)piperazin-1-yl)ethyl)-2-(furan-2-yl)-[1,2,4]triazolo[1,5-a][1,3,5]triazine-5,7-diamine 5-((4-(4-(2-((7-amino-2-(furan-2-yl)-[1,2,4]triazolo[1,5-a][1,3,5]triazin-5-yl)amino)ethyl)piperazin-1-yl)-3-fluorophenoxy)methyl)-1,3,4-oxadiazol-2(3H)-one 2-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)acetamide (S)—N5-(2-(4-(2-fluoro-4-(2-(methylsulfinyl)ethoxy)phenyl)piperazin-1-yl)ethyl)-2-(furan-2-yl)-[1,2,4]triazolo[1,5-a][1,3,5]triazine-5,7-diamine (R)—N5-(2-(4-(2-fluoro-4-(2-(methylsulfinyl)ethoxy)phenyl)piperazin-1-yl)ethyl)-2-(furan-2-yl)-[1,2,4]triazolo[1,5-a][1,3,5]triazine-5,7-diamine N5-(2-(4-(2,4-difluoro-5-(2-(methylsulfinyl)ethoxy)phenyl)piperazin-1-yl)ethyl)-2-(furan-2-yl)-[1,2,4]triazolo[1,5-a][1,3,5]triazine-5,7-diamine (S)—N5-(2-(4-(2,4-difluoro-5-(2-(methylsulfinyl)ethoxy)phenyl)piperazin-1-yl)ethyl)-2-(furan-2-yl)-[1,2,4]triazolo[1,5-a][1,3,5]triazine-5,7-diamine (Example 10)

(R)—N5-(2-(4-(2,4-difluoro-5-(2-(methylsulfinyl)ethoxy)phenyl)piperazin-1-yl)ethyl)-2-(furan-2-yl)-[1,2,4]triazolo[1,5-a][1,3,5]triazine-5,7-diamine (Example 11)

2-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)-1-(piperazin-1-yl)ethanone N5-(2-(4-(2-fluoro-4-(piperidin-4-ylmethoxy)phenyl)piperazin-1-yl)ethyl)-2-(furan-2-yl)-[1,2,4]triazolo[1,5-a][1,3,5]triazine-5,7-diamine (4-(4-(2-((7-amino-2-(furan-2-yl)-[1,2,4]triazolo[1,5-a][1,3,5]triazin-5-yl)amino)ethyl)piperazin-1-yl)-3-fluorophenyl)(piperazin-1-yl)methanone N5-(2-(4-(2-fluoro-4-(2-(piperazin-1-yl)ethoxy)phenyl)piperazin-1-yl)ethyl)-2-(furan-2-yl)-[1,2,4]triazolo[1,5-a][1,3,5]triazine-5,7-diamine N5-(2-(4-(2-fluoro-4-(piperazin-1-ylsulfonyl)phenyl)piperazin-1-yl)ethyl)-2-(furan-2-yl)-[1,2,4]triazolo[1,5-a][1,3,5]triazine-5,7-diamine N5-(2-(4-(2-fluoro-4-(methylsulfonyl)phenyl)piperazin-1-yl)ethyl)-2-(furan-2-yl)-[1,2,4]triazolo[1,5-a][1,3,5]triazine-5,7-diamine 4-(4-(2-((7-amino-2-(furan-2-yl)-[1,2,4]triazolo[1,5-a][1,3,5]triazin-5-yl)amino)ethyl)piperazin-1-yl)-N-(2-aminoethyl)-3-fluorobenzamide 4-(4-(2-((7-amino-2-(furan-2-yl)-[1,2,4]triazolo[1,5-a][1,3,5]triazin-5-yl)amino)ethyl)piperazin-1-yl)-3-fluoro-N-(2-(methylamino)ethyl)benzamide 4-(4-(2-((7-amino-2-(furan-2-yl)-[1,2,4]triazolo[1,5-a][1,3,5]triazin-5-yl)amino)ethyl)piperazin-1-yl)-N-(2-(dimethylamino)ethyl)-3-fluorobenzamide 4-(4-(2-((7-amino-2-(furan-2-yl)-[1,2,4]triazolo[1,5-a][1,3,5]triazin-5-yl)amino)ethyl)piperazin-1-yl)-3-fluoro-N-(2-hydroxyethyl)benzamide 4-(4-(2-((7-amino-2-(furan-2-yl)-[1,2,4]triazolo[1,5-a][1,3,5]triazin-5-yl)amino)ethyl)piperazin-1-yl)-N-(2,3-dihydroxypropyl)-3-fluorobenzamide 2-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)acetic acid 2-(4-(4-(2-((7-amino-2-(furan-2-yl)-[1,2,4]triazolo[1,5-a][1,3,5]triazin-5-yl)amino)ethyl)piperazin-1-yl)-3,5-difluorophenoxy)acetic acid 2-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)propanoic acid (S)-2-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)propanoic acid 2-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)-2-methylpropanoic acid 3-(4-(4-(2-((7-amino-2-(furan-2-yl)-[1,2,4]triazolo[1,5-a][1,3,5]triazin-5-yl)amino)ethyl)piperazin-1-yl)-3-fluorophenyl)propanoic acid 4-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)butanoic acid 2-(3-(4-(2-((7-amino-2-(furan-2-yl)-[1,2,4]triazolo[1,5-a][1,3,5]triazin-5-yl)amino)ethyl)piperazin-1-yl)-2,6-difluorophenoxy)acetic acid 2-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)acetic acid 4-(4-(2-((7-amino-2-(furan-2-yl)-[1,2,4]triazolo[1,5-a][1,3,5]triazin-5-yl)amino)ethyl)piperazin-1-yl)-3-fluorobenzoic acid 2-((2-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)ethyl)amino)acetamide 2-((2-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)ethyl)(methyl)amino)acetamide N5-(2-(4-(2-fluoro-4-(piperidin-4-yloxy)phenyl)piperazin-1-yl)ethyl)-2-(furan-2-yl)-[1,2,4]triazolo[1,5-a][1,3,5]triazine-5,7-diamine N5-(2-(4-(2-fluoro-4-(pyrrolidin-3-yloxy)phenyl)piperazin-1-yl)ethyl)-2-(furan-2-yl)-[1,2,4]triazolo[1,5-a][1,3,5]triazine-5,7-diamine N5-(2-(4-(4-((4H-1,2,4-triazol-3-yl)methoxy)-2-fluorophenyl)piperazin-1-yl)ethyl)-2-(furan-2-yl)-[1,2,4]triazolo[1,5-a][1,3,5]triazine-5,7-diamine 2-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)-N-(2-(methylamino)ethyl)acetamide 2-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)-N-(2-(dimethylamino)ethyl)acetamide 2-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)-N-(2-aminoethyl)acetamide (R)-2-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)propanoic acid 2-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)acetamide 4-(4-(2-((7-amino-2-(furan-2-yl)-[1,2,4]triazolo[1,5-a][1,3,5]triazin-5-yl)amino)ethyl)piperazin-1-yl)-3-fluoro-N-methyl-N-(2-(methylamino)ethyl)benzamide 4-(4-(2-((7-amino-2-(furan-2-yl)-[1,2,4]triazolo[1,5-a][1,3,5]triazin-5-yl)amino)ethyl)piperazin-1-yl)-N-(2-(dimethylamino)ethyl)-3-fluoro-N-methylbenzamide (R)-4-(4-(2-((7-amino-2-(furan-2-yl)-[1,2,4]triazolo[1,5-a][1,3,5]triazin-5-yl)amino)ethyl)piperazin-1-yl)-N-(1-(dimethylamino)propan-2-yl)-3-fluorobenzamide 2-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)-N-methyl-N-(2-(methylamino)ethyl)acetamide 2-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)-2-methylpropanoic acid (S)-2-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)propanoic acid (R)-2-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)propanoic acid 2-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)-N-(2-(methylamino)ethyl)acetamide 2-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)-N-(2-(dimethylamino)ethyl)acetamide 5-(4-(2-((7-amino-2-(furan-2-yl)-[1,2,4]triazolo[1,5-a][1,3,5]triazin-5-yl)amino)ethyl)piperazin-1-yl)-N-(2-(dimethylamino)ethyl)-2,4-difluoro-N-methylbenzamide 5-(4-(2-((7-amino-2-(furan-2-yl)-[1,2,4]triazolo[1,5-a][1,3,5]triazin-5-yl)amino)ethyl)piperazin-1-yl)-2,4-difluoro-N-methylbenzamide 4-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)butanoic acid N5-(2-(4-(5-((1H-tetrazol-5-yl)methoxy)-2,4-difluorophenyl)piperazin-1-yl)ethyl)-2-(furan-2-yl)-[1,2,4]triazolo[1,5-a][1,3,5]triazine-5,7-diamine N5-(2-(4-(2-fluoro-4-((1-methyl-1H-1,2,4-triazol-3-yl)methoxy)phenyl)piperazin-1-yl)ethyl)-2-(furan-2-yl)-[1,2,4]triazolo[1,5-a][1,3,5]triazine-5,7-diamine N5-(2-(4-(2,4-difluoro-5-((1-methyl-1H-1,2,4-triazol-3-yl)methoxy)phenyl)piperazin-1-yl)ethyl)-2-(furan-2-yl)-[1,2,4]triazolo[1,5-a][1,3,5]triazine-5,7-diamine 4-(4-(2-((7-amino-2-(furan-2-yl)-[1,2,4]triazolo[1,5-a][1,3,5]triazin-5-yl)amino)ethyl)piperazin-1-yl)-3-fluoro-N-(2-(methyl(oxetan-3-yl)amino)ethyl)benzamide 4-(4-(2-((7-amino-2-(furan-2-yl)-[1,2,4]triazolo[1,5-a][1,3,5]triazin-5-yl)amino)ethyl)piperazin-1-yl)-3-fluoro-N-(2-((2-hydroxyethyl)amino)ethyl)benzamide 2-amino-N-(2-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)ethyl)acetamide (S)-2-amino-N-(2-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)ethyl)-3-methylbutanamide N5-(2-(4-(2,4-difluoro-5-(2-(methylsulfonyl)ethoxy)phenyl)piperazin-1-yl)ethyl)-2-(furan-2-yl)-[1,2,4]triazolo[1,5-a][1,3,5]triazine-5,7-diamine (Example 6)

N5-(2-(4-(2-fluoro-4-(2-(methylsulfonyl)ethoxy)phenyl)piperazin-1-yl)ethyl)-2-(furan-2-yl)-[1,2,4]triazolo[1,5-a][1,3,5]triazine-5,7-diamine 5-(4-(2-((7-amino-2-(furan-2-yl)-[1,2,4]triazolo[1,5-a][1,3,5]triazin-5-yl)amino)ethyl)piperazin-1-yl)-6-fluoroindolin-2-one N5-(2-(4-(2-fluoro-4-(S-methylsulfonimidoyl)phenyl)piperazin-1-yl)ethyl)-2-(furan-2-yl)-[1,2,4]triazolo[1,5-a][1,3,5]triazine-5,7-diamine 5-(4-(2-((7-amino-2-(furan-2-yl)-[1,2,4]triazolo[1,5-a][1,3,5]triazin-5-yl)amino)ethyl)piperazin-1-yl)-N-(2-(dimethylamino)ethyl)-2,4-difluorobenzamide (3R,4R)-4-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)tetrahydrofuran-3-ol (3S,4S)-4-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)tetrahydrofuran-3-ol 1-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)-2-methylpropan-2-ol 2-(4-(4-(2-((7-amino-2-(furan-2-yl)-[1,2,4]triazolo[1,5-a][1,3,5]triazin-5-yl)amino)ethyl)piperazin-1-yl)-3-fluorophenyl)propan-2-ol 3-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)-1,1,1-trifluoropropan-2-ol 2-(3-(4-(2-((7-amino-2-(furan-2-yl)-[1,2,4]triazolo[1,5-a][1,3,5]triazin-5-yl)amino)ethyl)piperazin-1-yl)-4-fluorophenoxy)ethanol N5-(2-(4-(2,4-difluoro-5-(morpholin-2-ylmethoxy)phenyl)piperazin-1-yl)ethyl)-2-(furan-2-yl)-[1,2,4]triazolo[1,5-a][1,3,5]triazine-5,7-diamine N5-(2-(4-(2,4-difluoro-5-(morpholin-3-ylmethoxy)phenyl)piperazin-1-yl)ethyl)-2-(furan-2-yl)-[1,2,4]triazolo[1,5-a][1,3,5]triazine-5,7-diamine N5-(2-(4-(2,4-difluoro-5-(((3S,4S)-4-fluoropyrrolidin-3-yl)oxy)phenyl)piperazin-1-yl)ethyl)-2-(furan-2-yl)-[1,2,4]triazolo[1,5-a][1,3,5]triazine-5,7-diamine N5-(2-(4-(2,4-difluoro-5-(((3R,4S)-4-fluoropyrrolidin-3-yl)oxy)phenyl)piperazin-1-yl)ethyl)-2-(furan-2-yl)-[1,2,4]triazolo[1,5-a][1,3,5]triazine-5,7-diamine N5-(2-(4-(2,4-difluoro-5-(((3S,4R)-4-fluoropyrrolidin-3-yl)oxy)phenyl)piperazin-1-yl)ethyl)-2-(furan-2-yl)-[1,2,4]triazolo[1,5-a][1,3,5]triazine-5,7-diamine (S)-3-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)pyrrolidin-2-one (R)-3-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)pyrrolidin-2-one 2-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)-N-(2-morpholinoethyl)acetamide 5-(4-(2-((7-amino-2-(furan-2-yl)-[1,2,4]triazolo[1,5-a][1,3,5]triazin-5-yl)amino)ethyl)piperazin-1-yl)-2,4-difluoro-N-(morpholin-3-ylmethyl)benzamide N5-(2-(4-(2-fluoro-4-(morpholin-3-ylmethoxy)phenyl)piperazin-1-yl)ethyl)-2-(furan-2-yl)-[1,2,4]triazolo[1,5-a][1,3,5]triazine-5,7-diamine N5-(2-(4-(2-fluoro-4-(morpholin-2-ylmethoxy)phenyl)piperazin-1-yl)ethyl)-2-(furan-2-yl)-[1,2,4]triazolo[1,5-a][1,3,5]triazine-5,7-diamine N5-(2-(4-(2-fluoro-4-(((3R,4R)-4-fluoropyrrolidin-3-yl)oxy)phenyl)piperazin-1-yl)ethyl)-2-(furan-2-yl)-[1,2,4]triazolo[1,5-a][1,3,5]triazine-5,7-diamine N5-(2-(4-(2-fluoro-4-(((3S,4S)-4-fluoropyrrolidin-3-yl)oxy)phenyl)piperazin-1-yl)ethyl)-2-(furan-2-yl)-[1,2,4]triazolo[1,5-a][1,3,5]triazine-5,7-diamine N5-(2-(4-(2-fluoro-4-(((3R,4S)-4-fluoropyrrolidin-3-yl)oxy)phenyl)piperazin-1-yl)ethyl)-2-(furan-2-yl)-[1,2,4]triazolo[1,5-a][1,3,5]triazine-5,7-diamine N5-(2-(4-(2-fluoro-4-(((3S,4R)-4-fluoropyrrolidin-3-yl)oxy)phenyl)piperazin-1-yl)ethyl)-2-(furan-2-yl)-[1,2,4]triazolo[1,5-a][1,3,5]triazine-5,7-diamine 2-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)-N-(2-morpholinoethyl)acetamide 4-(4-(2-((7-amino-2-(furan-2-yl)-[1,2,4]triazolo[1,5-a][1,3,5]triazin-5-yl)amino)ethyl)piperazin-1-yl)-3-fluoro-N-(2-morpholinoethyl)benzamide 4-(4-(2-((7-amino-2-(furan-2-yl)-[1,2,4]triazolo[1,5-a][1,3,5]triazin-5-yl)amino)ethyl)piperazin-1-yl)-3-fluoro-N-(morpholin-3-ylmethyl)benzamide (S)—N5-(2-(4-(2,4-difluoro-5-(methylsulfinyl)phenyl)piperazin-1-yl)ethyl)-2-(furan-2-yl)-[1,2,4]triazolo[1,5-a][1,3,5]triazine-5,7-diamine (Example 17)

(R)—N5-(2-(4-(2,4-difluoro-5-(methylsulfinyl)phenyl)piperazin-1-yl)ethyl)-2-(furan-2-yl)-[1,2,4]triazolo[1,5-a][1,3,5]triazine-5,7-diamine (Example 16)

(1s,4s)-4-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)tetrahydro-2H-thiopyran 1-oxide (Example 14)

(1r,4r)-4-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)tetrahydro-2H-thiopyran 1-oxide (S)-5-(4-(2-((7-amino-2-(furan-2-yl)-[1,2,4]triazolo[1,5-a][1,3,5]triazin-5-yl)amino)ethyl)piperazin-1-yl)-2,4-difluoro-N-(2-(methylsulfinyl)ethyl)benzamide (R)-5-(4-(2-((7-amino-2-(furan-2-yl)-[1,2,4]triazolo[1,5-a][1,3,5]triazin-5-yl)amino)ethyl)piperazin-1-yl)-2,4-difluoro-N-(2-(methylsulfinyl)ethyl)benzamide (S)-5-(4-(2-((7-amino-2-(furan-2-yl)-[1,2,4]triazolo[1,5-a][1,3,5]triazin-5-yl)amino)ethyl)piperazin-1-yl)-2,4-difluoro-N-methyl-N-(2-(methylsulfinyl)ethyl)benzamide (R)-5-(4-(2-((7-amino-2-(furan-2-yl)-[1,2,4]triazolo[1,5-a][1,3,5]triazin-5-yl)amino)ethyl)piperazin-1-yl)-2,4-difluoro-N-methyl-N-(2-(methylsulfinyl)ethyl)benzamide (5-(4-(2-((7-amino-2-(furan-2-yl)-[1,2,4]triazolo[1,5-a][1,3,5]triazin-5-yl)amino)ethyl)piperazin-1-yl)-2,4-difluorophenyl)(1-oxidothiomorpholino)methanone 4-(5-(4-(2-((7-amino-2-(furan-2-yl)-[1,2,4]triazolo[1,5-a][1,3,5]triazin-5-yl)amino)ethyl)piperazin-1-yl)-2,4-difluorophenyl)thiomorpholine 1-oxide (Example 15)

(R)—N5-(2-(4-(2-fluoro-4-(methylsulfinyl)phenyl)piperazin-1-yl)ethyl)-2-(furan-2-yl)-[1,2,4]triazolo[1,5-a][1,3,5]triazine-5,7-diamine (S)—N5-(2-(4-(2-fluoro-4-(methylsulfinyl)phenyl)piperazin-1-yl)ethyl)-2-(furan-2-yl)-[1,2,4]triazolo[1,5-a][1,3,5]triazine-5,7-diamine (1s,4s)-4-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)tetrahydro-2H-thiopyran 1-oxide (Example 19)

(1r,4r)-4-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)tetrahydro-2H-thiopyran 1-oxide (S)-4-(4-(2-((7-amino-2-(furan-2-yl)-[1,2,4]triazolo[1,5-a][1,3,5]triazin-5-yl)amino)ethyl)piperazin-1-yl)-3-fluoro-N-(2-(methylsulfinyl)ethyl)benzamide (R)-4-(4-(2-((7-amino-2-(furan-2-yl)-[1,2,4]triazolo[1,5-a][1,3,5]triazin-5-yl)amino)ethyl)piperazin-1-yl)-3-fluoro-N-(2-(methylsulfinyl)ethyl)benzamide (4-(4-(2-((7-amino-2-(furan-2-yl)-[1,2,4]triazolo[1,5-a][1,3,5]triazin-5-yl)amino)ethyl)piperazin-1-yl)-3-fluorophenyl)(1-oxidothiomorpholino)methanone (Example 18)

4-(4-(4-(2-((7-amino-2-(furan-2-yl)-[1,2,4]triazolo[1,5-a][1,3,5]triazin-5-yl)amino)ethyl)piperazin-1-yl)-3-fluorophenyl)thiomorpholine 1-oxide (S)-3-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)propane-1,2-diol (R)-3-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)propane-1,2-diol (S)-5-(4-(2-((7-amino-2-(furan-2-yl)-[1,2,4]triazolo[1,5-a][1,3,5]triazin-5-yl)amino)ethyl)piperazin-1-yl)-N-(2,3-dihydroxypropyl)-2,4-difluorobenzamide (R)-5-(4-(2-((7-amino-2-(furan-2-yl)-[1,2,4]triazolo[1,5-a][1,3,5]triazin-5-yl)amino)ethyl)piperazin-1-yl)-N-(2,3-dihydroxypropyl)-2,4-difluorobenzamide N5-(2-(4-(4-(azetidin-3-yloxy)-2-fluorophenyl)piperazin-1-yl)ethyl)-2-(furan-2-yl)-[1,2,4]triazolo[1,5-a][1,3,5]triazine-5,7-diamine N5-(2-(4-(5-(azetidin-3-yloxy)-2,4-difluorophenyl)piperazin-1-yl)ethyl)-2-(furan-2-yl)-[1,2,4]triazolo[1,5-a][1,3,5]triazine-5,7-diamine (S)—N5-(2-(4-(2,4-difluoro-5-(3-(methylsulfinyl)propoxy)phenyl)piperazin-1-yl)ethyl)-2-(furan-2-yl)-[1,2,4]triazolo[1,5-a][1,3,5]triazine-5,7-diamine Heteroaryl Scaffold (2)

2-(4-(4-(2-((7-amino-2-(furan-2-yl)-[1,2,4]triazolo[1,5-a][1,3,5]triazin-5-yl)(methyl)amino)ethyl)piperazin-1-yl)phenoxy)ethanol 2-(4-(4-(2-((7-amino-2-(furan-2-yl)-[1,2,4]triazolo[1,5-a][1,3,5]triazin-5-yl)(methyl)amino)ethyl)piperazin-1-yl)phenoxy)acetic acid 2-(4-(4-(2-((7-amino-2-(furan-2-yl)-[1,2,4]triazolo[1,5-a]
[1,3,5]triazin-5-yl)(methyl)amino)ethyl)piperazin-1-yl)
phenoxy)acetamide 3-(4-(4-(2-((7-amino-2-(furan-2-yl)-[1,2,4]triazolo[1,5-a]
[1,3,5]triazin-5-yl)(methyl)amino)ethyl)piperazin-1-yl)
phenoxy)propane-1,2-diol N5-(2-(4-(4-(2-aminoethoxy)phenyl)piperazin-1-yl)ethyl)-
2-(furan-2-yl)-N5-methyl-[1,2,4]triazolo[1,5-a][1,3,5]tri-
azine-5,7-diamine 4-(4-(2-((7-amino-2-(furan-2-yl)-[1,2,4]triazolo[1,5-a][1,3,
5]triazin-5-yl)(methyl)amino)ethyl)piperazin-1-yl)benz-
amide 4-(4-(2-((7-amino-2-(furan-2-yl)-[1,2,4]triazolo[1,5-a][1,3,
5]triazin-5-yl)(methyl)amino)ethyl)piperazin-1-yl)-N-
methylbenzamide 2-(furan-2-yl)-N5-methyl-N5-(2-(4-(4-(2-morpholino
ethoxy)phenyl)piperazin-1-yl)ethyl)-[1,2,4]triazolo[1,5-
a][1,3,5]triazine-5,7-diamine N5-(2-(4-(4-(2-(dimethylamino)ethoxy)phenyl)piperazin-1-
yl)ethyl)-2-(furan-2-yl)-N5-methyl-[1,2,4]triazolo[1,5-a]
[1,3,5]triazine-5,7-diamine 4-(4-(2-((7-amino-2-(furan-2-yl)-[1,2,4]triazolo[1,5-a][1,3,
5]triazin-5-yl)(methyl)amino)ethyl)piperazin-1-yl)benze-
nesulfonamide 4-(4-(2-((7-amino-2-(furan-2-yl)-[1,2,4]triazolo[1,5-a][1,3,
5]triazin-5-yl)(methyl)amino)ethyl)piperazin-1-yl)-N-
methylbenzenesulfonamide 2-(furan-2-yl)-N5-methyl-N5-(2-(4-(4-(methylsulfonyl)
phenyl)piperazin-1-yl)ethyl)-[1,2,4]triazolo[1,5-a][1,3,5]
triazine-5,7-diamine 2-(furan-2-yl)-N5-methyl-N5-(2-(4-(4-(methylsulfinyl)phe-
nyl)piperazin-1-yl)ethyl)-[1,2,4]triazolo[1,5-a][1,3,5]tri-
azine-5,7-diamine 3-(4-(2-((7-amino-2-(furan-2-yl)-[1,2,4]triazolo[1,5-a][1,3,
5]triazin-5-yl)(methyl)amino)ethyl)piperazin-1-yl)benz-
amide 2-(3-(4-(2-((7-amino-2-(furan-2-yl)-[1,2,4]triazolo[1,5-a]
[1,3,5]triazin-5-yl)(methyl)amino)ethyl)piperazin-1-yl)
phenoxy)ethanol N5-(2-(4-(4-(azetidin-3-yloxy)phenyl)piperazin-1-yl)
ethyl)-2-(furan-2-yl)-N5-methyl-[1,2,4]triazolo[1,5-a][1,
3,5]triazine-5,7-diamine N5-(2-(4-(4-((2H-1,2,3-triazol-4-yl)methoxy)-2-fluorophe-
nyl)piperazin-1-yl)ethyl)-2-(furan-2-yl)-N5-methyl-[1,2,
4]triazolo[1,5-a][1,3,5]triazine-5,7-diamine 5-((4-(4-(2-((7-amino-2-(furan-2-yl)-[1,2,4]triazolo[1,5-a]
[1,3,5]triazin-5-yl)(methyl)amino)ethyl)piperazin-1-yl)-
3-fluorophenoxy)methyl)-1,3,4-oxadiazol-2(3H)-one 2-(5-(4-(2-((7-amino-2-(furan-2-yl)-[1,2,4]triazolo[1,5-a]
[1,3,5]triazin-5-yl)(methyl)amino)ethyl)piperazin-1-yl)-
2,4-difluorophenoxy)acetamide (S)—N5-(2-(4-(2-fluoro-4-(2-(methylsulfinyl)ethoxy)phe-
nyl)piperazin-1-yl)ethyl)-2-(furan-2-yl)-N5-methyl-[1,2,
4]triazolo[1,5-a][1,3,5]triazine-5,7-diamine (R)—N5-(2-(4-(2-fluoro-4-(2-(methylsulfinyl)ethoxy)phe-
nyl)piperazin-1-yl)ethyl)-2-(furan-2-yl)-N5-methyl-[1,2,
4]triazolo[1,5-a][1,3,5]triazine-5,7-diamine N5-(2-(4-(2,4-difluoro-5-(2-(methylsulfinyl)ethoxy)phenyl)
piperazin-1-yl)ethyl)-2-(furan-2-yl)-N5-methyl-[1,2,4]
triazolo[1,5-a][1,3,5]triazine-5,7-diamine (S)—N5-(2-(4-(2,4-difluoro-5-(2-(methylsulfinyl)ethoxy)
phenyl)piperazin-1-yl)ethyl)-2-(furan-2-yl)-N5-methyl-
[1,2,4]triazolo[1,5-a][1,3,5]triazine-5,7-diamine (Ex-
ample 1)

(R)—N5-(2-(4-(2,4-difluoro-5-(2-(methylsulfinyl)ethoxy)
phenyl)piperazin-1-yl)ethyl)-2-(furan-2-yl)-N5-methyl-
[1,2,4]triazolo[1,5-a][1,3,5]triazine-5,7-diamine (Ex-
ample 2)

2-(4-(4-(2-((7-amino-2-(furan-2-yl)-[1,2,4]triazolo[1,5-a]
[1,3,5]triazin-5-yl)(methyl)amino)ethyl)piperazin-1-yl)-
3-fluorophenoxy)-1-(piperazin-1-yl)ethanone N5-(2-(4-(2-fluoro-4-(piperidin-4-ylmethoxy)phenyl)piper-
azin-1-yl)ethyl)-2-(furan-2-yl)-N5-methyl-[1,2,4]triazolo
[1,5-a][1,3,5]triazine-5,7-diamine (4-(4-(2-((7-amino-2-(furan-2-yl)-[1,2,4]triazolo[1,5-a][1,3,
5]triazin-5-yl)(methyl)amino)ethyl)piperazin-1-yl)-3-
fluorophenyl)(piperazin-1-yl)methanone N5-(2-(4-(2-fluoro-4-(2-(piperazin-1-yl)ethoxy)phenyl)pip-
erazin-1-yl)ethyl)-2-(furan-2-yl)-N5-methyl-[1,2,4]tri-
azolo[1,5-a][1,3,5]triazine-5,7-diamine N5-(2-(4-(2-fluoro-4-(piperazin-1-ylsulfonyl)phenyl)piper-
azin-1-yl)ethyl)-2-(furan-2-yl)-N5-methyl-[1,2,4]triazolo
[1,5-a][1,3,5]triazine-5,7-diamine N5-(2-(4-(2-fluoro-4-(methylsulfonyl)phenyl)piperazin-1-
yl)ethyl)-2-(furan-2-yl)-N5-methyl-[1,2,4]triazolo[1,5-a]
[1,3,5]triazine-5,7-diamine 4-(4-(2-((7-amino-2-(furan-2-yl)-[1,2,4]triazolo[1,5-a][1,3,
5]triazin-5-yl)(methyl)amino)ethyl)piperazin-1-yl)-N-(2-
aminoethyl)-3-fluorobenzamide 4-(4-(2-((7-amino-2-(furan-2-yl)-[1,2,4]triazolo[1,5-a][1,3,
5]triazin-5-yl)(methyl)amino)ethyl)piperazin-1-yl)-3-
fluoro-N-(2-(methylamino)ethyl)benzamide 4-(4-(2-((7-amino-2-(furan-2-yl)-[1,2,4]triazolo[1,5-a][1,3,
5]triazin-5-yl)(methyl)amino)ethyl)piperazin-1-yl)-N-(2-
(dimethylamino)ethyl)-3-fluorobenzamide 4-(4-(2-((7-amino-2-(furan-2-yl)-[1,2,4]triazolo[1,5-a][1,3,
5]triazin-5-yl)(methyl)amino)ethyl)piperazin-1-yl)-3-
fluoro-N-(2-hydroxyethyl)benzamide 4-(4-(2-((7-amino-2-(furan-2-yl)-[1,2,4]triazolo[1,5-a][1,3,
5]triazin-5-yl)(methyl)amino)ethyl)piperazin-1-yl)-N-(2,
3-dihydroxypropyl)-3-fluorobenzamide 2-(4-(4-(2-((7-amino-2-(furan-2-yl)-[1,2,4]triazolo[1,5-a]
[1,3,5]triazin-5-yl)(methyl)amino)ethyl)piperazin-1-yl)-
3-fluorophenoxy)acetic acid 2-(4-(4-(2-((7-amino-2-(furan-2-yl)-[1,2,4]triazolo[1,5-a]
[1,3,5]triazin-5-yl)(methyl)amino)ethyl)piperazin-1-yl)-
3,5-difluorophenoxy)acetic acid 2-(4-(4-(2-((7-amino-2-(furan-2-yl)-[1,2,4]triazolo[1,5-a]
[1,3,5]triazin-5-yl)(methyl)amino)ethyl)piperazin-1-yl)-
3-fluorophenoxy)propanoic acid (S)-2-(4-(4-(2-((7-amino-2-(furan-2-yl)-[1,2,4]triazolo[1,5-
a][1,3,5]triazin-5-yl)(methyl)amino)ethyl)piperazin-1-
yl)-3-fluorophenoxy)propanoic acid 2-(4-(4-(2-((7-amino-2-(furan-2-yl)-[1,2,4]triazolo[1,5-a]
[1,3,5]triazin-5-yl)(methyl)amino)ethyl)piperazin-1-yl)-
3-fluorophenoxy)-2-methylpropanoic acid 3-(4-(4-(2-((7-amino-2-(furan-2-yl)-[1,2,4]triazolo[1,5-a]
[1,3,5]triazin-5-yl)(methyl)amino)ethyl)piperazin-1-yl)-
3-fluorophenyl)propanoic acid 4-(4-(4-(2-((7-amino-2-(furan-2-yl)-[1,2,4]triazolo[1,5-a]
[1,3,5]triazin-5-yl)(methyl)amino)ethyl)piperazin-1-yl)-
3-fluorophenoxy)butanoic acid 2-(3-(4-(2-((7-amino-2-(furan-2-yl)-[1,2,4]triazolo[1,5-a]
[1,3,5]triazin-5-yl)(methyl)amino)ethyl)piperazin-1-yl)-
2,6-difluorophenoxy)acetic acid 2-(5-(4-(2-((7-amino-2-(furan-2-yl)-[1,2,4]triazolo[1,5-a]
[1,3,5]triazin-5-yl)(methyl)amino)ethyl)piperazin-1-yl)-
2,4-difluorophenoxy)acetic acid 4-(4-(2-((7-amino-2-(furan-2-yl)-[1,2,4]triazolo[1,5-a][1,3,
5]triazin-5-yl)(methyl)amino)ethyl)piperazin-1-yl)-3-
fluorobenzoic acid 2-((2-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)ethyl)amino)acetamide
2-((2-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)ethyl)(methyl)amino)acetamide
N5-(2-(4-(2-fluoro-4-(piperidin-4-yloxy)phenyl)piperazin-1-yl)ethyl)-2-(furan-2-yl)-N5-methyl-[1,2,4]triazolo[1,5-a][1,3,5]triazine-5,7-diamine
N5-(2-(4-(2-fluoro-4-(pyrrolidin-3-yloxy)phenyl)piperazin-1-yl)ethyl)-2-(furan-2-yl)-N5-methyl-[1,2,4]triazolo[1,5-a][1,3,5]triazine-5,7-diamine
N5-(2-(4-(4-((4H-1,2,4-triazol-3-yl)methoxy)-2-fluorophenyl)piperazin-1-yl)ethyl)-2-(furan-2-yl)-N5-methyl-[1,2,4]triazolo[1,5-a][1,3,5]triazine-5,7-diamine
2-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)-N-(2-(methylamino)ethyl)acetamide
2-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)-N-(2-(dimethylamino)ethyl)acetamide
2-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)-N-(2-aminoethyl)acetamide
(R)-2-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)propanoic acid
2-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)acetamide
4-(4-(2-((7-amino-2-(furan-2-yl)-[1,2,4]triazolo[1,5-a][1,3,5]triazin-5-yl)(methyl)amino)ethyl)piperazin-1-yl)-3-fluoro-N-methyl-N-(2-(methylamino)ethyl)benzamide
4-(4-(2-((7-amino-2-(furan-2-yl)-[1,2,4]triazolo[1,5-a][1,3,5]triazin-5-yl)(methyl)amino)ethyl)piperazin-1-yl)-N-(2-(dimethylamino)ethyl)-3-fluoro-N-methylbenzamide
(R)-4-(4-(2-((7-amino-2-(furan-2-yl)-[1,2,4]triazolo[1,5-a][1,3,5]triazin-5-yl)(methyl)amino)ethyl)piperazin-1-yl)-N-(1-(dimethylamino)propan-2-yl)-3-fluorobenzamide
2-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)-N-methyl-N-(2-(methylamino)ethyl)acetamide
2-(5-(4-(2-((7-amino-2-(furan-2-yl)-[1,2,4]triazolo[1,5-a][1,3,5]triazin-5-yl)(methyl)amino)ethyl)piperazin-1-yl)-2,4-difluorophenoxy)-2-methylpropanoic acid
(S)-2-(5-(4-(2-((7-amino-2-(furan-2-yl)-[1,2,4]triazolo[1,5-a][1,3,5]triazin-5-yl)(methyl)amino)ethyl)piperazin-1-yl)-2,4-difluorophenoxy)propanoic acid
(R)-2-(5-(4-(2-((7-amino-2-(furan-2-yl)-[1,2,4]triazolo[1,5-a][1,3,5]triazin-5-yl)(methyl)amino)ethyl)piperazin-1-yl)-2,4-difluorophenoxy)propanoic acid
2-(5-(4-(2-((7-amino-2-(furan-2-yl)-[1,2,4]triazolo[1,5-a][1,3,5]triazin-5-yl)(methyl)amino)ethyl)piperazin-1-yl)-2,4-difluorophenoxy)-N-(2-(methylamino)ethyl)acetamide
2-(5-(4-(2-((7-amino-2-(furan-2-yl)-[1,2,4]triazolo[1,5-a][1,3,5]triazin-5-yl)(methyl)amino)ethyl)piperazin-1-yl)-2,4-difluorophenoxy)-N-(2-(dimethylamino)ethyl)acetamide
5-(4-(2-((7-amino-2-(furan-2-yl)-[1,2,4]triazolo[1,5-a][1,3,5]triazin-5-yl)(methyl)amino)ethyl)piperazin-1-yl)-N-(2-(dimethylamino)ethyl)-2,4-difluoro-N-methylbenzamide
5-(4-(2-((7-amino-2-(furan-2-yl)-[1,2,4]triazolo[1,5-a][1,3,5]triazin-5-yl)(methyl)amino)ethyl)piperazin-1-yl)-2,4-difluoro-N-methylbenzamide
4-(5-(4-(2-((7-amino-2-(furan-2-yl)-[1,2,4]triazolo[1,5-a][1,3,5]triazin-5-yl)(methyl)amino)ethyl)piperazin-1-yl)-2,4-difluorophenoxy)butanoic acid
N5-(2-(4-(5-((1H-tetrazol-5-yl)methoxy)-2,4-difluorophenyl)piperazin-1-yl)ethyl)-2-(furan-2-yl)-N5-methyl-[1,2,4]triazolo[1,5-a][1,3,5]triazine-5,7-diamine
N5-(2-(4-(2-fluoro-4-((1-methyl-1H-1,2,4-triazol-3-yl)methoxy)phenyl)piperazin-1-yl)ethyl)-2-(furan-2-yl)-N5-methyl-[1,2,4]triazolo[1,5-a][1,3,5]triazine-5,7-diamine
N5-(2-(4-(2,4-difluoro-5-((1-methyl-1H-1,2,4-triazol-3-yl)methoxy)phenyl)piperazin-1-yl)ethyl)-2-(furan-2-yl)-N5-methyl-[1,2,4]triazolo[1,5-a][1,3,5]triazine-5,7-diamine
4-(4-(2-((7-amino-2-(furan-2-yl)-[1,2,4]triazolo[1,5-a][1,3,5]triazin-5-yl)(methyl)amino)ethyl)piperazin-1-yl)-3-fluoro-N-(2-(methyl(oxetan-3-yl)amino)ethyl)benzamide
4-(4-(2-((7-amino-2-(furan-2-yl)-[1,2,4]triazolo[1,5-a][1,3,5]triazin-5-yl)(methyl)amino)ethyl)piperazin-1-yl)-3-fluoro-N-(2-((2-hydroxyethyl)amino)ethyl)benzamide
2-amino-N-(2-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)ethyl)acetamide
(S)-2-amino-N-(2-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)ethyl)-3-methylbutanamide
N5-(2-(4-(2,4-difluoro-5-(2-(methylsulfonyl)ethoxy)phenyl)piperazin-1-yl)ethyl)-2-(furan-2-yl)-N5-methyl-[1,2,4]triazolo[1,5-a][1,3,5]triazine-5,7-diamine (Example 5)
N5-(2-(4-(2-fluoro-4-(2-(methylsulfonyl)ethoxy)phenyl)piperazin-1-yl)ethyl)-2-(furan-2-yl)-N5-methyl-[1,2,4]triazolo[1,5-a][1,3,5]triazine-5,7-diamine
5-(4-(2-((7-amino-2-(furan-2-yl)-[1,2,4]triazolo[1,5-a][1,3,5]triazin-5-yl)(methyl)amino)ethyl)piperazin-1-yl)-6-fluoroindolin-2-one
N5-(2-(4-(2-fluoro-4-(S-methylsulfonimidoyl)phenyl)piperazin-1-yl)ethyl)-2-(furan-2-yl)-N5-methyl-[1,2,4]triazolo[1,5-a][1,3,5]triazine-5,7-diamine
5-(4-(2-((7-amino-2-(furan-2-yl)-[1,2,4]triazolo[1,5-a][1,3,5]triazin-5-yl)(methyl)amino)ethyl)piperazin-1-yl)-N-(2-(dimethylamino)ethyl)-2,4-difluorobenzamide
(3R,4R)-4-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)tetrahydrofuran-3-ol
(3S,4S)-4-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)tetrahydrofuran-3-ol
1-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)-2-methylpropan-2-ol
2-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenyl)propan-2-ol
3-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)-1,1,1-trifluoropropan-2-ol
2-(3-(4-(2-((7-amino-2-(furan-2-yl)-[1,2,4]triazolo[1,5-a][1,3,5]triazin-5-yl)(methyl)amino)ethyl)piperazin-1-yl)-4-fluorophenoxy)ethanol
N5-(2-(4-(2,4-difluoro-5-(morpholin-2-ylmethoxy)phenyl)piperazin-1-yl)ethyl)-2-(furan-2-yl)-N5-methyl-[1,2,4]triazolo[1,5-a][1,3,5]triazine-5,7-diamine
N5-(2-(4-(2,4-difluoro-5-(morpholin-3-ylmethoxy)phenyl)piperazin-1-yl)ethyl)-2-(furan-2-yl)-N5-methyl-[1,2,4]triazolo[1,5-a][1,3,5]triazine-5,7-diamine
N5-(2-(4-(2,4-difluoro-5-(((3S,4S)-4-fluoropyrrolidin-3-yl)oxy)phenyl)piperazin-1-yl)ethyl)-2-(furan-2-yl)-N5-methyl-[1,2,4]triazolo[1,5-a][1,3,5]triazine-5,7-diamine N5-(2-(4-(2,4-difluoro-5-(((3R,4S)-4-fluoropyrrolidin-3-yl) oxy)phenyl)piperazin-1-yl)ethyl)-2-(furan-2-yl)-N5-methyl-[1,2,4]triazolo[1,5-a][1,3,5]triazine-5,7-diamine N5-(2-(4-(2,4-difluoro-5-(((3S,4R)-4-fluoropyrrolidin-3-yl) oxy)phenyl)piperazin-1-yl)ethyl)-2-(furan-2-yl)-N5-methyl-[1,2,4]triazolo[1,5-a][1,3,5]triazine-5,7-diamine (S)-3-(5-(4-(2-((7-amino-2-(furan-2-yl)-[1,2,4]triazolo[1,5-a][1,3,5]triazin-5-yl)(methyl)amino)ethyl)piperazin-1-yl)-2,4-difluorophenoxy)pyrrolidin-2-one (R)-3-(5-(4-(2-((7-amino-2-(furan-2-yl)-[1,2,4]triazolo[1,5-a][1,3,5]triazin-5-yl)(methyl)amino)ethyl)piperazin-1-yl)-2,4-difluorophenoxy)pyrrolidin-2-one 2-(5-(4-(2-((7-amino-2-(furan-2-yl)-[1,2,4]triazolo[1,5-a][1,3,5]triazin-5-yl)(methyl)amino)ethyl)piperazin-1-yl)-2,4-difluorophenoxy)-N-(2-morpholinoethyl)acetamide 5-(4-(2-((7-amino-2-(furan-2-yl)-[1,2,4]triazolo[1,5-a][1,3,5]triazin-5-yl)(methyl)amino)ethyl)piperazin-1-yl)-2,4-difluoro-N-(morpholin-3-ylmethyl)benzamide N5-(2-(4-(2-fluoro-4-(morpholin-3-ylmethoxy)phenyl)piperazin-1-yl)ethyl)-2-(furan-2-yl)-N5-methyl-[1,2,4]triazolo[1,5-a][1,3,5]triazine-5,7-diamine N5-(2-(4-(2-fluoro-4-(morpholin-2-ylmethoxy)phenyl)piperazin-1-yl)ethyl)-2-(furan-2-yl)-N5-methyl-[1,2,4]triazolo[1,5-a][1,3,5]triazine-5,7-diamine N5-(2-(4-(2-fluoro-4-(((3R,4R)-4-fluoropyrrolidin-3-yl) oxy)phenyl)piperazin-1-yl)ethyl)-2-(furan-2-yl)-N5-methyl-[1,2,4]triazolo[1,5-a][1,3,5]triazine-5,7-diamine N5-(2-(4-(2-fluoro-4-(((3S,4S)-4-fluoropyrrolidin-3-yl) oxy)phenyl)piperazin-1-yl)ethyl)-2-(furan-2-yl)-N5-methyl-[1,2,4]triazolo[1,5-a][1,3,5]triazine-5,7-diamine N5-(2-(4-(2-fluoro-4-(((3R,4S)-4-fluoropyrrolidin-3-yl) oxy)phenyl)piperazin-1-yl)ethyl)-2-(furan-2-yl)-N5-methyl-[1,2,4]triazolo[1,5-a][1,3,5]triazine-5,7-diamine N5-(2-(4-(2-fluoro-4-(((3S,4R)-4-fluoropyrrolidin-3-yl) oxy)phenyl)piperazin-1-yl)ethyl)-2-(furan-2-yl)-N5-methyl-[1,2,4]triazolo[1,5-a][1,3,5]triazine-5,7-diamine 2-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)-N-(2-morpholinoethyl)acetamide 4-(4-(2-((7-amino-2-(furan-2-yl)-[1,2,4]triazolo[1,5-a][1,3,5]triazin-5-yl)(methyl)amino)ethyl)piperazin-1-yl)-3-fluoro-N-(2-morpholinoethyl)benzamide 4-(4-(2-((7-amino-2-(furan-2-yl)-[1,2,4]triazolo[1,5-a][1,3,5]triazin-5-yl)(methyl)amino)ethyl)piperazin-1-yl)-3-fluoro-N-(morpholin-3-ylmethyl)benzamide (S)—N5-(2-(4-(2,4-difluoro-5-(methylsulfinyl)phenyl)piperazin-1-yl)ethyl)-2-(furan-2-yl)-N5-methyl-[1,2,4]triazolo[1,5-a][1,3,5]triazine-5,7-diamine (R)—N5-(2-(4-(2,4-difluoro-5-(methylsulfinyl)phenyl)piperazin-1-yl)ethyl)-2-(furan-2-yl)-N5-methyl-[1,2,4]triazolo[1,5-a][1,3,5]triazine-5,7-diamine (1s,4s)-4-(5-(4-(2-((7-amino-2-(furan-2-yl)-[1,2,4]triazolo[1,5-a][1,3,5]triazin-5-yl)(methyl)amino)ethyl)piperazin-1-yl)-2,4-difluorophenoxy)tetrahydro-2H-thiopyran 1-oxide (1r,4r)-4-(5-(4-(2-((7-amino-2-(furan-2-yl)-[1,2,4]triazolo[1,5-a][1,3,5]triazin-5-yl)(methyl)amino)ethyl)piperazin-1-yl)-2,4-difluorophenoxy)tetrahydro-2H-thiopyran 1-oxide (S)-5-(4-(2-((7-amino-2-(furan-2-yl)-[1,2,4]triazolo[1,5-a][1,3,5]triazin-5-yl)(methyl)amino)ethyl)piperazin-1-yl)-2,4-difluoro-N-(2-(methylsulfinyl)ethyl)benzamide (R)-5-(4-(2-((7-amino-2-(furan-2-yl)-[1,2,4]triazolo[1,5-a][1,3,5]triazin-5-yl)(methyl)amino)ethyl)piperazin-1-yl)-2,4-difluoro-N-(2-(methylsulfinyl)ethyl)benzamide (S)-5-(4-(2-((7-amino-2-(furan-2-yl)-[1,2,4]triazolo[1,5-a][1,3,5]triazin-5-yl)(methyl)amino)ethyl)piperazin-1-yl)-2,4-difluoro-N-methyl-N-(2-(methylsulfinyl)ethyl)benzamide (R)-5-(4-(2-((7-amino-2-(furan-2-yl)-[1,2,4]triazolo[1,5-a][1,3,5]triazin-5-yl)(methyl)amino)ethyl)piperazin-1-yl)-2,4-difluoro-N-methyl-N-(2-(methylsulfinyl)ethyl)benzamide (5-(4-(2-((7-amino-2-(furan-2-yl)-[1,2,4]triazolo[1,5-a][1,3,5]triazin-5-yl)(methyl)amino)ethyl)piperazin-1-yl)-2,4-difluorophenyl)(1-oxidothiomorpholino)methanone 4-(5-(4-(2-((7-amino-2-(furan-2-yl)-[1,2,4]triazolo[1,5-a][1,3,5]triazin-5-yl)(methyl)amino)ethyl)piperazin-1-yl)-2,4-difluorophenyl)thiomorpholine 1-oxide (R)—N5-(2-(4-(2-fluoro-4-(methylsulfinyl)phenyl)piperazin-1-yl)ethyl)-2-(furan-2-yl)-N5-methyl-[1,2,4]triazolo[1,5-a][1,3,5]triazine-5,7-diamine (S)—N5-(2-(4-(2-fluoro-4-(methylsulfinyl)phenyl)piperazin-1-yl)ethyl)-2-(furan-2-yl)-N5-methyl-[1,2,4]triazolo[1,5-a][1,3,5]triazine-5,7-diamine (1s,4s)-4-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)tetrahydro-2H-thiopyran 1-oxide (1r,4r)-4-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenoxy)tetrahydro-2H-thiopyran 1-oxide (S)-4-(4-(2-((7-amino-2-(furan-2-yl)-[1,2,4]triazolo[1,5-a][1,3,5]triazin-5-yl)(methyl)amino)ethyl)piperazin-1-yl)-3-fluoro-N-(2-(methylsulfinyl)ethyl)benzamide (R)-4-(4-(2-((7-amino-2-(furan-2-yl)-[1,2,4]triazolo[1,5-a][1,3,5]triazin-5-yl)(methyl)amino)ethyl)piperazin-1-yl)-3-fluoro-N-(2-(methylsulfinyl)ethyl)benzamide (4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenyl)(1-oxidothiomorpholino)methanone 4-(4-(4-(2-((7-amino-2-(furan-2-yl)-[1,2,4]triazolo[1,5-a][1,3,5]triazin-5-yl)(methyl)amino)ethyl)piperazin-1-yl)-3-fluorophenyl)thiomorpholine 1-oxide (S)-3-(5-(4-(2-((7-amino-2-(furan-2-yl)-[1,2,4]triazolo[1,5-a][1,3,5]triazin-5-yl)(methyl)amino)ethyl)piperazin-1-yl)-2,4-difluorophenoxy)propane-1,2-diol (R)-3-(5-(4-(2-((7-amino-2-(furan-2-yl)-[1,2,4]triazolo[1,5-a][1,3,5]triazin-5-yl)(methyl)amino)ethyl)piperazin-1-yl)-2,4-difluorophenoxy)propane-1,2-diol (S)-5-(4-(2-((7-amino-2-(furan-2-yl)-[1,2,4]triazolo[1,5-a][1,3,5]triazin-5-yl)(methyl)amino)ethyl)piperazin-1-yl)-N-(2,3-dihydroxypropyl)-2,4-difluorobenzamide (R)-5-(4-(2-((7-amino-2-(furan-2-yl)-[1,2,4]triazolo[1,5-a][1,3,5]triazin-5-yl)(methyl)amino)ethyl)piperazin-1-yl)-N-(2,3-dihydroxypropyl)-2,4-difluorobenzamide N5-(2-(4-(4-(azetidin-3-yloxy)-2-fluorophenyl)piperazin-1-yl)ethyl)-2-(furan-2-yl)-N5-methyl-[1,2,4]triazolo[1,5-a][1,3,5]triazine-5,7-diamine N5-(2-(4-(5-(azetidin-3-yloxy)-2,4-difluorophenyl)piperazin-1-yl)ethyl)-2-(furan-2-yl)-N5-methyl-[1,2,4]triazolo[1,5-a][1,3,5]triazine-5,7-diamine (S)—N5-(2-(4-(2,4-difluoro-5-(3-(methylsulfinyl)propoxy) phenyl)piperazin-1-yl)ethyl)-2-(furan-2-yl)-N5-methyl-[1,2,4]triazolo[1,5-a][1,3,5]triazine-5,7-diamine Heteroaryl Scaffold (3)

5-amino-8-(furan-2-yl)-3-(2-(4-(4-(2-hydroxyethoxy)phenyl)piperazin-1-yl)ethyl)-1-methyl-1H-[1,2,4]triazolo[5,1-i]purin-2(3H)-one 2-(4-(4-(2-(5-amino-8-(furan-2-yl)-1-methyl-2-oxo-1H-[1,2,4]triazolo[5,1-i]purin-3(2H)-yl)ethyl)piperazin-1-yl) phenoxy)acetic acid 2-(4-(4-(2-(5-amino-8-(furan-2-yl)-1-methyl-2-oxo-1H-[1,2,4]triazolo[5,1-i]purin-3(2H)-yl)ethyl)piperazin-1-yl)phenoxy)acetamide 5-amino-3-(2-(4-(4-(2,3-dihydroxypropoxy)phenyl)piperazin-1-yl)ethyl)-8-(furan-2-yl)-1-methyl-1H-[1,2,4]triazolo[5,1-i]purin-2(3H)-one 5-amino-3-(2-(4-(4-(2-aminoethoxy)phenyl)piperazin-1-yl)ethyl)-8-(furan-2-yl)-1-methyl-1H-[1,2,4]triazolo[5,1-i]purin-2(3H)-one 4-(4-(2-(5-amino-8-(furan-2-yl)-1-methyl-2-oxo-1H-[1,2,4]triazolo[5,1-i]purin-3 (2H)-yl)ethyl)piperazin-1-yl)benzamide 4-(4-(2-(5-amino-8-(furan-2-yl)-1-methyl-2-oxo-1H-[1,2,4]triazolo[5,1-i]purin-3 (2H)-yl)ethyl)piperazin-1-yl)-N-methylbenzamide 5-amino-8-(furan-2-yl)-1-methyl-3-(2-(4-(4-(2-morpholinoethoxy)phenyl)piperazin-1-yl)ethyl)-1H-[1,2,4]triazolo[5,1-i]purin-2(3H)-one 5-amino-3-(2-(4-(4-(2-(dimethylamino)ethoxy)phenyl)piperazin-1-yl)ethyl)-8-(furan-2-yl)-1-methyl-1H-[1,2,4]triazolo[5,1-i]purin-2(3H)-one 4-(4-(2-(5-amino-8-(furan-2-yl)-1-methyl-2-oxo-1H-[1,2,4]triazolo[5,1-i]purin-3 (2H)-yl)ethyl)piperazin-1-yl)benzenesulfonamide 4-(4-(2-(5-amino-8-(furan-2-yl)-1-methyl-2-oxo-1H-[1,2,4]triazolo[5,1-i]purin-3 (2H)-yl)ethyl)piperazin-1-yl)-N-methylbenzenesulfonamide 5-amino-8-(furan-2-yl)-1-methyl-3-(2-(4-(4-(methylsulfonyl)phenyl)piperazin-1-yl)ethyl)-1H-[1,2,4]triazolo[5,1-i]purin-2(3H)-one 5-amino-8-(furan-2-yl)-1-methyl-3-(2-(4-(4-(methylsulfinyl)phenyl)piperazin-1-yl)ethyl)-1H-[1,2,4]triazolo[5,1-i]purin-2(3H)-one 3-(4-(2-(5-amino-8-(furan-2-yl)-1-methyl-2-oxo-1H-[1,2,4]triazolo[5,1-i]purin-3(2H)-yl)ethyl)piperazin-1-yl)benzamide 5-amino-8-(furan-2-yl)-3-(2-(4-(3-(2-hydroxyethoxy)phenyl)piperazin-1-yl)ethyl)-1-methyl-1H-[1,2,4]triazolo[5,1-i]purin-2(3H)-one 5-amino-3-(2-(4-(4-(azetidin-3-yloxy)phenyl)piperazin-1-yl)ethyl)-8-(furan-2-yl)-1-methyl-1H-[1,2,4]triazolo[5,1-i]purin-2(3H)-one 3-(2-(4-(4-((2H-1,2,3-triazol-4-yl)methoxy)-2-fluorophenyl)piperazin-1-yl)ethyl)-5-amino-8-(furan-2-yl)-1-methyl-1H-[1,2,4]triazolo[5,1-i]purin-2(3H)-one 5-((4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)methyl)-1,3,4-oxadiazol-2(3H)-one 2-(5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluorophenoxy)acetamide 5-amino-3-(2-(4-(2-fluoro-4-(2-(methylsulfinyl)ethoxy)phenyl)piperazin-1-yl)ethyl)-8-(furan-2-yl)-1-methyl-1H-[1,2,4]triazolo[5,1-i]purin-2(3H)-one (Example 20)

(S)-5-amino-3-(2-(4-(2-fluoro-4-(2-(methylsulfinyl)ethoxy)phenyl)piperazin-1-yl)ethyl)-8-(furan-2-yl)-1-methyl-1H-[1,2,4]triazolo[5,1-i]purin-2(3H)-one (R)-5-amino-3-(2-(4-(2-fluoro-4-(2-(methylsulfinyl)ethoxy)phenyl)piperazin-1-yl)ethyl)-8-(furan-2-yl)-1-methyl-1H-[1,2,4]triazolo[5,1-i]purin-2(3H)-one 5-amino-3-(2-(4-(2,4-difluoro-5-(2-(methylsulfinyl)ethoxy)phenyl)piperazin-1-yl)ethyl)-8-(furan-2-yl)-1-methyl-1H-[1,2,4]triazolo[5,1-i]purin-2(3H)-one (S)-5-amino-3-(2-(4-(2,4-difluoro-5-(2-(methylsulfinyl)ethoxy)phenyl)piperazin-1-yl)ethyl)-8-(furan-2-yl)-1-methyl-1H-[1,2,4]triazolo[5,1-i]purin-2(3H)-one (Example 7)

(R)-5-amino-3-(2-(4-(2,4-difluoro-5-(2-(methylsulfinyl)ethoxy)phenyl)piperazin-1-yl)ethyl)-8-(furan-2-yl)-1-methyl-1H-[1,2,4]triazolo[5,1-i]purin-2(3H)-one (Example 7)

5-amino-3-(2-(4-(2-fluoro-4-(2-oxo-2-(piperazin-1-yl)ethoxy)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(piperidin-4-ylmethoxy)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(piperazine-1-carbonyl)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(2-(piperazin-1-yl)ethoxy)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(piperazin-1-ylsulfonyl)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(methylsulfonyl)phenyl)piperazin-1-yl)ethyl)-8-(furan-2-yl)-1-methyl-1H-[1,2,4]triazolo[5,1-i]purin-2(3H)-one 4-(4-(2-(5-amino-8-(furan-2-yl)-1-methyl-2-oxo-1H-[1,2,4]triazolo[5,1-i]purin-3(2H)-yl)ethyl)piperazin-1-yl)-N-(2-aminoethyl)-3-fluorobenzamide 4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluoro-N-(2-(methylamino)ethyl)benzamide 4-(4-(2-(5-amino-8-(furan-2-yl)-1-methyl-2-oxo-1H-[1,2,4]triazolo[5,1-i]purin-3(2H)-yl)ethyl)piperazin-1-yl)-N-(2-(dimethylamino)ethyl)-3-fluorobenzamide 4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluoro-N-(2-hydroxyethyl)benzamide 4-(4-(2-(5-amino-8-(furan-2-yl)-1-methyl-2-oxo-1H-[1,2,4]triazolo[5,1-i]purin-3(2H)-yl)ethyl)piperazin-1-yl)-N-(2,3-dihydroxypropyl)-3-fluorobenzamide 2-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)acetic acid 2-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3,5-difluorophenoxy)acetic acid 2-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)propanoic acid (S)-2-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)propanoic acid 2-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)-2-methylpropanoic acid 3-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenyl)propanoic acid 4-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)butanoic acid 2-(3-(4-(2-(5-amino-8-(furan-2-yl)-1-methyl-2-oxo-1H-[1,2,4]triazolo[5,1-i]purin-3(2H)-yl)ethyl)piperazin-1-yl)-2,6-difluorophenoxy)acetic acid 2-(5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluorophenoxy)acetic acid 4-(4-(2-(5-amino-8-(furan-2-yl)-1-methyl-2-oxo-1H-[1,2,4]triazolo[5,1-i]purin-3 (2H)-yl)ethyl)piperazin-1-yl)-3-fluorobenzoic acid 2-((2-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)ethyl)amino)acetamide 2-((2-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)ethyl)(methyl)amino)acetamide 5-amino-3-(2-(4-(2-fluoro-4-(piperidin-4-yloxy)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(pyrrolidin-3-yloxy)phenyl)piperazin-1-yl)ethyl)-8-(furan-2-yl)-1-methyl-1H-[1,2,4]triazolo[5,1-i]purin-2(3H)-one 3-(2-(4-(4-((4H-1,2,4-triazol-3-yl)methoxy)-2-fluorophenyl)piperazin-1-yl)ethyl)-5-amino-8-(furan-2-yl)-1-methyl-1H-[1,2,4]triazolo[5,1-i]purin-2(3H)-one 2-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)-N-(2-(methylamino)ethyl)acetamide 2-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)-N-(2-(dimethylamino)ethyl)acetamide 2-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)-N-(2-aminoethyl)acetamide (R)-2-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)propanoic acid 2-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)acetamide 4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluoro-N-methyl-N-(2-(methylamino)ethyl)benzamide 4-(4-(2-(5-amino-8-(furan-2-yl)-1-methyl-2-oxo-1H-[1,2,4]triazolo[5,1-i]purin-3 (2H)-yl)ethyl)piperazin-1-yl)-N-(2-(dimethylamino)ethyl)-3-fluoro-N-methylbenzamide (R)-4-(4-(2-(5-amino-8-(furan-2-yl)-1-methyl-2-oxo-1H-[1,2,4]triazolo[5,1-i]purin-3(2H)-yl)ethyl)piperazin-1-yl)-N-(1-(dimethylamino)propan-2-yl)-3-fluorobenzamide 2-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)-N-methyl-N-(2-(methylamino)ethyl)acetamide 2-(5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluorophenoxy)-2-methylpropanoic acid (S)-2-(5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluorophenoxy)propanoic acid (R)-2-(5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluorophenoxy)propanoic acid 2-(5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluorophenoxy)-N-(2-(methylamino)ethyl)acetamide 2-(5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluorophenoxy)-N-(2-(dimethylamino)ethyl)acetamide 5-(4-(2-(5-amino-8-(furan-2-yl)-1-methyl-2-oxo-1H-[1,2,4]triazolo[5,1-i]purin-3(2H)-yl)ethyl)piperazin-1-yl)-N-(2-(dimethylamino)ethyl)-2,4-difluoro-N-methylbenzamide 5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluoro-N-methylbenzamide (Example 3)

4-(5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluorophenoxy)butanoic acid 3-(2-(4-(5-((1H-tetrazol-5-yl)methoxy)-2,4-difluorophenyl)piperazin-1-yl)ethyl)-5-amino-8-(furan-2-yl)-1-methyl-1H-[1,2,4]triazolo[5,1-i]purin-2(3H)-one 5-amino-3-(2-(4-(2-fluoro-4-((1-methyl-1H-1,2,4-triazol-3-yl)methoxy)phenyl)piperazin-1-yl)ethyl)-8-(furan-2-yl)-1-methyl-1H-[1,2,4]triazolo[5,1-i]purin-2(3H)-one 5-amino-3-(2-(4-(2,4-difluoro-5-((1-methyl-1H-1,2,4-triazol-3-yl)methoxy)phenyl)piperazin-1-yl)ethyl)-8-(furan-2-yl)-1-methyl-1H-[1,2,4]triazolo[5,1-i]purin-2 (3H)-one 4-(4-(2-(5-amino-8-(furan-2-yl)-1-methyl-2-oxo-1H-[1,2,4]triazolo[5,1-i]purin-3 (2H)-yl)ethyl)piperazin-1-yl)-3-fluoro-N-(2-(methyl(oxetan-3-yl)amino)ethyl)benzamide 4-(4-(2-(5-amino-8-(furan-2-yl)-1-methyl-2-oxo-1H-[1,2,4]triazolo[5,1-i]purin-3 (2H)-yl)ethyl)piperazin-1-yl)-3-fluoro-N-(2-((2-hydroxyethyl)amino)ethyl)benzamide 2-amino-N-(2-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)ethyl)acetamide (S)-2-amino-N-(2-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)ethyl)-3-methylbutanamide 5-amino-3-(2-(4-(2,4-difluoro-5-(2-(methylsulfonyl)ethoxy)phenyl)piperazin-1-yl)ethyl)-8-(furan-2-yl)-1-methyl-1H-[1,2,4]triazolo[5,1-i]purin-2(3H)-one (Example 9) 5-amino-3-(2-(4-(2-fluoro-4-(2-(methylsulfonyl)ethoxy)phenyl)piperazin-1-yl)ethyl)-8-(furan-2-yl)-1-methyl-1H-[1,2,4]triazolo[5,1-i]purin-2 (3H)-one 5-amino-3-(2-(4-(6-fluoro-2-oxoindolin-5-yl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(S-methylsulfonimidoyl)phenyl)piperazin-1-yl)ethyl)-8-(furan-2-yl)-1-methyl-1H-[1,2,4]triazolo[5,1-i]purin-2(3H)-one 5-(4-(2-(5-amino-8-(furan-2-yl)-1-methyl-2-oxo-1H-[1,2,4]triazolo[5,1-i]purin-3(2H)-yl)ethyl)piperazin-1-yl)-N-(2-(dimethylamino)ethyl)-2,4-difluorobenzamide 5-amino-3-(2-(4-(2-fluoro-4-(((3R,4R)-4-hydroxytetrahydrofuran-3-yl)oxy)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(((3S,4S)-4-hydroxytetrahydrofuran-3-yl)oxy)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(2-hydroxy-2-methylpropoxy)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(2-hydroxypropan-2-yl)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(3,3,3-trifluoro-2-hydroxypropoxy)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-5-(2-hydroxyethoxy)phenyl)piperazin-1-yl)ethyl)-8-(furan-2-yl)-1-methyl-1H-[1,2,4]triazolo[5,1-i]purin-2(3H)-one 5-amino-3-(2-(4-(2,4-difluoro-5-(morpholin-2-ylmethoxy)phenyl)piperazin-1-yl)ethyl)-8-(furan-2-yl)-1-methyl-1H-[1,2,4]triazolo[5,1-i]purin-2(3H)-one 5-amino-3-(2-(4-(2,4-difluoro-5-(morpholin-3-ylmethoxy)phenyl)piperazin-1-yl)ethyl)-8-(furan-2-yl)-1-methyl-1H-[1,2,4]triazolo[5,1-i]purin-2(3H)-one 5-amino-3-(2-(4-(2,4-difluoro-5-(((3S,4S)-4-fluoropyrrolidin-3-yl)oxy)phenyl)piperazin-1-yl)ethyl)-8-(furan-2-yl)-1-methyl-1H-[1,2,4]triazolo[5,1-i]purin-2(3H)-one 5-amino-3-(2-(4-(2,4-difluoro-5-(((3R,4S)-4-fluoropyrrolidin-3-yl)oxy)phenyl)piperazin-1-yl)ethyl)-8-(furan-2-yl)-1-methyl-1H-[1,2,4]triazolo[5,1-i]purin-2(3H)-one 5-amino-3-(2-(4-(2,4-difluoro-5-(((3S,4R)-4-fluoropyrrolidin-3-yl)oxy)phenyl)piperazin-1-yl)ethyl)-8-(furan-2-yl)-1-methyl-1H-[1,2,4]triazolo[5,1-i]purin-2(3H)-one 5-amino-3-(2-(4-(2,4-difluoro-5-((2-oxopyrrolidin-3-yl)oxy)phenyl)piperazin-1-yl)ethyl)-8-(furan-2-yl)-1-methyl-1H-[1,2,4]triazolo[5,1-i]purin-2(3H)-one (Example 21)

(S)-5-amino-3-(2-(4-(2,4-difluoro-5-((2-oxopyrrolidin-3-yl)oxy)phenyl)piperazin-1-yl)ethyl)-8-(furan-2-yl)-1-methyl-1H-[1,2,4]triazolo[5,1-i]purin-2(3H)-one (R)-5-amino-3-(2-(4-(2,4-difluoro-5-((2-oxopyrrolidin-3-yl)oxy)phenyl)piperazin-1-yl)ethyl)-8-(furan-2-yl)-1-methyl-1H-[1,2,4]triazolo[5,1-i]purin-2(3H)-one 2-(5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluorophenoxy)-N-(2-morpholinoethyl)acetamide 5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluoro-N-(morpholin-3-ylmethyl)benzamide 5-amino-3-(2-(4-(2-fluoro-4-(morpholin-3-ylmethoxy)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(morpholin-2-ylmethoxy)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(((3R,4R)-4-fluoropyrrolidin-3-yl)oxy)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(((3S,4S)-4-fluoropyrrolidin-3-yl)oxy)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(((3R,4S)-4-fluoropyrrolidin-3-yl)oxy)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(((3S,4R)-4-fluoropyrrolidin-3-yl)oxy)phenyl)piperazin-1-yl)ethyl)-8-(furan-2-yl)-1-methyl-1H-[1,2,4]triazolo[5,1-i]purin-2(3H)-one 2-(4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluorophenoxy)-N-(2-morpholinoethyl)acetamide 4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluoro-N-(2-morpholinoethyl)benzamide 4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluoro-N-(morpholin-3-ylmethyl)benzamide (S)-5-amino-3-(2-(4-(2,4-difluoro-5-(methylsulfinyl)phenyl)piperazin-1-yl)ethyl)-8-(furan-2-yl)-1-methyl-1H-[1,2,4]triazolo[5,1-i]purin-2(3H)-one (R)-5-amino-3-(2-(4-(2,4-difluoro-5-(methylsulfinyl)phenyl)piperazin-1-yl)ethyl)-8-(furan-2-yl)-1-methyl-1H-[1,2,4]triazolo[5,1-i]purin-2(3H)-one 5-amino-3-(2-(4-(2,4-difluoro-5-(((1s,4s)-1-oxidotetrahydro-2H-thiopyran-4-yl)oxy)phenyl)piperazin-1-yl)ethyl)-8-(furan-2-yl)-1-methyl-1H-[1,2,4]triazolo[5,1-i]purin-2(3H)-one 5-amino-3-(2-(4-(2,4-difluoro-5-(((1r,4r)-1-oxidotetrahydro-2H-thiopyran-4-yl)oxy)phenyl)piperazin-1-yl)ethyl)-8-(furan-2-yl)-1-methyl-1H-[1,2,4]triazolo[5,1-i]purin-2(3H)-one (S)-5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluoro-N-(2-(methylsulfinyl)ethyl)benzamide (R)-5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluoro-N-(2-(methylsulfinyl)ethyl)benzamide (S)-5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluoro-N-methyl-N-(2-(methylsulfinyl)ethyl)benzamide (R)-5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluoro-N-methyl-N-(2-(methylsulfinyl)ethyl)benzamide 5-amino-3-(2-(4-(2,4-difluoro-5-(1-oxidothiomorpholine-4-carbonyl)phenyl)piperazin-1-yl)ethyl)-8-(furan-2-yl)-1-methyl-1H-[1,2,4]triazolo[5,1-i]purin-2(3H)-one 5-amino-3-(2-(4-(2,4-difluoro-5-(1-oxidothiomorpholino)phenyl)piperazin-1-yl)ethyl)-8-(furan-2-yl)-1-methyl-1H-[1,2,4]triazolo[5,1-i]purin-2(3H)-one (R)-5-amino-3-(2-(4-(2-fluoro-4-(methylsulfinyl)phenyl)piperazin-1-yl)ethyl)-8-(furan-2-yl)-1-methyl-1H-[1,2,4]triazolo[5,1-i]purin-2(3H)-one (S)-5-amino-3-(2-(4-(2-fluoro-4-(methylsulfinyl)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(((1s,4s)-1-oxidotetrahydro-2H-thiopyran-4-yl)oxy)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(((1r,4r)-1-oxidotetrahydro-2H-thiopyran-4-yl)oxy)phenyl)piperazin-1-yl)ethyl)-8-(furan-2-yl)-1-methyl-1H-[1,2,4]triazolo[5,1-i]purin-2(3H)-one (S)-4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluoro-N-(2-(methylsulfinyl)ethyl)benzamide (R)-4-(4-(2-(5-amino-8-(furan-2-yl)-1-methyl-2-oxo-1H-[1,2,4]triazolo[5,1-i]purin-3(2H)-yl)ethyl)piperazin-1-yl)-3-fluoro-N-(2-(methylsulfinyl)ethyl)benzamide 5-amino-3-(2-(4-(2-fluoro-4-(1-oxidothiomorpholine-4-carbonyl)phenyl)piperazin-1-yl)ethyl)-8-(furan-2-yl)-1-methyl-1H-[1,2,4]triazolo[5,1-i]purin-2(3H)-one 5-amino-3-(2-(4-(2-fluoro-4-(1-oxidothiomorpholino)phenyl)piperazin-1-yl)ethyl)-8-(furan-2-yl)-1-methyl-1H-[1,2,4]triazolo[5,1-i]purin-2(3H)-one (S)-5-amino-3-(2-(4-(5-(2,3-dihydroxypropoxy)-2,4-difluorophenyl)piperazin-1-yl)ethyl)-8-(furan-2-yl)-1-methyl-1H-[1,2,4]triazolo[5,1-i]purin-2(3H)-one (R)-5-amino-3-(2-(4-(5-(2,3-dihydroxypropoxy)-2,4-difluorophenyl)piperazin-1-yl)ethyl)-8-(furan-2-yl)-1-methyl-1H-[1,2,4]triazolo[5,1-i]purin-2(3H)-one (S)-5-(4-(2-(5-amino-8-(furan-2-yl)-1-methyl-2-oxo-1H-[1,2,4]triazolo[5,1-i]purin-3(2H)-yl)ethyl)piperazin-1-yl)-N-(2,3-dihydroxypropyl)-2,4-difluorobenzamide (R)-5-(4-(2-(5-amino-8-(furan-2-yl)-1-methyl-2-oxo-1H-[1,2,4]triazolo[5,1-i]purin-3(2H)-yl)ethyl)piperazin-1-yl)-N-(2,3-dihydroxypropyl)-2,4-difluorobenzamide 5-amino-3-(2-(4-(4-(azetidin-3-yloxy)-2-fluorophenyl)piperazin-1-yl)ethyl)-8-(furan-2-yl)-1-methyl-1H-[1,2,4]triazolo[5,1-i]purin-2(3H)-one 5-amino-3-(2-(4-(5-(azetidin-3-yloxy)-2,4-difluorophenyl)piperazin-1-yl)ethyl)-8-(furan-2-yl)-1-methyl-1H-[1,2,4]triazolo[5,1-i]purin-2(3H)-one (S)-5-amino-3-(2-(4-(2,4-difluoro-5-(3-(methylsulfinyl)propoxy)phenyl)piperazin-1-yl)ethyl)-8-(furan-2-yl)-1-methyl-1H-[1,2,4]triazolo[5,1-i]purin-2(3H)-one Heteroaryl Scaffold (4)

2-(4-(4-(2-(5-amino-8-(furan-2-yl)-3H-[1,2,4]triazolo[5,1-i]purin-3-yl)ethyl)piperazin-1-yl)phenoxy)ethanol 2-(4-(4-(2-(5-amino-8-(furan-2-yl)-3H-[1,2,4]triazolo[5,1-i]purin-3-yl)ethyl)piperazin-1-yl)phenoxy)acetic acid 2-(4-(4-(2-(5-amino-8-(furan-2-yl)-3H-[1,2,4]triazolo[5,1-i]purin-3-yl)ethyl)piperazin-1-yl)phenoxy)acetamide 3-(4-(4-(2-(5-amino-8-(furan-2-yl)-3H-[1,2,4]triazolo[5,1-i]purin-3-yl)ethyl)piperazin-1-yl)phenoxy)propane-1,2-diol 3-(2-(4-(4-(2-aminoethoxy)phenyl)piperazin-1-yl)ethyl)-8-(furan-2-yl)-3H-[1,2,4]triazolo[5,1-i]purin-5-amine 4-(4-(2-(5-amino-8-(furan-2-yl)-3H-[1,2,4]triazolo[5,1-i]purin-3-yl)ethyl)piperazin-1-yl)benzamide 4-(4-(2-(5-amino-8-(furan-2-yl)-3H-[1,2,4]triazolo[5,1-i]purin-3-yl)ethyl)piperazin-1-yl)-N-methylbenzamide 8-(furan-2-yl)-3-(2-(4-(4-(2-morpholinoethoxy)phenyl)piperazin-1-yl)ethyl)-3H-[1,2,4]triazolo[5,1-i]purin-5-amine 3-(2-(4-(4-(2-(dimethylamino)ethoxy)phenyl)piperazin-1-yl)ethyl)-8-(furan-2-yl)-3H-[1,2,4]triazolo[5,1-i]purin-5-amine 4-(4-(2-(5-amino-8-(furan-2-yl)-3H-[1,2,4]triazolo[5,1-i]purin-3-yl)ethyl)piperazin-1-yl)benzenesulfonamide 4-(4-(2-(5-amino-8-(furan-2-yl)-3H-[1,2,4]triazolo[5,1-i]purin-3-yl)ethyl)piperazin-1-yl)-N-methylbenzenesulfonamide 8-(furan-2-yl)-3-(2-(4-(4-(methylsulfonyl)phenyl)piperazin-1-yl)ethyl)-3H-[1,2,4]triazolo[5,1-i]purin-5-amine 8-(furan-2-yl)-3-(2-(4-(4-(methylsulfinyl)phenyl)piperazin-1-yl)ethyl)-3H-[1,2,4]triazolo[5,1-i]purin-5-amine 3-(4-(2-(5-amino-8-(furan-2-yl)-3H-[1,2,4]triazolo[5,1-i]purin-3-yl)ethyl)piperazin-1-yl)benzamide 2-(3-(4-(2-(5-amino-8-(furan-2-yl)-3H-[1,2,4]triazolo[5,1-i]purin-3-yl)ethyl)piperazin-1-yl)phenoxy)ethanol 3-(2-(4-(4-(azetidin-3-yloxy)phenyl)piperazin-1-yl)ethyl)-8-(furan-2-yl)-3H-[1,2,4]triazolo[5,1-i]purin-5-amine 3-(2-(4-(4-((2H-1,2,3-triazol-4-yl)methoxy)-2-fluorophenyl)piperazin-1-yl)ethyl)-8-(furan-2-yl)-3H-[1,2,4]triazolo[5,1-i]purin-5-amine 5-((4-(4-(2-(5-amino-8-(furan-2-yl)-3H-[1,2,4]triazolo[5,1-i]purin-3-yl)ethyl)piperazin-1-yl)-3-fluorophenoxy)methyl)-1,3,4-oxadiazol-2(3H)-one 2-(5-(4-(2-(5-amino-8-(furan-2-yl)-3H-[1,2,4]triazolo[5,1-i]purin-3-yl)ethyl)piperazin-1-yl)-2,4-difluorophenoxy)acetamide (S)-3-(2-(4-(2-fluoro-4-(2-(methylsulfinyl)ethoxy)phenyl)piperazin-1-yl)ethyl)-8-(furan-2-yl)-3H-[1,2,4]triazolo[5,1-i]purin-5-amine (R)-3-(2-(4-(2-fluoro-4-(2-(methylsulfinyl)ethoxy)phenyl)piperazin-1-yl)ethyl)-8-(furan-2-yl)-3H-[1,2,4]triazolo[5,1-i]purin-5-amine 3-(2-(4-(2,4-difluoro-5-(2-(methylsulfinyl)ethoxy)phenyl)piperazin-1-yl)ethyl)-8-(furan-2-yl)-3H-[1,2,4]triazolo[5,1-i]purin-5-amine 2-(4-(4-(2-(5-amino-8-(furan-2-yl)-3H-[1,2,4]triazolo[5,1-i]purin-3-yl)ethyl)piperazin-1-yl)-3-fluorophenoxy)-1-(piperazin-1-yl)ethanone 3-(2-(4-(2-fluoro-4-(piperidin-4-ylmethoxy)phenyl)piperazin-1-yl)ethyl)-8-(furan-2-yl)-3H-[1,2,4]triazolo[5,1-i]purin-5-amine (4-(4-(2-(5-amino-8-(furan-2-yl)-3H-[1,2,4]triazolo[5,1-i]purin-3-yl)ethyl)piperazin-1-yl)-3-fluorophenyl)(piperazin-1-yl)methanone 3-(2-(4-(2-fluoro-4-(2-(piperazin-1-yl)ethoxy)phenyl)piperazin-1-yl)ethyl)-8-(furan-2-yl)-3H-[1,2,4]triazolo[5,1-i]purin-5-amine 3-(2-(4-(2-fluoro-4-(piperazin-1-ylsulfonyl)phenyl)piperazin-1-yl)ethyl)-8-(furan-2-yl)-3H-[1,2,4]triazolo[5,1-i]purin-5-amine 3-(2-(4-(2-fluoro-4-(methylsulfonyl)phenyl)piperazin-1-yl)ethyl)-8-(furan-2-yl)-3H-[1,2,4]triazolo[5,1-i]purin-5-amine 4-(4-(2-(5-amino-8-(furan-2-yl)-3H-[1,2,4]triazolo[5,1-i]purin-3-yl)ethyl)piperazin-1-yl)-N-(2-aminoethyl)-3-fluorobenzamide 4-(4-(2-(5-amino-8-(furan-2-yl)-3H-[1,2,4]triazolo[5,1-i]purin-3-yl)ethyl)piperazin-1-yl)-3-fluoro-N-(2-(methylamino)ethyl)benzamide 4-(4-(2-(5-amino-8-(furan-2-yl)-3H-[1,2,4]triazolo[5,1-i]purin-3-yl)ethyl)piperazin-1-yl)-N-(2-(dimethylamino)ethyl)-3-fluorobenzamide 4-(4-(2-(5-amino-8-(furan-2-yl)-3H-[1,2,4]triazolo[5,1-i]purin-3-yl)ethyl)piperazin-1-yl)-3-fluoro-N-(2-hydroxyethyl)benzamide 4-(4-(2-(5-amino-8-(furan-2-yl)-3H-[1,2,4]triazolo[5,1-i]purin-3-yl)ethyl)piperazin-1-yl)-N-(2,3-dihydroxypropyl)-3-fluorobenzamide 2-(4-(4-(2-(5-amino-8-(furan-2-yl)-3H-[1,2,4]triazolo[5,1-i]purin-3-yl)ethyl)piperazin-1-yl)-3-fluorophenoxy)acetic acid 2-(4-(4-(2-(5-amino-8-(furan-2-yl)-3H-[1,2,4]triazolo[5,1-i]purin-3-yl)ethyl)piperazin-1-yl)-3,5-difluorophenoxy)acetic acid 2-(4-(4-(2-(5-amino-8-(furan-2-yl)-3H-[1,2,4]triazolo[5,1-i]purin-3-yl)ethyl)piperazin-1-yl)-3-fluorophenoxy)propanoic acid (S)-2-(4-(4-(2-(5-amino-8-(furan-2-yl)-3H-[1,2,4]triazolo[5,1-i]purin-3-yl)ethyl)piperazin-1-yl)-3-fluorophenoxy)propanoic acid 2-(4-(4-(2-(5-amino-8-(furan-2-yl)-3H-[1,2,4]triazolo[5,1-i]purin-3-yl)ethyl)piperazin-1-yl)-3-fluorophenoxy)-2-methylpropanoic acid 3-(4-(4-(2-(5-amino-8-(furan-2-yl)-3H-[1,2,4]triazolo[5,1-i]purin-3-yl)ethyl)piperazin-1-yl)-3-fluorophenyl)propanoic acid 4-(4-(4-(2-(5-amino-8-(furan-2-yl)-3H-[1,2,4]triazolo[5,1-i]purin-3-yl)ethyl)piperazin-1-yl)-3-fluorophenoxy)butanoic acid 2-(3-(4-(2-(5-amino-8-(furan-2-yl)-3H-[1,2,4]triazolo[5,1-i]purin-3-yl)ethyl)piperazin-1-yl)-2,6-difluorophenoxy)acetic acid 2-(5-(4-(2-(5-amino-8-(furan-2-yl)-3H-[1,2,4]triazolo[5,1-i]purin-3-yl)ethyl)piperazin-1-yl)-2,4-difluorophenoxy)acetic acid 4-(4-(2-(5-amino-8-(furan-2-yl)-3H-[1,2,4]triazolo[5,1-i]purin-3-yl)ethyl)piperazin-1-yl)-3-fluorobenzoic acid 2-((2-(4-(4-(2-(5-amino-8-(furan-2-yl)-3H-[1,2,4]triazolo[5,1-i]purin-3-yl)ethyl)piperazin-1-yl)-3-fluorophenoxy)ethyl)amino)acetamide 2-((2-(4-(4-(2-(5-amino-8-(furan-2-yl)-3H-[1,2,4]triazolo[5,1-i]purin-3-yl)ethyl)piperazin-1-yl)-3-fluorophenoxy)ethyl)(methyl)amino)acetamide 3-(2-(4-(2-fluoro-4-(piperidin-4-yloxy)phenyl)piperazin-1-yl)ethyl)-8-(furan-2-yl)-3H-[1,2,4]triazolo[5,1-i]purin-5-amine 3-(2-(4-(2-fluoro-4-(pyrrolidin-3-yloxy)phenyl)piperazin-1-yl)ethyl)-8-(furan-2-yl)-3H-[1,2,4]triazolo[5,1-i]purin-5-amine 3-(2-(4-(4-((4H-1,2,4-triazol-3-yl)methoxy)-2-fluorophenyl)piperazin-1-yl)ethyl)-8-(furan-2-yl)-3H-[1,2,4]triazolo[5,1-i]purin-5-amine 2-(4-(4-(2-(5-amino-8-(furan-2-yl)-3H-[1,2,4]triazolo[5,1-i]purin-3-yl)ethyl)piperazin-1-yl)-3-fluorophenoxy)-N-(2-(methylamino)ethyl)acetamide 2-(4-(4-(2-(5-amino-8-(furan-2-yl)-3H-[1,2,4]triazolo[5,1-i]purin-3-yl)ethyl)piperazin-1-yl)-3-fluorophenoxy)-N-(2-(dimethylamino)ethyl)acetamide 2-(4-(4-(2-(5-amino-8-(furan-2-yl)-3H-[1,2,4]triazolo[5,1-i]purin-3-yl)ethyl)piperazin-1-yl)-3-fluorophenoxy)-N-(2-aminoethyl)acetamide (R)-2-(4-(4-(2-(5-amino-8-(furan-2-yl)-3H-[1,2,4]triazolo[5,1-i]purin-3-yl)ethyl)piperazin-1-yl)-3-fluorophenoxy)propanoic acid 2-(4-(4-(2-(5-amino-8-(furan-2-yl)-3H-[1,2,4]triazolo[5,1-i]purin-3-yl)ethyl)piperazin-1-yl)-3-fluorophenoxy)acetamide 4-(4-(2-(5-amino-8-(furan-2-yl)-3H-[1,2,4]triazolo[5,1-i]purin-3-yl)ethyl)piperazin-1-yl)-3-fluoro-N-methyl-N-(2-(methylamino)ethyl)benzamide 4-(4-(2-(5-amino-8-(furan-2-yl)-3H-[1,2,4]triazolo[5,1-i]purin-3-yl)ethyl)piperazin-1-yl)-N-(2-(dimethylamino)ethyl)-3-fluoro-N-methylbenzamide (R)-4-(4-(2-(5-amino-8-(furan-2-yl)-3H-[1,2,4]triazolo[5,1-i]purin-3-yl)ethyl)piperazin-1-yl)-N-(1-(dimethylamino)propan-2-yl)-3-fluorobenzamide 2-(4-(4-(2-(5-amino-8-(furan-2-yl)-3H-[1,2,4]triazolo[5,1-i]purin-3-yl)ethyl)piperazin-1-yl)-3-fluorophenoxy)-N-methyl-N-(2-(methylamino)ethyl)acetamide 2-(5-(4-(2-(5-amino-8-(furan-2-yl)-3H-[1,2,4]triazolo[5,1-i]purin-3-yl)ethyl)piperazin-1-yl)-2,4-difluorophenoxy)-2-methylpropanoic acid (S)-2-(5-(4-(2-(5-amino-8-(furan-2-yl)-3H-[1,2,4]triazolo[5,1-i]purin-3-yl)ethyl)piperazin-1-yl)-2,4-difluorophenoxy)propanoic acid (R)-2-(5-(4-(2-(5-amino-8-(furan-2-yl)-3H-[1,2,4]triazolo[5,1-i]purin-3-yl)ethyl)piperazin-1-yl)-2,4-difluorophenoxy)propanoic acid 2-(5-(4-(2-(5-amino-8-(furan-2-yl)-3H-[1,2,4]triazolo[5,1-i]purin-3-yl)ethyl)piperazin-1-yl)-2,4-difluorophenoxy)-N-(2-(methylamino)ethyl)acetamide 2-(5-(4-(2-(5-amino-8-(furan-2-yl)-3H-[1,2,4]triazolo[5,1-i]purin-3-yl)ethyl)piperazin-1-yl)-2,4-difluorophenoxy)-N-(2-(dimethylamino)ethyl)acetamide 5-(4-(2-(5-amino-8-(furan-2-yl)-3H-[1,2,4]triazolo[5,1-i]purin-3-yl)ethyl)piperazin-1-yl)-N-(2-(dimethylamino)ethyl)-2,4-difluoro-N-methylbenzamide 5-(4-(2-(5-amino-8-(furan-2-yl)-3H-[1,2,4]triazolo[5,1-i]purin-3-yl)ethyl)piperazin-1-yl)-2,4-difluoro-N-methylbenzamide 4-(5-(4-(2-(5-amino-8-(furan-2-yl)-3H-[1,2,4]triazolo[5,1-i]purin-3-yl)ethyl)piperazin-1-yl)-2,4-difluorophenoxy)butanoic acid 3-(2-(4-(5-((1H-tetrazol-5-yl)methoxy)-2,4-difluorophenyl)piperazin-1-yl)ethyl)-8-(furan-2-yl)-3H-[1,2,4]triazolo[5,1-i]purin-5-amine 3-(2-(4-(2-fluoro-4-((1-methyl-1H-1,2,4-triazol-3-yl)methoxy)phenyl)piperazin-1-yl)ethyl)-8-(furan-2-yl)-3H-[1,2,4]triazolo[5,1-i]purin-5-amine 3-(2-(4-(2,4-difluoro-5-((1-methyl-1H-1,2,4-triazol-3-yl)methoxy)phenyl)piperazin-1-yl)ethyl)-8-(furan-2-yl)-3H-[1,2,4]triazolo[5,1-i]purin-5-amine 4-(4-(2-(5-amino-8-(furan-2-yl)-3H-[1,2,4]triazolo[5,1-i]purin-3-yl)ethyl)piperazin-1-yl)-3-fluoro-N-(2-(methyl(oxetan-3-yl)amino)ethyl)benzamide 4-(4-(2-(5-amino-8-(furan-2-yl)-3H-[1,2,4]triazolo[5,1-i]purin-3-yl)ethyl)piperazin-1-yl)-3-fluoro-N-(2-((2-hydroxyethyl)amino)ethyl)benzamide 2-amino-N-(2-(4-(4-(2-(5-amino-8-(furan-2-yl)-3H-[1,2,4]triazolo[5,1-i]purin-3-yl)ethyl)piperazin-1-yl)-3-fluorophenoxy)ethyl)acetamide (S)-2-amino-N-(2-(4-(4-(2-(5-amino-8-(furan-2-yl)-3H-[1,2,4]triazolo[5,1-i]purin-3-yl)ethyl)piperazin-1-yl)-3-fluorophenoxy)ethyl)-3-methylbutanamide 3-(2-(4-(2,4-difluoro-5-(2-(methylsulfonyl)ethoxy)phenyl)piperazin-1-yl)ethyl)-8-(furan-2-yl)-3H-[1,2,4]triazolo[5,1-i]purin-5-amine 3-(2-(4-(2-fluoro-4-(2-(methylsulfonyl)ethoxy)phenyl)piperazin-1-yl)ethyl)-8-(furan-2-yl)-3H-[1,2,4]triazolo[5,1-i]purin-5-amine 5-(4-(2-(5-amino-8-(furan-2-yl)-3H-[1,2,4]triazolo[5,1-i]purin-3-yl)ethyl)piperazin-1-yl)-6-fluoroindolin-2-one 3-(2-(4-(2-fluoro-4-(S-methylsulfonimidoyl)phenyl)piperazin-1-yl)ethyl)-8-(furan-2-yl)-3H-[1,2,4]triazolo[5,1-i]purin-5-amine 5-(4-(2-(5-amino-8-(furan-2-yl)-3H-[1,2,4]triazolo[5,1-i]purin-3-yl)ethyl)piperazin-1-yl)-N-(2-(dimethylamino)ethyl)-2,4-difluorobenzamide (3R,4R)-4-(4-(4-(2-(5-amino-8-(furan-2-yl)-3H-[1,2,4]triazolo[5,1-i]purin-3-yl)ethyl)piperazin-1-yl)-3-fluorophenoxy)tetrahydrofuran-3-ol (3S,4S)-4-(4-(4-(2-(5-amino-8-(furan-2-yl)-3H-[1,2,4]triazolo[5,1-i]purin-3-yl)ethyl)piperazin-1-yl)-3-fluorophenoxy)tetrahydrofuran-3-ol 1-(4-(4-(2-(5-amino-8-(furan-2-yl)-3H-[1,2,4]triazolo[5,1-i]purin-3-yl)ethyl)piperazin-1-yl)-3-fluorophenoxy)-2-methylpropan-2-ol 2-(4-(4-(2-(5-amino-8-(furan-2-yl)-3H-[1,2,4]triazolo[5,1-i]purin-3-yl)ethyl)piperazin-1-yl)-3-fluorophenyl)propan-2-ol 3-(4-(4-(2-(5-amino-8-(furan-2-yl)-3H-[1,2,4]triazolo[5,1-i]purin-3-yl)ethyl)piperazin-1-yl)-3-fluorophenoxy)-1,1,1-trifluoropropan-2-ol 2-(3-(4-(2-(5-amino-8-(furan-2-yl)-3H-[1,2,4]triazolo[5,1-i]purin-3-yl)ethyl)piperazin-1-yl)-4-fluorophenoxy)ethanol 3-(2-(4-(2,4-difluoro-5-(morpholin-2-ylmethoxy)phenyl)piperazin-1-yl)ethyl)-8-(furan-2-yl)-3H-[1,2,4]triazolo[5,1-i]purin-5-amine 3-(2-(4-(2,4-difluoro-5-(morpholin-3-ylmethoxy)phenyl)piperazin-1-yl)ethyl)-8-(furan-2-yl)-3H-[1,2,4]triazolo[5,1-i]purin-5-amine 3-(2-(4-(2,4-difluoro-5-(((3S,4S)-4-fluoropyrrolidin-3-yl)oxy)phenyl)piperazin-1-yl)ethyl)-8-(furan-2-yl)-3H-[1,2,4]triazolo[5,1-i]purin-5-amine 3-(2-(4-(2,4-difluoro-5-(((3R,4S)-4-fluoropyrrolidin-3-yl)oxy)phenyl)piperazin-1-yl)ethyl)-8-(furan-2-yl)-3H-[1,2,4]triazolo[5,1-i]purin-5-amine 3-(2-(4-(2,4-difluoro-5-(((3S,4R)-4-fluoropyrrolidin-3-yl)oxy)phenyl)piperazin-1-yl)ethyl)-8-(furan-2-yl)-3H-[1,2,4]triazolo[5,1-i]purin-5-amine (S)-3-(5-(4-(2-(5-amino-8-(furan-2-yl)-3H-[1,2,4]triazolo[5,1-i]purin-3-yl)ethyl)piperazin-1-yl)-2,4-difluorophenoxy)pyrrolidin-2-one (R)-3-(5-(4-(2-(5-amino-8-(furan-2-yl)-3H-[1,2,4]triazolo[5,1-i]purin-3-yl)ethyl)piperazin-1-yl)-2,4-difluorophenoxy)pyrrolidin-2-one 2-(5-(4-(2-(5-amino-8-(furan-2-yl)-3H-[1,2,4]triazolo[5,1-i]purin-3-yl)ethyl)piperazin-1-yl)-2,4-difluorophenoxy)-N-(2-morpholinoethyl)acetamide 5-(4-(2-(5-amino-8-(furan-2-yl)-3H-[1,2,4]triazolo[5,1-i]purin-3-yl)ethyl)piperazin-1-yl)-2,4-difluoro-N-(morpholin-3-ylmethyl)benzamide 3-(2-(4-(2-fluoro-4-(morpholin-3-ylmethoxy)phenyl)piperazin-1-yl)ethyl)-8-(furan-2-yl)-3H-[1,2,4]triazolo[5,1-i]purin-5-amine 3-(2-(4-(2-fluoro-4-(morpholin-2-ylmethoxy)phenyl)piperazin-1-yl)ethyl)-8-(furan-2-yl)-3H-[1,2,4]triazolo[5,1-i]purin-5-amine 3-(2-(4-(2-fluoro-4-(((3R,4R)-4-fluoropyrrolidin-3-yl)oxy)phenyl)piperazin-1-yl)ethyl)-8-(furan-2-yl)-3H-[1,2,4]triazolo[5,1-i]purin-5-amine 3-(2-(4-(2-fluoro-4-(((3 S,4S)-4-fluoropyrrolidin-3-yl)oxy)phenyl)piperazin-1-yl)ethyl)-8-(furan-2-yl)-3H-[1,2,4]triazolo[5,1-i]purin-5-amine 3-(2-(4-(2-fluoro-4-(((3R,4S)-4-fluoropyrrolidin-3-yl)oxy)phenyl)piperazin-1-yl)ethyl)-8-(furan-2-yl)-3H-[1,2,4]triazolo[5,1-i]purin-5-amine 3-(2-(4-(2-fluoro-4-(((3S,4R)-4-fluoropyrrolidin-3-yl)oxy)phenyl)piperazin-1-yl)ethyl)-8-(furan-2-yl)-3H-[1,2,4]triazolo[5,1-i]purin-5-amine 2-(4-(4-(2-(5-amino-8-(furan-2-yl)-3H-[1,2,4]triazolo[5,1-i]purin-3-yl)ethyl)piperazin-1-yl)-3-fluorophenoxy)-N-(2-morpholinoethyl)acetamide 4-(4-(2-(5-amino-8-(furan-2-yl)-3H-[1,2,4]triazolo[5,1-i]purin-3-yl)ethyl)piperazin-1-yl)-3-fluoro-N-(2-morpholinoethyl)benzamide 4-(4-(2-(5-amino-8-(furan-2-yl)-3H-[1,2,4]triazolo[5,1-i]purin-3-yl)ethyl)piperazin-1-yl)-3-fluoro-N-(morpholin-3-ylmethyl)benzamide (S)-3-(2-(4-(2,4-difluoro-5-(methylsulfinyl)phenyl)piperazin-1-yl)ethyl)-8-(furan-2-yl)-3H-[1,2,4]triazolo[5,1-i]purin-5-amine (R)-3-(2-(4-(2,4-difluoro-5-(methylsulfinyl)phenyl)piperazin-1-yl)ethyl)-8-(furan-2-yl)-3H-[1,2,4]triazolo[5,1-i]purin-5-amine (1s,4s)-4-(5-(4-(2-(5-amino-8-(furan-2-yl)-3H-[1,2,4]triazolo[5,1-i]purin-3-yl)ethyl)piperazin-1-yl)-2,4-difluorophenoxy)tetrahydro-2H-thiopyran 1-oxide (1r,4r)-4-(5-(4-(2-(5-amino-8-(furan-2-yl)-3H-[1,2,4]triazolo[5,1-i]purin-3-yl)ethyl)piperazin-1-yl)-2,4-difluorophenoxy)tetrahydro-2H-thiopyran 1-oxide (S)-5-(4-(2-(5-amino-8-(furan-2-yl)-3H-[1,2,4]triazolo[5,1-i]purin-3-yl)ethyl)piperazin-1-yl)-2,4-difluoro-N-(2-(methylsulfinyl)ethyl)benzamide (R)-5-(4-(2-(5-amino-8-(furan-2-yl)-3H-[1,2,4]triazolo[5,1-i]purin-3-yl)ethyl)piperazin-1-yl)-2,4-difluoro-N-(2-(methylsulfinyl)ethyl)benzamide (S)-5-(4-(2-(5-amino-8-(furan-2-yl)-3H-[1,2,4]triazolo[5,1-i]purin-3-yl)ethyl)piperazin-1-yl)-2,4-difluoro-N-methyl-N-(2-(methylsulfinyl)ethyl)benzamide (R)-5-(4-(2-(5-amino-8-(furan-2-yl)-3H-[1,2,4]triazolo[5,1-i]purin-3-yl)ethyl)piperazin-1-yl)-2,4-difluoro-N-methyl-N-(2-(methylsulfinyl)ethyl)benzamide (5-(4-(2-(5-amino-8-(furan-2-yl)-3H-[1,2,4]triazolo[5,1-i]purin-3-yl)ethyl)piperazin-1-yl)-2,4-difluorophenyl)(1-oxidothiomorpholino)methanone 4-(5-(4-(2-(5-amino-8-(furan-2-yl)-3H-[1,2,4]triazolo[5,1-i]purin-3-yl)ethyl)piperazin-1-yl)-2,4-difluorophenyl)thiomorpholine 1-oxide (R)-3-(2-(4-(2-fluoro-4-(methylsulfinyl)phenyl)piperazin-1-yl)ethyl)-8-(furan-2-yl)-3H-[1,2,4]triazolo[5,1-i]purin-5-amine (S)-3-(2-(4-(2-fluoro-4-(methylsulfinyl)phenyl)piperazin-1-yl)ethyl)-8-(furan-2-yl)-3H-[1,2,4]triazolo[5,1-i]purin-5-amine (1s,4s)-4-(4-(4-(2-(5-amino-8-(furan-2-yl)-3H-[1,2,4]triazolo[5,1-i]purin-3-yl)ethyl)piperazin-1-yl)-3-fluorophenoxy)tetrahydro-2H-thiopyran 1-oxide (1r,4r)-4-(4-(4-(2-(5-amino-8-(furan-2-yl)-3H-[1,2,4]triazolo[5,1-i]purin-3-yl)ethyl)piperazin-1-yl)-3-fluorophenoxy)tetrahydro-2H-thiopyran 1-oxide (S)-4-(4-(2-(5-amino-8-(furan-2-yl)-3H-[1,2,4]triazolo[5,1-i]purin-3-yl)ethyl)piperazin-1-yl)-3-fluoro-N-(2-(methylsulfinyl)ethyl)benzamide (R)-4-(4-(2-(5-amino-8-(furan-2-yl)-3H-[1,2,4]triazolo[5,1-i]purin-3-yl)ethyl)piperazin-1-yl)-3-fluoro-N-(2-(methylsulfinyl)ethyl)benzamide (4-(4-(2-(5-amino-8-(furan-2-yl)-3H-[1,2,4]triazolo[5,1-i]purin-3-yl)ethyl)piperazin-1-yl)-3-fluorophenyl)(1-oxidothiomorpholino)methanone 4-(4-(2-(5-amino-8-(furan-2-yl)-3H-[1,2,4]triazolo[5,1-i]purin-3-yl)ethyl)piperazin-1-yl)-3-fluorophenyl)thiomorpholine 1-oxide (S)-3-(5-(4-(2-(5-amino-8-(furan-2-yl)-3H-[1,2,4]triazolo[5,1-i]purin-3-yl)ethyl)piperazin-1-yl)-2,4-difluorophenoxy)propane-1,2-diol (R)-3-(5-(4-(2-(5-amino-8-(furan-2-yl)-3H-[1,2,4]triazolo[5,1-i]purin-3-yl)ethyl)piperazin-1-yl)-2,4-difluorophenoxy)propane-1,2-diol (S)-5-(4-(2-(5-amino-8-(furan-2-yl)-3H-[1,2,4]triazolo[5,1-i]purin-3-yl)ethyl)piperazin-1-yl)-N-(2,3-dihydroxypropyl)-2,4-difluorobenzamide (R)-5-(4-(2-(5-amino-8-(furan-2-yl)-3H-[1,2,4]triazolo[5,1-i]purin-3-yl)ethyl)piperazin-1-yl)-N-(2,3-dihydroxypropyl)-2,4-difluorobenzamide 3-(2-(4-(4-(azetidin-3-yloxy)-2-fluorophenyl)piperazin-1-yl)ethyl)-8-(furan-2-yl)-3H-[1,2,4]triazolo[5,1-i]purin-5-amine 3-(2-(4-(5-(azetidin-3-yloxy)-2,4-difluorophenyl)piperazin-1-yl)ethyl)-8-(furan-2-yl)-3H-[1,2,4]triazolo[5,1-i]purin-5-amine (S)-3-(2-(4-(2,4-difluoro-5-(3-(methylsulfinyl)propoxy)phenyl)piperazin-1-yl)ethyl)-8-(furan-2-yl)-3H-[1,2,4]triazolo[5,1-i]purin-5-amine Heteroaryl Scaffold (5)

2-(4-(4-(2-(5-amino-2-(furan-2-yl)-7H-pyrazolo[4,3-e][1,2,4]triazolo[1,5-c]pyrimidin-7-yl)ethyl)piperazin-1-yl)phenoxy)ethanol 2-(4-(4-(2-(5-amino-2-(furan-2-yl)-7H-pyrazolo[4,3-e][1,2,4]triazolo[1,5-c]pyrimidin-7-yl)ethyl)piperazin-1-yl)phenoxy)acetic acid 2-(4-(4-(2-(5-amino-2-(furan-2-yl)-7H-pyrazolo[4,3-e][1,2,4]triazolo[1,5-c]pyrimidin-7-yl)ethyl)piperazin-1-yl)phenoxy)acetamide 3-(4-(4-(2-(5-amino-2-(furan-2-yl)-7H-pyrazolo[4,3-e][1,2,4]triazolo[1,5-c]pyrimidin-7-yl)ethyl)piperazin-1-yl)phenoxy)propane-1,2-diol 7-(2-(4-(4-(2-aminoethoxy)phenyl)piperazin-1-yl)ethyl)-2-(furan-2-yl)-7H-pyrazolo[4,3-e][1,2,4]triazolo[1,5-c]pyrimidin-5-amine 4-(4-(2-(5-amino-2-(furan-2-yl)-7H-pyrazolo[4,3-e][1,2,4]triazolo[1,5-c]pyrimidin-7-yl)ethyl)piperazin-1-yl)benzamide 4-(4-(2-(5-amino-2-(furan-2-yl)-7H-pyrazolo[4,3-e][1,2,4]triazolo[1,5-c]pyrimidin-7-yl)ethyl)piperazin-1-yl)-N-methylbenzamide 2-(furan-2-yl)-7-(2-(4-(4-(2-morpholinoethoxy)phenyl)piperazin-1-yl)ethyl)-7H-pyrazolo[4,3-e][1,2,4]triazolo[1,5-c]pyrimidin-5-amine 7-(2-(4-(4-(2-(dimethylamino)ethoxy)phenyl)piperazin-1-yl)ethyl)-2-(furan-2-yl)-7H-pyrazolo[4,3-e][1,2,4]triazolo[1,5-c]pyrimidin-5-amine 4-(4-(2-(5-amino-2-(furan-2-yl)-7H-pyrazolo[4,3-e][1,2,4]triazolo[1,5-c]pyrimidin-7-yl)ethyl)piperazin-1-yl)benzenesulfonamide 4-(4-(2-(5-amino-2-(furan-2-yl)-7H-pyrazolo[4,3-e][1,2,4]triazolo[1,5-c]pyrimidin-7-yl)ethyl)piperazin-1-yl)-N-methylbenzenesulfonamide 2-(furan-2-yl)-7-(2-(4-(4-(methylsulfonyl)phenyl)piperazin-1-yl)ethyl)-7H-pyrazolo[4,3-e][1,2,4]triazolo[1,5-c]pyrimidin-5-amine 2-(furan-2-yl)-7-(2-(4-(4-(methylsulfinyl)phenyl)piperazin-1-yl)ethyl)-7H-pyrazolo[4,3-e][1,2,4]triazolo[1,5-c]pyrimidin-5-amine 3-(4-(2-(5-amino-2-(furan-2-yl)-7H-pyrazolo[4,3-e][1,2,4]triazolo[1,5-c]pyrimidin-7-yl)ethyl)piperazin-1-yl)benzamide 2-(3-(4-(2-(5-amino-2-(furan-2-yl)-7H-pyrazolo[4,3-e][1,2,4]triazolo[1,5-c]pyrimidin-7-yl)ethyl)piperazin-1-yl)phenoxy)ethanol 7-(2-(4-(4-(azetidin-3-yloxy)phenyl)piperazin-1-yl)ethyl)-2-(furan-2-yl)-7H-pyrazolo[4,3-e][1,2,4]triazolo[1,5-c]pyrimidin-5-amine 7-(2-(4-(4-((2H-1,2,3-triazol-4-yl)methoxy)-2-fluorophenyl)piperazin-1-yl)ethyl)-2-(furan-2-yl)-7H-pyrazolo[4,3-e][1,2,4]triazolo[1,5-c]pyrimidin-5-amine 5-((4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)methyl)-1,3,4-oxadiazol-2(3H)-one 2-(5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenoxy)acetamide (S)-7-(2-(4-(2-fluoro-4-(2-(methylsulfinyl)ethoxy)phenyl)piperazin-1-yl)ethyl)-2-(furan-2-yl)-7H-pyrazolo[4,3-e][1,2,4]triazolo[1,5-c]pyrimidin-5-amine (R)-7-(2-(4-(2-fluoro-4-(2-(methylsulfinyl)ethoxy)phenyl)piperazin-1-yl)ethyl)-2-(furan-2-yl)-7H-pyrazolo[4,3-e][1,2,4]triazolo[1,5-c]pyrimidin-5-amine 7-(2-(4-(2,4-difluoro-5-(2-(methylsulfinyl)ethoxy)phenyl)piperazin-1-yl)ethyl)-2-(furan-2-yl)-7H-pyrazolo[4,3-e][1,2,4]triazolo[1,5-c]pyrimidin-5-amine (S)-7-(2-(4-(2,4-difluoro-5-(2-(methylsulfinyl)ethoxy)phenyl)piperazin-1-yl)ethyl)-2-(furan-2-yl)-7H-pyrazolo[4,3-e][1,2,4]triazolo[1,5-c]pyrimidin-5-amine (Example 12)

(R)-7-(2-(4-(2,4-difluoro-5-(2-(methylsulfinyl)ethoxy)phenyl)piperazin-1-yl)ethyl)-2-(furan-2-yl)-7H-pyrazolo[4,3-e][1,2,4]triazolo[1,5-c]pyrimidin-5-amine (Example 12)

2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)-1-(piperazin-1-yl)ethanone 7-(2-(4-(2-fluoro-4-(piperidin-4-ylmethoxy)phenyl)piperazin-1-yl)ethyl)-2-(furan-2-yl)-7H-pyrazolo[4,3-e][1,2,4]triazolo[1,5-c]pyrimidin-5-amine (4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenyl)(piperazin-1-yl)methanone 7-(2-(4-(2-fluoro-4-(2-(piperazin-1-yl)ethoxy)phenyl)piperazin-1-yl)ethyl)-2-(furan-2-yl)-7H-pyrazolo[4,3-e][1,2,4]triazolo[1,5-c]pyrimidin-5-amine 7-(2-(4-(2-fluoro-4-(piperazin-1-ylsulfonyl)phenyl)piperazin-1-yl)ethyl)-2-(furan-2-yl)-7H-pyrazolo[4,3-e][1,2,4]triazolo[1,5-c]pyrimidin-5-amine 7-(2-(4-(2-fluoro-4-(methylsulfonyl)phenyl)piperazin-1-yl)ethyl)-2-(furan-2-yl)-7H-pyrazolo[4,3-e][1,2,4]triazolo[1,5-c]pyrimidin-5-amine 4-(4-(2-(5-amino-2-(furan-2-yl)-7H-pyrazolo[4,3-e][1,2,4]triazolo[1,5-c]pyrimidin-7-yl)ethyl)piperazin-1-yl)-N-(2-aminoethyl)-3-fluorobenzamide 4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluoro-N-(2-(methylamino)ethyl)benzamide 4-(4-(2-(5-amino-2-(furan-2-yl)-7H-pyrazolo[4,3-e][1,2,4]triazolo[1,5-c]pyrimidin-7-yl)ethyl)piperazin-1-yl)-N-(2-(dimethylamino)ethyl)-3-fluorobenzamide 4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluoro-N-(2-hydroxyethyl)benzamide 4-(4-(2-(5-amino-2-(furan-2-yl)-7H-pyrazolo[4,3-e][1,2,4]triazolo[1,5-c]pyrimidin-7-yl)ethyl)piperazin-1-yl)-N-(2,3-dihydroxypropyl)-3-fluorobenzamide 2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)acetic acid 2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3,5-difluorophenoxy)acetic acid 2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)propanoic acid (S)-2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)propanoic acid 2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)-2-methylpropanoic acid 3-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenyl)propanoic acid 4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)butanoic acid 2-(3-(4-(2-(5-amino-2-(furan-2-yl)-7H-pyrazolo[4,3-e][1,2,4]triazolo[1,5-c]pyrimidin-7-yl)ethyl)piperazin-1-yl)-2,6-difluorophenoxy)acetic acid 2-(5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenoxy)acetic acid 4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorobenzoic acid 2-((2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)ethyl)amino)acetamide 2-((2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)ethyl)(methyl)amino)acetamide 7-(2-(4-(2-fluoro-4-(piperidin-4-yloxy)phenyl)piperazin-1-yl)ethyl)-2-(furan-2-yl)-7H-pyrazolo[4,3-e][1,2,4]triazolo[1,5-c]pyrimidin-5-amine 7-(2-(4-(2-fluoro-4-(pyrrolidin-3-yloxy)phenyl)piperazin-1-yl)ethyl)-2-(furan-2-yl)-7H-pyrazolo[4,3-e][1,2,4]triazolo[1,5-c]pyrimidin-5-amine 7-(2-(4-(4-((4H-1,2,4-triazol-3-yl)methoxy)-2-fluorophenyl)piperazin-1-yl)ethyl)-2-(furan-2-yl)-7H-pyrazolo[4,3-e][1,2,4]triazolo[1,5-c]pyrimidin-5-amine 2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)-N-(2-(methylamino)ethyl)acetamide 2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)-N-(2-(dimethylamino)ethyl)acetamide 2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)-N-(2-aminoethyl)acetamide (R)-2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)propanoic acid 2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)acetamide 4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluoro-N-methyl-N-(2-(methylamino)ethyl)benzamide 4-(4-(2-(5-amino-2-(furan-2-yl)-7H-pyrazolo[4,3-e][1,2,4]triazolo[1,5-c]pyrimidin-7-yl)ethyl)piperazin-1-yl)-N-(2-(dimethylamino)ethyl)-3-fluoro-N-methylbenzamide (R)-4-(4-(2-(5-amino-2-(furan-2-yl)-7H-pyrazolo[4,3-e][1,2,4]triazolo[1,5-c]pyrimidin-7-yl)ethyl)piperazin-1-yl)-N-(1-(dimethylamino)propan-2-yl)-3-fluorobenzamide 2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)-N-methyl-N-(2-(methylamino)ethyl)acetamide 2-(5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenoxy)-2-methylpropanoic acid (S)-2-(5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenoxy)propanoic acid (R)-2-(5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenoxy)propanoic acid 2-(5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenoxy)-N-(2-(methylamino)ethyl)acetamide 2-(5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenoxy)-N-(2-(dimethylamino)ethyl)acetamide 5-(4-(2-(5-amino-2-(furan-2-yl)-7H-pyrazolo[4,3-e][1,2,4]triazolo[1,5-c]pyrimidin-7-yl)ethyl)piperazin-1-yl)-N-(2-(dimethylamino)ethyl)-2,4-difluoro-N-methylbenzamide 5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluoro-N-methylbenzamide (Example 4)

4-(5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenoxy)butanoic acid 7-(2-(4-(4-(5-((1H-tetrazol-5-yl)methoxy)-2,4-difluorophenyl)piperazin-1-yl)ethyl)-2-(furan-2-yl)-7H-pyrazolo[4,3-e][1,2,4]triazolo[1,5-c]pyrimidin-5-amine 7-(2-(4-(2-fluoro-4-((1-methyl-1H-1,2,4-triazol-3-yl)methoxy)phenyl)piperazin-1-yl)ethyl)-2-(furan-2-yl)-7H-pyrazolo[4,3-e][1,2,4]triazolo[1,5-c]pyrimidin-5-amine 7-(2-(4-(2,4-difluoro-5-((1-methyl-1H-1,2,4-triazol-3-yl)methoxy)phenyl)piperazin-1-yl)ethyl)-2-(furan-2-yl)-7H-pyrazolo[4,3-e][1,2,4]triazolo[1,5-c]pyrimidin-5-amine 4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluoro-N-(2-(methyl(oxetan-3-yl)amino)ethyl)benzamide 4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluoro-N-(2-((2-hydroxyethyl)amino)ethyl)benzamide 2-amino-N-(2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)ethyl)acetamide (S)-2-amino-N-(2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)ethyl)-3-methylbutanamide 7-(2-(4-(2,4-difluoro-5-(2-(methylsulfonyl)ethoxy)phenyl)piperazin-1-yl)ethyl)-2-(furan-2-yl)-7H-pyrazolo[4,3-e][1,2,4]triazolo[1,5-c]pyrimidin-5-amine 7-(2-(4-(2-fluoro-4-(2-(methylsulfonyl)ethoxy)phenyl)piperazin-1-yl)ethyl)-2-(furan-2-yl)-7H-pyrazolo[4,3-e][1,2,4]triazolo[1,5-c]pyrimidin-5-amine 5-(4-(2-(5-amino-2-(furan-2-yl)-7H-pyrazolo[4,3-e][1,2,4]triazolo[1,5-c]pyrimidin-7-yl)ethyl)piperazin-1-yl)-6-fluoroindolin-2-one 7-(2-(4-(2-fluoro-4-(S-methylsulfonimidoyl)phenyl)piperazin-1-yl)ethyl)-2-(furan-2-yl)-7H-pyrazolo[4,3-e][1,2,4]triazolo[1,5-c]pyrimidin-5-amine 5-(4-(2-(5-amino-2-(furan-2-yl)-7H-pyrazolo[4,3-e][1,2,4]triazolo[1,5-c]pyrimidin-7-yl)ethyl)piperazin-1-yl)-N-(2-(dimethylamino)ethyl)-2,4-difluorobenzamide (3R,4R)-4-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)tetrahydrofuran-3-ol (3S,4S)-4-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)tetrahydrofuran-3-ol 1-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)-2-methylpropan-2-ol 2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenyl)propan-2-ol 3-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)-1,1,1-trifluoropropan-2-ol 2-(3-(4-(2-(5-amino-2-(furan-2-yl)-7H-pyrazolo[4,3-e][1,2,4]triazolo[1,5-c]pyrimidin-7-yl)ethyl)piperazin-1-yl)-4-fluorophenoxy)ethanol 7-(2-(4-(2,4-difluoro-5-(morpholin-2-ylmethoxy)phenyl)piperazin-1-yl)ethyl)-2-(furan-2-yl)-7H-pyrazolo[4,3-e][1,2,4]triazolo[1,5-c]pyrimidin-5-amine 7-(2-(4-(2,4-difluoro-5-(morpholin-3-ylmethoxy)phenyl)piperazin-1-yl)ethyl)-2-(furan-2-yl)-7H-pyrazolo[4,3-e][1,2,4]triazolo[1,5-c]pyrimidin-5-amine 7-(2-(4-(2,4-difluoro-5-(((3 S,4S)-4-fluoropyrrolidin-3-yl)oxy)phenyl)piperazin-1-yl)ethyl)-2-(furan-2-yl)-7H-pyrazolo[4,3-e][1,2,4]triazolo[1,5-c]pyrimidin-5-amine 7-(2-(4-(2,4-difluoro-5-(((3R,4S)-4-fluoropyrrolidin-3-yl)oxy)phenyl)piperazin-1-yl)ethyl)-2-(furan-2-yl)-7H-pyrazolo[4,3-e][1,2,4]triazolo[1,5-c]pyrimidin-5-amine 7-(2-(4-(2,4-difluoro-5-(((3S,4R)-4-fluoropyrrolidin-3-yl)oxy)phenyl)piperazin-1-yl)ethyl)-2-(furan-2-yl)-7H-pyrazolo[4,3-e][1,2,4]triazolo[1,5-c]pyrimidin-5-amine (S)-3-(5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenoxy)pyrrolidin-2-one (R)-3-(5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenoxy)pyrrolidin-2-one 2-(5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenoxy)-N-(2-morpholinoethyl)acetamide 5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluoro-N-(morpholin-3-ylmethyl)benzamide 7-(2-(4-(2-fluoro-4-(morpholin-3-ylmethoxy)phenyl)piperazin-1-yl)ethyl)-2-(furan-2-yl)-7H-pyrazolo[4,3-e][1,2,4]triazolo[1,5-c]pyrimidin-5-amine 7-(2-(4-(2-fluoro-4-(morpholin-2-ylmethoxy)phenyl)piperazin-1-yl)ethyl)-2-(furan-2-yl)-7H-pyrazolo[4,3-e][1,2,4]triazolo[1,5-c]pyrimidin-5-amine 7-(2-(4-(2-fluoro-4-(((3R,4R)-4-fluoropyrrolidin-3-yl)oxy)phenyl)piperazin-1-yl)ethyl)-2-(furan-2-yl)-7H-pyrazolo[4,3-e][1,2,4]triazolo[1,5-c]pyrimidin-5-amine 7-(2-(4-(2-fluoro-4-(((3 S,4S)-4-fluoropyrrolidin-3-yl)oxy)phenyl)piperazin-1-yl)ethyl)-2-(furan-2-yl)-7H-pyrazolo[4,3-e][1,2,4]triazolo[1,5-c]pyrimidin-5-amine 7-(2-(4-(2-fluoro-4-(((3R,4S)-4-fluoropyrrolidin-3-yl)oxy)phenyl)piperazin-1-yl)ethyl)-2-(furan-2-yl)-7H-pyrazolo[4,3-e][1,2,4]triazolo[1,5-c]pyrimidin-5-amine 7-(2-(4-(2-fluoro-4-(((3S,4R)-4-fluoropyrrolidin-3-yl)oxy)phenyl)piperazin-1-yl)ethyl)-2-(furan-2-yl)-7H-pyrazolo[4,3-e][1,2,4]triazolo[1,5-c]pyrimidin-5-amine 2-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)-N-(2-morpholinoethyl)acetamide 4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluoro-N-(2-morpholinoethyl)benzamide 4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluoro-N-(morpholin-3-ylmethyl)benzamide (S)-7-(2-(4-(2,4-difluoro-5-(methylsulfinyl)phenyl)piperazin-1-yl)ethyl)-2-(furan-2-yl)-7H-pyrazolo[4,3-e][1,2,4]triazolo[1,5-c]pyrimidin-5-amine (R)-7-(2-(4-(2,4-difluoro-5-(methylsulfinyl)phenyl)piperazin-1-yl)ethyl)-2-(furan-2-yl)-7H-pyrazolo[4,3-e][1,2,4]triazolo[1,5-c]pyrimidin-5-amine (1s,4s)-4-(5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenoxy)tetrahydro-2H-thiopyran 1-oxide (1r,4r)-4-(5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenoxy)tetrahydro-2H-thiopyran 1-oxide (S)-5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluoro-N-(2-(methylsulfinyl)ethyl)benzamide (R)-5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluoro-N-(2-(methylsulfinyl)ethyl)benzamide (S)-5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluoro-N-methyl-N-(2-(methylsulfinyl)ethyl)benzamide (R)-5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluoro-N-methyl-N-(2-(methylsulfinyl)ethyl)benzamide (5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenyl)(1-oxidothiomorpholino)methanone 4-(5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenyl)thiomorpholine 1-oxide (R)-7-(2-(4-(2-fluoro-4-(methylsulfinyl)phenyl)piperazin-1-yl)ethyl)-2-(furan-2-yl)-7H-pyrazolo[4,3-e][1,2,4]triazolo[1,5-c]pyrimidin-5-amine (S)-7-(2-(4-(2-fluoro-4-(methylsulfinyl)phenyl)piperazin-1-yl)ethyl)-2-(furan-2-yl)-7H-pyrazolo[4,3-e][1,2,4]triazolo[1,5-c]pyrimidin-5-amine (1s,4s)-4-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)tetrahydro-2H-thiopyran 1-oxide (1r,4r)-4-(4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenoxy)tetrahydro-2H-thiopyran 1-oxide (S)-4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluoro-N-(2-(methylsulfinyl)ethyl)benzamide (R)-4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluoro-N-(2-(methylsulfinyl)ethyl)benzamide (4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenyl)(1-oxidothiomorpholino)methanone 4-(4-(2-(5-amino-2-(furan-2-yl)-7H-pyrazolo[4,3-e][1,2,4]triazolo[1,5-c]pyrimidin-7-yl)ethyl)piperazin-1-yl)-3-fluorophenyl)thiomorpholine 1-oxide (S)-3-(5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenoxy)propane-1,2-diol (R)-3-(5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluorophenoxy)propane-1,2-diol (S)-5-(4-(2-(5-amino-2-(furan-2-yl)-7H-pyrazolo[4,3-e][1,2,4]triazolo[1,5-c]pyrimidin-7-yl)ethyl)piperazin-1-yl)-N-(2,3-dihydroxypropyl)-2,4-difluorobenzamide (R)-5-(4-(2-(5-amino-2-(furan-2-yl)-7H-pyrazolo[4,3-e][1,2,4]triazolo[1,5-c]pyrimidin-7-yl)ethyl)piperazin-1-yl)-N-(2,3-dihydroxypropyl)-2,4-difluorobenzamide 7-(2-(4-(4-(azetidin-3-yloxy)-2-fluorophenyl)piperazin-1-yl)ethyl)-2-(furan-2-yl)-7H-pyrazolo[4,3-e][1,2,4]triazolo[1,5-c]pyrimidin-5-amine 7-(2-(4-(5-(azetidin-3-yloxy)-2,4-difluorophenyl)piperazin-1-yl)ethyl)-2-(furan-2-yl)-7H-pyrazolo[4,3-e][1,2,4]triazolo[1,5-c]pyrimidin-5-amine (S)-7-(2-(4-(2,4-difluoro-5-(3-(methylsulfinyl)propoxy)phenyl)piperazin-1-yl)ethyl)-2-(furan-2-yl)-7H-pyrazolo[4,3-e][1,2,4]triazolo[1,5-c]pyrimidin-5-amine Heteroaryl Scaffold (6)

2-(4-(4-(2-((4-amino-7-(furan-2-yl)pyrazolo[1,5-a][1,3,5]triazin-2-yl)amino)ethyl)piperazin-1-yl)phenoxy)ethanol 2-(4-(4-(2-((4-amino-7-(furan-2-yl)pyrazolo[1,5-a][1,3,5]triazin-2-yl)amino)ethyl)piperazin-1-yl)phenoxy)acetic acid 2-(4-(4-(2-((4-amino-7-(furan-2-yl)pyrazolo[1,5-a][1,3,5]triazin-2-yl)amino)ethyl)piperazin-1-yl)phenoxy)acetamide 3-(4-(4-(2-((4-amino-7-(furan-2-yl)pyrazolo[1,5-a][1,3,5]triazin-2-yl)amino)ethyl)piperazin-1-yl)phenoxy)propane-1,2-diol N2-(2-(4-(4-(2-aminoethoxy)phenyl)piperazin-1-yl)ethyl)-7-(furan-2-yl)pyrazolo[1,5-a][1,3,5]triazine-2,4-diamine 4-(4-(2-((4-amino-7-(furan-2-yl)pyrazolo[1,5-a][1,3,5]triazin-2-yl)amino)ethyl)piperazin-1-yl)benzamide 4-(4-(2-((4-amino-7-(furan-2-yl)pyrazolo[1,5-a][1,3,5]triazin-2-yl)amino)ethyl)piperazin-1-yl)-N-methylbenzamide 7-(furan-2-yl)-N2-(2-(4-(4-(2-morpholinoethoxy)phenyl)piperazin-1-yl)ethyl)pyrazolo[1,5-a][1,3,5]triazine-2,4-diamine N2-(2-(4-(4-(2-(dimethylamino)ethoxy)phenyl)piperazin-1-yl)ethyl)-7-(furan-2-yl)pyrazolo[1,5-a][1,3,5]triazine-2,4-diamine 4-(4-(2-((4-amino-7-(furan-2-yl)pyrazolo[1,5-a][1,3,5]triazin-2-yl)amino)ethyl)piperazin-1-yl)benzenesulfonamide 4-(4-(2-((4-amino-7-(furan-2-yl)pyrazolo[1,5-a][1,3,5]triazin-2-yl)amino)ethyl)piperazin-1-yl)-N-methylbenzenesulfonamide 7-(furan-2-yl)-N2-(2-(4-(4-(methylsulfonyl)phenyl)piperazin-1-yl)ethyl)pyrazolo[1,5-a][1,3,5]triazine-2,4-diamine 7-(furan-2-yl)-N2-(2-(4-(4-(methylsulfinyl)phenyl)piperazin-1-yl)ethyl)pyrazolo[1,5-a][1,3,5]triazine-2,4-diamine 3-(4-(2-((4-amino-7-(furan-2-yl)pyrazolo[1,5-a][1,3,5]triazin-2-yl)amino)ethyl)piperazin-1-yl)benzamide 2-(3-(4-(2-((4-amino-7-(furan-2-yl)pyrazolo[1,5-a][1,3,5]triazin-2-yl)amino)ethyl)piperazin-1-yl)phenoxy)ethanol N2-(2-(4-(4-(azetidin-3-yloxy)phenyl)piperazin-1-yl)ethyl)-7-(furan-2-yl)pyrazolo[1,5-a][1,3,5]triazine-2,4-diamine N2-(2-(4-(4-((2H-1,2,3-triazol-4-yl)methoxy)-2-fluorophenyl)piperazin-1-yl)ethyl)-7-(furan-2-yl)pyrazolo[1,5-a][1,3,5]triazine-2,4-diamine 5-((4-(4-(2-((4-amino-7-(furan-2-yl)pyrazolo[1,5-a][1,3,5]triazin-2-yl)amino)ethyl)piperazin-1-yl)-3-fluorophenoxy)methyl)-1,3,4-oxadiazol-2(3H)-one 2-(5-(4-(2-((4-amino-7-(furan-2-yl)pyrazolo[1,5-a][1,3,5]triazin-2-yl)amino)ethyl)piperazin-1-yl)-2,4-difluorophenoxy)acetamide (S)—N2-(2-(4-(2-fluoro-4-(2-(methylsulfinyl)ethoxy)phenyl)piperazin-1-yl)ethyl)-7-(furan-2-yl)pyrazolo[1,5-a][1,3,5]triazine-2,4-diamine (R)—N2-(2-(4-(2-fluoro-4-(2-(methylsulfinyl)ethoxy)phenyl)piperazin-1-yl)ethyl)-7-(furan-2-yl)pyrazolo[1,5-a][1,3,5]triazine-2,4-diamine N2-(2-(4-(2,4-difluoro-5-(2-(methylsulfinyl)ethoxy)phenyl)piperazin-1-yl)ethyl)-7-(furan-2-yl)pyrazolo[1,5-a][1,3,5]triazine-2,4-diamine 2-(4-(4-(2-((4-amino-7-(furan-2-yl)pyrazolo[1,5-a][1,3,5]triazin-2-yl)amino)ethyl)piperazin-1-yl)-3-fluorophenoxy)-1-(piperazin-1-yl)ethanone N2-(2-(4-(2-fluoro-4-(piperidin-4-ylmethoxy)phenyl)piperazin-1-yl)ethyl)-7-(furan-2-yl)pyrazolo[1,5-a][1,3,5]triazine-2,4-diamine (4-(4-(2-((4-amino-7-(furan-2-yl)pyrazolo[1,5-a][1,3,5]triazin-2-yl)amino)ethyl)piperazin-1-yl)-3-fluorophenyl)(piperazin-1-yl)methanone N2-(2-(4-(2-fluoro-4-(2-(piperazin-1-yl)ethoxy)phenyl)piperazin-1-yl)ethyl)-7-(furan-2-yl)pyrazolo[1,5-a][1,3,5]triazine-2,4-diamine N2-(2-(4-(2-fluoro-4-(piperazin-1-ylsulfonyl)phenyl)piperazin-1-yl)ethyl)-7-(furan-2-yl)pyrazolo[1,5-a][1,3,5]triazine-2,4-diamine N2-(2-(4-(2-fluoro-4-(methylsulfonyl)phenyl)piperazin-1-yl)ethyl)-7-(furan-2-yl)pyrazolo[1,5-a][1,3,5]triazine-2,4-diamine 4-(4-(2-((4-amino-7-(furan-2-yl)pyrazolo[1,5-a][1,3,5]triazin-2-yl)amino)ethyl)piperazin-1-yl)-N-(2-aminoethyl)-3-fluorobenzamide 4-(4-(2-((4-amino-7-(furan-2-yl)pyrazolo[1,5-a][1,3,5]triazin-2-yl)amino)ethyl)piperazin-1-yl)-3-fluoro-N-(2-(methylamino)ethyl)benzamide 4-(4-(2-((4-amino-7-(furan-2-yl)pyrazolo[1,5-a][1,3,5]triazin-2-yl)amino)ethyl)piperazin-1-yl)-N-(2-(dimethylamino)ethyl)-3-fluorobenzamide 4-(4-(2-((4-amino-7-(furan-2-yl)pyrazolo[1,5-a][1,3,5]triazin-2-yl)amino)ethyl)piperazin-1-yl)-3-fluoro-N-(2-hydroxyethyl)benzamide 4-(4-(2-((4-amino-7-(furan-2-yl)pyrazolo[1,5-a][1,3,5]triazin-2-yl)amino)ethyl)piperazin-1-yl)-N-(2,3-dihydroxypropyl)-3-fluorobenzamide 2-(4-(4-(2-((4-amino-7-(furan-2-yl)pyrazolo[1,5-a][1,3,5]triazin-2-yl)amino)ethyl)piperazin-1-yl)-3-fluorophenoxy)acetic acid 2-(4-(4-(2-((4-amino-7-(furan-2-yl)pyrazolo[1,5-a][1,3,5]triazin-2-yl)amino)ethyl)piperazin-1-yl)-3,5-difluorophenoxy)acetic acid 2-(4-(4-(2-((4-amino-7-(furan-2-yl)pyrazolo[1,5-a][1,3,5]triazin-2-yl)amino)ethyl)piperazin-1-yl)-3-fluorophenoxy)propanoic acid (S)-2-(4-(4-(2-((4-amino-7-(furan-2-yl)pyrazolo[1,5-a][1,3,5]triazin-2-yl)amino)ethyl)piperazin-1-yl)-3-fluorophenoxy)propanoic acid 2-(4-(4-(2-((4-amino-7-(furan-2-yl)pyrazolo[1,5-a][1,3,5]triazin-2-yl)amino)ethyl)piperazin-1-yl)-3-fluorophenoxy)-2-methylpropanoic acid 3-(4-(4-(2-((4-amino-7-(furan-2-yl)pyrazolo[1,5-a][1,3,5]triazin-2-yl)amino)ethyl)piperazin-1-yl)-3-fluorophenyl)propanoic acid 4-(4-(4-(2-((4-amino-7-(furan-2-yl)pyrazolo[1,5-a][1,3,5]triazin-2-yl)amino)ethyl)piperazin-1-yl)-3-fluorophenoxy)butanoic acid 2-(3-(4-(2-((4-amino-7-(furan-2-yl)pyrazolo[1,5-a][1,3,5]triazin-2-yl)amino)ethyl)piperazin-1-yl)-2,6-difluorophenoxy)acetic acid 2-(5-(4-(2-((4-amino-7-(furan-2-yl)pyrazolo[1,5-a][1,3,5]triazin-2-yl)amino)ethyl)piperazin-1-yl)-2,4-difluorophenoxy)acetic acid 4-(4-(2-((4-amino-7-(furan-2-yl)pyrazolo[1,5-a][1,3,5]triazin-2-yl)amino)ethyl)piperazin-1-yl)-3-fluorobenzoic acid 2-((2-(4-(4-(2-((4-amino-7-(furan-2-yl)pyrazolo[1,5-a][1,3,5]triazin-2-yl)amino)ethyl)piperazin-1-yl)-3-fluorophenoxy)ethyl)amino)acetamide 2-((2-(4-(4-(2-((4-amino-7-(furan-2-yl)pyrazolo[1,5-a][1,3,5]triazin-2-yl)amino)ethyl)piperazin-1-yl)-3-fluorophenoxy)ethyl)(methyl)amino)acetamide N2-(2-(4-(2-fluoro-4-(piperidin-4-yloxy)phenyl)piperazin-1-yl)ethyl)-7-(furan-2-yl)pyrazolo[1,5-a][1,3,5]triazine-2,4-diamine N2-(2-(4-(2-fluoro-4-(pyrrolidin-3-yloxy)phenyl)piperazin-1-yl)ethyl)-7-(furan-2-yl)pyrazolo[1,5-a][1,3,5]triazine-2,4-diamine N2-(2-(4-(4-((4H-1,2,4-triazol-3-yl)methoxy)-2-fluorophenyl)piperazin-1-yl)ethyl)-7-(furan-2-yl)pyrazolo[1,5-a][1,3,5]triazine-2,4-diamine 2-(4-(4-(2-((4-amino-7-(furan-2-yl)pyrazolo[1,5-a][1,3,5]triazin-2-yl)amino)ethyl)piperazin-1-yl)-3-fluorophenoxy)-N-(2-(methylamino)ethyl)acetamide 2-(4-(4-(2-((4-amino-7-(furan-2-yl)pyrazolo[1,5-a][1,3,5]triazin-2-yl)amino)ethyl)piperazin-1-yl)-3-fluorophenoxy)-N-(2-(dimethylamino)ethyl)acetamide 2-(4-(4-(2-((4-amino-7-(furan-2-yl)pyrazolo[1,5-a][1,3,5]triazin-2-yl)amino)ethyl)piperazin-1-yl)-3-fluorophenoxy)-N-(2-aminoethyl)acetamide (R)-2-(4-(4-(2-((4-amino-7-(furan-2-yl)pyrazolo[1,5-a][1,3,5]triazin-2-yl)amino)ethyl)piperazin-1-yl)-3-fluorophenoxy)propanoic acid 2-(4-(4-(2-((4-amino-7-(furan-2-yl)pyrazolo[1,5-a][1,3,5]triazin-2-yl)amino)ethyl)piperazin-1-yl)-3-fluorophenoxy)acetamide 4-(4-(2-((4-amino-7-(furan-2-yl)pyrazolo[1,5-a][1,3,5]triazin-2-yl)amino)ethyl)piperazin-1-yl)-3-fluoro-N-methyl-N-(2-(methylamino)ethyl)benzamide 4-(4-(2-((4-amino-7-(furan-2-yl)pyrazolo[1,5-a][1,3,5]triazin-2-yl)amino)ethyl)piperazin-1-yl)-N-(2-(dimethylamino)ethyl)-3-fluoro-N-methylbenzamide (R)-4-(4-(2-((4-amino-7-(furan-2-yl)pyrazolo[1,5-a][1,3,5]triazin-2-yl)amino)ethyl)piperazin-1-yl)-N-(1-(dimethylamino)propan-2-yl)-3-fluorobenzamide 2-(4-(4-(2-((4-amino-7-(furan-2-yl)pyrazolo[1,5-a][1,3,5]triazin-2-yl)amino)ethyl)piperazin-1-yl)-3-fluorophenoxy)-N-methyl-N-(2-(methylamino)ethyl)acetamide 2-(5-(4-(2-((4-amino-7-(furan-2-yl)pyrazolo[1,5-a][1,3,5]triazin-2-yl)amino)ethyl)piperazin-1-yl)-2,4-difluorophenoxy)-2-methylpropanoic acid (S)-2-(5-(4-(2-((4-amino-7-(furan-2-yl)pyrazolo[1,5-a][1,3,5]triazin-2-yl)amino)ethyl)piperazin-1-yl)-2,4-difluorophenoxy)propanoic acid (R)-2-(5-(4-(2-((4-amino-7-(furan-2-yl)pyrazolo[1,5-a][1,3,5]triazin-2-yl)amino)ethyl)piperazin-1-yl)-2,4-difluorophenoxy)propanoic acid 2-(5-(4-(2-((4-amino-7-(furan-2-yl)pyrazolo[1,5-a][1,3,5]triazin-2-yl)amino)ethyl)piperazin-1-yl)-2,4-difluorophenoxy)-N-(2-(methylamino)ethyl)acetamide 2-(5-(4-(2-((4-amino-7-(furan-2-yl)pyrazolo[1,5-a][1,3,5]triazin-2-yl)amino)ethyl)piperazin-1-yl)-2,4-difluorophenoxy)-N-(2-(dimethylamino)ethyl)acetamide 5-(4-(2-((4-amino-7-(furan-2-yl)pyrazolo[1,5-a][1,3,5]triazin-2-yl)amino)ethyl)piperazin-1-yl)-N-(2-(dimethylamino)ethyl)-2,4-difluoro-N-methylbenzamide 5-(4-(2-((4-amino-7-(furan-2-yl)pyrazolo[1,5-a][1,3,5]triazin-2-yl)amino)ethyl)piperazin-1-yl)-2,4-difluoro-N-methylbenzamide 4-(5-(4-(2-((4-amino-7-(furan-2-yl)pyrazolo[1,5-a][1,3,5]triazin-2-yl)amino)ethyl)piperazin-1-yl)-2,4-difluorophenoxy)butanoic acid N2-(2-(4-(5-((1H-tetrazol-5-yl)methoxy)-2,4-difluorophenyl)piperazin-1-yl)ethyl)-7-(furan-2-yl)pyrazolo[1,5-a][1,3,5]triazine-2,4-diamine N2-(2-(4-(2-fluoro-4-((1-methyl-1H-1,2,4-triazol-3-yl)methoxy)phenyl)piperazin-1-yl)ethyl)-7-(furan-2-yl)pyrazolo[1,5-a][1,3,5]triazine-2,4-diamine N2-(2-(4-(2,4-difluoro-5-((1-methyl-1H-1,2,4-triazol-3-yl)methoxy)phenyl)piperazin-1-yl)ethyl)-7-(furan-2-yl)pyrazolo[1,5-a][1,3,5]triazine-2,4-diamine 4-(4-(2-((4-amino-7-(furan-2-yl)pyrazolo[1,5-a][1,3,5]triazin-2-yl)amino)ethyl)piperazin-1-yl)-3-fluoro-N-(2-(methyl(oxetan-3-yl)amino)ethyl)benzamide 4-(4-(2-((4-amino-7-(furan-2-yl)pyrazolo[1,5-a][1,3,5]triazin-2-yl)amino)ethyl)piperazin-1-yl)-3-fluoro-N-(2-((2-hydroxyethyl)amino)ethyl)benzamide 2-amino-N-(2-(4-(4-(2-((4-amino-7-(furan-2-yl)pyrazolo[1,5-a][1,3,5]triazin-2-yl)amino)ethyl)piperazin-1-yl)-3-fluorophenoxy)ethyl)acetamide (S)-2-amino-N-(2-(4-(4-(2-((4-amino-7-(furan-2-yl)pyrazolo[1,5-a][1,3,5]triazin-2-yl)amino)ethyl)piperazin-1-yl)-3-fluorophenoxy)ethyl)-3-methylbutanamide N2-(2-(4-(2,4-difluoro-5-(2-(methylsulfonyl)ethoxy)phenyl)piperazin-1-yl)ethyl)-7-(furan-2-yl)pyrazolo[1,5-a][1,3,5]triazine-2,4-diamine N2-(2-(4-(2-fluoro-4-(2-(methylsulfonyl)ethoxy)phenyl)piperazin-1-yl)ethyl)-7-(furan-2-yl)pyrazolo[1,5-a][1,3,5]triazine-2,4-diamine 5-(4-(2-((4-amino-7-(furan-2-yl)pyrazolo[1,5-a][1,3,5]triazin-2-yl)amino)ethyl)piperazin-1-yl)-6-fluoroindolin-2-one N2-(2-(4-(2-fluoro-4-(S-methylsulfonimidoyl)phenyl)piperazin-1-yl)ethyl)-7-(furan-2-yl)pyrazolo[1,5-a][1,3,5]triazine-2,4-diamine 5-(4-(2-((4-amino-7-(furan-2-yl)pyrazolo[1,5-a][1,3,5]triazin-2-yl)amino)ethyl)piperazin-1-yl)-N-(2-(dimethylamino)ethyl)-2,4-difluorobenzamide (3R,4R)-4-(4-(2-((4-amino-7-(furan-2-yl)pyrazolo[1,5-a][1,3,5]triazin-2-yl)amino)ethyl)piperazin-1-yl)-3-fluorophenoxy)tetrahydrofuran-3-ol (3S,4S)-4-(4-(2-((4-amino-7-(furan-2-yl)pyrazolo[1,5-a][1,3,5]triazin-2-yl)amino)ethyl)piperazin-1-yl)-3-fluorophenoxy)tetrahydrofuran-3-ol 1-(4-(4-(2-((4-amino-7-(furan-2-yl)pyrazolo[1,5-a][1,3,5]triazin-2-yl)amino)ethyl)piperazin-1-yl)-3-fluorophenoxy)-2-methylpropan-2-ol 2-(4-(4-(2-((4-amino-7-(furan-2-yl)pyrazolo[1,5-a][1,3,5]triazin-2-yl)amino)ethyl)piperazin-1-yl)-3-fluorophenyl)propan-2-ol 3-(4-(4-(2-((4-amino-7-(furan-2-yl)pyrazolo[1,5-a][1,3,5]triazin-2-yl)amino)ethyl)piperazin-1-yl)-3-fluorophenoxy)-1,1,1-trifluoropropan-2-ol 2-(3-(4-(2-((4-amino-7-(furan-2-yl)pyrazolo[1,5-a][1,3,5]triazin-2-yl)amino)ethyl)piperazin-1-yl)-4-fluorophenoxy)ethanol N2-(2-(4-(2,4-difluoro-5-(morpholin-2-ylmethoxy)phenyl)piperazin-1-yl)ethyl)-7-(furan-2-yl)pyrazolo[1,5-a][1,3,5]triazine-2,4-diamine N2-(2-(4-(2,4-difluoro-5-(morpholin-3-ylmethoxy)phenyl)piperazin-1-yl)ethyl)-7-(furan-2-yl)pyrazolo[1,5-a][1,3,5]triazine-2,4-diamine N2-(2-(4-(2,4-difluoro-5-(((3S,4S)-4-fluoropyrrolidin-3-yl)oxy)phenyl)piperazin-1-yl)ethyl)-7-(furan-2-yl)pyrazolo[1,5-a][1,3,5]triazine-2,4-diamine N2-(2-(4-(2,4-difluoro-5-(((3R,4S)-4-fluoropyrrolidin-3-yl)oxy)phenyl)piperazin-1-yl)ethyl)-7-(furan-2-yl)pyrazolo[1,5-a][1,3,5]triazine-2,4-diamine N2-(2-(4-(2,4-difluoro-5-(((3S,4R)-4-fluoropyrrolidin-3-yl)oxy)phenyl)piperazin-1-yl)ethyl)-7-(furan-2-yl)pyrazolo[1,5-a][1,3,5]triazine-2,4-diamine (S)-3-(5-(4-(2-((4-amino-7-(furan-2-yl)pyrazolo[1,5-a][1,3,5]triazin-2-yl)amino)ethyl)piperazin-1-yl)-2,4-difluorophenoxy)pyrrolidin-2-one (R)-3-(5-(4-(2-((4-amino-7-(furan-2-yl)pyrazolo[1,5-a][1,3,5]triazin-2-yl)amino)ethyl)piperazin-1-yl)-2,4-difluorophenoxy)pyrrolidin-2-one 2-(5-(4-(2-((4-amino-7-(furan-2-yl)pyrazolo[1,5-a][1,3,5]triazin-2-yl)amino)ethyl)piperazin-1-yl)-2,4-difluorophenoxy)-N-(2-morpholinoethyl)acetamide 5-(4-(2-((4-amino-7-(furan-2-yl)pyrazolo[1,5-a][1,3,5]triazin-2-yl)amino)ethyl)piperazin-1-yl)-2,4-difluoro-N-(morpholin-3-ylmethyl)benzamide N2-(2-(4-(2-fluoro-4-(morpholin-3-ylmethoxy)phenyl)piperazin-1-yl)ethyl)-7-(furan-2-yl)pyrazolo[1,5-a][1,3,5]triazine-2,4-diamine N2-(2-(4-(2-fluoro-4-(morpholin-2-ylmethoxy)phenyl)piperazin-1-yl)ethyl)-7-(furan-2-yl)pyrazolo[1,5-a][1,3,5]triazine-2,4-diamine N2-(2-(4-(2-fluoro-4-(((3R,4R)-4-fluoropyrrolidin-3-yl)oxy)phenyl)piperazin-1-yl)ethyl)-7-(furan-2-yl)pyrazolo[1,5-a][1,3,5]triazine-2,4-diamine N2-(2-(4-(2-fluoro-4-(((3S,4S)-4-fluoropyrrolidin-3-yl)oxy)phenyl)piperazin-1-yl)ethyl)-7-(furan-2-yl)pyrazolo[1,5-a][1,3,5]triazine-2,4-diamine N2-(2-(4-(2-fluoro-4-(((3R,4S)-4-fluoropyrrolidin-3-yl)oxy)phenyl)piperazin-1-yl)ethyl)-7-(furan-2-yl)pyrazolo[1,5-a][1,3,5]triazine-2,4-diamine N2-(2-(4-(2-fluoro-4-(((3S,4R)-4-fluoropyrrolidin-3-yl)oxy)phenyl)piperazin-1-yl)ethyl)-7-(furan-2-yl)pyrazolo[1,5-a][1,3,5]triazine-2,4-diamine 2-(4-(4-(2-((4-amino-7-(furan-2-yl)pyrazolo[1,5-a][1,3,5]triazin-2-yl)amino)ethyl)piperazin-1-yl)-3-fluorophenoxy)-N-(2-morpholinoethyl)acetamide 4-(4-(2-((4-amino-7-(furan-2-yl)pyrazolo[1,5-a][1,3,5]triazin-2-yl)amino)ethyl)piperazin-1-yl)-3-fluoro-N-(2-morpholinoethyl)benzamide 4-(4-(2-((4-amino-7-(furan-2-yl)pyrazolo[1,5-a][1,3,5]triazin-2-yl)amino)ethyl)piperazin-1-yl)-3-fluoro-N-(morpholin-3-ylmethyl)benzamide (S)—N2-(2-(4-(2,4-difluoro-5-(methylsulfinyl)phenyl)piperazin-1-yl)ethyl)-7-(furan-2-yl)pyrazolo[1,5-a][1,3,5]triazine-2,4-diamine (R)—N2-(2-(4-(2,4-difluoro-5-(methylsulfinyl)phenyl)piperazin-1-yl)ethyl)-7-(furan-2-yl)pyrazolo[1,5-a][1,3,5]triazine-2,4-diamine (1s,4s)-4-(5-(4-(2-((4-amino-7-(furan-2-yl)pyrazolo[1,5-a][1,3,5]triazin-2-yl)amino)ethyl)piperazin-1-yl)-2,4-difluorophenoxy)tetrahydro-2H-thiopyran 1-oxide (1r,4r)-4-(5-(4-(2-((4-amino-7-(furan-2-yl)pyrazolo[1,5-a][1,3,5]triazin-2-yl)amino)ethyl)piperazin-1-yl)-2,4-difluorophenoxy)tetrahydro-2H-thiopyran 1-oxide (S)-5-(4-(2-((4-amino-7-(furan-2-yl)pyrazolo[1,5-a][1,3,5]triazin-2-yl)amino)ethyl)piperazin-1-yl)-2,4-difluoro-N-(2-(methylsulfinyl)ethyl)benzamide (R)-5-(4-(2-((4-amino-7-(furan-2-yl)pyrazolo[1,5-a][1,3,5]triazin-2-yl)amino)ethyl)piperazin-1-yl)-2,4-difluoro-N-(2-(methylsulfinyl)ethyl)benzamide (S)-5-(4-(2-((4-amino-7-(furan-2-yl)pyrazolo[1,5-a][1,3,5]triazin-2-yl)amino)ethyl)piperazin-1-yl)-2,4-difluoro-N-methyl-N-(2-(methylsulfinyl)ethyl)benzamide (R)-5-(4-(2-((4-amino-7-(furan-2-yl)pyrazolo[1,5-a][1,3,5]triazin-2-yl)amino)ethyl)piperazin-1-yl)-2,4-difluoro-N-methyl-N-(2-(methylsulfinyl)ethyl)benzamide (5-(4-(2-((4-amino-7-(furan-2-yl)pyrazolo[1,5-a][1,3,5]triazin-2-yl)amino)ethyl)piperazin-1-yl)-2,4-difluorophenyl)(1-oxidothiomorpholino)methanone 4-(5-(4-(2-((4-amino-7-(furan-2-yl)pyrazolo[1,5-a][1,3,5]triazin-2-yl)amino)ethyl)piperazin-1-yl)-2,4-difluorophenyl)thiomorpholine 1-oxide (R)—N2-(2-(4-(2-fluoro-4-(methylsulfinyl)phenyl)piperazin-1-yl)ethyl)-7-(furan-2-yl)pyrazolo[1,5-a][1,3,5]triazine-2,4-diamine (S)—N2-(2-(4-(2-fluoro-4-(methylsulfinyl)phenyl)piperazin-1-yl)ethyl)-7-(furan-2-yl)pyrazolo[1,5-a][1,3,5]triazine-2,4-diamine (1s,4s)-4-(4-(4-(2-((4-amino-7-(furan-2-yl)pyrazolo[1,5-a][1,3,5]triazin-2-yl)amino)ethyl)piperazin-1-yl)-3-fluorophenoxy)tetrahydro-2H-thiopyran 1-oxide (1r,4r)-4-(4-(4-(2-((4-amino-7-(furan-2-yl)pyrazolo[1,5-a][1,3,5]triazin-2-yl)amino)ethyl)piperazin-1-yl)-3-fluorophenoxy)tetrahydro-2H-thiopyran 1-oxide (S)-4-(4-(2-((4-amino-7-(furan-2-yl)pyrazolo[1,5-a][1,3,5]triazin-2-yl)amino)ethyl)piperazin-1-yl)-3-fluoro-N-(2-(methylsulfinyl)ethyl)benzamide (R)-4-(4-(2-((4-amino-7-(furan-2-yl)pyrazolo[1,5-a][1,3,5]triazin-2-yl)amino)ethyl)piperazin-1-yl)-3-fluoro-N-(2-(methylsulfinyl)ethyl)benzamide (4-(4-(2-((4-amino-7-(furan-2-yl)pyrazolo[1,5-a][1,3,5]triazin-2-yl)amino)ethyl)piperazin-1-yl)-3-fluorophenyl)(1-oxidothiomorpholino)methanone 4-(4-(4-(2-((4-amino-7-(furan-2-yl)pyrazolo[1,5-a][1,3,5]triazin-2-yl)amino)ethyl)piperazin-1-yl)-3-fluorophenyl)thiomorpholine 1-oxide (S)-3-(5-(4-(2-((4-amino-7-(furan-2-yl)pyrazolo[1,3,5]triazin-2-yl)amino)ethyl)piperazin-1-yl)-2,4-difluorophenoxy)propane-1,2-diol (R)-3-(5-(4-(2-((4-amino-7-(furan-2-yl)pyrazolo[1,3,5]triazin-2-yl)amino)ethyl)piperazin-1-yl)-2,4-difluorophenoxy)propane-1,2-diol (S)-5-(4-(2-((4-amino-7-(furan-2-yl)pyrazolo[1,5-a][1,3,5]triazin-2-yl)amino)ethyl)piperazin-1-yl)-N-(2,3-dihydroxypropyl)-2,4-difluorobenzamide (R)-5-(4-(2-((4-amino-7-(furan-2-yl)pyrazolo[1,5-a][1,3,5]triazin-2-yl)amino)ethyl)piperazin-1-yl)-N-(2,3-dihydroxypropyl)-2,4-difluorobenzamide N2-(2-(4-(4-(azetidin-3-yloxy)-2-fluorophenyl)piperazin-1-yl)ethyl)-7-(furan-2-yl)pyrazolo[1,5-a][1,3,5]triazine-2,4-diamine N2-(2-(4-(5-(azetidin-3-yloxy)-2,4-difluorophenyl)piperazin-1-yl)ethyl)-7-(furan-2-yl)pyrazolo[1,5-a][1,3,5]triazine-2,4-diamine (S)—N2-(2-(4-(2,4-difluoro-5-(3-(methylsulfinyl)propoxy)phenyl)piperazin-1-yl)ethyl)-7-(furan-2-yl)pyrazolo[1,5-a][1,3,5]triazine-2,4-diamine Heteroaryl Scaffold (7)

2-(4-(4-(2-((4-amino-7-(furan-2-yl)pyrazolo[1,5-a][1,3,5]triazin-2-yl)(methyl)amino)ethyl)piperazin-1-yl)phenoxy)ethanol 2-(4-(4-(2-((4-amino-7-(furan-2-yl)pyrazolo[1,5-a][1,3,5]triazin-2-yl)(methyl)amino)ethyl)piperazin-1-yl)phenoxy)acetic acid 2-(4-(4-(2-((4-amino-7-(furan-2-yl)pyrazolo[1,5-a][1,3,5]triazin-2-yl)(methyl)amino)ethyl)piperazin-1-yl)phenoxy)acetamide 3-(4-(4-(2-((4-amino-7-(furan-2-yl)pyrazolo[1,5-a][1,3,5]triazin-2-yl)(methyl)amino)ethyl)piperazin-1-yl)phenoxy)propane-1,2-diol N2-(2-(4-(4-(2-aminoethoxy)phenyl)piperazin-1-yl)ethyl)-7-(furan-2-yl)-N2-methylpyrazolo[1,5-a][1,3,5]triazine-2,4-diamine 4-(4-(2-((4-amino-7-(furan-2-yl)pyrazolo[1,5-a][1,3,5]triazin-2-yl)(methyl)amino)ethyl)piperazin-1-yl)benzamide 4-(4-(2-((4-amino-7-(furan-2-yl)pyrazolo[1,5-a][1,3,5]triazin-2-yl)(methyl)amino)ethyl)piperazin-1-yl)-N-methylbenzamide 7-(furan-2-yl)-N2-methyl-N2-(2-(4-(4-(2-morpholinoethoxy)phenyl)piperazin-1-yl)ethyl)pyrazolo[1,5-a][1,3,5]triazine-2,4-diamine N2-(2-(4-(4-(2-(dimethylamino)ethoxy)phenyl)piperazin-1-yl)ethyl)-7-(furan-2-yl)-N2-methylpyrazolo[1,5-a][1,3,5]triazine-2,4-diamine 4-(4-(2-((4-amino-7-(furan-2-yl)pyrazolo[1,5-a][1,3,5]triazin-2-yl)(methyl)amino)ethyl)piperazin-1-yl)benzenesulfonamide 4-(4-(2-((4-amino-7-(furan-2-yl)pyrazolo[1,5-a][1,3,5]triazin-2-yl)(methyl)amino)ethyl)piperazin-1-yl)-N-methylbenzenesulfonamide 7-(furan-2-yl)-N2-methyl-N2-(2-(4-(4-(methylsulfonyl)phenyl)piperazin-1-yl)ethyl)pyrazolo[1,5-a][1,3,5]triazine-2,4-diamine 7-(furan-2-yl)-N2-methyl-N2-(2-(4-(4-(methylsulfinyl)phenyl)piperazin-1-yl)ethyl)pyrazolo[1,5-a][1,3,5]triazine-2,4-diamine 3-(4-(2-((4-amino-7-(furan-2-yl)pyrazolo[1,5-a][1,3,5]triazin-2-yl)(methyl)amino)ethyl)piperazin-1-yl)benzamide 2-(3-(4-(2-((4-amino-7-(furan-2-yl)pyrazolo[1,5-a][1,3,5]triazin-2-yl)(methyl)amino)ethyl)piperazin-1-yl)phenoxy)ethanol N2-(2-(4-(4-(azetidin-3-yloxy)phenyl)piperazin-1-yl)ethyl)-7-(furan-2-yl)-N2-methylpyrazolo[1,5-a][1,3,5]triazine-2,4-diamine N2-(2-(4-(4-((2H-1,2,3-triazol-4-yl)methoxy)-2-fluorophenyl)piperazin-1-yl)ethyl)-7-(furan-2-yl)-N2-methylpyrazolo[1,5-a][1,3,5]triazine-2,4-diamine 5-((4-(4-(2-((4-amino-7-(furan-2-yl)pyrazolo[1,5-a][1,3,5]triazin-2-yl)(methyl)amino)ethyl)piperazin-1-yl)-3-fluorophenoxy)methyl)-1,3,4-oxadiazol-2(3H)-one 2-(5-(4-(2-((4-amino-7-(furan-2-yl)pyrazolo[1,5-a][1,3,5]triazin-2-yl)(methyl)amino)ethyl)piperazin-1-yl)-2,4-difluorophenoxy)acetamide (S)—N2-(2-(4-(2-fluoro-4-(2-(methylsulfinyl)ethoxy)phenyl)piperazin-1-yl)ethyl)-7-(furan-2-yl)-N2-methylpyrazolo[1,5-a][1,3,5]triazine-2,4-diamine (R)—N2-(2-(4-(2-fluoro-4-(2-(methylsulfinyl)ethoxy)phenyl)piperazin-1-yl)ethyl)-7-(furan-2-yl)-N2-methylpyrazolo[1,5-a][1,3,5]triazine-2,4-diamine N2-(2-(4-(2,4-difluoro-5-(2-(methylsulfinyl)ethoxy)phenyl)piperazin-1-yl)ethyl)-7-(furan-2-yl)-N2-methylpyrazolo[1,5-a][1,3,5]triazine-2,4-diamine 2-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)-1-(piperazin-1-yl)ethanone N2-(2-(4-(2-fluoro-4-(piperidin-4-ylmethoxy)phenyl)piperazin-1-yl)ethyl)-7-(furan-2-yl)-N2-methylpyrazolo[1,5-a][1,3,5]triazine-2,4-diamine (4-(4-(2-((4-amino-7-(furan-2-yl)pyrazolo[1,5-a][1,3,5]triazin-2-yl)(methyl)amino)ethyl)piperazin-1-yl)-3-fluorophenyl)(piperazin-1-yl)methanone N2-(2-(4-(2-fluoro-4-(2-(piperazin-1-yl)ethoxy)phenyl)piperazin-1-yl)ethyl)-7-(furan-2-yl)-N2-methylpyrazolo[1,5-a][1,3,5]triazine-2,4-diamine N2-(2-(4-(2-fluoro-4-(piperazin-1-ylsulfonyl)phenyl)piperazin-1-yl)ethyl)-7-(furan-2-yl)-N2-methylpyrazolo[1,5-a][1,3,5]triazine-2,4-diamine N2-(2-(4-(2-fluoro-4-(methylsulfonyl)phenyl)piperazin-1-yl)ethyl)-7-(furan-2-yl)-N2-methylpyrazolo[1,5-a][1,3,5]triazine-2,4-diamine 4-(4-(2-((4-amino-7-(furan-2-yl)pyrazolo[1,5-a][1,3,5]triazin-2-yl)(methyl)amino)ethyl)piperazin-1-yl)-N-(2-aminoethyl)-3-fluorobenzamide 4-(4-(2-((4-amino-7-(furan-2-yl)pyrazolo[1,5-a][1,3,5]triazin-2-yl)(methyl)amino)ethyl)piperazin-1-yl)-3-fluoro-N-(2-(methylamino)ethyl)benzamide 4-(4-(2-((4-amino-7-(furan-2-yl)pyrazolo[1,5-a][1,3,5]triazin-2-yl)(methyl)amino)ethyl)piperazin-1-yl)-N-(2-(dimethylamino)ethyl)-3-fluorobenzamide 4-(4-(2-((4-amino-7-(furan-2-yl)pyrazolo[1,5-a][1,3,5]triazin-2-yl)(methyl)amino)ethyl)piperazin-1-yl)-3-fluoro-N-(2-hydroxyethyl)benzamide 4-(4-(2-((4-amino-7-(furan-2-yl)pyrazolo[1,5-a][1,3,5]triazin-2-yl)(methyl)amino)ethyl)piperazin-1-yl)-N-(2,3-dihydroxypropyl)-3-fluorobenzamide 2-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)acetic acid 2-(4-(4-(2-((4-amino-7-(furan-2-yl)pyrazolo[1,5-a][1,3,5]triazin-2-yl)(methyl)amino)ethyl)piperazin-1-yl)-3,5-difluorophenoxy)acetic acid 2-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)propanoic acid (S)-2-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)propanoic acid 2-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)-2-methylpropanoic acid 3-(4-(4-(2-((4-amino-7-(furan-2-yl)pyrazolo[1,5-a][1,3,5]triazin-2-yl)(methyl)amino)ethyl)piperazin-1-yl)-3-fluorophenyl)propanoic acid 4-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)butanoic acid 2-(3-(4-(2-((4-amino-7-(furan-2-yl)pyrazolo[1,5-a][1,3,5]triazin-2-yl)(methyl)amino)ethyl)piperazin-1-yl)-2,6-difluorophenoxy)acetic acid 2-(5-(4-(2-((4-amino-7-(furan-2-yl)pyrazolo[1,5-a][1,3,5]triazin-2-yl)(methyl)amino)ethyl)piperazin-1-yl)-2,4-difluorophenoxy)acetic acid 4-(4-(2-((4-amino-7-(furan-2-yl)pyrazolo[1,5-a][1,3,5]triazin-2-yl)(methyl)amino)ethyl)piperazin-1-yl)-3-fluorobenzoic acid 2-((2-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)ethyl)amino)acetamide 2-((2-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)ethyl)(methyl)amino)acetamide N2-(2-(4-(2-fluoro-4-(piperidin-4-yloxy)phenyl)piperazin-1-yl)ethyl)-7-(furan-2-yl)-N2-methylpyrazolo[1,5-a][1,3,5]triazine-2,4-diamine N2-(2-(4-(2-fluoro-4-(pyrrolidin-3-yloxy)phenyl)piperazin-1-yl)ethyl)-7-(furan-2-yl)-N2-methylpyrazolo[1,5-a][1,3,5]triazine-2,4-diamine N2-(2-(4-(4-((4H-1,2,4-triazol-3-yl)methoxy)-2-fluorophenyl)piperazin-1-yl)ethyl)-7-(furan-2-yl)-N2-methylpyrazolo[1,5-a][1,3,5]triazine-2,4-diamine 2-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)-N-(2-(methylamino)ethyl)acetamide 2-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)-N-(2-(dimethylamino)ethyl)acetamide 2-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)-N-(2-aminoethyl)acetamide (R)-2-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)propanoic acid 2-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)acetamide 4-(4-(2-((4-amino-7-(furan-2-yl)pyrazolo[1,5-a][1,3,5]triazin-2-yl)(methyl)amino)ethyl)piperazin-1-yl)-3-fluoro-N-methyl-N-(2-(methylamino)ethyl)benzamide 4-(4-(2-((4-amino-7-(furan-2-yl)pyrazolo[1,5-a][1,3,5]triazin-2-yl)(methyl)amino)ethyl)piperazin-1-yl)-N-(2-(dimethylamino)ethyl)-3-fluoro-N-methylbenzamide (R)-4-(4-(2-((4-amino-7-(furan-2-yl)pyrazolo[1,5-a][1,3,5]triazin-2-yl)(methyl)amino)ethyl)piperazin-1-yl)-N-(1-(dimethylamino)propan-2-yl)-3-fluorobenzamide 2-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)-N-methyl-N-(2-(methylamino)ethyl)acetamide 2-(5-(4-(2-((4-amino-7-(furan-2-yl)pyrazolo[1,5-a][1,3,5]triazin-2-yl)(methyl)amino)ethyl)piperazin-1-yl)-2,4-difluorophenoxy)-2-methylpropanoic acid (S)-2-(5-(4-(2-((4-amino-7-(furan-2-yl)pyrazolo[1,5-a][1,3,5]triazin-2-yl)(methyl)amino)ethyl)piperazin-1-yl)-2,4-difluorophenoxy)propanoic acid (R)-2-(5-(4-(2-((4-amino-7-(furan-2-yl)pyrazolo[1,5-a][1,3,5]triazin-2-yl)(methyl)amino)ethyl)piperazin-1-yl)-2,4-difluorophenoxy)propanoic acid 2-(5-(4-(2-((4-amino-7-(furan-2-yl)pyrazolo[1,5-a][1,3,5]triazin-2-yl)(methyl)amino)ethyl)piperazin-1-yl)-2,4-difluorophenoxy)-N-(2-(methylamino)ethyl)acetamide 2-(5-(4-(2-((4-amino-7-(furan-2-yl)pyrazolo[1,5-a][1,3,5]triazin-2-yl)(methyl)amino)ethyl)piperazin-1-yl)-2,4-difluorophenoxy)-N-(2-(dimethylamino)ethyl)acetamide 5-(4-(2-((4-amino-7-(furan-2-yl)pyrazolo[1,5-a][1,3,5]triazin-2-yl)(methyl)amino)ethyl)piperazin-1-yl)-N-(2-(dimethylamino)ethyl)-2,4-difluoro-N-methylbenzamide 5-(4-(2-((4-amino-7-(furan-2-yl)pyrazolo[1,5-a][1,3,5]triazin-2-yl)(methyl)amino)ethyl)piperazin-1-yl)-2,4-difluoro-N-methylbenzamide 4-(5-(4-(2-((4-amino-7-(furan-2-yl)pyrazolo[1,5-a][1,3,5]triazin-2-yl)(methyl)amino)ethyl)piperazin-1-yl)-2,4-difluorophenoxy)butanoic acid N2-(2-(4-(5-((1H-tetrazol-5-yl)methoxy)-2,4-difluorophenyl)piperazin-1-yl)ethyl)-7-(furan-2-yl)-N2-methylpyrazolo[1,5-a][1,3,5]triazine-2,4-diamine N2-(2-(4-(2-fluoro-4-((1-methyl-1H-1,2,4-triazol-3-yl)methoxy)phenyl)piperazin-1-yl)ethyl)-7-(furan-2-yl)-N2-methylpyrazolo[1,5-a][1,3,5]triazine-2,4-diamine N2-(2-(4-(2,4-difluoro-5-((1-methyl-1H-1,2,4-triazol-3-yl)methoxy)phenyl)piperazin-1-yl)ethyl)-7-(furan-2-yl)-N2-methylpyrazolo[1,5-a][1,3,5]triazine-2,4-diamine 4-(4-(2-((4-amino-7-(furan-2-yl)pyrazolo[1,5-a][1,3,5]triazin-2-yl)(methyl)amino)ethyl)piperazin-1-yl)-3-fluoro-N-(2-(methyl(oxetan-3-yl)amino)ethyl)benzamide 4-(4-(2-((4-amino-7-(furan-2-yl)pyrazolo[1,5-a][1,3,5]triazin-2-yl)(methyl)amino)ethyl)piperazin-1-yl)-3-fluoro-N-(2-((2-hydroxyethyl)amino)ethyl)benzamide 2-amino-N-(2-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)ethyl)acetamide (S)-2-amino-N-(2-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)ethyl)-3-methylbutanamide N2-(2-(4-(2,4-difluoro-5-(2-(methylsulfonyl)ethoxy)phenyl)piperazin-1-yl)ethyl)-7-(furan-2-yl)-N2-methylpyrazolo[1,5-a][1,3,5]triazine-2,4-diamine N2-(2-(4-(2-fluoro-4-(2-(methylsulfonyl)ethoxy)phenyl)piperazin-1-yl)ethyl)-7-(furan-2-yl)-N2-methylpyrazolo[1,5-a][1,3,5]triazine-2,4-diamine 5-(4-(2-((4-amino-7-(furan-2-yl)pyrazolo[1,5-a][1,3,5]triazin-2-yl)(methyl)amino)ethyl)piperazin-1-yl)-6-fluoroindolin-2-one N2-(2-(4-(2-fluoro-4-(S-methylsulfonimidoyl)phenyl)piperazin-1-yl)ethyl)-7-(furan-2-yl)-N2-methylpyrazolo[1,5-a][1,3,5]triazine-2,4-diamine 5-(4-(2-((4-amino-7-(furan-2-yl)pyrazolo[1,5-a][1,3,5]triazin-2-yl)(methyl)amino)ethyl)piperazin-1-yl)-N-(2-(dimethylamino)ethyl)-2,4-difluorobenzamide (3R,4R)-4-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)tetrahydrofuran-3-ol (3S,4S)-4-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)tetrahydrofuran-3-ol 1-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)-2-methylpropan-2-ol 2-(4-(4-(2-((4-amino-7-(furan-2-yl)pyrazolo[1,5-a][1,3,5]triazin-2-yl)(methyl)amino)ethyl)piperazin-1-yl)-3-fluorophenyl)propan-2-ol 3-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)-1,1,1-trifluoropropan-2-ol 2-(3-(4-(2-((4-amino-7-(furan-2-yl)pyrazolo[1,5-a][1,3,5]triazin-2-yl)(methyl)amino)ethyl)piperazin-1-yl)-4-fluorophenoxy)ethanol N2-(2-(4-(2,4-difluoro-5-(morpholin-2-ylmethoxy)phenyl)piperazin-1-yl)ethyl)-7-(furan-2-yl)-N2-methylpyrazolo[1,5-a][1,3,5]triazine-2,4-diamine N2-(2-(4-(2,4-difluoro-5-(morpholin-3-ylmethoxy)phenyl)piperazin-1-yl)ethyl)-7-(furan-2-yl)-N2-methylpyrazolo[1,5-a][1,3,5]triazine-2,4-diamine N2-(2-(4-(2,4-difluoro-5-(((3S,4S)-4-fluoropyrrolidin-3-yl)oxy)phenyl)piperazin-1-yl)ethyl)-7-(furan-2-yl)-N2-methylpyrazolo[1,5-a][1,3,5]triazine-2,4-diamine N2-(2-(4-(2,4-difluoro-5-(((3R,4S)-4-fluoropyrrolidin-3-yl)oxy)phenyl)piperazin-1-yl)ethyl)-7-(furan-2-yl)-N2-methylpyrazolo[1,5-a][1,3,5]triazine-2,4-diamine N2-(2-(4-(2,4-difluoro-5-(((3S,4R)-4-fluoropyrrolidin-3-yl)oxy)phenyl)piperazin-1-yl)ethyl)-7-(furan-2-yl)-N2-methylpyrazolo[1,5-a][1,3,5]triazine-2,4-diamine (S)-3-(5-(4-(2-((4-amino-7-(furan-2-yl)pyrazolo[1,5-a][1,3,5]triazin-2-yl)(methyl)amino)ethyl)piperazin-1-yl)-2,4-difluorophenoxy)pyrrolidin-2-one (R)-3-(5-(4-(2-((4-amino-7-(furan-2-yl)pyrazolo[1,5-a][1,3,5]triazin-2-yl)(methyl)amino)ethyl)piperazin-1-yl)-2,4-difluorophenoxy)pyrrolidin-2-one 2-(5-(4-(2-((4-amino-7-(furan-2-yl)pyrazolo[1,5-a][1,3,5]triazin-2-yl)(methyl)amino)ethyl)piperazin-1-yl)-2,4-difluorophenoxy)-N-(2-morpholinoethyl)acetamide 5-(4-(2-((4-amino-7-(furan-2-yl)pyrazolo[1,5-a][1,3,5]triazin-2-yl)(methyl)amino)ethyl)piperazin-1-yl)-2,4-difluoro-N-(morpholin-3-ylmethyl)benzamide N2-(2-(4-(2-fluoro-4-(morpholin-3-ylmethoxy)phenyl)piperazin-1-yl)ethyl)-7-(furan-2-yl)-N2-methylpyrazolo[1,5-a][1,3,5]triazine-2,4-diamine N2-(2-(4-(2-fluoro-4-(morpholin-2-ylmethoxy)phenyl)piperazin-1-yl)ethyl)-7-(furan-2-yl)-N2-methylpyrazolo[1,5-a][1,3,5]triazine-2,4-diamine N2-(2-(4-(2-fluoro-4-(((3R,4R)-4-fluoropyrrolidin-3-yl)oxy)phenyl)piperazin-1-yl)ethyl)-7-(furan-2-yl)-N2-methylpyrazolo[1,5-a][1,3,5]triazine-2,4-diamine N2-(2-(4-(2-fluoro-4-(((3S,4S)-4-fluoropyrrolidin-3-yl)oxy)phenyl)piperazin-1-yl)ethyl)-7-(furan-2-yl)-N2-methylpyrazolo[1,5-a][1,3,5]triazine-2,4-diamine N2-(2-(4-(2-fluoro-4-(((3R,4S)-4-fluoropyrrolidin-3-yl)oxy)phenyl)piperazin-1-yl)ethyl)-7-(furan-2-yl)-N2-methylpyrazolo[1,5-a][1,3,5]triazine-2,4-diamine N2-(2-(4-(2-fluoro-4-(((3S,4R)-4-fluoropyrrolidin-3-yl)oxy)phenyl)piperazin-1-yl)ethyl)-7-(furan-2-yl)-N2-methylpyrazolo[1,5-a][1,3,5]triazine-2,4-diamine 2-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)-N-(2-morpholinoethyl)acetamide 4-(4-(2-((4-amino-7-(furan-2-yl)pyrazolo[1,5-a][1,3,5]triazin-2-yl)(methyl)amino)ethyl)piperazin-1-yl)-3-fluoro-N-(2-morpholinoethyl)benzamide 4-(4-(2-((4-amino-7-(furan-2-yl)pyrazolo[1,5-a][1,3,5]triazin-2-yl)(methyl)amino)ethyl)piperazin-1-yl)-3-fluoro-N-(morpholin-3-ylmethyl)benzamide (S)—N2-(2-(4-(2,4-difluoro-5-(methylsulfinyl)phenyl)piperazin-1-yl)ethyl)-7-(furan-2-yl)-N2-methylpyrazolo[1,5-a][1,3,5]triazine-2,4-diamine (R)—N2-(2-(4-(2,4-difluoro-5-(methylsulfinyl)phenyl)piperazin-1-yl)ethyl)-7-(furan-2-yl)-N2-methylpyrazolo[1,5-a][1,3,5]triazine-2,4-diamine (1s,4s)-4-(5-(4-(2-((4-amino-7-(furan-2-yl)pyrazolo[1,5-a][1,3,5]triazin-2-yl)(methyl)amino)ethyl)piperazin-1-yl)-2,4-difluorophenoxy)tetrahydro-2H-thiopyran 1-oxide (1r,4r)-4-(5-(4-(2-((4-amino-7-(furan-2-yl)pyrazolo[1,5-a][1,3,5]triazin-2-yl)(methyl)amino)ethyl)piperazin-1-yl)-2,4-difluorophenoxy)tetrahydro-2H-thiopyran 1-oxide (S)-5-(4-(2-((4-amino-7-(furan-2-yl)pyrazolo[1,5-a][1,3,5]triazin-2-yl)(methyl)amino)ethyl)piperazin-1-yl)-2,4-difluoro-N-(2-(methylsulfinyl)ethyl)benzamide (R)-5-(4-(2-((4-amino-7-(furan-2-yl)pyrazolo[1,5-a][1,3,5]triazin-2-yl)(methyl)amino)ethyl)piperazin-1-yl)-2,4-difluoro-N-(2-(methylsulfinyl)ethyl)benzamide (S)-5-(4-(2-((4-amino-7-(furan-2-yl)pyrazolo[1,5-a][1,3,5]triazin-2-yl)(methyl)amino)ethyl)piperazin-1-yl)-2,4-difluoro-N-methyl-N-(2-(methylsulfinyl)ethyl)benzamide (R)-5-(4-(2-((4-amino-7-(furan-2-yl)pyrazolo[1,5-a][1,3,5]triazin-2-yl)(methyl)amino)ethyl)piperazin-1-yl)-2,4-difluoro-N-methyl-N-(2-(methylsulfinyl)ethyl)benzamide (5-(4-(2-((4-amino-7-(furan-2-yl)pyrazolo[1,5-a][1,3,5]triazin-2-yl)(methyl)amino)ethyl)piperazin-1-yl)-2,4-difluorophenyl)(1-oxidothiomorpholino)methanone 4-(5-(4-(2-((4-amino-7-(furan-2-yl)pyrazolo[1,5-a][1,3,5]triazin-2-yl)(methyl)amino)ethyl)piperazin-1-yl)-2,4-difluorophenyl)thiomorpholine 1-oxide (R)—N2-(2-(4-(2-fluoro-4-(methylsulfinyl)phenyl)piperazin-1-yl)ethyl)-7-(furan-2-yl)-N2-methylpyrazolo[1,5-a][1,3,5]triazine-2,4-diamine (S)—N2-(2-(4-(2-fluoro-4-(methylsulfinyl)phenyl)piperazin-1-yl)ethyl)-7-(furan-2-yl)-N2-methylpyrazolo[1,5-a][1,3,5]triazine-2,4-diamine (1s,4s)-4-(4-(4-(2-((4-amino-7-(furan-2-yl)pyrazolo[1,3,5]triazin-2-yl)(methyl)amino)ethyl)piperazin-1-yl)-3-fluorophenoxy)tetrahydro-2H-thiopyran 1-oxide (1r,4r)-4-(4-(4-(2-((4-amino-7-(furan-2-yl)pyrazolo[1,5-a][1,3,5]triazin-2-yl)(methyl)amino)ethyl)piperazin-1-yl)-3-fluorophenoxy)tetrahydro-2H-thiopyran 1-oxide (S)-4-(4-(2-((4-amino-7-(furan-2-yl)pyrazolo[1,5-a][1,3,5]triazin-2-yl)(methyl)amino)ethyl)piperazin-1-yl)-3-fluoro-N-(2-(methylsulfinyl)ethyl)benzamide (R)-4-(4-(2-((4-amino-7-(furan-2-yl)pyrazolo[1,5-a][1,3,5]triazin-2-yl)(methyl)amino)ethyl)piperazin-1-yl)-3-fluoro-N-(2-(methylsulfinyl)ethyl)benzamide (4-(4-(2-((4-amino-7-(furan-2-yl)pyrazolo[1,5-a][1,3,5]triazin-2-yl)(methyl)amino)ethyl)piperazin-1-yl)-3-fluorophenyl)(1-oxidothiomorpholino)methanone 4-(4-(4-(2-((4-amino-7-(furan-2-yl)pyrazolo[1,5-a][1,3,5]triazin-2-yl)(methyl)amino)ethyl)piperazin-1-yl)-3-fluorophenyl)thiomorpholine 1-oxide (S)-3-(5-(4-(2-((4-amino-7-(furan-2-yl)pyrazolo[1,5-a][1,3,5]triazin-2-yl)(methyl)amino)ethyl)piperazin-1-yl)-2,4-difluorophenoxy)propane-1,2-diol (R)-3-(5-(4-(2-((4-amino-7-(furan-2-yl)pyrazolo[1,5-a][1,3,5]triazin-2-yl)(methyl)amino)ethyl)piperazin-1-yl)-2,4-difluorophenoxy)propane-1,2-diol (S)-5-(4-(2-((4-amino-7-(furan-2-yl)pyrazolo[1,5-a][1,3,5]triazin-2-yl)(methyl)amino)ethyl)piperazin-1-yl)-N-(2,3-dihydroxypropyl)-2,4-difluorobenzamide (R)-5-(4-(2-((4-amino-7-(furan-2-yl)pyrazolo[1,5-a][1,3,5]triazin-2-yl)(methyl)amino)ethyl)piperazin-1-yl)-N-(2,3-dihydroxypropyl)-2,4-difluorobenzamide N2-(2-(4-(4-(azetidin-3-yloxy)-2-fluorophenyl)piperazin-1-yl)ethyl)-7-(furan-2-yl)-N2-methylpyrazolo[1,5-a][1,3,5]triazine-2,4-diamine N2-(2-(4-(5-(azetidin-3-yloxy)-2,4-difluorophenyl)piperazin-1-yl)ethyl)-7-(furan-2-yl)-N2-methylpyrazolo[1,5-a][1,3,5]triazine-2,4-diamine (S)—N2-(2-(4-(2,4-difluoro-5-(3-(methylsulfinyl)propoxy)phenyl)piperazin-1-yl)ethyl)-7-(furan-2-yl)-N2-methylpyrazolo[1,5-a][1,3,5]triazine-2,4-diamine Heteroaryl Scaffold (8)

5-amino-8-(furan-2-yl)-3-(2-(4-(4-(2-hydroxyethoxy)phenyl)piperazin-1-yl)ethyl)-1-methyl-1H-pyrazolo[5,1-i]purin-2(3H)-one 2-(4-(4-(2-(5-amino-8-(furan-2-yl)-1-methyl-2-oxo-1H-pyrazolo[5,1-i]purin-3(2H)-yl)ethyl)piperazin-1-yl)phenoxy)acetic acid 2-(4-(4-(2-(5-amino-8-(furan-2-yl)-1-methyl-2-oxo-1H-pyrazolo[5,1-i]purin-3(2H)-yl)ethyl)piperazin-1-yl)phenoxy)acetamide 5-amino-3-(2-(4-(4-(2,3-dihydroxypropoxy)phenyl)piperazin-1-yl)ethyl)-8-(furan-2-yl)-1-methyl-1H-pyrazolo[5,1-i]purin-2(3H)-one 5-amino-3-(2-(4-(4-(2-aminoethoxy)phenyl)piperazin-1-yl)ethyl)-8-(furan-2-yl)-1-methyl-1H-pyrazolo[5,1-i]purin-2(3H)-one 4-(4-(2-(5-amino-8-(furan-2-yl)-1-methyl-2-oxo-1H-pyrazolo[5,1-i]purin-3 (2H)-yl)ethyl)piperazin-1-yl)benzamide 4-(4-(2-(5-amino-8-(furan-2-yl)-1-methyl-2-oxo-1H-pyrazolo[5,1-i]purin-3 (2H)-yl)ethyl)piperazin-1-yl)-N-methylbenzamide 5-amino-8-(furan-2-yl)-1-methyl-3-(2-(4-(4-(2-morpholinoethoxy)phenyl)piperazin-1-yl)ethyl)-1H-pyrazolo[5,1-i]purin-2(3H)-one 5-amino-3-(2-(4-(4-(2-(dimethylamino)ethoxy)phenyl)piperazin-1-yl)ethyl)-8-(furan-2-yl)-1-methyl-1H-pyrazolo[5,1-i]purin-2(3H)-one 4-(4-(2-(5-amino-8-(furan-2-yl)-1-methyl-2-oxo-1H-pyrazolo[5,1-i]purin-3 (2H)-yl)ethyl)piperazin-1-yl)benzenesulfonamide 4-(4-(2-(5-amino-8-(furan-2-yl)-1-methyl-2-oxo-1H-pyrazolo[5,1-i]purin-3 (2H)-yl)ethyl)piperazin-1-yl)-N-methylbenzenesulfonamide 5-amino-8-(furan-2-yl)-1-methyl-3-(2-(4-(4-(methylsulfonyl)phenyl)piperazin-1-yl)ethyl)-1H-pyrazolo[5,1-i]purin-2(3H)-one 5-amino-8-(furan-2-yl)-1-methyl-3-(2-(4-(4-(methylsulfinyl)phenyl)piperazin-1-yl)ethyl)-1H-pyrazolo[5,1-i]purin-2(3H)-one 3-(4-(2-(5-amino-8-(furan-2-yl)-1-methyl-2-oxo-1H-pyrazolo[5,1-i]purin-3 (2H)-yl)ethyl)piperazin-1-yl)benzamide 5-amino-8-(furan-2-yl)-3-(2-(4-(3-(2-hydroxyethoxy)phenyl)piperazin-1-yl)ethyl)-1-methyl-1H-pyrazolo[5,1-i]purin-2(3H)-one 5-amino-3-(2-(4-(4-(azetidin-3-yloxy)phenyl)piperazin-1-yl)ethyl)-8-(furan-2-yl)-1-methyl-1H-pyrazolo[5,1-i]purin-2(3H)-one 3-(2-(4-(4-((2H-1,2,3-triazol-4-yl)methoxy)-2-fluorophenyl)piperazin-1-yl)ethyl)-5-amino-8-(furan-2-yl)-1-methyl-1H-pyrazolo[5,1-i]purin-2(3H)-one 5-((4-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)methyl)-1,3,4-oxadiazol-2(3H)-one 2-(5-(4-(2-(5-amino-8-(furan-2-yl)-1-methyl-2-oxo-1H-pyrazolo[5,1-i]purin-3(2H)-yl)ethyl)piperazin-1-yl)-2,4-difluorophenoxy)acetamide (S)-5-amino-3-(2-(4-(2-fluoro-4-(2-(methylsulfinyl)ethoxy)phenyl)piperazin-1-yl)ethyl)-8-(furan-2-yl)-1-methyl-1H-pyrazolo[5,1-i]purin-2(3H)-one (R)-5-amino-3-(2-(4-(2-fluoro-4-(2-(methylsulfinyl)ethoxy)phenyl)piperazin-1-yl)ethyl)-8-(furan-2-yl)-1-methyl-1H-pyrazolo[5,1-i]purin-2(3H)-one 5-amino-3-(2-(4-(2,4-difluoro-5-(2-(methylsulfinyl)ethoxy)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(2-oxo-2-(piperazin-1-yl)ethoxy)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(piperidin-4-ylmethoxy)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(piperazine-1-carbonyl)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(2-(piperazin-1-yl)ethoxy)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(piperazin-1-ylsulfonyl)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(methylsulfonyl)phenyl)piperazin-1-yl)ethyl)-8-(furan-2-yl)-1-methyl-1H-pyrazolo[5,1-i]purin-2(3H)-one 4-(4-(2-(5-amino-8-(furan-2-yl)-1-methyl-2-oxo-1H-pyrazolo[5,1-i]purin-3 (2H)-yl)ethyl)piperazin-1-yl)-N-(2-aminoethyl)-3-fluorobenzamide 4-(4-(2-(5-amino-8-(furan-2-yl)-1-methyl-2-oxo-1H-pyrazolo[5,1-i]purin-3 (2H)-yl)ethyl)piperazin-1-yl)-3-fluoro-N-(2-(methylamino)ethyl)benzamide 4-(4-(2-(5-amino-8-(furan-2-yl)-1-methyl-2-oxo-1H-pyrazolo[5,1-i]purin-3 (2H)-yl)ethyl)piperazin-1-yl)-N-(2-(dimethylamino)ethyl)-3-fluorobenzamide 4-(4-(2-(5-amino-8-(furan-2-yl)-1-methyl-2-oxo-1H-pyrazolo[5,1-i]purin-3 (2H)-yl)ethyl)piperazin-1-yl)-3-fluoro-N-(2-hydroxyethyl)benzamide 4-(4-(2-(5-amino-8-(furan-2-yl)-1-methyl-2-oxo-1H-pyrazolo[5,1-i]purin-3 (2H)-yl)ethyl)piperazin-1-yl)-N-(2,3-dihydroxypropyl)-3-fluorobenzamide 2-(4-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)acetic acid 2-(4-(4-(2-(5-amino-8-(furan-2-yl)-1-methyl-2-oxo-1H-pyrazolo[5,1-i]purin-3(2H)-yl)ethyl)piperazin-1-yl)-3,5-difluorophenoxy)acetic acid 2-(4-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)propanoic acid (S)-2-(4-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)propanoic acid 2-(4-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)-2-methylpropanoic acid 3-(4-(4-(2-(5-amino-8-(furan-2-yl)-1-methyl-2-oxo-1H-pyrazolo[5,1-i]purin-3(2H)-yl)ethyl)piperazin-1-yl)-3-fluorophenyl)propanoic acid 4-(4-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)butanoic acid 2-(3-(4-(2-(5-amino-8-(furan-2-yl)-1-methyl-2-oxo-1H-pyrazolo[5,1-i]purin-3(2H)-yl)ethyl)piperazin-1-yl)-2,6-difluorophenoxy)acetic acid 2-(5-(4-(2-(5-amino-8-(furan-2-yl)-1-methyl-2-oxo-1H-pyrazolo[5,1-i]purin-3(2H)-yl)ethyl)piperazin-1-yl)-2,4-difluorophenoxy)acetic acid 4-(4-(2-(5-amino-8-(furan-2-yl)-1-methyl-2-oxo-1H-pyrazolo[5,1-i]purin-3 (2H)-yl)ethyl)piperazin-1-yl)-3-fluorobenzoic acid 2-((2-(4-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)ethyl)amino)acetamide 2-((2-(4-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)ethyl)(methyl)amino)acetamide 5-amino-3-(2-(4-(2-fluoro-4-(piperidin-4-yloxy)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(pyrrolidin-3-yloxy)phenyl)piperazin-1-yl)ethyl)-8-(furan-2-yl)-1-methyl-1H-pyrazolo[5,1-i]purin-2(3H)-one 3-(2-(4-(4-((4H-1,2,4-triazol-3-yl)methoxy)-2-fluorophenyl)piperazin-1-yl)ethyl)-5-amino-8-(furan-2-yl)-1-methyl-1H-pyrazolo[5,1-i]purin-2(3H)-one 2-(4-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)-N-(2-(methylamino)ethyl)acetamide 2-(4-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)-N-(2-(dimethylamino)ethyl)acetamide 2-(4-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)-N-(2-aminoethyl)acetamide (R)-2-(4-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)propanoic acid 2-(4-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)acetamide 4-(4-(2-(5-amino-8-(furan-2-yl)-1-methyl-2-oxo-1H-pyrazolo[5,1-i]purin-3 (2H)-yl)ethyl)piperazin-1-yl)-3-fluoro-N-methyl-N-(2-(methylamino)ethyl)benzamide 4-(4-(2-(5-amino-8-(furan-2-yl)-1-methyl-2-oxo-1H-pyrazolo[5,1-i]purin-3 (2H)-yl)ethyl)piperazin-1-yl)-N-(2-(dimethylamino)ethyl)-3-fluoro-N-methylbenzamide (R)-4-(4-(2-(5-amino-8-(furan-2-yl)-1-methyl-2-oxo-1H-pyrazolo[5,1-i]purin-3(2H)-yl)ethyl)piperazin-1-yl)-N-(1-(dimethylamino)propan-2-yl)-3-fluorobenzamide 2-(4-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)-N-methyl-N-(2-(methylamino)ethyl)acetamide 2-(5-(4-(2-(5-amino-8-(furan-2-yl)-1-methyl-2-oxo-1H-pyrazolo[5,1-i]purin-3(2H)-yl)ethyl)piperazin-1-yl)-2,4-difluorophenoxy)-2-methylpropanoic acid (S)-2-(5-(4-(2-(5-amino-8-(furan-2-yl)-1-methyl-2-oxo-1H-pyrazolo[5,1-i]purin-3(2H)-yl)ethyl)piperazin-1-yl)-2,4-difluorophenoxy)propanoic acid (R)-2-(5-(4-(2-(5-amino-8-(furan-2-yl)-1-methyl-2-oxo-1H-pyrazolo[5,1-i]purin-3 (2H)-yl)ethyl)piperazin-1-yl)-2,4-difluorophenoxy)propanoic acid 2-(5-(4-(2-(5-amino-8-(furan-2-yl)-1-methyl-2-oxo-1H-pyrazolo[5,1-i]purin-3(2H)-yl)ethyl)piperazin-1-yl)-2,4-difluorophenoxy)-N-(2-(methylamino)ethyl)acetamide 2-(5-(4-(2-(5-amino-8-(furan-2-yl)-1-methyl-2-oxo-1H-pyrazolo[5,1-i]purin-3(2H)-yl)ethyl)piperazin-1-yl)-2,4-difluorophenoxy)-N-(2-(dimethylamino)ethyl)acetamide 5-(4-(2-(5-amino-8-(furan-2-yl)-1-methyl-2-oxo-1H-pyrazolo[5,1-i]purin-3 (2H)-yl)ethyl)piperazin-1-yl)-N-(2-(dimethylamino)ethyl)-2,4-difluoro-N-methylbenzamide 5-(4-(2-(5-amino-8-(furan-2-yl)-1-methyl-2-oxo-1H-pyrazolo[5,1-i]purin-3 (2H)-yl)ethyl)piperazin-1-yl)-2,4-difluoro-N-methylbenzamide 4-(5-(4-(2-(5-amino-8-(furan-2-yl)-1-methyl-2-oxo-1H-pyrazolo[5,1-i]purin-3(2H)-yl)ethyl)piperazin-1-yl)-2,4-difluorophenoxy)butanoic acid 3-(2-(4-(5-((1H-tetrazol-5-yl)methoxy)-2,4-difluorophenyl)piperazin-1-yl)ethyl)-5-amino-8-(furan-2-yl)-1-methyl-1H-pyrazolo[5,1-i]purin-2(3H)-one 5-amino-3-(2-(4-(2-fluoro-4-((1-methyl-1H-1,2,4-triazol-3-yl)methoxy)phenyl)piperazin-1-yl)ethyl)-8-(furan-2-yl)-1-methyl-1H-pyrazolo[5,1-i]purin-2(3H)-one 5-amino-3-(2-(4-(2,4-difluoro-5-((1-methyl-1H-1,2,4-triazol-3-yl)methoxy)phenyl)piperazin-1-yl)ethyl)-8-(furan-2-yl)-1-methyl-1H-pyrazolo[5,1-i]purin-2(3H)-one 4-(4-(2-(5-amino-8-(furan-2-yl)-1-methyl-2-oxo-1H-pyrazolo[5,1-i]purin-3 (2H)-yl)ethyl)piperazin-1-yl)-3-fluoro-N-(2-(methyl(oxetan-3-yl)amino)ethyl)benzamide 4-(4-(2-(5-amino-8-(furan-2-yl)-1-methyl-2-oxo-1H-pyrazolo[5,1-i]purin-3 (2H)-yl)ethyl)piperazin-1-yl)-3-fluoro-N-(2-((2-hydroxyethyl)amino)ethyl)benzamide 2-amino-N-(2-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)ethyl)acetamide (S)-2-amino-N-(2-(4-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)ethyl)-3-methylbutanamide 5-amino-3-(2-(4-(2,4-difluoro-5-(2-(methylsulfonyl)ethoxy)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(2-(methylsulfonyl)ethoxy)phenyl)piperazin-1-yl)ethyl)-8-(furan-2-yl)-1-methyl-1H-pyrazolo[5,1-i]purin-2(3H)-one 5-amino-3-(2-(4-(6-fluoro-2-oxoindolin-5-yl)piperazin-1-yl)ethyl)-8-(furan-2-yl)-1-methyl-1H-pyrazolo[5,1-i]purin-2(3H)-one 5-amino-3-(2-(4-(2-fluoro-4-(S-methylsulfonimidoyl)phenyl)piperazin-1-yl)ethyl)-8-(furan-2-yl)-1-methyl-1H-pyrazolo[5,1-i]purin-2(3H)-one 5-(4-(2-(5-amino-8-(furan-2-yl)-1-methyl-2-oxo-1H-pyrazolo[5,1-i]purin-3 (2H)-yl)ethyl)piperazin-1-yl)-N-(2-(dimethylamino)ethyl)-2,4-difluorobenzamide 5-amino-3-(2-(4-(2-fluoro-4-(((3R,4R)-4-hydroxytetrahydrofuran-3-yl)oxy)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(((3S,4S)-4-hydroxytetrahydrofuran-3-yl)oxy)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(2-hydroxy-2-methylpropoxy)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(2-hydroxypropan-2-yl)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(3,3,3-trifluoro-2-hydroxypropoxy)phenyl)piperazin-1-yl)ethyl)-8-(furan-2-yl)-1-methyl-1H-pyrazolo[5,1-i]purin-2(3H)-one 5-amino-3-(2-(4-(2-fluoro-5-(2-hydroxyethoxy)phenyl)piperazin-1-yl)ethyl)-8-(furan-2-yl)-1-methyl-1H-pyrazolo[5,1-i]purin-2(3H)-one 5-amino-3-(2-(4-(2,4-difluoro-5-(morpholin-2-ylmethoxy)phenyl)piperazin-1-yl)ethyl)-8-(furan-2-yl)-1-methyl-1H-pyrazolo[5,1-i]purin-2(3H)-one 5-amino-3-(2-(4-(2,4-difluoro-5-(morpholin-3-ylmethoxy)phenyl)piperazin-1-yl)ethyl)-8-(furan-2-yl)-1-methyl-1H-pyrazolo[5,1-i]purin-2(3H)-one 5-amino-3-(2-(4-(2,4-difluoro-5-(((3 S,4S)-4-fluoropyrrolidin-3-yl)oxy)phenyl)piperazin-1-yl)ethyl)-8-(furan-2-yl)-1-methyl-1H-pyrazolo[5,1-i]purin-2(3H)-one 5-amino-3-(2-(4-(2,4-difluoro-5-(((3R,4S)-4-fluoropyrrolidin-3-yl)oxy)phenyl)piperazin-1-yl)ethyl)-8-(furan-2-yl)-1-methyl-1H-pyrazolo[5,1-i]purin-2(3H)-one 5-amino-3-(2-(4-(2,4-difluoro-5-(((3S,4R)-4-fluoropyrrolidin-3-yl)oxy)phenyl)piperazin-1-yl)ethyl)-8-(furan-2-yl)-1-methyl-1H-pyrazolo[5,1-i]purin-2(3H)-one (S)-5-amino-3-(2-(4-(2,4-difluoro-5-((2-oxopyrrolidin-3-yl)oxy)phenyl)piperazin-1-yl)ethyl)-8-(furan-2-yl)-1-methyl-1H-pyrazolo[5,1-i]purin-2(3H)-one (R)-5-amino-3-(2-(4-(2,4-difluoro-5-((2-oxopyrrolidin-3-yl)oxy)phenyl)piperazin-1-yl)ethyl)-8-(furan-2-yl)-1-methyl-1H-pyrazolo[5,1-i]purin-2(3H)-one 2-(5-(4-(2-(5-amino-8-(furan-2-yl)-1-methyl-2-oxo-1H-pyrazolo[5,1-i]purin-3(2H)-yl)ethyl)piperazin-1-yl)-2,4-difluorophenoxy)-N-(2-morpholinoethyl)acetamide 5-(4-(2-(5-amino-8-(furan-2-yl)-1-methyl-2-oxo-1H-pyrazolo[5,1-i]purin-3 (2H)-yl)ethyl)piperazin-1-yl)-2,4-difluoro-N-(morpholin-3-ylmethyl)benzamide 5-amino-3-(2-(4-(2-fluoro-4-(morpholin-3-ylmethoxy)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(morpholin-2-ylmethoxy)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(((3R,4R)-4-fluoropyrrolidin-3-yl)oxy)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(((3S,4S)-4-fluoropyrrolidin-3-yl)oxy)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(((3R,4S)-4-fluoropyrrolidin-3-yl)oxy)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(((3S,4R)-4-fluoropyrrolidin-3-yl)oxy)phenyl)piperazin-1-yl)ethyl)-8-(furan-2-yl)-1-methyl-1H-pyrazolo[5,1-i]purin-2(3H)-one 2-(4-(4-(2-(5-amino-8-(furan-2-yl)-1-methyl-2-oxo-1H-pyrazolo[5,1-i]purin-3(2H)-yl)ethyl)piperazin-1-yl)-3-fluorophenoxy)-N-(2-morpholinoethyl)acetamide 4-(4-(2-(5-amino-8-(furan-2-yl)-1-methyl-2-oxo-1H-pyrazolo[5,1-i]purin-3 (2H)-yl)ethyl)piperazin-1-yl)-3-fluoro-N-(2-morpholinoethyl)benzamide 4-(4-(2-(5-amino-8-(furan-2-yl)-1-methyl-2-oxo-1H-pyrazolo[5,1-i]purin-3 (2H)-yl)ethyl)piperazin-1-yl)-3-fluoro-N-(morpholin-3-ylmethyl)benzamide (S)-5-amino-3-(2-(4-(2,4-difluoro-5-(methylsulfinyl)phenyl)piperazin-1-yl)ethyl)-8-(furan-2-yl)-1-methyl-1H-pyrazolo[5,1-i]purin-2(3H)-one (R)-5-amino-3-(2-(4-(2,4-difluoro-5-(methylsulfinyl)phenyl)piperazin-1-yl)ethyl)-8-(furan-2-yl)-1-methyl-1H-pyrazolo[5,1-i]purin-2(3H)-one 5-amino-3-(2-(4-(2,4-difluoro-5-(((1s,4s)-1-oxidotetrahydro-2H-thiopyran-4-yl)oxy)phenyl)piperazin-1-yl)ethyl)-8-(furan-2-yl)-1-methyl-1H-pyrazolo[5,1-i]purin-2(3H)-one 5-amino-3-(2-(4-(2,4-difluoro-5-(((1r,4r)-1-oxidotetrahydro-2H-thiopyran-4-yl)oxy)phenyl)piperazin-1-yl)ethyl)-8-(furan-2-yl)-1-methyl-1H-pyrazolo[5,1-i]purin-2(3H)-one (S)-5-(4-(2-(5-amino-8-(furan-2-yl)-1-methyl-2-oxo-1H-pyrazolo[5,1-i]purin-3(2H)-yl)ethyl)piperazin-1-yl)-2,4-difluoro-N-(2-(methylsulfinyl)ethyl)benzamide (R)-5-(4-(2-(5-amino-8-(furan-2-yl)-1-methyl-2-oxo-1H-pyrazolo[5,1-i]purin-3(2H)-yl)ethyl)piperazin-1-yl)-2,4-difluoro-N-(2-(methylsulfinyl)ethyl)benzamide (S)-5-(4-(2-(5-amino-8-(furan-2-yl)-1-methyl-2-oxo-1H-pyrazolo[5,1-i]purin-3(2H)-yl)ethyl)piperazin-1-yl)-2,4-difluoro-N-methyl-N-(2-(methylsulfinyl)ethyl)benzamide (R)-5-(4-(2-(5-amino-8-(furan-2-yl)-1-methyl-2-oxo-1H-pyrazolo[5,1-i]purin-3(2H)-yl)ethyl)piperazin-1-yl)-2,4-difluoro-N-methyl-N-(2-(methylsulfinyl)ethyl)benzamide 5-amino-3-(2-(4-(2,4-difluoro-5-(1-oxidothiomorpholine-4-carbonyl)phenyl)piperazin-1-yl)ethyl)-8-(furan-2-yl)-1-methyl-1H-pyrazolo[5,1-i]purin-2(3H)-one 5-amino-3-(2-(4-(2,4-difluoro-5-(1-oxidothiomorpholino)phenyl)piperazin-1-yl)ethyl)-8-(furan-2-yl)-1-methyl-1H-pyrazolo[5,1-i]purin-2(3H)-one (R)-5-amino-3-(2-(4-(2-fluoro-4-(methylsulfinyl)phenyl)piperazin-1-yl)ethyl)-8-(furan-2-yl)-1-methyl-1H-pyrazolo[5,1-i]purin-2(3H)-one (S)-5-amino-3-(2-(4-(2-fluoro-4-(methylsulfinyl)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(((1s,4s)-1-oxidotetrahydro-2H-thiopyran-4-yl)oxy)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(((1r,4r)-1-oxidotetrahydro-2H-thiopyran-4-yl)oxy)phenyl)piperazin-1-yl)ethyl)-8-(furan-2-yl)-1-methyl-1H-pyrazolo[5,1-i]purin-2(3H)-one (S)-4-(4-(2-(5-amino-8-(furan-2-yl)-1-methyl-2-oxo-1H-pyrazolo[5,1-i]purin-3(2H)-yl)ethyl)piperazin-1-yl)-3-fluoro-N-(2-(methylsulfinyl)ethyl)benzamide (R)-4-(4-(2-(5-amino-8-(furan-2-yl)-1-methyl-2-oxo-1H-pyrazolo[5,1-i]purin-3(2H)-yl)ethyl)piperazin-1-yl)-3-fluoro-N-(2-(methylsulfinyl)ethyl)benzamide 5-amino-3-(2-(4-(2-fluoro-4-(1-oxidothiomorpholine-4-carbonyl)phenyl)piperazin-1-yl)ethyl)-8-(furan-2-yl)-1-methyl-1H-pyrazolo[5,1-i]purin-2(3H)-one 5-amino-3-(2-(4-(2-fluoro-4-(1-oxidothiomorpholino)phenyl)piperazin-1-yl)ethyl)-8-(furan-2-yl)-1-methyl-1H-pyrazolo[5,1-i]purin-2(3H)-one (S)-5-amino-3-(2-(4-(5-(2,3-dihydroxypropoxy)-2,4-difluorophenyl)piperazin-1-yl)ethyl)-8-(furan-2-yl)-1-methyl-1H-pyrazolo[5,1-i]purin-2(3H)-one (R)-5-amino-3-(2-(4-(5-(2,3-dihydroxypropoxy)-2,4-difluorophenyl)piperazin-1-yl)ethyl)-8-(furan-2-yl)-1-methyl-1H-pyrazolo[5,1-i]purin-2(3H)-one (S)-5-(4-(2-(5-amino-8-(furan-2-yl)-1-methyl-2-oxo-1H-pyrazolo[5,1-i]purin-3(2H)-yl)ethyl)piperazin-1-yl)-N-(2,3-dihydroxypropyl)-2,4-difluorobenzamide (R)-5-(4-(2-(5-amino-8-(furan-2-yl)-1-methyl-2-oxo-1H-pyrazolo[5,1-i]purin-3(2H)-yl)ethyl)piperazin-1-yl)-N-(2,3-dihydroxypropyl)-2,4-difluorobenzamide 5-amino-3-(2-(4-(4-(azetidin-3-yloxy)-2-fluorophenyl)piperazin-1-yl)ethyl)-8-(furan-2-yl)-1-methyl-1H-pyrazolo[5,1-i]purin-2(3H)-one 5-amino-3-(2-(4-(5-(azetidin-3-yloxy)-2,4-difluorophenyl)piperazin-1-yl)ethyl)-8-(furan-2-yl)-1-methyl-1H-pyrazolo[5,1-i]purin-2(3H)-one (S)-5-amino-3-(2-(4-(2,4-difluoro-5-(3-(methylsulfinyl)propoxy)phenyl)piperazin-1-yl)ethyl)-8-(furan-2-yl)-1-methyl-1H-pyrazolo[5,1-i]purin-2(3H)-one Heteroaryl Scaffold (9)

2-(4-(4-(2-(5-amino-8-(furan-2-yl)-3H-pyrazolo[5,1-i]purin-3-yl)ethyl)piperazin-1-yl)phenoxy)ethanol 2-(4-(4-(2-(5-amino-8-(furan-2-yl)-3H-pyrazolo[5,1-i]purin-3-yl)ethyl)piperazin-1-yl)phenoxy)acetic acid 2-(4-(4-(2-(5-amino-8-(furan-2-yl)-3H-pyrazolo[5,1-i]purin-3-yl)ethyl)piperazin-1-yl)phenoxy)acetamide 3-(4-(4-(2-(5-amino-8-(furan-2-yl)-3H-pyrazolo[5,1-i]purin-3-yl)ethyl)piperazin-1-yl)phenoxy)propane-1,2-diol 3-(2-(4-(4-(2-aminoethoxy)phenyl)piperazin-1-yl)ethyl)-8-(furan-2-yl)-3H-pyrazolo[5,1-i]purin-5-amine 4-(4-(2-(5-amino-8-(furan-2-yl)-3H-pyrazolo[5,1-i]purin-3-yl)ethyl)piperazin-1-yl)benzamide 4-(4-(2-(5-amino-8-(furan-2-yl)-3H-pyrazolo[5,1-i]purin-3-yl)ethyl)piperazin-1-yl)-N-methylbenzamide 8-(furan-2-yl)-3-(2-(4-(4-(2-morpholinoethoxy)phenyl)piperazin-1-yl)ethyl)-3H-pyrazolo[5,1-i]purin-5-amine 3-(2-(4-(4-(2-(dimethylamino)ethoxy)phenyl)piperazin-1-yl)ethyl)-8-(furan-2-yl)-3H-pyrazolo[5,1-i]purin-5-amine 4-(4-(2-(5-amino-8-(furan-2-yl)-3H-pyrazolo[5,1-i]purin-3-yl)ethyl)piperazin-1-yl)benzenesulfonamide 4-(4-(2-(5-amino-8-(furan-2-yl)-3H-pyrazolo[5,1-i]purin-3-yl)ethyl)piperazin-1-yl)-N-methylbenzenesulfonamide 8-(furan-2-yl)-3-(2-(4-(4-(methylsulfonyl)phenyl)piperazin-1-yl)ethyl)-3H-pyrazolo[5,1-i]purin-5-amine 8-(furan-2-yl)-3-(2-(4-(4-(methylsulfinyl)phenyl)piperazin-1-yl)ethyl)-3H-pyrazolo[5,1-i]purin-5-amine 3-(4-(2-(5-amino-8-(furan-2-yl)-3H-pyrazolo[5,1-i]purin-3-yl)ethyl)piperazin-1-yl)benzamide 2-(3-(4-(2-(5-amino-8-(furan-2-yl)-3H-pyrazolo[5,1-i]purin-3-yl)ethyl)piperazin-1-yl)phenoxy)ethanol 3-(2-(4-(4-(azetidin-3-yloxy)phenyl)piperazin-1-yl)ethyl)-8-(furan-2-yl)-3H-pyrazolo[5,1-i]purin-5-amine 3-(2-(4-(4-((2H-1,2,3-triazol-4-yl)methoxy)-2-fluorophenyl)piperazin-1-yl)ethyl)-8-(furan-2-yl)-3H-pyrazolo[5,1-i]purin-5-amine 5-((4-(4-(2-(5-amino-8-(furan-2-yl)-3H-pyrazolo[5,1-i]purin-3-yl)ethyl)piperazin-1-yl)-3-fluorophenoxy)methyl)-1,3,4-oxadiazol-2(3H)-one 2-(5-(4-(2-(5-amino-8-(furan-2-yl)-3H-pyrazolo[5,1-i]purin-3-yl)ethyl)piperazin-1-yl)-2,4-difluorophenoxy)acetamide (S)-3-(2-(4-(2-fluoro-4-(2-(methylsulfinyl)ethoxy)phenyl)piperazin-1-yl)ethyl)-8-(furan-2-yl)-3H-pyrazolo[5,1-i]purin-5-amine (R)-3-(2-(4-(2-fluoro-4-(2-(methylsulfinyl)ethoxy)phenyl)piperazin-1-yl)ethyl)-8-(furan-2-yl)-3H-pyrazolo[5,1-i]purin-5-amine 3-(2-(4-(2,4-difluoro-5-(2-(methylsulfinyl)ethoxy)phenyl)piperazin-1-yl)ethyl)-8-(furan-2-yl)-3H-pyrazolo[5,1-i]purin-5-amine 2-(4-(4-(2-(5-amino-8-(furan-2-yl)-3H-pyrazolo[5,1-i]purin-3-yl)ethyl)piperazin-1-yl)-3-fluorophenoxy)-1-(piperazin-1-yl)ethanone 3-(2-(4-(2-fluoro-4-(piperidin-4-ylmethoxy)phenyl)piperazin-1-yl)ethyl)-8-(furan-2-yl)-3H-pyrazolo[5,1-i]purin-5-amine (4-(4-(2-(5-amino-8-(furan-2-yl)-3H-pyrazolo[5,1-i]purin-3-yl)ethyl)piperazin-1-yl)-3-fluorophenyl)(piperazin-1-yl)methanone 3-(2-(4-(2-fluoro-4-(2-(piperazin-1-yl)ethoxy)phenyl)piperazin-1-yl)ethyl)-8-(furan-2-yl)-3H-pyrazolo[5,1-i]purin-5-amine 3-(2-(4-(2-fluoro-4-(piperazin-1-ylsulfonyl)phenyl)piperazin-1-yl)ethyl)-8-(furan-2-yl)-3H-pyrazolo[5,1-i]purin-5-amine 3-(2-(4-(2-fluoro-4-(methylsulfonyl)phenyl)piperazin-1-yl)ethyl)-8-(furan-2-yl)-3H-pyrazolo[5,1-i]purin-5-amine 4-(4-(2-(5-amino-8-(furan-2-yl)-3H-pyrazolo[5,1-i]purin-3-yl)ethyl)piperazin-1-yl)-N-(2-aminoethyl)-3-fluorobenzamide 4-(4-(2-(5-amino-8-(furan-2-yl)-3H-pyrazolo[5,1-i]purin-3-yl)ethyl)piperazin-1-yl)-3-fluoro-N-(2-(methylamino)ethyl)benzamide 4-(4-(2-(5-amino-8-(furan-2-yl)-3H-pyrazolo[5,1-i]purin-3-yl)ethyl)piperazin-1-yl)-N-(2-(dimethylamino)ethyl)-3-fluorobenzamide 4-(4-(2-(5-amino-8-(furan-2-yl)-3H-pyrazolo[5,1-i]purin-3-yl)ethyl)piperazin-1-yl)-3-fluoro-N-(2-hydroxyethyl)benzamide 4-(4-(2-(5-amino-8-(furan-2-yl)-3H-pyrazolo[5,1-i]purin-3-yl)ethyl)piperazin-1-yl)-N-(2,3-dihydroxypropyl)-3-fluorobenzamide 2-(4-(4-(2-(5-amino-8-(furan-2-yl)-3H-pyrazolo[5,1-i]purin-3-yl)ethyl)piperazin-1-yl)-3-fluorophenoxy)acetic acid 2-(4-(4-(2-(5-amino-8-(furan-2-yl)-3H-pyrazolo[5,1-i]purin-3-yl)ethyl)piperazin-1-yl)-3,5-difluorophenoxy)acetic acid 2-(4-(4-(2-(5-amino-8-(furan-2-yl)-3H-pyrazolo[5,1-i]purin-3-yl)ethyl)piperazin-1-yl)-3-fluorophenoxy)propanoic acid (S)-2-(4-(4-(2-(5-amino-8-(furan-2-yl)-3H-pyrazolo[5,1-i]purin-3-yl)ethyl)piperazin-1-yl)-3-fluorophenoxy)propanoic acid 2-(4-(4-(2-(5-amino-8-(furan-2-yl)-3H-pyrazolo[5,1-i]purin-3-yl)ethyl)piperazin-1-yl)-3-fluorophenoxy)-2-methylpropanoic acid 3-(4-(4-(2-(5-amino-8-(furan-2-yl)-3H-pyrazolo[5,1-i]purin-3-yl)ethyl)piperazin-1-yl)-3-fluorophenyl)propanoic acid 4-(4-(4-(2-(5-amino-8-(furan-2-yl)-3H-pyrazolo[5,1-i]purin-3-yl)ethyl)piperazin-1-yl)-3-fluorophenoxy)butanoic acid 2-(3-(4-(2-(5-amino-8-(furan-2-yl)-3H-pyrazolo[5,1-i]purin-3-yl)ethyl)piperazin-1-yl)-2,6-difluorophenoxy)acetic acid 2-(5-(4-(2-(5-amino-8-(furan-2-yl)-3H-pyrazolo[5,1-i]purin-3-yl)ethyl)piperazin-1-yl)-2,4-difluorophenoxy)acetic acid 4-(4-(2-(5-amino-8-(furan-2-yl)-3H-pyrazolo[5,1-i]purin-3-yl)ethyl)piperazin-1-yl)-3-fluorobenzoic acid 2-((2-(4-(4-(2-(5-amino-8-(furan-2-yl)-3H-pyrazolo[5,1-i]purin-3-yl)ethyl)piperazin-1-yl)-3-fluorophenoxy)ethyl)amino)acetamide 2-((2-(4-(4-(2-(5-amino-8-(furan-2-yl)-3H-pyrazolo[5,1-i]purin-3-yl)ethyl)piperazin-1-yl)-3-fluorophenoxy)ethyl)(methyl)amino)acetamide 3-(2-(4-(2-fluoro-4-(piperidin-4-yloxy)phenyl)piperazin-1-yl)ethyl)-8-(furan-2-yl)-3H-pyrazolo[5,1-i]purin-5-amine 3-(2-(4-(2-fluoro-4-(pyrrolidin-3-yloxy)phenyl)piperazin-1-yl)ethyl)-8-(furan-2-yl)-3H-pyrazolo[5,1-i]purin-5-amine 3-(2-(4-(4-((4H-1,2,4-triazol-3-yl)methoxy)-2-fluorophenyl)piperazin-1-yl)ethyl)-8-(furan-2-yl)-3H-pyrazolo[5,1-i]purin-5-amine 2-(4-(4-(2-(5-amino-8-(furan-2-yl)-3H-pyrazolo[5,1-i]purin-3-yl)ethyl)piperazin-1-yl)-3-fluorophenoxy)-N-(2-(methylamino)ethyl)acetamide 2-(4-(4-(2-(5-amino-8-(furan-2-yl)-3H-pyrazolo[5,1-i]purin-3-yl)ethyl)piperazin-1-yl)-3-fluorophenoxy)-N-(2-(dimethylamino)ethyl)acetamide 2-(4-(4-(2-(5-amino-8-(furan-2-yl)-3H-pyrazolo[5,1-i]purin-3-yl)ethyl)piperazin-1-yl)-3-fluorophenoxy)-N-(2-aminoethyl)acetamide (R)-2-(4-(4-(2-(5-amino-8-(furan-2-yl)-3H-pyrazolo[5,1-i]purin-3-yl)ethyl)piperazin-1-yl)-3-fluorophenoxy)propanoic acid 2-(4-(4-(2-(5-amino-8-(furan-2-yl)-3H-pyrazolo[5,1-i]purin-3-yl)ethyl)piperazin-1-yl)-3-fluorophenoxy)acetamide 4-(4-(2-(5-amino-8-(furan-2-yl)-3H-pyrazolo[5,1-i]purin-3-yl)ethyl)piperazin-1-yl)-3-fluoro-N-methyl-N-(2-(methylamino)ethyl)benzamide 4-(4-(2-(5-amino-8-(furan-2-yl)-3H-pyrazolo[5,1-i]purin-3-yl)ethyl)piperazin-1-yl)-N-(2-(dimethylamino)ethyl)-3-fluoro-N-methylbenzamide (R)-4-(4-(2-(5-amino-8-(furan-2-yl)-3H-pyrazolo[5,1-i]purin-3-yl)ethyl)piperazin-1-yl)-N-(1-(dimethylamino)propan-2-yl)-3-fluorobenzamide 2-(4-(4-(2-(5-amino-8-(furan-2-yl)-3H-pyrazolo[5,1-i]purin-3-yl)ethyl)piperazin-1-yl)-3-fluorophenoxy)-N-methyl-N-(2-(methylamino)ethyl)acetamide 2-(5-(4-(2-(5-amino-8-(furan-2-yl)-3H-pyrazolo[5,1-i]purin-3-yl)ethyl)piperazin-1-yl)-2,4-difluorophenoxy)-2-methylpropanoic acid (S)-2-(5-(4-(2-(5-amino-8-(furan-2-yl)-3H-pyrazolo[5,1-i]purin-3-yl)ethyl)piperazin-1-yl)-2,4-difluorophenoxy)propanoic acid (R)-2-(5-(4-(2-(5-amino-8-(furan-2-yl)-3H-pyrazolo[5,1-i]purin-3-yl)ethyl)piperazin-1-yl)-2,4-difluorophenoxy)propanoic acid 2-(5-(4-(2-(5-amino-8-(furan-2-yl)-3H-pyrazolo[5,1-i]purin-3-yl)ethyl)piperazin-1-yl)-2,4-difluorophenoxy)-N-(2-(methylamino)ethyl)acetamide 2-(5-(4-(2-(5-amino-8-(furan-2-yl)-3H-pyrazolo[5,1-i]purin-3-yl)ethyl)piperazin-1-yl)-2,4-difluorophenoxy)-N-(2-(dimethylamino)ethyl)acetamide 5-(4-(2-(5-amino-8-(furan-2-yl)-3H-pyrazolo[5,1-i]purin-3-yl)ethyl)piperazin-1-yl)-N-(2-(dimethylamino)ethyl)-2,4-difluoro-N-methylbenzamide 5-(4-(2-(5-amino-8-(furan-2-yl)-3H-pyrazolo[5,1-i]purin-3-yl)ethyl)piperazin-1-yl)-2,4-difluoro-N-methylbenzamide 4-(5-(4-(2-(5-amino-8-(furan-2-yl)-3H-pyrazolo[5,1-i]purin-3-yl)ethyl)piperazin-1-yl)-2,4-difluorophenoxy)butanoic acid 3-(2-(4-(5-((1H-tetrazol-5-yl)methoxy)-2,4-difluorophenyl)piperazin-1-yl)ethyl)-8-(furan-2-yl)-3H-pyrazolo[5,1-i]purin-5-amine 3-(2-(4-(2-fluoro-4-((1-methyl-1H-1,2,4-triazol-3-yl)methoxy)phenyl)piperazin-1-yl)ethyl)-8-(furan-2-yl)-3H-pyrazolo[5,1-i]purin-5-amine 3-(2-(4-(2,4-difluoro-5-((1-methyl-1H-1,2,4-triazol-3-yl)methoxy)phenyl)piperazin-1-yl)ethyl)-8-(furan-2-yl)-3H-pyrazolo[5,1-i]purin-5-amine 4-(4-(2-(5-amino-8-(furan-2-yl)-3H-pyrazolo[5,1-i]purin-3-yl)ethyl)piperazin-1-yl)-3-fluoro-N-(2-(methyl(oxetan-3-yl)amino)ethyl)benzamide 4-(4-(2-(5-amino-8-(furan-2-yl)-3H-pyrazolo[5,1-i]purin-3-yl)ethyl)piperazin-1-yl)-3-fluoro-N-(2-((2-hydroxyethyl)amino)ethyl)benzamide 2-amino-N-(2-(4-(4-(2-(5-amino-8-(furan-2-yl)-3H-pyrazolo[5,1-i]purin-3-yl)ethyl)piperazin-1-yl)-3-fluorophenoxy)ethyl)acetamide (S)-2-amino-N-(2-(4-(4-(2-(5-amino-8-(furan-2-yl)-3H-pyrazolo[5,1-i]purin-3-yl)ethyl)piperazin-1-yl)-3-fluorophenoxy)ethyl)-3-methylbutanamide 3-(2-(4-(2,4-difluoro-5-(2-(methylsulfonyl)ethoxy)phenyl)piperazin-1-yl)ethyl)-8-(furan-2-yl)-3H-pyrazolo[5,1-i]purin-5-amine 3-(2-(4-(2-fluoro-4-(2-(methylsulfonyl)ethoxy)phenyl)piperazin-1-yl)ethyl)-8-(furan-2-yl)-3H-pyrazolo[5,1-i]purin-5-amine 5-(4-(2-(5-amino-8-(furan-2-yl)-3H-pyrazolo[5,1-i]purin-3-yl)ethyl)piperazin-1-yl)-6-fluoroindolin-2-one 3-(2-(4-(2-fluoro-4-(S-methylsulfonimidoyl)phenyl)piperazin-1-yl)ethyl)-8-(furan-2-yl)-3H-pyrazolo[5,1-i]purin-5-amine 5-(4-(2-(5-amino-8-(furan-2-yl)-3H-pyrazolo[5,1-i]purin-3-yl)ethyl)piperazin-1-yl)-N-(2-(dimethylamino)ethyl)-2,4-difluorobenzamide (3R,4R)-4-(4-(4-(2-(5-amino-8-(furan-2-yl)-3H-pyrazolo[5,1-i]purin-3-yl)ethyl)piperazin-1-yl)-3-fluorophenoxy)tetrahydrofuran-3-ol (3S,4S)-4-(4-(4-(2-(5-amino-8-(furan-2-yl)-3H-pyrazolo[5,1-i]purin-3-yl)ethyl)piperazin-1-yl)-3-fluorophenoxy)tetrahydrofuran-3-ol 1-(4-(4-(2-(5-amino-8-(furan-2-yl)-3H-pyrazolo[5,1-i]purin-3-yl)ethyl)piperazin-1-yl)-3-fluorophenoxy)-2-methylpropan-2-ol 2-(4-(4-(2-(5-amino-8-(furan-2-yl)-3H-pyrazolo[5,1-i]purin-3-yl)ethyl)piperazin-1-yl)-3-fluorophenyl)propan-2-ol 3-(4-(4-(2-(5-amino-8-(furan-2-yl)-3H-pyrazolo[5,1-i]purin-3-yl)ethyl)piperazin-1-yl)-3-fluorophenoxy)-1,1,1-trifluoropropan-2-ol 2-(3-(4-(2-(5-amino-8-(furan-2-yl)-3H-pyrazolo[5,1-i]purin-3-yl)ethyl)piperazin-1-yl)-4-fluorophenoxy)ethanol 3-(2-(4-(2,4-difluoro-5-(morpholin-2-ylmethoxy)phenyl)piperazin-1-yl)ethyl)-8-(furan-2-yl)-3H-pyrazolo[5,1-i]purin-5-amine 3-(2-(4-(2,4-difluoro-5-(morpholin-3-ylmethoxy)phenyl)piperazin-1-yl)ethyl)-8-(furan-2-yl)-3H-pyrazolo[5,1-i]purin-5-amine 3-(2-(4-(2,4-difluoro-5-(((3S,4S)-4-fluoropyrrolidin-3-yl)oxy)phenyl)piperazin-1-yl)ethyl)-8-(furan-2-yl)-3H-pyrazolo[5,1-i]purin-5-amine 3-(2-(4-(2,4-difluoro-5-(((3R,4S)-4-fluoropyrrolidin-3-yl)oxy)phenyl)piperazin-1-yl)ethyl)-8-(furan-2-yl)-3H-pyrazolo[5,1-i]purin-5-amine 3-(2-(4-(2,4-difluoro-5-(((3S,4R)-4-fluoropyrrolidin-3-yl)oxy)phenyl)piperazin-1-yl)ethyl)-8-(furan-2-yl)-3H-pyrazolo[5,1-i]purin-5-amine (S)-3-(5-(4-(2-(5-amino-8-(furan-2-yl)-3H-pyrazolo[5,1-i]purin-3-yl)ethyl)piperazin-1-yl)-2,4-difluorophenoxy)pyrrolidin-2-one (R)-3-(5-(4-(2-(5-amino-8-(furan-2-yl)-3H-pyrazolo[5,1-i]purin-3-yl)ethyl)piperazin-1-yl)-2,4-difluorophenoxy)pyrrolidin-2-one 2-(5-(4-(2-(5-amino-8-(furan-2-yl)-3H-pyrazolo[5,1-i]purin-3-yl)ethyl)piperazin-1-yl)-2,4-difluorophenoxy)-N-(2-morpholinoethyl)acetamide 5-(4-(2-(5-amino-8-(furan-2-yl)-3H-pyrazolo[5,1-i]purin-3-yl)ethyl)piperazin-1-yl)-2,4l-difluoro-N-(morpholin-3-ylmethyl)benzamide 3-(2-(4-(2-fluoro-4-(morpholin-3-ylmethoxy)phenyl)piperazin-1-yl)ethyl)-8-(furan-2-yl)-3H-pyrazolo[5,1-i]purin-5-amine 3-(2-(4-(2-fluoro-4-(morpholin-2-ylmethoxy)phenyl)piperazin-1-yl)ethyl)-8-(furan-2-yl)-3H-pyrazolo[5,1-i]purin-5-amine 3-(2-(4-(2-fluoro-4-(((3R,4R)-4-fluoropyrrolidin-3-yl)oxy)phenyl)piperazin-1-yl)ethyl)-8-(furan-2-yl)-3H-pyrazolo[5,1-i]purin-5-amine 3-(2-(4-(2-fluoro-4-(((3S,4S)-4-fluoropyrrolidin-3-yl)oxy)phenyl)piperazin-1-yl)ethyl)-8-(furan-2-yl)-3H-pyrazolo[5,1-i]purin-5-amine 3-(2-(4-(2-fluoro-4-(((3R,4S)-4-fluoropyrrolidin-3-yl)oxy)phenyl)piperazin-1-yl)ethyl)-8-(furan-2-yl)-3H-pyrazolo[5,1-i]purin-5-amine 3-(2-(4-(2-fluoro-4-(((3S,4R)-4-fluoropyrrolidin-3-yl)oxy)phenyl)piperazin-1-yl)ethyl)-8-(furan-2-yl)-3H-pyrazolo[5,1-i]purin-5-amine 2-(4-(4-(2-(5-amino-8-(furan-2-yl)-3H-pyrazolo[5,1-i]purin-3-yl)ethyl)piperazin-1-yl)-3-fluorophenoxy)-N-(2-morpholinoethyl)acetamide 4-(4-(2-(5-amino-8-(furan-2-yl)-3H-pyrazolo[5,1-i]purin-3-yl)ethyl)piperazin-1-yl)-3-fluoro-N-(2-morpholinoethyl)benzamide 4-(4-(2-(5-amino-8-(furan-2-yl)-3H-pyrazolo[5,1-i]purin-3-yl)ethyl)piperazin-1-yl)-3-fluoro-N-(morpholin-3-ylmethyl)benzamide (S)-3-(2-(4-(2,4-difluoro-5-(methylsulfinyl)phenyl)piperazin-1-yl)ethyl)-8-(furan-2-yl)-3H-pyrazolo[5,1-i]purin-5-amine (R)-3-(2-(4-(2,4-difluoro-5-(methylsulfinyl)phenyl)piperazin-1-yl)ethyl)-8-(furan-2-yl)-3H-pyrazolo[5,1-i]purin-5-amine (1s,4s)-4-(5-(4-(2-(5-amino-8-(furan-2-yl)-3H-pyrazolo[5,1-i]purin-3-yl)ethyl)piperazin-1-yl)-2,4-difluorophenoxy)tetrahydro-2H-thiopyran 1-oxide (1r,4r)-4-(5-(4-(2-(5-amino-8-(furan-2-yl)-3H-pyrazolo[5,1-i]purin-3-yl)ethyl)piperazin-1-yl)-2,4-difluorophenoxy)tetrahydro-2H-thiopyran 1-oxide (S)-5-(4-(2-(5-amino-8-(furan-2-yl)-3H-pyrazolo[5,1-i]purin-3-yl)ethyl)piperazin-1-yl)-2,4-difluoro-N-(2-(methylsulfinyl)ethyl)benzamide (R)-5-(4-(2-(5-amino-8-(furan-2-yl)-3H-pyrazolo[5,1-i]purin-3-yl)ethyl)piperazin-1-yl)-2,4-difluoro-N-(2-(methylsulfinyl)ethyl)benzamide (S)-5-(4-(2-(5-amino-8-(furan-2-yl)-3H-pyrazolo[5,1-i]purin-3-yl)ethyl)piperazin-1-yl)-2,4-difluoro-N-methyl-N-(2-(methylsulfinyl)ethyl)benzamide (R)-5-(4-(2-(5-amino-8-(furan-2-yl)-3H-pyrazolo[5,1-i]purin-3-yl)ethyl)piperazin-1-yl)-2,4-difluoro-N-methyl-N-(2-(methylsulfinyl)ethyl)benzamide (5-(4-(2-(5-amino-8-(furan-2-yl)-3H-pyrazolo[5,1-i]purin-3-yl)ethyl)piperazin-1-yl)-2,4-difluorophenyl)(1-oxidothiomorpholino)methanone 4-(5-(4-(2-(5-amino-8-(furan-2-yl)-3H-pyrazolo[5,1-i]purin-3-yl)ethyl)piperazin-1-yl)-2,4-difluorophenyl)thiomorpholine 1-oxide (R)-3-(2-(4-(2-fluoro-4-(methylsulfinyl)phenyl)piperazin-1-yl)ethyl)-8-(furan-2-yl)-3H-pyrazolo[5,1-i]purin-5-amine (S)-3-(2-(4-(2-fluoro-4-(methylsulfinyl)phenyl)piperazin-1-yl)ethyl)-8-(furan-2-yl)-3H-pyrazolo[5,1-i]purin-5-amine (1s,4s)-4-(4-(4-(2-(5-amino-8-(furan-2-yl)-3H-pyrazolo[5,1-i]purin-3-yl)ethyl)piperazin-1-yl)-3-fluorophenoxy)tetrahydro-2H-thiopyran 1-oxide (1r,4r)-4-(4-(4-(2-(5-amino-8-(furan-2-yl)-3H-pyrazolo[5,1-i]purin-3-yl)ethyl)piperazin-1-yl)-3-fluorophenoxy)tetrahydro-2H-thiopyran 1-oxide (S)-4-(4-(2-(5-amino-8-(furan-2-yl)-3H-pyrazolo[5,1-i]purin-3-yl)ethyl)piperazin-1-yl)-3-fluoro-N-(2-(methylsulfinyl)ethyl)benzamide (R)-4-(4-(2-(5-amino-8-(furan-2-yl)-3H-pyrazolo[5,1-i]purin-3-yl)ethyl)piperazin-1-yl)-3-fluoro-N-(2-(methylsulfinyl)ethyl)benzamide (4-(4-(2-(5-amino-8-(furan-2-yl)-3H-pyrazolo[5,1-i]purin-3-yl)ethyl)piperazin-1-yl)-3-fluorophenyl)(1-oxidothiomorpholino)methanone 4-(4-(4-(2-(5-amino-8-(furan-2-yl)-3H-pyrazolo[n5,1-i]purin-3-yl)ethyl)piperazin-1-yl)-3-fluorophenyl)thiomorpholine 1-oxide (S)-3-(5-(4-(2-(5-amino-8-(furan-2-yl)-3H-pyrazolo[5,1-i]purin-3-yl)ethyl)piperazin-1-yl)-2,4-difluorophenoxy)propane-1,2-diol (R)-3-(5-(4-(2-(5-amino-8-(furan-2-yl)-3H-pyrazolo[5,1-i]purin-3-yl)ethyl)piperazin-1-yl)-2,4-difluorophenoxy)propane-1,2-diol (S)-5-(4-(2-(5-amino-8-(furan-2-yl)-3H-pyrazolo[5,1-i]purin-3-yl)ethyl)piperazin-1-yl)-N-(2,3-dihydroxypropyl)-2,4-difluorobenzamide (R)-5-(4-(2-(5-amino-8-(furan-2-yl)-3H-pyrazolo[5,1-i]purin-3-yl)ethyl)piperazin-1-yl)-N-(2,3-dihydroxypropyl)-2,4-difluorobenzamide 3-(2-(4-(4-(azetidin-3-yloxy)-2-fluorophenyl)piperazin-1-yl)ethyl)-8-(furan-2-yl)-3H-pyrazolo[5,1-i]purin-5-amine 3-(2-(4-(5-(azetidin-3-yloxy)-2,4-difluorophenyl)piperazin-1-yl)ethyl)-8-(furan-2-yl)-3H-pyrazolo[5,1-i]purin-5-amine (S)-3-(2-(4-(2,4-difluoro-5-(3-(methylsulfinyl)propoxy)phenyl)piperazin-1-yl)ethyl)-8-(furan-2-yl)-3H-pyrazolo[5,1-i]purin-5-amine Heteroaryl Scaffold (10)

2-(4-(4-(2-(5-amino-8-(furan-2-yl)-3H-dipyrazolo[1,5-c:4',3'-e]pyrimidin-3-yl)ethyl)piperazin-1-yl)phenoxy)ethanol 2-(4-(4-(2-(5-amino-8-(furan-2-yl)-3H-dipyrazolo[1,5-c:4',3'-e]pyrimidin-3-yl)ethyl)piperazin-1-yl)phenoxy)acetic acid 2-(4-(4-(2-(5-amino-8-(furan-2-yl)-3H-dipyrazolo[1,5-c:4',3'-e]pyrimidin-3-yl)ethyl)piperazin-1-yl)phenoxy)acetamide 3-(4-(4-(2-(5-amino-8-(furan-2-yl)-3H-dipyrazolo[1,5-c:4',3'-e]pyrimidin-3-yl)ethyl)piperazin-1-yl)phenoxy)propane-1,2-diol 3-(2-(4-(4-(2-aminoethoxy)phenyl)piperazin-1-yl)ethyl)-8-(furan-2-yl)-3H-dipyrazolo[1,5-c:4',3'-e]pyrimidin-5-amine 4-(4-(2-(5-amino-8-(furan-2-yl)-3H-dipyrazolo[1,5-c:4',3'-e]pyrimidin-3-yl)ethyl)piperazin-1-yl)benzamide 4-(4-(2-(5-amino-8-(furan-2-yl)-3H-dipyrazolo[1,5-c:4',3'-e]pyrimidin-3-yl)ethyl)piperazin-1-yl)-N-methylbenzamide 8-(furan-2-yl)-3-(2-(4-(4-(2-morpholinoethoxy)phenyl)piperazin-1-yl)ethyl)-3H-dipyrazolo[1,5-c:4',3'-e]pyrimidin-5-amine 3-(2-(4-(4-(2-(dimethylamino)ethoxy)phenyl)piperazin-1-yl)ethyl)-8-(furan-2-yl)-3H-dipyrazolo[1,5-c:4',3'-e]pyrimidin-5-amine 4-(4-(2-(5-amino-8-(furan-2-yl)-3H-dipyrazolo[1,5-c:4',3'-e]pyrimidin-3-yl)ethyl)piperazin-1-yl)benzenesulfonamide 4-(4-(2-(5-amino-8-(furan-2-yl)-3H-dipyrazolo[1,5-c:4',3'-e]pyrimidin-3-yl)ethyl)piperazin-1-yl)-N-methylbenzenesulfonamide 8-(furan-2-yl)-3-(2-(4-(4-(methylsulfonyl)phenyl)piperazin-1-yl)ethyl)-3H-dipyrazolo[1,5-c:4',3'-e]pyrimidin-5-amine 8-(furan-2-yl)-3-(2-(4-(4-(methylsulfinyl)phenyl)piperazin-1-yl)ethyl)-3H-dipyrazolo[1,5-c:4',3'-e]pyrimidin-5-amine 3-(4-(2-(5-amino-8-(furan-2-yl)-3H-dipyrazolo[1,5-c:4',3'-e]pyrimidin-3-yl)ethyl)piperazin-1-yl)benzamide 2-(3-(4-(2-(5-amino-8-(furan-2-yl)-3H-dipyrazolo[1,5-c:4',3'-e]pyrimidin-3-yl)ethyl)piperazin-1-yl)phenoxy)ethanol 3-(2-(4-(4-(azetidin-3-yloxy)phenyl)piperazin-1-yl)ethyl)-8-(furan-2-yl)-3H-dipyrazolo[1,5-c:4',3'-e]pyrimidin-5-amine 3-(2-(4-(4-((2H-1,2,3-triazol-4-yl)methoxy)-2-fluorophenyl)piperazin-1-yl)ethyl)-8-(furan-2-yl)-3H-dipyrazolo[1,5-c:4',3'-e]pyrimidin-5-amine 5-((4-(4-(2-(5-amino-8-(furan-2-yl)-3H-dipyrazolo[1,5-c:4',3'-e]pyrimidin-3-yl)ethyl)piperazin-1-yl)-3-fluorophenoxy)methyl)-1,3,4-oxadiazol-2(3H)-one 2-(5-(4-(2-(5-amino-8-(furan-2-yl)-3H-dipyrazolo[1,5-c:4',3'-e]pyrimidin-3-yl)ethyl)piperazin-1-yl)-2,4-difluorophenoxy)acetamide (S)-3-(2-(4-(2-fluoro-4-(2-(methylsulfinyl)ethoxy)phenyl)piperazin-1-yl)ethyl)-8-(furan-2-yl)-3H-dipyrazolo[1,5-c:4',3'-e]pyrimidin-5-amine (R)-3-(2-(4-(2-fluoro-4-(2-(methylsulfinyl)ethoxy)phenyl)piperazin-1-yl)ethyl)-8-(furan-2-yl)-3H-dipyrazolo[1,5-c:4',3'-e]pyrimidin-5-amine 3-(2-(4-(2,4-difluoro-5-(2-(methylsulfinyl)ethoxy)phenyl)piperazin-1-yl)ethyl)-8-(furan-2-yl)-3H-dipyrazolo[1,5-c:4',3'-e]pyrimidin-5-amine 2-(4-(4-(2-(5-amino-8-(furan-2-yl)-3H-dipyrazolo[1,5-c:4',3'-e]pyrimidin-3-yl)ethyl)piperazin-1-yl)-3-fluorophenoxy)-1-(piperazin-1-yl)ethanone 3-(2-(4-(2-fluoro-4-(piperidin-4-ylmethoxy)phenyl)piperazin-1-yl)ethyl)-8-(furan-2-yl)-3H-dipyrazolo[1,5-c:4',3'-e]pyrimidin-5-amine (4-(4-(2-(5-amino-8-(furan-2-yl)-3H-dipyrazolo[1,5-c:4',3'-e]pyrimidin-3-yl)ethyl)piperazin-1-yl)-3-fluorophenyl)(piperazin-1-yl)methanone 3-(2-(4-(2-fluoro-4-(2-(piperazin-1-yl)ethoxy)phenyl)piperazin-1-yl)ethyl)-8-(furan-2-yl)-3H-dipyrazolo[1,5-c:4',3'-e]pyrimidin-5-amine 3-(2-(4-(2-fluoro-4-(piperazin-1-ylsulfonyl)phenyl)piperazin-1-yl)ethyl)-8-(furan-2-yl)-3H-dipyrazolo[1,5-c:4',3'-e]pyrimidin-5-amine 3-(2-(4-(2-fluoro-4-(methylsulfonyl)phenyl)piperazin-1-yl)ethyl)-8-(furan-2-yl)-3H-dipyrazolo[1,5-c:4',3'-e]pyrimidin-5-amine 4-(4-(2-(5-amino-8-(furan-2-yl)-3H-dipyrazolo[1,5-c:4',3'-e]pyrimidin-3-yl)ethyl)piperazin-1-yl)-N-(2-aminoethyl)-3-fluorobenzamide 4-(4-(2-(5-amino-8-(furan-2-yl)-3H-dipyrazolo[1,5-c:4',3'-e]pyrimidin-3-yl)ethyl)piperazin-1-yl)-3-fluoro-N-(2-(methylamino)ethyl)benzamide 4-(4-(2-(5-amino-8-(furan-2-yl)-3H-dipyrazolo[1,5-c:4',3'-e]pyrimidin-3-yl)ethyl)piperazin-1-yl)-N-(2-(dimethylamino)ethyl)-3-fluorobenzamide 4-(4-(2-(5-amino-8-(furan-2-yl)-3H-dipyrazolo[1,5-c:4',3'-e]pyrimidin-3-yl)ethyl)piperazin-1-yl)-3-fluoro-N-(2-hydroxyethyl)benzamide 4-(4-(2-(5-amino-8-(furan-2-yl)-3H-dipyrazolo[1,5-c:4',3'-e]pyrimidin-3-yl)ethyl)piperazin-1-yl)-N-(2,3-dihydroxypropyl)-3-fluorobenzamide 2-(4-(4-(2-(5-amino-8-(furan-2-yl)-3H-dipyrazolo[1,5-c:4',3'-e]pyrimidin-3-yl)ethyl)piperazin-1-yl)-3-fluorophenoxy)acetic acid 2-(4-(4-(2-(5-amino-8-(furan-2-yl)-3H-dipyrazolo[1,5-c:4',3'-e]pyrimidin-3-yl)ethyl)piperazin-1-yl)-3,5-difluorophenoxy)acetic acid 2-(4-(4-(2-(5-amino-8-(furan-2-yl)-3H-dipyrazolo[1,5-c:4',3'-e]pyrimidin-3-yl)ethyl)piperazin-1-yl)-3-fluorophenoxy)propanoic acid (S)-2-(4-(4-(2-(5-amino-8-(furan-2-yl)-3H-dipyrazolo[1,5-c:4',3'-e]pyrimidin-3-yl)ethyl)piperazin-1-yl)-3-fluorophenoxy)propanoic acid 2-(4-(4-(2-(5-amino-8-(furan-2-yl)-3H-dipyrazolo[1,5-c:4',3'-e]pyrimidin-3-yl)ethyl)piperazin-1-yl)-3-fluorophenoxy)-2-methylpropanoic acid 3-(4-(4-(2-(5-amino-8-(furan-2-yl)-3H-dipyrazolo[1,5-c:4',3'-e]pyrimidin-3-yl)ethyl)piperazin-1-yl)-3-fluorophenyl)propanoic acid 4-(4-(4-(2-(5-amino-8-(furan-2-yl)-3H-dipyrazolo[1,5-c:4',3'-e]pyrimidin-3-yl)ethyl)piperazin-1-yl)-3-fluorophenoxy)butanoic acid 2-(3-(4-(2-(5-amino-8-(furan-2-yl)-3H-dipyrazolo[1,5-c:4', 3'-e]pyrimidin-3-yl)ethyl)piperazin-1-yl)-2,6-difluorophenoxy)acetic acid 2-(5-(4-(2-(5-amino-8-(furan-2-yl)-3H-dipyrazolo[1,5-c:4', 3'-e]pyrimidin-3-yl)ethyl)piperazin-1-yl)-2,4-difluorophenoxy)acetic acid 4-(4-(2-(5-amino-8-(furan-2-yl)-3H-dipyrazolo[1,5-c:4',3'-e]pyrimidin-3-yl)ethyl)piperazin-1-yl)-3-fluorobenzoic acid 2-((2-(4-(4-(2-(5-amino-8-(furan-2-yl)-3H-dipyrazolo[1,5-c:4',3'-e]pyrimidin-3-yl)ethyl)piperazin-1-yl)-3-fluorophenoxy)ethyl)amino)acetamide 2-((2-(4-(4-(2-(5-amino-8-(furan-2-yl)-3H-dipyrazolo[1,5-c:4',3'-e]pyrimidin-3-yl)ethyl)piperazin-1-yl)-3-fluorophenoxy)ethyl)(methyl)amino)acetamide 3-(2-(4-(2-fluoro-4-(piperidin-4-yloxy)phenyl)piperazin-1-yl)ethyl)-8-(furan-2-yl)-3H-dipyrazolo[1,5-c:4',3'-e]pyrimidin-5-amine 3-(2-(4-(2-fluoro-4-(pyrrolidin-3-yloxy)phenyl)piperazin-1-yl)ethyl)-8-(furan-2-yl)-3H-dipyrazolo[1,5-c:4',3'-e]pyrimidin-5-amine 3-(2-(4-(4-((4H-1,2,4-triazol-3-yl)methoxy)-2-fluorophenyl)piperazin-1-yl)ethyl)-8-(furan-2-yl)-3H-dipyrazolo[1,5-c:4',3'-e]pyrimidin-5-amine 2-(4-(4-(2-(5-amino-8-(furan-2-yl)-3H-dipyrazolo[1,5-c:4', 3'-e]pyrimidin-3-yl)ethyl)piperazin-1-yl)-3-fluorophenoxy)-N-(2-(methylamino)ethyl)acetamide 2-(4-(4-(2-(5-amino-8-(furan-2-yl)-3H-dipyrazolo[1,5-c:4', 3'-e]pyrimidin-3-yl)ethyl)piperazin-1-yl)-3-fluorophenoxy)-N-(2-(dimethylamino)ethyl)acetamide 2-(4-(4-(2-(5-amino-8-(furan-2-yl)-3H-dipyrazolo[1,5-c:4', 3'-e]pyrimidin-3-yl)ethyl)piperazin-1-yl)-3-fluorophenoxy)-N-(2-aminoethyl)acetamide (R)-2-(4-(4-(2-(5-amino-8-(furan-2-yl)-3H-dipyrazolo[1,5-c:4',3'-e]pyrimidin-3-yl)ethyl)piperazin-1-yl)-3-fluorophenoxy)propanoic acid 2-(4-(4-(2-(5-amino-8-(furan-2-yl)-3H-dipyrazolo[1,5-c:4', 3'-e]pyrimidin-3-yl)ethyl)piperazin-1-yl)-3-fluorophenoxy)acetamide 4-(4-(2-(5-amino-8-(furan-2-yl)-3H-dipyrazolo[1,5-c:4',3'-e]pyrimidin-3-yl)ethyl)piperazin-1-yl)-3-fluoro-N-methyl-N-(2-(methylamino)ethyl)benzamide 4-(4-(2-(5-amino-8-(furan-2-yl)-3H-dipyrazolo[1,5-c:4',3'-e]pyrimidin-3-yl)ethyl)piperazin-1-yl)-N-(2-(dimethylamino)ethyl)-3-fluoro-N-methylbenzamide (R)-4-(4-(2-(5-amino-8-(furan-2-yl)-3H-dipyrazolo[1,5-c:4',3'-e]pyrimidin-3-yl)ethyl)piperazin-1-yl)-N-(1-(dimethylamino)propan-2-yl)-3-fluorobenzamide 2-(4-(4-(2-(5-amino-8-(furan-2-yl)-3H-dipyrazolo[1,5-c:4', 3'-e]pyrimidin-3-yl)ethyl)piperazin-1-yl)-3-fluorophenoxy)-N-methyl-N-(2-(methylamino)ethyl)acetamide 2-(5-(4-(2-(5-amino-8-(furan-2-yl)-3H-dipyrazolo[1,5-c:4', 3'-e]pyrimidin-3-yl)ethyl)piperazin-1-yl)-2,4-difluorophenoxy)-2-methylpropanoic acid (S)-2-(5-(4-(2-(5-amino-8-(furan-2-yl)-3H-dipyrazolo[1,5-c:4',3'-e]pyrimidin-3-yl)ethyl)piperazin-1-yl)-2,4-difluorophenoxy)propanoic acid (R)-2-(5-(4-(2-(5-amino-8-(furan-2-yl)-3H-dipyrazolo[1,5-c:4',3'-e]pyrimidin-3-yl)ethyl)piperazin-1-yl)-2,4-difluorophenoxy)propanoic acid 2-(5-(4-(2-(5-amino-8-(furan-2-yl)-3H-dipyrazolo[1,5-c:4', 3'-e]pyrimidin-3-yl)ethyl)piperazin-1-yl)-2,4-difluorophenoxy)-N-(2-(methylamino)ethyl)acetamide 2-(5-(4-(2-(5-amino-8-(furan-2-yl)-3H-dipyrazolo[1,5-c:4', 3'-e]pyrimidin-3-yl)ethyl)piperazin-1-yl)-2,4-difluorophenoxy)-N-(2-(dimethylamino)ethyl)acetamide 5-(4-(2-(5-amino-8-(furan-2-yl)-3H-dipyrazolo[1,5-c:4',3'-e]pyrimidin-3-yl)ethyl)piperazin-1-yl)-N-(2-(dimethylamino)ethyl)-2,4-difluoro-N-methylbenzamide 5-(4-(2-(5-amino-8-(furan-2-yl)-3H-dipyrazolo[1,5-c:4',3'-e]pyrimidin-3-yl)ethyl)piperazin-1-yl)-2,4-difluoro-N-methylbenzamide 4-(5-(4-(2-(5-amino-8-(furan-2-yl)-3H-dipyrazolo[1,5-c:4', 3'-e]pyrimidin-3-yl)ethyl)piperazin-1-yl)-2,4-difluorophenoxy)butanoic acid 3-(2-(4-(5-((1H-tetrazol-5-yl)methoxy)-2,4-difluorophenyl) piperazin-1-yl)ethyl)-8-(furan-2-yl)-3H-dipyrazolo[1,5-c:4',3'-e]pyrimidin-5-amine 3-(2-(4-(2-fluoro-4-((1-methyl-1H-1,2,4-triazol-3-yl)methoxy)phenyl)piperazin-1-yl)ethyl)-8-(furan-2-yl)-3H-dipyrazolo[1,5-c:4',3'-e]pyrimidin-5-amine 3-(2-(4-(2,4-difluoro-5-((1-methyl-1H-1,2,4-triazol-3-yl)methoxy)phenyl)piperazin-1-yl)ethyl)-8-(furan-2-yl)-3H-dipyrazolo[1,5-c:4',3'-e]pyrimidin-5-amine 4-(4-(2-(5-amino-8-(furan-2-yl)-3H-dipyrazolo[1,5-c:4',3'-e]pyrimidin-3-yl)ethyl)piperazin-1-yl)-3-fluoro-N-(2-(methyl(oxetan-3-yl)amino)ethyl)benzamide 4-(4-(2-(5-amino-8-(furan-2-yl)-3H-dipyrazolo[1,5-c:4',3'-e]pyrimidin-3-yl)ethyl)piperazin-1-yl)-3-fluoro-N-(2-((2-hydroxyethyl)amino)ethyl)benzamide 2-amino-N-(2-(4-(4-(2-(5-amino-8-(furan-2-yl)-3H-dipyrazolo[1,5-c:4',3'-e]pyrimidin-3-yl)ethyl)piperazin-1-yl)-3-fluorophenoxy)ethyl)acetamide (S)-2-amino-N-(2-(4-(4-(2-(5-amino-8-(furan-2-yl)-3H-dipyrazolo[1,5-c:4',3'-e]pyrimidin-3-yl)ethyl)piperazin-1-yl)-3-fluorophenoxy)ethyl)-3-methylbutanamide 3-(2-(4-(2,4-difluoro-5-(2-(methylsulfonyl)ethoxy)phenyl) piperazin-1-yl)ethyl)-8-(furan-2-yl)-3H-dipyrazolo[1,5-c:4',3'-e]pyrimidin-5-amine 3-(2-(4-(2-fluoro-4-(2-(methylsulfonyl)ethoxy)phenyl)piperazin-1-yl)ethyl)-8-(furan-2-yl)-3H-dipyrazolo[1,5-c:4', 3'-e]pyrimidin-5-amine 5-(4-(2-(5-amino-8-(furan-2-yl)-3H-dipyrazolo[1,5-c:4',3'-e]pyrimidin-3-yl)ethyl)piperazin-1-yl)-6-fluoroindolin-2-one 3-(2-(4-(2-fluoro-4-(S-methylsulfonimidoyl)phenyl)piperazin-1-yl)ethyl)-8-(furan-2-yl)-3H-dipyrazolo[1,5-c:4',3'-e]pyrimidin-5-amine 5-(4-(2-(5-amino-8-(furan-2-yl)-3H-dipyrazolo[1,5-c:4',3'-e]pyrimidin-3-yl)ethyl)piperazin-1-yl)-N-(2-(dimethylamino)ethyl)-2,4-difluorobenzamide (3R,4R)-4-(4-(4-(2-(5-amino-8-(furan-2-yl)-3H-dipyrazolo [1,5-c:4',3'-e]pyrimidin-3-yl)ethyl)piperazin-1-yl)-3-fluorophenoxy)tetrahydrofuran-3-ol (3S,4S)-4-(4-(4-(2-(5-amino-8-(furan-2-yl)-3H-dipyrazolo [1,5-c:4',3'-e]pyrimidin-3-yl)ethyl)piperazin-1-yl)-3-fluorophenoxy)tetrahydrofuran-3-ol 1-(4-(4-(2-(5-amino-8-(furan-2-yl)-3H-dipyrazolo[1,5-c:4', 3'-e]pyrimidin-3-yl)ethyl)piperazin-1-yl)-3-fluorophenoxy)-2-methylpropan-2-ol 2-(4-(4-(2-(5-amino-8-(furan-2-yl)-3H-dipyrazolo[1,5-c:4', 3'-e]pyrimidin-3-yl)ethyl)piperazin-1-yl)-3-fluorophenyl)propan-2-ol 3-(4-(4-(2-(5-amino-8-(furan-2-yl)-3H-dipyrazolo[1,5-c:4', 3'-e]pyrimidin-3-yl)ethyl)piperazin-1-yl)-3-fluorophenoxy)-1,1,1-trifluoropropan-2-ol 2-(3-(4-(2-(5-amino-8-(furan-2-yl)-3H-dipyrazolo[1,5-c:4', 3'-e]pyrimidin-3-yl)ethyl)piperazin-1-yl)-4-fluorophenoxy)ethanol 3-(2-(4-(2,4-difluoro-5-(morpholin-2-ylmethoxy)phenyl) piperazin-1-yl)ethyl)-8-(furan-2-yl)-3H-dipyrazolo[1,5-c:4',3'-e]pyrimidin-5-amine 3-(2-(4-(2,4-difluoro-5-(morpholin-3-ylmethoxy)phenyl)
piperazin-1-yl)ethyl)-8-(furan-2-yl)-3H-dipyrazolo[1,5-
c:4',3'-e]pyrimidin-5-amine
3-(2-(4-(2,4-difluoro-5-(((3 S,4S)-4-fluoropyrrolidin-3-yl)
oxy)phenyl)piperazin-1-yl)ethyl)-8-(furan-2-yl)-3H-
dipyrazolo[1,5-c:4',3'-e]pyrimidin-5-amine
3-(2-(4-(2,4-difluoro-5-(((3R,4S)-4-fluoropyrrolidin-3-yl)
oxy)phenyl)piperazin-1-yl)ethyl)-8-(furan-2-yl)-3H-
dipyrazolo[1,5-c:4',3'-e]pyrimidin-5-amine
3-(2-(4-(2,4-difluoro-5-(((3S,4R)-4-fluoropyrrolidin-3-yl)
oxy)phenyl)piperazin-1-yl)ethyl)-8-(furan-2-yl)-3H-
dipyrazolo[1,5-c:4',3'-e]pyrimidin-5-amine
(S)-3-(5-(4-(2-(5-amino-8-(furan-2-yl)-3H-dipyrazolo[1,5-
c:4',3'-e]pyrimidin-3-yl)ethyl)piperazin-1-yl)-2,4-difluo-
rophenoxy)pyrrolidin-2-one
(R)-3-(5-(4-(2-(5-amino-8-(furan-2-yl)-3H-dipyrazolo[1,5-
c:4',3'-e]pyrimidin-3-yl)ethyl)piperazin-1-yl)-2,4-difluo-
rophenoxy)pyrrolidin-2-one
2-(5-(4-(2-(5-amino-8-(furan-2-yl)-3H-dipyrazolo[1,5-c:4',
3'-e]pyrimidin-3-yl)ethyl)piperazin-1-yl)-2,4-difluoro-
phenoxy)-N-(2-morpholinoethyl)acetamide
5-(4-(2-(5-amino-8-(furan-2-yl)-3H-dipyrazolo[1,5-c:4',3'-
e]pyrimidin-3-yl)ethyl)piperazin-1-yl)-2,4-difluoro-N-
(morpholin-3-ylmethyl)benzamide
3-(2-(4-(2-fluoro-4-(morpholin-3-ylmethoxy)phenyl)piper-
azin-1-yl)ethyl)-8-(furan-2-yl)-3H-dipyrazolo[1,5-c:4',3'-
e]pyrimidin-5-amine
3-(2-(4-(2-fluoro-4-(morpholin-2-ylmethoxy)phenyl)piper-
azin-1-yl)ethyl)-8-(furan-2-yl)-3H-dipyrazolo[1,5-c:4',3'-
e]pyrimidin-5-amine
3-(2-(4-(2-fluoro-4-(((3R,4R)-4-fluoropyrrolidin-3-yl)oxy)
phenyl)piperazin-1-yl)ethyl)-8-(furan-2-yl)-3H-dipyra-
zolo[1,5-c:4',3'-e]pyrimidin-5-amine
3-(2-(4-(2-fluoro-4-(((3 S,4S)-4-fluoropyrrolidin-3-yl)oxy)
phenyl)piperazin-1-yl)ethyl)-8-(furan-2-yl)-3H-dipyra-
zolo[1,5-c:4',3'-e]pyrimidin-5-amine
3-(2-(4-(2-fluoro-4-(((3R,4S)-4-fluoropyrrolidin-3-yl)oxy)
phenyl)piperazin-1-yl)ethyl)-8-(furan-2-yl)-3H-dipyra-
zolo[1,5-c:4',3'-e]pyrimidin-5-amine
3-(2-(4-(2-fluoro-4-(((3S,4R)-4-fluoropyrrolidin-3-yl)oxy)
phenyl)piperazin-1-yl)ethyl)-8-(furan-2-yl)-3H-dipyra-
zolo[1,5-c:4',3'-e]pyrimidin-5-amine
2-(4-(2-(5-amino-8-(furan-2-yl)-3H-dipyrazolo[1,5-c:4',
3'-e]pyrimidin-3-yl)ethyl)piperazin-1-yl)-3-fluorophe-
noxy)-N-(2-morpholinoethyl)acetamide
4-(4-(2-(5-amino-8-(furan-2-yl)-3H-dipyrazolo[1,5-c:4',3'-
e]pyrimidin-3-yl)ethyl)piperazin-1-yl)-3-fluoro-N-(2-
morpholinoethyl)benzamide
4-(4-(2-(5-amino-8-(furan-2-yl)-3H-dipyrazolo[1,5-c:4',3'-
e]pyrimidin-3-yl)ethyl)piperazin-1-yl)-3-fluoro-N-(mor-
pholin-3-ylmethyl)benzamide
(S)-3-(2-(4-(2,4-difluoro-5-(methylsulfinyl)phenyl)piper-
azin-1-yl)ethyl)-8-(furan-2-yl)-3H-dipyrazolo[1,5-c:4',3'-
e]pyrimidin-5-amine
(R)-3-(2-(4-(2,4-difluoro-5-(methylsulfinyl)phenyl)piper-
azin-1-yl)ethyl)-8-(furan-2-yl)-3H-dipyrazolo[1,5-c:4',3'-
e]pyrimidin-5-amine
(1s,4s)-4-(5-(4-(2-(5-amino-8-(furan-2-yl)-3H-dipyrazolo
[1,5-c:4',3'-e]pyrimidin-3-yl)ethyl)piperazin-1-yl)-2,4-di-
fluorophenoxy)tetrahydro-2H-thiopyran 1-oxide
(1r,4r)-4-(5-(4-(2-(5-amino-8-(furan-2-yl)-3H-dipyrazolo[1,
5-c:4',3'-e]pyrimidin-3-yl)ethyl)piperazin-1-yl)-2,4-dif-
luorophenoxy)tetrahydro-2H-thiopyran 1-oxide
(S)-5-(4-(2-(5-amino-8-(furan-2-yl)-3H-dipyrazolo[1,5-c:4',
3'-e]pyrimidin-3-yl)ethyl)piperazin-1-yl)-2,4-difluoro-N-
(2-(methylsulfinyl)ethyl)benzamide (R)-5-(4-(2-(5-amino-8-(furan-2-yl)-3H-dipyrazolo[1,5-c:
4',3'-e]pyrimidin-3-yl)ethyl)piperazin-1-yl)-2,4-difluoro-
N-(2-(methylsulfinyl)ethyl)benzamide
(S)-5-(4-(2-(5-amino-8-(furan-2-yl)-3H-dipyrazolo[1,5-c:4',
3'-e]pyrimidin-3-yl)ethyl)piperazin-1-yl)-2,4-difluoro-N-
methyl-N-(2-(methylsulfinyl)ethyl)benzamide
(R)-5-(4-(2-(5-amino-8-(furan-2-yl)-3H-dipyrazolo[1,5-c:
4',3'-e]pyrimidin-3-yl)ethyl)piperazin-1-yl)-2,4-difluoro-
N-methyl-N-(2-(methylsulfinyl)ethyl)benzamide
(5-(4-(2-(5-amino-8-(furan-2-yl)-3H-dipyrazolo[1,5-c:4',3'-
e]pyrimidin-3-yl)ethyl)piperazin-1-yl)-2,4-difluorophe-
nyl)(1-oxidothiomorpholino)methanone
4-(5-(4-(2-(5-amino-8-(furan-2-yl)-3H-dipyrazolo[1,5-c:4',
3'-e]pyrimidin-3-yl)ethyl)piperazin-1-yl)-2,4-difluoro-
phenyl)thiomorpholine 1-oxide
(R)-3-(2-(4-(2-fluoro-4-(methylsulfinyl)phenyl)piperazin-
1-yl)ethyl)-8-(furan-2-yl)-3H-dipyrazolo[1,5-c:4',3'-e]
pyrimidin-5-amine
(S)-3-(2-(4-(2-fluoro-4-(methylsulfinyl)phenyl)piperazin-1-
yl)ethyl)-8-(furan-2-yl)-3H-dipyrazolo[1,5-c:4',3'-e]py-
rimidin-5-amine
(1s,4s)-4-(4-(4-(2-(5-amino-8-(furan-2-yl)-3H-dipyrazolo
[1,5-c:4',3'-e]pyrimidin-3-yl)ethyl)piperazin-1-yl)-3-
fluorophenoxy)tetrahydro-2H-thiopyran 1-oxide
(1r,4r)-4-(4-(4-(2-(5-amino-8-(furan-2-yl)-3H-dipyrazol[1,
5-c:4',3'-e]pyrimidin-3-yl)ethyl)piperazin-1-yl)-3-fluoro-
phenoxy)tetrahydro-2H-thiopyran 1-oxide
(S)-4-(4-(2-(5-amino-8-(furan-2-yl)-3H-dipyrazolo[1,5-c:4',
3'-e]pyrimidin-3-yl)ethyl)piperazin-1-yl)-3-fluoro-N-(2-
(methylsulfinyl)ethyl)benzamide
(R)-4-(4-(2-(5-amino-8-(furan-2-yl)-3H-dipyrazolo[1,5-c:
4',3'-e]pyrimidin-3-yl)ethyl)piperazin-1-yl)-3-fluoro-N-
(2-(methylsulfinyl)ethyl)benzamide
(4-(4-(2-(5-amino-8-(furan-2-yl)-3H-dipyrazolo[1,5-c:4',3'-
e]pyrimidin-3-yl)ethyl)piperazin-1-yl)-3-fluorophenyl)
(1-oxidothiomorpholino)methanone
4-(4-(4-(2-(5-amino-8-(furan-2-yl)-3H-dipyrazolo[1,5-c:4',
3'-e]pyrimidin-3-yl)ethyl)piperazin-1-yl)-3-fluorophenyl)
thiomorpholine 1-oxide
(S)-3-(5-(4-(2-(5-amino-8-(furan-2-yl)-3H-dipyrazolo[1,5-
c:4',3'-e]pyrimidin-3-yl)ethyl)piperazin-1-yl)-2,4-difluo-
rophenoxy)propane-1,2-diol
(R)-3-(5-(4-(2-(5-amino-8-(furan-2-yl)-3H-dipyrazolo[1,5-
c:4',3'-e]pyrimidin-3-yl)ethyl)piperazin-1-yl)-2,4-difluo-
rophenoxy)propane-1,2-diol
(S)-5-(4-(2-(5-amino-8-(furan-2-yl)-3H-dipyrazolo[1,5-c:4',
3'-e]pyrimidin-3-yl)ethyl)piperazin-1-yl)-N-(2,3-dihy-
droxypropyl)-2,4-difluorobenzamide
(R)-5-(4-(2-(5-amino-8-(furan-2-yl)-3H-dipyrazolo[1,5-c:
4',3'-e]pyrimidin-3-yl)ethyl)piperazin-1-yl)-N-(2,3-dihy-
droxypropyl)-2,4-difluorobenzamide
3-(2-(4-(4-(azetidin-3-yloxy)-2-fluorophenyl)piperazin-1-
yl)ethyl)-8-(furan-2-yl)-3H-dipyrazolo[1,5-c:4',3'-e]py-
rimidin-5-amine
3-(2-(4-(5-(azetidin-3-yloxy)-2,4-difluorophenyl)piperazin-
1-yl)ethyl)-8-(furan-2-yl)-3H-dipyrazolo[1,5-c:4',3'-e]
pyrimidin-5-amine
(S)-3-(2-(4-(2,4-difluoro-5-(3-(methylsulfinyl)propoxy)
phenyl)piperazin-1-yl)ethyl)-8-(furan-2-yl)-3H-dipyra-
zolo[1,5-c:4',3'-e]pyrimidin-5-amine
Heteroaryl Scaffold (11)
5-amino-8-(furan-2-yl)-3-(2-(4-(4-(2-hydroxyethoxy)phe-
nyl)piperazin-1-yl)ethyl)pyrazolo[1,5-c]thiazolo[5,4-e]
pyrimidin-2(3H)-one
2-(4-(4-(2-(5-amino-8-(furan-2-yl)-2-oxopyrazolo[1,5-c]
thiazolo[5,4-e]pyrimidin-3(2H)-yl)ethyl)piperazin-1-yl)
phenoxy)acetic acid 2-(4-(4-(2-(5-amino-8-(furan-2-yl)-2-oxopyrazolo[1,5-c]thiazolo[5,4-e]pyrimidin-3(2H)-yl)ethyl)piperazin-1-yl)phenoxy)acetamide 5-amino-3-(2-(4-(4-(2,3-dihydroxypropoxy)phenyl)piperazin-1-yl)ethyl)-8-(furan-2-yl)pyrazolo[1,5-c]thiazolo[5,4-e]pyrimidin-2(3H)-one 5-amino-3-(2-(4-(4-(2-aminoethoxy)phenyl)piperazin-1-yl)ethyl)-8-(furan-2-yl)pyrazolo[1,5-c]thiazolo[5,4-e]pyrimidin-2(3H)-one 4-(4-(2-(5-amino-8-(furan-2-yl)-2-oxopyrazolo[1,5-c]thiazolo[5,4-e]pyrimidin-3(2H)-yl)ethyl)piperazin-1-yl)benzamide 4-(4-(2-(5-amino-8-(furan-2-yl)-2-oxopyrazolo[1,5-c]thiazolo[5,4-e]pyrimidin-3(2H)-yl)ethyl)piperazin-1-yl)-N-methylbenzamide 5-amino-8-(furan-2-yl)-3-(2-(4-(4-(2-morpholinoethoxy)phenyl)piperazin-1-yl)ethyl)pyrazolo[1,5-c]thiazolo[5,4-e]pyrimidin-2(3H)-one 5-amino-3-(2-(4-(4-(2-(dimethylamino)ethoxy)phenyl)piperazin-1-yl)ethyl)-8-(furan-2-yl)pyrazolo[1,5-c]thiazolo[5,4-e]pyrimidin-2(3H)-one 4-(4-(2-(5-amino-8-(furan-2-yl)-2-oxopyrazolo[1,5-c]thiazolo[5,4-e]pyrimidin-3(2H)-yl)ethyl)piperazin-1-yl)benzenesulfonamide 4-(4-(2-(5-amino-8-(furan-2-yl)-2-oxopyrazolo[1,5-c]thiazolo[5,4-e]pyrimidin-3(2H)-yl)ethyl)piperazin-1-yl)-N-methylbenzenesulfonamide 5-amino-8-(furan-2-yl)-3-(2-(4-(4-(methylsulfonyl)phenyl)piperazin-1-yl)ethyl)pyrazolo[1,5-c]thiazolo[5,4-e]pyrimidin-2(3H)-one 5-amino-8-(furan-2-yl)-3-(2-(4-(4-(methylsulfinyl)phenyl)piperazin-1-yl)ethyl)pyrazolo[1,5-c]thiazolo[5,4-e]pyrimidin-2(3H)-one 3-(4-(2-(5-amino-8-(furan-2-yl)-2-oxopyrazolo[1,5-c]thiazolo[5,4-e]pyrimidin-3(2H)-yl)ethyl)piperazin-1-yl)benzamide 5-amino-8-(furan-2-yl)-3-(2-(4-(3-(2-hydroxyethoxy)phenyl)piperazin-1-yl)ethyl)pyrazolo[1,5-c]thiazolo[5,4-e]pyrimidin-2(3H)-one 5-amino-3-(2-(4-(4-(azetidin-3-yloxy)phenyl)piperazin-1-yl)ethyl)-8-(furan-2-yl)pyrazolo[1,5-c]thiazolo[5,4-e]pyrimidin-2(3H)-one 3-(2-(4-(4-((2H-1,2,3-triazol-4-yl)methoxy)-2-fluorophenyl)piperazin-1-yl)ethyl)-5-amino-8-(furan-2-yl)pyrazolo[1,5-c]thiazolo[5,4-e]pyrimidin-2(3H)-one 5-((4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenoxy)methyl)-1,3,4-oxadiazol-2(3H)-one 2-(5-(4-(2-(5-amino-8-(furan-2-yl)-2-oxopyrazolo[1,5-c]thiazolo[5,4-e]pyrimidin-3(2H)-yl)ethyl)piperazin-1-yl)-2,4-difluorophenoxy)acetamide (S)-5-amino-3-(2-(4-(2-fluoro-4-(2-(methylsulfinyl)ethoxy)phenyl)piperazin-1-yl)ethyl)-8-(furan-2-yl)pyrazolo[1,5-c]thiazolo[5,4-e]pyrimidin-2(3H)-one (R)-5-amino-3-(2-(4-(2-fluoro-4-(2-(methylsulfinyl)ethoxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2,4-difluoro-5-(2-(methylsulfinyl)ethoxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(2-oxo-2-(piperazin-1-yl)ethoxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(piperidin-4-ylmethoxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(piperazine-1-carbonyl)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(2-(piperazin-1-yl)ethoxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(piperazin-1-ylsulfonyl)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(methylsulfonyl)phenyl)piperazin-1-yl)ethyl)-8-(furan-2-yl)pyrazolo[1,5-c]thiazolo[5,4-e]pyrimidin-2(3H)-one 4-(4-(2-(5-amino-8-(furan-2-yl)-2-oxopyrazolo[1,5-c]thiazolo[5,4-e]pyrimidin-3(2H)-yl)ethyl)piperazin-1-yl)-N-(2-aminoethyl)-3-fluorobenzamide 4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluoro-N-(2-(methylamino)ethyl)benzamide 4-(4-(2-(5-amino-8-(furan-2-yl)-2-oxopyrazolo[1,5-c]thiazolo[5,4-e]pyrimidin-3(2H)-yl)ethyl)piperazin-1-yl)-N-(2-(dimethylamino)ethyl)-3-fluorobenzamide 4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluoro-N-(2-hydroxyethyl)benzamide 4-(4-(2-(5-amino-8-(furan-2-yl)-2-oxopyrazolo[1,5-c]thiazolo[5,4-e]pyrimidin-3(2H)-yl)ethyl)piperazin-1-yl)-N-(2,3-dihydroxypropyl)-3-fluorobenzamide 2-(4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenoxy)acetic acid 2-(4-(4-(2-(5-amino-8-(furan-2-yl)-2-oxopyrazolo[1,5-c]thiazolo[5,4-e]pyrimidin-3(2H)-yl)ethyl)piperazin-1-yl)-3,5-difluorophenoxy)acetic acid 2-(4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenoxy)propanoic acid (S)-2-(4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenoxy)propanoic acid 2-(4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenoxy)-2-methylpropanoic acid 3-(4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenyl)propanoic acid 4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenoxy)butanoic acid 2-(3-(4-(2-(5-amino-8-(furan-2-yl)-2-oxopyrazolo[1,5-c]thiazolo[5,4-e]pyrimidin-3(2H)-yl)ethyl)piperazin-1-yl)-2,6-difluorophenoxy)acetic acid 2-(5-(4-(2-(5-amino-8-(furan-2-yl)-2-oxopyrazolo[1,5-c]thiazolo[5,4-e]pyrimidin-3(2H)-yl)ethyl)piperazin-1-yl)-2,4-difluorophenoxy)acetic acid 4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorobenzoic acid 2-((2-(4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenoxy)ethyl)amino)acetamide 2-((2-(4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenoxy)ethyl)(methyl)amino)acetamide 5-amino-3-(2-(4-(2-fluoro-4-(piperidin-4-yloxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(pyrrolidin-3-yloxy)phenyl)piperazin-1-yl)ethyl)-8-(furan-2-yl)pyrazolo[1,5-c]thiazolo[5,4-e]pyrimidin-2(3H)-one 3-(2-(4-(4-((4H-1,2,4-triazol-3-yl)methoxy)-2-fluorophenyl)piperazin-1-yl)ethyl)-5-amino-8-(furan-2-yl)pyrazolo[1,5-c]thiazolo[5,4-e]pyrimidin-2(3H)-one 2-(4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenoxy)-N-(2-(methylamino)ethyl)acetamide 2-(4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenoxy)-N-(2-(dimethylamino)ethyl)acetamide 2-(4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenoxy)-N-(2-aminoethyl)acetamide (R)-2-(4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenoxy)propanoic acid 2-(4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenoxy)acetamide 4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluoro-N-methyl-N-(2-(methylamino)ethyl)benzamide 4-(4-(2-(5-amino-8-(furan-2-yl)-2-oxopyrazolo[1,5-c]thiazolo[5,4-e]pyrimidin-3(2H)-yl)ethyl)piperazin-1-yl)-N-(2-(dimethylamino)ethyl)-3-fluoro-N-methylbenzamide (R)-4-(4-(2-(5-amino-8-(furan-2-yl)-2-oxopyrazolo[1,5-c]thiazolo[5,4-e]pyrimidin-3(2H)-yl)ethyl)piperazin-1-yl)-N-(1-(dimethylamino)propan-2-yl)-3-fluorobenzamide 2-(4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenoxy)-N-methyl-N-(2-(methylamino)ethyl)acetamide 2-(5-(4-(2-(5-amino-8-(furan-2-yl)-2-oxopyrazolo[1,5-c]thiazolo[5,4-e]pyrimidin-3(2H)-yl)ethyl)piperazin-1-yl)-2,4-difluorophenoxy)-2-methylpropanoic acid (S)-2-(5-(4-(2-(5-amino-8-(furan-2-yl)-2-oxopyrazolo[1,5-c]thiazolo[5,4-e]pyrimidin-3(2H)-yl)ethyl)piperazin-1-yl)-2,4-difluorophenoxy)propanoic acid (R)-2-(5-(4-(2-(5-amino-8-(furan-2-yl)-2-oxopyrazolo[1,5-c]thiazolo[5,4-e]pyrimidin-3(2H)-yl)ethyl)piperazin-1-yl)-2,4-difluorophenoxy)propanoic acid 2-(5-(4-(2-(5-amino-8-(furan-2-yl)-2-oxopyrazolo[1,5-c]thiazolo[5,4-e]pyrimidin-3(2H)-yl)ethyl)piperazin-1-yl)-2,4-difluorophenoxy)-N-(2-(methylamino)ethyl)acetamide 2-(5-(4-(2-(5-amino-8-(furan-2-yl)-2-oxopyrazolo[1,5-c]thiazolo[5,4-e]pyrimidin-3(2H)-yl)ethyl)piperazin-1-yl)-2,4-difluorophenoxy)-N-(2-(dimethylamino)ethyl)acetamide 5-(4-(2-(5-amino-8-(furan-2-yl)-2-oxopyrazolo[1,5-c]thiazolo[5,4-e]pyrimidin-3(2H)-yl)ethyl)piperazin-1-yl)-N-(2-(dimethylamino)ethyl)-2,4-difluoro-N-methylbenzamide 5-(4-(2-(5-amino-8-(furan-2-yl)-2-oxopyrazolo[1,5-c]thiazolo[5,4-e]pyrimidin-3(2H)-yl)ethyl)piperazin-1-yl)-2,4-difluoro-N-methylbenzamide 4-(5-(4-(2-(5-amino-8-(furan-2-yl)-2-oxopyrazolo[1,5-c]thiazolo[5,4-e]pyrimidin-3(2H)-yl)ethyl)piperazin-1-yl)-2,4-difluorophenoxy)butanoic acid 3-(2-(4-(5-(((1H-tetrazol-5-yl)methoxy)-2,4-difluorophenyl)piperazin-1-yl)ethyl)-5-amino-8-(furan-2-yl)pyrazolo[1,5-c]thiazolo[5,4-e]pyrimidin-2(3H)-one 5-amino-3-(2-(4-(2-fluoro-4-((1-methyl-1H-1,2,4-triazol-3-yl)methoxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2,4-difluoro-5-((1-methyl-1H-1,2,4-triazol-3-yl)methoxy)phenyl)piperazin-1-yl)ethyl)-8-(furan-2-yl)pyrazolo[1,5-c]thiazolo[5,4-e]pyrimidin-2(3H)-one 4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluoro-N-(2-(methyl(oxetan-3-yl)amino)ethyl)benzamide 4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluoro-N-(2-((2-hydroxyethyl)amino)ethyl)benzamide 2-amino-N-(2-(4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenoxy)ethyl)acetamide (S)-2-amino-N-(2-(4-(4-(2-(5-amino-8-(furan-2-yl)-2-oxopyrazolo[1,5-c]thiazolo[5,4-e]pyrimidin-3 (2H)-yl)ethyl)piperazin-1-yl)-3-fluorophenoxy)ethyl)-3-methylbutanamide 5-amino-3-(2-(4-(2,4-difluoro-5-(2-(methylsulfonyl)ethoxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(2-(methylsulfonyl)ethoxy)phenyl)piperazin-1-yl)ethyl)-8-(furan-2-yl)pyrazolo[1,5-c]thiazolo[5,4-e]pyrimidin-2(3H)-one 5-amino-3-(2-(4-(6-fluoro-2-oxoindolin-5-yl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(S-methylsulfonimidoyl)phenyl)piperazin-1-yl)ethyl)-8-(furan-2-yl)pyrazolo[1,5-c]thiazolo[5,4-e]pyrimidin-2(3H)-one 5-(4-(2-(5-amino-8-(furan-2-yl)-2-oxopyrazolo[1,5-c]thiazolo[5,4-e]pyrimidin-3(2H)-yl)ethyl)piperazin-1-yl)-N-(2-(dimethylamino)ethyl)-2,4-difluorobenzamide 5-amino-3-(2-(4-(2-fluoro-4-(((3R,4R)-4-hydroxytetrahydrofuran-3-yl)oxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(((3 S,4S)-4-hydroxytetrahydrofuran-3-yl)oxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(2-hydroxy-2-methylpropoxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(2-hydroxypropan-2-yl)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(3,3,3-trifluoro-2-hydroxypropoxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-5-(2-hydroxyethoxy)phenyl)piperazin-1-yl)ethyl)-8-(furan-2-yl)pyrazolo[5,4-e]pyrimidin-2(3H)-one 5-amino-3-(2-(4-(2,4-difluoro-5-(morpholin-2-ylmethoxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2,4-difluoro-5-(morpholin-3-ylmethoxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2,4-difluoro-5-(((3 S,4S)-4-fluoropyrrolidin-3-yl)oxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2,4-difluoro-5-(((3R,4S)-4-fluoropyrrolidin-3-yl)oxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2,4-difluoro-5-(((3 S,4R)-4-fluoropyrrolidin-3-yl)oxy)phenyl)piperazin-1-yl)ethyl)-8-(furan-2-yl)pyrazolo[1,5-c]thiazolo[5,4-e]pyrimidin-2(3H)-one (S)-5-amino-3-(2-(4-(2,4-difluoro-5-((2-oxopyrrolidin-3-yl)oxy)phenyl)piperazin-1-yl)ethyl)-8-(furan-2-yl)pyrazolo[1,5-c]thiazolo[5,4-e]pyrimidin-2(3H)-one (R)-5-amino-3-(2-(4-(2,4-difluoro-5-((2-oxopyrrolidin-3-yl)oxy)phenyl)piperazin-1-yl)ethyl)-8-(furan-2-yl)pyrazolo[1,5-c]thiazolo[5,4-e]pyrimidin-2(3H)-one 2-(5-(4-(2-(5-amino-8-(furan-2-yl)-2-oxopyrazolo[1,5-c]thiazolo[5,4-e]pyrimidin-3(2H)-yl)ethyl)piperazin-1-yl)-2,4-difluorophenoxy)-N-(2-morpholinoethyl)acetamide 5-(4-(2-(5-amino-8-(furan-2-yl)-2-oxopyrazolo[1,5-c]thiazolo[5,4-e]pyrimidin-3(2H)-yl)ethyl)piperazin-1-yl)-2,4-difluoro-N-(morpholin-3-ylmethyl)benzamide 5-amino-3-(2-(4-(2-fluoro-4-(morpholin-3-ylmethoxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(morpholin-2-ylmethoxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(((3R,4R)-4-fluoropyrrolidin-3-yl)oxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(((3 S,4S)-4-fluoropyrrolidin-3-yl)oxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(((3R,4S)-4-fluoropyrrolidin-3-yl)oxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(((3 S,4R)-4-fluoropyrrolidin-3-yl)oxy)phenyl)piperazin-1-yl)ethyl)-8-(furan-2-yl)pyrazolo[1,5-c]thiazolo[5,4-e]pyrimidin-2(3H)-one 2-(4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluorophenoxy)-N-(2-morpholinoethyl)acetamide 4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluoro-N-(2-morpholinoethyl)benzamide 4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluoro-N-(morpholin-3-ylmethyl)benzamide (S)-5-amino-3-(2-(4-(2,4-difluoro-5-(methylsulfinyl)phenyl)piperazin-1-yl)ethyl)-8-(furan-2-yl)pyrazolo[1,5-c]thiazolo[5,4-e]pyrimidin-2(3H)-one (R)-5-amino-3-(2-(4-(2,4-difluoro-5-(methylsulfinyl)phenyl)piperazin-1-yl)ethyl)-8-(furan-2-yl)pyrazolo[1,5-c]thiazolo[5,4-e]pyrimidin-2(3H)-one 5-amino-3-(2-(4-(2,4-difluoro-5-(((1s,4s)-1-oxidotetrahydro-2H-thiopyran-4-yl)oxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2,4-difluoro-5-(((1r,4r)-1-oxidotetrahydro-2H-thiopyran-4-yl)oxy)phenyl)piperazin-1-yl)ethyl)-8-(furan-2-yl)pyrazolo[1,5-c]thiazolo[5,4-e]pyrimidin-2(3H)-one (S)-5-(4-(2-(5-amino-8-(furan-2-yl)-2-oxopyrazolo[1,5-c]thiazolo[5,4-e]pyrimidin-3(2H)-yl)ethyl)piperazin-1-yl)-2,4-difluoro-N-(2-(methylsulfinyl)ethyl)benzamide (R)-5-(4-(2-(5-amino-8-(furan-2-yl)-2-oxopyrazolo[1,5-c]thiazolo[5,4-e]pyrimidin-3(2H)-yl)ethyl)piperazin-1-yl)-2,4-difluoro-N-(2-(methylsulfinyl)ethyl)benzamide (S)-5-(4-(2-(5-amino-8-(furan-2-yl)-2-oxopyrazolo[1,5-c]thiazolo[5,4-e]pyrimidin-3(2H)-yl)ethyl)piperazin-1-yl)-2,4-difluoro-N-methyl-N-(2-(methylsulfinyl)ethyl)benzamide (R)-5-(4-(2-(5-amino-8-(furan-2-yl)-2-oxopyrazolo[1,5-c]thiazolo[5,4-e]pyrimidin-3(2H)-yl)ethyl)piperazin-1-yl)-2,4-difluoro-N-methyl-N-(2-(methylsulfinyl)ethyl)benzamide 5-amino-3-(2-(4-(2,4-difluoro-5-(1-oxidothiomorpholine-4-carbonyl)phenyl)piperazin-1-yl)ethyl)-8-(furan-2-yl)pyrazolo[1,5-c]thiazolo[5,4-e]pyrimidin-2(3H)-one 5-amino-3-(2-(4-(2,4-difluoro-5-(1-oxidothiomorpholino)phenyl)piperazin-1-yl)ethyl)-8-(furan-2-yl)pyrazolo[1,5-c]thiazolo[5,4-e]pyrimidin-2(3H)-one (R)-5-amino-3-(2-(4-(2-fluoro-4-(methylsulfinyl)phenyl)piperazin-1-yl)ethyl)-8-(furan-2-yl)pyrazolo[1,5-c]thiazolo[5,4-e]pyrimidin-2(3H)-one (S)-5-amino-3-(2-(4-(2-fluoro-4-(methylsulfinyl)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(((1s,4s)-1-oxidotetrahydro-2H-thiopyran-4-yl)oxy)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(((1r,4r)-1-oxidotetrahydro-2H-thiopyran-4-yl)oxy)phenyl)piperazin-1-yl)ethyl)-8-(furan-2-yl)pyrazolo[1,5-c]thiazolo[5,4-e]pyrimidin-2(3H)-one (S)-4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluoro-N-(2-(methylsulfinyl)ethyl)benzamide (R)-4-(4-(2-(5-amino-8-(furan-2-yl)-2-oxopyrazolo[1,5-c]thiazolo[5,4-e]pyrimidin-3(2H)-yl)ethyl)piperazin-1-yl)-3-fluoro-N-(2-(methylsulfinyl)ethyl)benzamide 5-amino-3-(2-(4-(2-fluoro-4-(1-oxidothiomorpholine-4-carbonyl)phenyl)piperazin-1-yl)ethyl)-8-(furan-2-yl)pyrazolo[1,5-c]thiazolo[5,4-e]pyrimidin-2(3H)-one 5-amino-3-(2-(4-(2-fluoro-4-(1-oxidothiomorpholino)phenyl)piperazin-1-yl)ethyl)-8-(furan-2-yl)pyrazolo[1,5-c]thiazolo[5,4-e]pyrimidin-2(3H)-one (S)-5-amino-3-(2-(4-(5-(2,3-dihydroxypropoxy)-2,4-difluorophenyl)piperazin-1-yl)ethyl)-8-(furan-2-yl)pyrazolo[1,5-c]thiazolo[5,4-e]pyrimidin-2(3H)-one (R)-5-amino-3-(2-(4-(5-(2,3-dihydroxypropoxy)-2,4-difluorophenyl)piperazin-1-yl)ethyl)-8-(furan-2-yl)pyrazolo[1,5-c]thiazolo[5,4-e]pyrimidin-2(3H)-one (S)-5-(4-(2-(5-amino-8-(furan-2-yl)-2-oxopyrazolo[1,5-c]thiazolo[5,4-e]pyrimidin-3(2H)-yl)ethyl)piperazin-1-yl)-N-(2,3-dihydroxypropyl)-2,4-difluorobenzamide (R)-5-(4-(2-(5-amino-8-(furan-2-yl)-2-oxopyrazolo[1,5-c]thiazolo[5,4-e]pyrimidin-3(2H)-yl)ethyl)piperazin-1-yl)-N-(2,3-dihydroxypropyl)-2,4-difluorobenzamide 5-amino-3-(2-(4-(4-(azetidin-3-yloxy)-2-fluorophenyl)piperazin-1-yl)ethyl)-8-(furan-2-yl)pyrazolo[1,5-c]thiazolo[5,4-e]pyrimidin-2(3H)-one 5-amino-3-(2-(4-(5-(azetidin-3-yloxy)-2,4-difluorophenyl)piperazin-1-yl)ethyl)-8-(furan-2-yl)pyrazolo[1,5-c]thiazolo[5,4-e]pyrimidin-2(3H)-one (S)-5-amino-3-(2-(4-(2,4-difluoro-5-(3-(methylsulfinyl)propoxy)phenyl)piperazin-1-yl)ethyl)-8-(furan-2-yl)pyrazolo[1,5-c]thiazolo[5,4-e]pyrimidin-2(3H)-one and pharmaceutically acceptable salts and solvates thereof.

In Table 1, the term "Cpd" means compound.

The compounds of Table 1 were named using ChemBioDraw® Ultra version 12.0 (PerkinElmer).

In one embodiment, compounds of Formula (I) of the invention are selected from:

(S)—N5-(2-(4-(2,4-difluoro-5-(2-(methylsulfinyl)ethoxy)phenyl)piperazin-1-yl)ethyl)-2-(furan-2-yl)-N5-methyl-[1,2,4]triazolo[1,5-a][1,3,5]triazine-5,7-diamine, (R)—N5-(2-(4-(2,4-difluoro-5-(2-(methylsulfinyl)ethoxy)phenyl)piperazin-1-yl)ethyl)-2-(furan-2-yl)-N5-methyl-[1,2,4]triazolo[1,5-a][1,3,5]triazine-5,7-diamine, 5-(4-(2-(5-amino-8-(furan-2-yl)-1-methyl-2-oxo-1H-[1,2,4]
triazolo[5,1-i]purin-3(2H)-yl)ethyl)piperazin-1-yl)-2,4-
difluoro-N-methylbenzamide,
5-(4-(2-(5-amino-2-(furan-2-yl)-7H-pyrazolo[4,3-e][1,2,4]
triazolo[1,5-c]pyrimidin-7-yl)ethyl)piperazin-1-yl)-2,4-
difluoro-N-methylbenzamide,
N5-(2-(4-(2,4-difluoro-5-(2-(methylsulfonyl)ethoxy)phe-
nyl)piperazin-1-yl)ethyl)-2-(furan-2-yl)-N5-methyl-[1,2,
4]triazolo[1,5-a][1,3,5]triazine-5,7-diamine,
N5-(2-(4-(2,4-difluoro-5-(2-(methylsulfonyl)ethoxy)phe-
nyl)piperazin-1-yl)ethyl)-2-(furan-2-yl)-[1,2,4]triazolo[1,
5-a][1,3,5]triazine-5,7-diamine,
(S)-5-amino-3-(2-(4-(2,4-difluoro-5-(2-(methylsulfinyl)
ethoxy)phenyl)piperazin-1-yl)ethyl)-8-(furan-2-yl)-1-
methyl-1H-[1,2,4]triazolo[5,1-i]purin-2(3H)-one,
(R)-5-amino-3-(2-(4-(2,4-difluoro-5-(2-(methylsulfinyl)
ethoxy)phenyl)piperazin-1-yl)ethyl)-8-(furan-2-yl)-1-
methyl-1H-[1,2,4]triazolo[5,1-i]purin-2(3H)-one,
5-amino-3-(2-(4-(2,4-difluoro-5-(2-(methylsulfonyl)
ethoxy)phenyl)piperazin-1-yl)ethyl)-8-(furan-2-yl)-1-
methyl-1H-[1,2,4]triazolo[5,1-i]purin-2(3H)-one,
(S)—N5-(2-(4-(2,4-difluoro-5-(2-(methylsulfinyl)ethoxy)
phenyl)piperazin-1-yl)ethyl)-2-(furan-2-yl)-[1,2,4]tri-
azolo[1,5-a][1,3,5]triazine-5,7-diamine,
(R)—N5-(2-(4-(2,4-difluoro-5-(2-(methylsulfinyl)ethoxy)
phenyl)piperazin-1-yl)ethyl)-2-(furan-2-yl)-[1,2,4]tri-
azolo[1,5-a][1,3,5]triazine-5,7-diamine,
(S)-7-(2-(4-(2,4-difluoro-5-(2-(methylsulfinyl)ethoxy)phe-
nyl)piperazin-1-yl)ethyl)-2-(furan-2-yl)-7H-pyrazolo[4,
3-e][1,2,4]triazolo[1,5-c]pyrimidin-5-amine,
(R)-7-(2-(4-(2,4-difluoro-5-(2-(methylsulfinyl)ethoxy)phe-
nyl)piperazin-1-yl)ethyl)-2-(furan-2-yl)-7H-pyrazolo[4,
3-e][1,2,4]triazolo[1,5-c]pyrimidin-5-amine,
(1s,4s)-4-(5-(4-(2-((7-amino-2-(furan-2-yl)-[1,2,4]triazolo
[1,5-a][1,3,5]triazin-5-yl)amino)ethyl)piperazin-1-yl)-2,
4-difluorophenoxy)tetrahydro-2H-thiopyran 1-oxide,
4-(5-(4-(2-((7-amino-2-(furan-2-yl)-[1,2,4]triazolo[1,5-a]
[1,3,5]triazin-5-yl)amino)ethyl)piperazin-1-yl)-2,4-dif-
luorophenyl)thiomorpholine 1-oxide,
(R)—N5-(2-(4-(2,4-difluoro-5-(methylsulfinyl)phenyl)pip-
erazin-1-yl)ethyl)-2-(furan-2-yl)-[1,2,4]triazolo[1,5-a][1,
3,5]triazine-5,7-diamine,
(S)—N5-(2-(4-(2,4-difluoro-5-(methylsulfinyl)phenyl)pip-
erazin-1-yl)ethyl)-2-(furan-2-yl)-[1,2,4]triazolo[1,5-a][1,
3,5]triazine-5,7-diamine,
(4-(4-(2-((7-amino-2-(furan-2-yl)-[1,2,4]triazolo[1,5-a][1,3,
5]triazin-5-yl)amino)ethyl)piperazin-1-yl)-3-fluorophe-
nyl)(1-oxidothiomorpholino)methanone,
(1s,4s)-4-(4-(4-(2-((7-amino-2-(furan-2-yl)-[1,2,4]triazolo
[1,5-a][1,3,5]triazin-5-yl)amino)ethyl)piperazin-1-yl)-3-
fluorophenoxy)tetrahydro-2H-thiopyran 1-oxide,
5-amino-3-(2-(4-(2-fluoro-4-(2-(methylsulfinyl)ethoxy)
phenyl)piperazin-1-yl)ethyl)-8-(furan-2-yl)-1-methyl-
1H-[1,2,4]triazolo[5,1-i]purin-2(3H)-one,
5-amino-3-(2-(4-(2,4-difluoro-5-((2-oxopyrrolidin-3-yl)
oxy)phenyl)piperazin-1-yl)ethyl)-8-(furan-2-yl)-1-
methyl-1H-[1,2,4]triazolo[5,1-i]purin-2(3H)-one,
and pharmaceutically acceptable salts and solvates
thereof.

In one embodiment, the present invention also relates to enantiomers, salts, solvates, polymorphs, multicomponent complexes and liquid crystals of compounds of Formula (I) and subformulae thereof.

In one embodiment, the present invention also relates to polymorphs and crystal habits of compounds of Formula (I) and subformulae thereof, prodrugs and isomers thereof (including optical, geometric and tautomeric isomers) and isotopically labeled compounds of Formula (I) and subformulae thereof.

The compounds of Formula (I) and subformulae thereof may contain an asymmetric center and thus may exist as different stereoisomeric forms. Accordingly, the present invention includes all possible stereoisomers and includes not only racemic compounds but the individual enantiomers and their non-racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be performed by any suitable method known in the art.

The compounds of the invention may be in the form of pharmaceutically acceptable salts. Pharmaceutically acceptable salts of the compounds of Formula (I) and subformulae thereof include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of compounds of Formula (I) and subformulae thereof may be prepared by one or more of these methods:
(i) by reacting the compound of Formula (I) with the desired acid;
(ii) by reacting the compound of Formula (I) with the desired base;
(iii) by removing an acid- or base-labile protecting group from a suitable precursor of the compound of Formula (I) or by ring-opening a suitable cyclic precursor, for example, a lactone or lactam, using the desired acid; or
(iv) by converting one salt of the compound of Formula (I) to another by reaction with an appropriate acid or by means of a suitable ion exchange column.

All these reactions are typically carried out in solution. The salt, may precipitate from solution and be collected by filtration or may be recovered by evaporation of the solvent.

The degree of ionization in the salt may vary from completely ionized to almost non-ionized.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

These salts may be prepared by standard procedures, e.g. by reacting a free acid with a suitable organic or inorganic base. Where a basic group is present, such as amino, an acidic salt, i.e. hydrochloride, hydrobromide, acetate, palmoate, and the like, can be used as the dosage form.

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula (I) above.

The compounds of the invention may be in the form of pharmaceutically acceptable solvates. Pharmaceutically acceptable solvates of the compounds of Formula (I) and subformulae thereof contains stoichiometric or sub-stoichiometric amounts of one or more pharmaceutically acceptable solvent molecule such as ethanol or water. The term "hydrate" refers to when the said solvent is water.

The invention also generally covers all pharmaceutically acceptable predrugs and prodrugs of the compounds of Formula (I) and subformulae thereof.

Also, in the case of an alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

Process for Manufacturing

The compounds of Formula (I) can be prepared by different ways with reactions known to a person skilled in the art.

The invention further relates to a process for manufacturing of compounds of Formula (I):

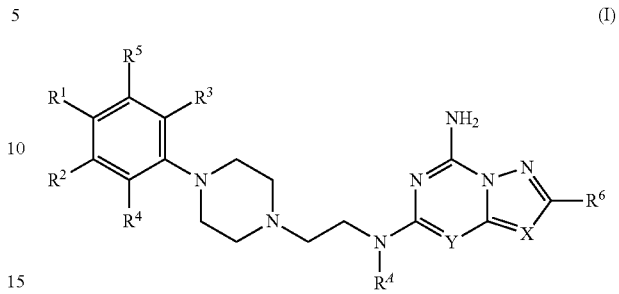

and pharmaceutically acceptable salts and solvates thereof, wherein X, Y, $R^{A}$, $R^1$, $R^2$, $R^3$, $R^4$, $R^5$ and $R^6$ are as defined above;
comprising:
(a1) reacting a compound of Formula (A)

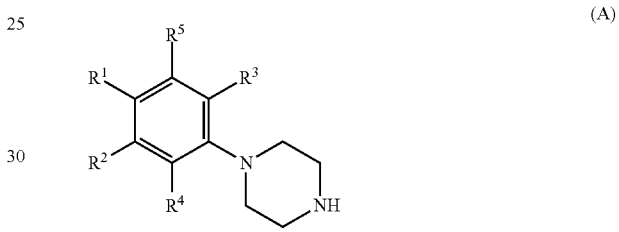

wherein $R^1$, $R^2$, $R^3$, $R^4$ and $R^5$ are as defined in Formula (I);
with a compound of Formula (B)

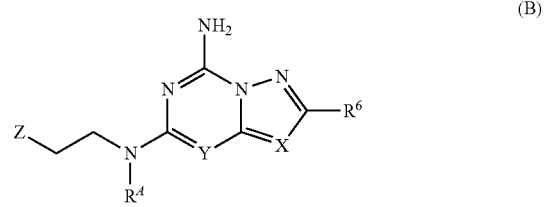

wherein X, Y, $R^{A}$ and $R^6$ are as defined in Formula (I); and represents a halogen (preferably iodine, bromine or chlorine), an alkylsulfonyloxy having 1-6 carbon atoms (preferably methylsulfonyloxy or trifluoro-methylsulfonyloxy) or arylsulfonyloxy having 6-10 carbon atoms (preferably phenyl- or p-tolylsulfonyloxy), or any leaving group known to those skilled in the art.

According to one embodiment, step (a1) of the process of the invention may be performed in the presence or absence of bases. In a specific embodiment, step (a1) of the process of the invention is performed in the presence of bases selected from the group consisting of but not limited to TEA, DIPEA, pyridine, NaOH, K3PO4, K2CO3, Na2CO3, preferably DIPEA or TEA.

According to one embodiment, step (a1) of the process of the invention may be performed in the presence of a suitable solvent such as but not limited to DMF, dioxane, THF, water or mixtures thereof, preferably in DMF.

According to one embodiment, step (a1) of the process of the invention may be performed at a temperature ranging from 20° C. to about 180° C., with or without microwave irradiation, for a period ranging from 10 minutes to a few hours, e.g. 10 minutes to 24 h.

Furthermore, the invention further relates to another process for manufacturing of compounds of Formula (I):

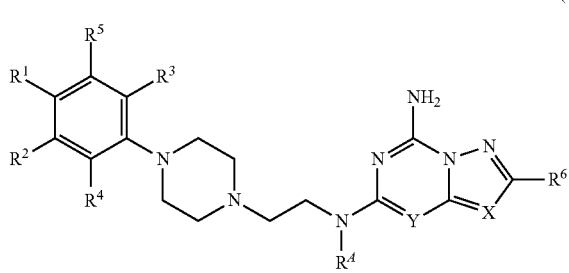

(I)

and pharmaceutically acceptable salts and solvates thereof, wherein X, Y, $R^4$, $R^1$, $R^2$, $R^3$, $R^4$, $R^5$ and $R^6$ are as defined above;
comprising:
(a2) reacting a compound of Formula (A)

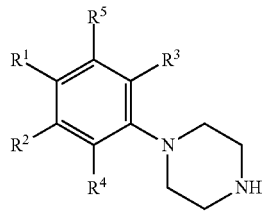

(A)

wherein $R^1$, $R^2$, $R^3$, $R^4$ and $R^5$ are as defined in Formula (I);
with a compound of Formula (C)

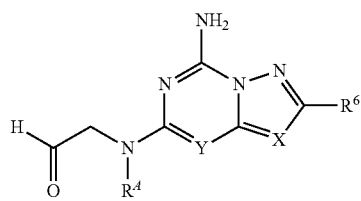

(C)

wherein X, Y, $R^4$ and $R^6$ are as defined in Formula (I).

According to one embodiment, step (a2) of the process of the invention may be performed in the presence of a reducing agent such as but not limited to NaBH4, LiBH4, NaB(OAc)3H or NaB(CN)H3.

According to one embodiment, step (a2) of the process of the invention may be performed in the presence or absence of bases. In a specific embodiment, step (a2) of the process of the invention is performed in the presence of bases selected from the group consisting of but not limited to TEA, DIPEA, pyridine, preferably DIPEA or TEA.

According to one embodiment, step (a2) of the process of the invention may be performed in the presence of a suitable solvent such as but not limited to dichloroethane, dichloromethane, DMF, dioxane, THF or mixtures thereof, preferably in dichloroethane.

According to one embodiment, step (a2) of the process of the invention may be performed at a temperature ranging from 20° C. to about 180° C., for a period ranging from 10 minutes to a few hours, e.g. 10 minutes to 24 h.

In general, the synthesis pathways for any individual compound of Formula (I) will depend on the specific substituents of each molecule and upon the ready availability of intermediates necessary; again such factors being appreciated by those of ordinary skill in the art.

According to a further general process, compounds of Formula (I) can be converted to alternative compounds of Formula (I), employing suitable interconversion techniques well known by a person skilled in the art.

Compounds of the Formula (I) and related formulae can furthermore be obtained by liberating compounds of the Formula (I) from one of their functional derivatives by treatment with a solvolysing or hydrogenolysing agent.

Preferred starting materials for the solvolysis or hydrogenolysis are those which conform to the Formula (I) and related formulae, but contain corresponding protected amino and/or hydroxyl groups instead of one or more free amino and/or hydroxyl groups, preferably those which carry an amino-protecting group instead of an H atom bonded to an N atom, in particular those which carry an R*—N group, in which R* denotes an amino-protecting group, instead of an HN group, and/or those which carry a hydroxyl-protecting group instead of the H atom of a hydroxyl group, for example those which conform to the Formula (I), but carry a —COOR group, in which R denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-carbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the Formula (I) and related formulae are liberated from their functional derivatives—depending on the protecting group used—for example strong inorganic acids, such as hydrochloric acid, perchloric acid or sulfuric acid, strong organic carboxylic acids, such as trichloroacetic acid, TFA or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBu and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be hydrolyzed, for example, using HCl, $H_2SO_4$, or using LiOH, NaOH or KOH in water, water/THF, water/THF/ethanol or water/dioxane, at temperatures between 0 and 100° C.

Free amino groups can furthermore be acylated in a conventional manner using an acyl chloride or anhydride or alkylated using an unsubstituted or substituted alkyl halide, advantageously in an inert solvent, such as dichloromethane or THF and/or in the presence of a base, such as triethylamine or pyridine, at temperatures between −60° C. and +30° C.

For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999.

Reaction schemes as described in the example section are illustrative only and should not be construed as limiting the invention in any way.

Uses

The invention is further directed to the use of the compounds of the invention or pharmaceutically acceptable salts and solvates thereof as A2A inhibitors.

Accordingly, in a particularly preferred embodiment, the invention relates to the use of compounds of Formula (I) and subformulae in particular those of Table 1 above, or pharmaceutically acceptable salts and solvates thereof, as A2A inhibitors.

Accordingly, in another aspect, the invention relates to the use of these compounds or salts and solvates thereof for the synthesis of pharmaceutical active ingredients, such as A2A inhibitors.

According to a further feature of the present invention there is provided a method for modulating A2A activity, in a patient, preferably a warm-blooded animal, and even more preferably a human, in need of such treatment, which comprises administering to said patient an effective amount of compound of the present invention, or a pharmaceutically acceptable salt and solvate thereof.

In one embodiment, the invention relates to the use of compounds of Formula (I) and subformulae in particular those of Table 1 above, or pharmaceutically acceptable salts and solvates thereof, for treating proliferative disorders, including cancers.

In one embodiment, the invention relates to the use of compounds of Formula (I) and subformulae in particular those of Table 1 above, or pharmaceutically acceptable salts and solvates thereof, for increasing immune recognition and destruction of the cancer cells.

The compounds of the invention are therefore useful as medicaments, in particular for the prevention and/or treatment of proliferative disorders, including cancer.

The invention further relates to a method for treatment or prevention of proliferative disorders, including cancers, which comprises administering to a mammal species in need thereof a therapeutically effective amount of the compound according to the invention or a pharmaceutically acceptable salt or solvate thereof.

The invention further provides the use of a compound of Formula (I) or a pharmaceutically acceptable salt and solvate thereof for the manufacture of a medicament for treating and/or preventing proliferative disorders, including cancers.

The invention also provides for a method for delaying in patient the onset of proliferative disorders, including cancers, comprising the administration of a pharmaceutically effective amount of a compound of Formula (I) or pharmaceutically acceptable salt and solvate thereof to a patient in need thereof.

Preferably, the patient is a warm-blooded animal, more preferably a human.

The invention further relates to the use of the compounds according to the invention or pharmaceutically acceptable salts or solvates thereof for the prevention and/or treatment of radiation-induced fibrosis, connective tissue diseases (such as for example Sjogrën syndrome, i.e. scleroderma), chronic bacterial infection (such as for example *Helicobacter Pylori*), abnormal scarring (keloids) and polymicrobial sepsis.

The invention further relates to a method for treatment or prevention of radiation-induced fibrosis, connective tissue diseases (such as for example Sjogrën syndrome, i.e. scleroderma), chronic bacterial infection (such as for example *Helicobacter Pylori*), abnormal scarring (keloids) and polymicrobial sepsis, which comprises administering to a mammal species in need thereof a therapeutically effective amount of the compound according to the invention or a pharmaceutically acceptable salt or solvate thereof.

The invention further provides the use of a compound of Formula (I) or a pharmaceutically acceptable salt and solvate thereof for the manufacture of a medicament for treating and/or preventing radiation-induced fibrosis, connective tissue diseases (such as for example Sjogrën syndrome, i.e. scleroderma), chronic bacterial infection (such as for example *Helicobacter Pylori*), abnormal scarring (keloids) and polymicrobial sepsis.

The invention also provides for a method for delaying in patient the onset of radiation-induced fibrosis, connective tissue diseases (such as for example Sjogrën syndrome, i.e. scleroderma), chronic bacterial infection (such as for example *Helicobacter Pylori*), abnormal scarring (keloids) and polymicrobial sepsis, comprising the administration of a pharmaceutically effective amount of a compound of Formula (I) or pharmaceutically acceptable salt and solvate thereof to a patient in need thereof.

Formulations

The invention also provides pharmaceutical compositions comprising a compound of Formula (I) or a pharmaceutically acceptable salt and solvate thereof and at least one pharmaceutically acceptable carrier, diluent, excipient and/or adjuvant. As indicated above, the invention also covers pharmaceutical compositions which contain, in addition to a compound of the present invention, a pharmaceutically acceptable salt and solvate thereof as active ingredient, additional therapeutic agents and/or active ingredients.

Another object of this invention is a medicament comprising at least one compound of the invention, or a pharmaceutically acceptable salt and solvate thereof, as active ingredient.

According to a further feature of the present invention there is provided the use of a compound of Formula (I) or a pharmaceutically acceptable salt and solvate thereof for the manufacture of a medicament for modulating A2A activity in a patient, in need of such treatment, which comprises administering to said patient an effective amount of compound of the present invention, or a pharmaceutically acceptable salt and solvate thereof.

Generally, for pharmaceutical use, the compounds of the invention may be formulated as a pharmaceutical preparation comprising at least one compound of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Depending on the condition to be prevented or treated and the route of administration, the active compound of the invention may be administered as a single daily dose, divided over one or more daily doses, or essentially continuously, e.g. using a drip infusion.

EXAMPLES

The present invention will be better understood with reference to the following examples. These examples are intended to representative of specific embodiments of the invention, and are not intended as limiting the scope of the invention.

The following abbreviations are used:
ACN: Acetonitrile,
BINAP: 2,2'-bis(diphenylphosphino)-1,1'-binaphthyl,
Boc: tert-Butoxycarbonyl,
BSA: Bis(trimethylsilyl)acetamide or bovine serum albumin, depending on the context,
Cpd: Compound, DABCO: 1,4-diazabicyclo[2.2.2]octane,
DCM: Dichloromethane,
DIPEA: N,N-Diisopropylethylamine,
DMF: Dimethylformamide,
DMSO: Dimethyl sulfoxide,
EDC-HCl: N'-ethylcarbodiimide hydrochloride,
EtOAc: Ethyl acetate,
h: Hour(s),
HAS: Human serum albumin,
HOBT: Hydroxybenzotriazole,
HPLC: High performance liquid chromatography,
IBX: 2-iodoxybenzoic acid,
LCMS: Liquid chromatography-mass spetrometry
M: $mol \cdot L^{-1}$,
mCPBA: meta-Chloroperoxybenzoic acid,
min: Minute(s),
mol: Mole(s),
MP-CNBH$_3$: macroporous polymer supported cyanoborohydride,
MTBE: Methyl tert-butyl ether,
NMR: Nuclear magnetic resonance spectroscopy,
Pd$_2$(dba)$_3$: Tris(dibenzylideneacetone)dipalladium(0),
pTSA: p-Toluenesulfonic acid,
SFC: Supercritical fluid chromatography,
rt or RT: Room temperature,
tBu: tert-Butyl,
TFA: Trifluoroacetic acid,
THF: Tetrahydrofuran,
TLC: Thin layer chromatography.

I. Chemistry Examples

The MS data provided in the examples described below were obtained as follows:
LCMS were recorded using Agilent 6130 or 6130B multimode (ESI+APCI).
LCMS Methods:
Column: XBridge C8 (50×4.6 mm) 5 μm; Method: A: 0.1% TFA in H$_2$O, B: 0.1% TFA in ACN, Flow Rate: 2.0 mL/min.
Column: Zorbax extend C18 (50×4.6 mm) 5 μm; Method: A: 10 mM NH$_4$OAc in H$_2$O, B: ACN, Flow Rate: 1.2 mL/min.
Column: Zorbax XDB C18 (50×4.6 mm) 3.5 μm; Method: A: 0.1% HCOOH in H$_2$O, B: ACN, Flow Rate: 1.5 mL/min.
Column: XBridge C8 (50×4.6 mm) 3.5 m; Method: A: 10 mM NH$_4$HCO$_3$ in H$_2$O, B: ACN, Flow Rate: 1.2 mL/min.
The NMR data provided in the examples described below were obtained as followed: 1H-NMR: Bruker DPX 400 MHz. Abbreviations for multiplicities observed in NMR spectra are as follows: s (singlet), d (doublet), t (triplet), q (quadruplet), m (multiplet), br (broad).
HPLC Purity were evaluated with either of two methods:
Method XB0595TF; COLUMN: XBridge C8 (50×4.6) mm, 3.5 μm; Gradient of eluents from 0.1% TFA in H$_2$O to 0.1% TFA in ACN, Flow Rate: 2.0 mL/min.
Method: AM9010A3; COLUMN: Phenomenex gemini NX-C18 (150×4.6), 3.0 μm; Gradient of eluents from 10 mM Ammonium acetate in water to ACN, Flow Rate: 1.0 mL/min.
Method: XB0595NHC; COLUMN: XBridge C8 (50×4.6) mm, 3.5 μm; Gradient of eluents from 10 mM Ammonium bicarbonate in water to ACN, Flow Rate: 1.0 mL/min.
Solvents, reagents and starting materials were purchased and used as received from commercial vendors unless otherwise specified.

The intermediates and compounds described below were named using ChemBioDraw® Ultra version 12.0 (PerkinElmer).

I.1. Synthesis of Intermediate Compounds

Intermediate 1: 2-((7-amino-2-(furan-2-yl)-[1,2,4]triazolo[1,5-a][1,3,5]triazin-5-yl)(methyl)amino)acetaldehyde hydrochloride

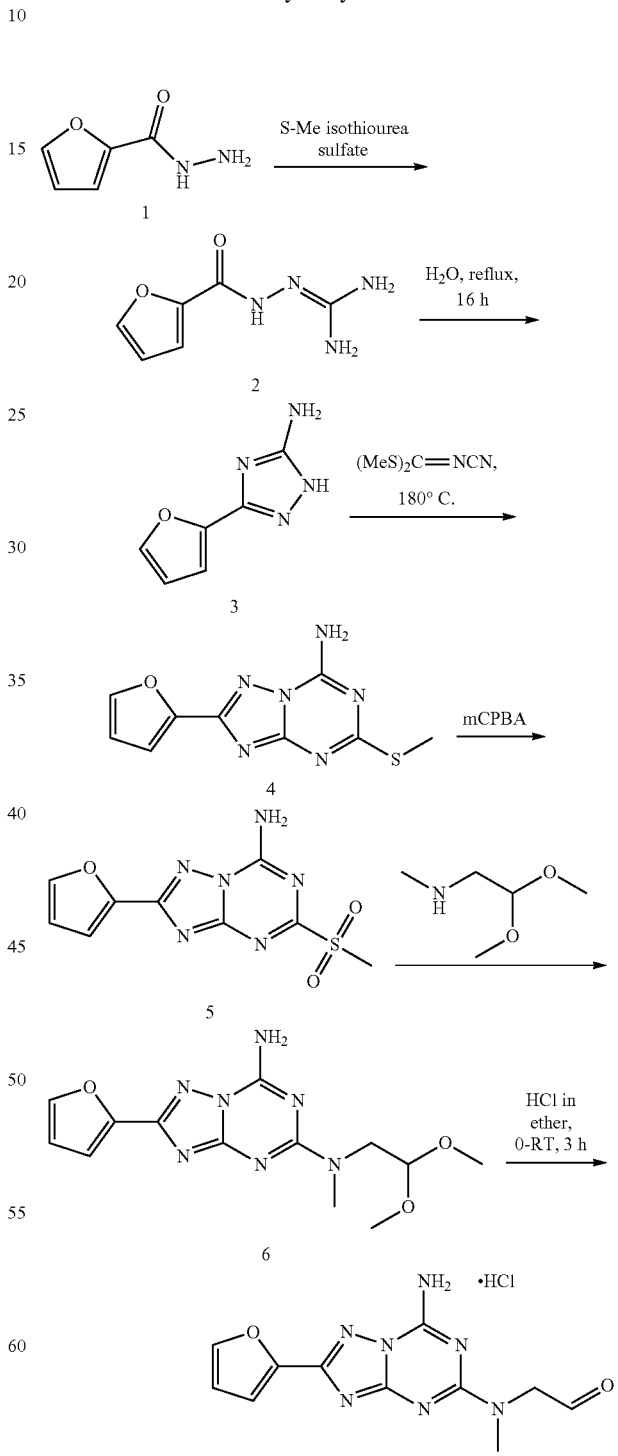

Step 1: Preparation of N-guanidinofuran-2-carboxamide (2)

A solution of sodium hydroxide (1% NaOH in water, 400 mL) was added to a mixture of furan-2-carbohydrazide (13 g, 0.103 mol), methylisothiourea.hemisulfate (14 g, 0.155 mol) with stirring. The resulting mixture was stirred at RT for 72 h. The white precipitated was filtered, washed with ice water and dried under vacuum. The solid product was analytically pure to be used as such for the next step. Yield: (9 g, 49%). 1H-NMR (400 MHz, DMSO-d6): δ 6.42-6.43 (m, 1H), 6.61 (s, 1H), 6.72 (brs, 3H), 10.44 (brs, 1H).

Step 2: Preparation of 3-(2-furyl)-1H-1,2,4-triazol-5-amine (3)

A stirred solution of N-guanidinofuran-2-carboxamide (2) (7 g, 0.042 mol) in water (100 mL) was heated to reflux for 16 h. The aqueous layer was concentrated under reduced pressure to afford the product as white solid. It was used as such for the next step without further purification. Yield: (6 g, 91%). 1H-NMR (400 MHz, DMSO-d6): δ 6.07 (s, 2H), 6.53 (s, 1H), 6.67 (s, 1H), 7.67 (s, 1H), 12.07 (brs, 1H).

Step 3: Preparation of 2-(furan-2-yl)-5-(methylthio)-[1,2,4]triazolo[1,5-a][1,3,5]triazin-7-amine (4)

A stirred mixture of 3-(2-furyl)-1H-1,2,4-triazol-5-amine (3) (5.5 g, 0.037 mol), bis(methyl-sulfanyl)methylenecyanamide (5.35 g, 0.037 mol) was heated to 180° C. for 3 h under nitrogen atmosphere. The reaction was monitored by TLC and LC-MS. After completion of the reaction, the reaction mixture was cooled to RT to afford a brown residue. It was purified by column chromatography over silica gel (230-400 mesh) using 15% Ethyl acetate in dichloromethane as eluent to obtain the title product as a yellow solid. Yield: (3.3 g, 36%). LCMS (ESI positive ion) m/z: calculated: 248; observed: 249 (M+1). 1H-NMR (400 MHz, DMSO-d6): δ 2.42 (s, 3H), 6.72-6.73 (m, 1H), 7.17 (d, J=3.20 Hz, 1H), 7.94 (s, 1H), 8.88 (2×1, brs, ratio 1:1, 2H).

Step 4: Preparation of 2-(furan-2-yl)-5-(methylsulfonyl)-[1,2,4]triazolo[1,5-a][1,3,5]-triazin-7-amine (5)

A solution of mCPBA (8.31 g, 0.048 mol) in dichloromethane (30 mL) was added dropwise at −5° C. to a stirred suspension of 2-(2-furyl)-5-methylsulfanyl-[1,2,4]triazolo[1,5-a][1,3,5]-triazin-7-amine (4) (3 g, 0.012 mol) in dichloromethane. After stirring at RT for 16 h, the volatiles were removed under reduced pressure. The crude residue obtained was suspended in ethanol (30 mL) and stirred at RT for 0.5 h. The solid formed was collected by filtration, washed well with ethanol (10 mL) and dried under vacuum to afford the title product as an off white solid. Yield: (3 g, 77%). LCMS (ESI positive ion) m/z: calculated: 280; observed: 281 (M+1). 1H-NMR (400 MHz, DMSO-d6): δ 3.34 (s, 3H), 6.75-6.77 (m, 1H), 7.27 (d, J=3.60 Hz, 1H), 7.99 (m, 1H), 9.65 (2×brs, ratio 1:1, 2H).

Step 5: Preparation of N5-(2,2-dimethoxyethyl)-2-(furan-2-yl)-N5-methyl-[1,2,4]triazolo[1,5-a][1,3,5]triazine-5,7-diamine (6)

To a solution of 2-(2-furyl)-5-methylsulfonyl-[1,2,4]triazolo[1,5-a][1,3,5]triazin-7-amine (5) (1.0 g, 0.004 mol) in DMF was added 3,3-dimethoxy-N-methylpropan-1-amine (0.713 g, 0.005 mol). The reaction mixture was stirred at RT for 6 h. After the completion of reaction, the reaction mixture was partitioned between water and ethyl acetate. The organic layer separated was concentrated under reduced pressure to afford crude product. It was purified by column chromatography over silica gel (230-400 mesh) using 5% methanol in dichloromethane as eluent, to afford the title product as an off white solid. Yield: (800 mg, 79%). LCMS (ESI positive ion) m/z: calculated: 305.3; observed: 306.1 (M+1).

Step 6: Preparation of 2-((7-amino-2-(furan-2-yl)-[1,2,4]triazolo[1,5-a][1,3,5]triazin-5-yl)(methyl)amino)acetaldehyde hydrochloride (Intermediate 1)

To an ice cold solution of N5-(2,2-dimethoxyethyl)-2-(2-furyl)-N5-methyl-[1,2,4]triazolo[1,5-a][1,3,5]triazine-5,7-diamine (6) (5 g, 0.016 mol) in dichloromethane (20 mL), 2M HCl in diethyl ether (2 mL) was added and the reaction mixture was stirred at 0° C. for 1 h. After completion of the reaction (monitored by TLC), the reaction mixture was concentrated under reduced pressure at RT. The residue obtained was triturated with diethyl ether to afford the pure product as an off white solid. (Yield 2.5 g, 46%). LCMS (ESI positive ion) m/z: calculated: 273.0; observed: 274.1 (M+1).

I.2. Synthesis of Final Compounds

Example 1: (S)—N5-(2-(4-(2,4-difluoro-5-(2-(methylsulfinyl)ethoxy)phenyl)piperazin-1-yl)ethyl)-2-(furan-2-yl)-N5-methyl-[1,2,4]triazolo[1,5-a][1,3,5]triazine-5,7-diamine

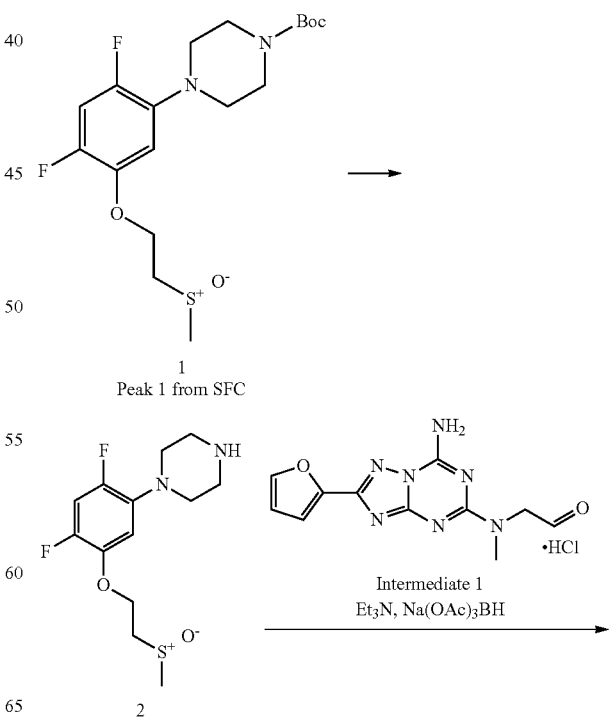

-continued

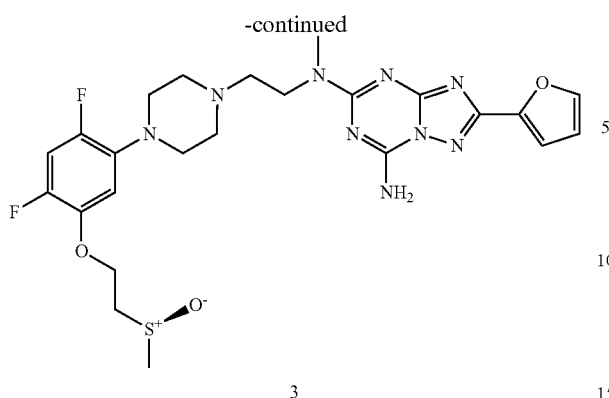

3

Step 1: Preparation of (S)-1-(2,4-difluoro-5-(2-(methylsulfinyl)ethoxy)phenyl) piperazine (2)

To an ice cold solution of tert-butyl (S)-4-(2,4-difluoro-5-(2-(methylsulfinyl)ethoxy)phenyl)-piperazine-1-carboxylate (1) (0.15 g, 0.371 mmol, 1 eq) in dichloromethane (2 mL), 4M HCl in dioxane (0.5 mL) was added and the reaction mixture was stirred at 0° C. for 1 h. After completion of the reaction (monitored by TLC), the reaction mixture was concentrated under reduced pressure at RT. The residue obtained was triturated with diethyl ether to afford the pure product. Then it was dissolved in methanol, passed through Si-Carbonate resin to afford the title product as free base. (Yield 0.360 g, 42%). LCMS (ESI positive ion) m/z: calculated: 304; observed: 305 (M+1).

Step 2: Preparation of (S)—N5-(2-(4-(2,4-difluoro-5-(2-(methylsulfinyl)ethoxy)phenyl)piperazin-1-yl)ethyl)-2-(furan-2-yl)-N5-methyl-[1,2,4]triazolo[1,5-a][1,3,5]triazine-5,7-diamine (3): An ice cold solution of 2-((7-amino-2-(furan-2-yl)-[1,2,4]triazolo[1,5-a][1,3,5]triazin-5-)(methyl)amino)acetaldehyde hydrochloride (Intermediate 1; 0.25 g, 0.807 mol, 1 eq) in dichloromethane (5 mL) was neutralized with triethylamine (0.5 mL). To the resulting mixture, (S)-1-(2,4-difluoro-5-(2-(methylsulfinyl)ethoxy)phenyl)piperazine (2) (0.28 g, 0.888 mol, 1.1 eq) was added. It was followed by the addition of sodium triacetoxyborohydride (0.341 g, 1.61 mol, 2 eq) in portion wise manner at same temperature. After that the reaction allowed to reach RT and continued there for 16 h. The progress of the reaction was monitored by both TLC and LCMS. The reaction mixture was diluted with water (10 mL) and extracted with dichloromethane. Organic layer was washed with saturated sodium bicarbonate solution, dried over anhydrous Na2SO4, filtered and concentrated under reduced pressure. The crude obtained was purified by column chromatography (5% Methanol/dichloromethane as eluent) to afford the product. It was purified by further by RP preparative HPLC to afford an off white solid. Yield: (16 mg, 3.5%). LCMS (ESI positive ion) m/z: calculated: 561.6; observed: 562.2 (M+1). 1H-NMR (400 MHz, DMSO-d6): δ 8.28 (s, 2H), 7.87-7.88 (m, 1H), 7.25 (s, 1H), 7.06 (d, J=2.80 Hz, 1H), 6.85 (t, J=8.00 Hz, 1H), 6.67-6.69 (m, 1H), 4.37-4.40 (m, 2H), 3.75 (d, J=6.00 Hz, 2H), 3.51 (s, 1H), 3.38-3.42 (m, 1H), 3.23-3.30 (m, 1H), 3.13 (s, 3H), 2.98-3.06 (m, 5H), and 2.56 (s, 9H).

Example 2: (R)—N5-(2-(4-(2,4-difluoro-5-(2-(methylsulfinyl)ethoxy)phenyl)piperazin-1-yl)ethyl)-2-(furan-2-yl)-N5-methyl-[1,2,4]triazolo[1,5-a][1,3,5]triazine-5,7-diamine

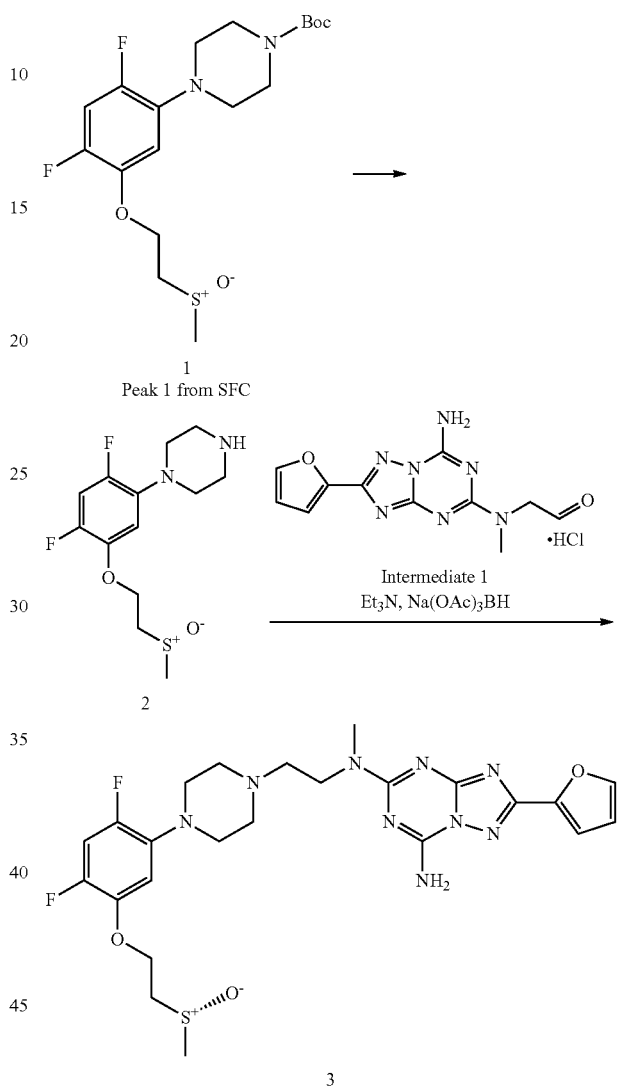

Step 1: Preparation of (R)-1-(2,4-difluoro-5-(2-methylsulfinyl)ethoxy)phenyl)piperazine (2)

To an ice cold solution of tert-butyl (R)-4-(2,4-difluoro-5-(2-(methylsulfinyl)ethoxy)-phenyl)piperazine-1-carboxylate (1) (0.15 g, 0.371 mmol, 1 eq) in dichloromethane (1 mL), 4M HCl in dioxane (0.5 mL) was added and the reaction mixture was stirred at 0° C. for 1 h. After completion (monitored by TLC), the reaction mixture was concentrated under reduced pressure at room temperature. The residue obtained was triturated with diethyl ether to afford the pure product. Then it was dissolved in methanol, passed through Si-Carbonate resin to afford the product as free base. Yield (0.09 g, 43%). LCMS (ESI positive ion) m/z: calculated: 304; observed: 305 (M+1).

Step 2: Preparation of (R)—N5-(2-(4-(2,4-difluoro-5-(2-(methylsulfinyl)ethoxy)phenyl)piperazin-1-yl)ethyl)-2-(furan-2-yl)-N5-methyl-[1,2,4]triazolo[1,5-a][1,3,5]triazine-5,7-diamine (3)

To a stirred suspension of 2-[[7-amino-2-(2-furyl)-[1,2,4]triazolo[1,5-a][1,3,5]triazin-5-yl]-methyl-amino]acetaldehyde hydrochloride (Intermediate 1, 0.106 g, 0.388 mmol) in dry dichloromethane (5 mL), triethyl amine (108 μL, 0.776 mmol, 2 eq) and (R)-1-(2,4-difluoro-5-(2-(methylsulfinyl)ethoxy)phenyl)piperazine (2) (0.130 g, 0.427 mmol, 1.1 eq) were added. After stirring at room temperature for 3 h, sodium triacetoxyborohydride (0.163 g, 0.776 mmol, 2.0 eq) was added. The resulting mixture was stirred at room temperature for 24 h. After completion, the reaction mixture was diluted with dichloromethane. The organic layer separated was washed successively with saturated bicarbonate solution and saturated brine solution. Then it was dried over anhydrous Na2SO4, filtered and concentrated under reduced pressure. The crude obtained was purified by column chromatography (230-400 silica gel, 5% methanol in dichloromethane as an eluent) to afford the title product as an off white solid. Yield (40 mg, 18%). LCMS (ESI positive ion) m/z: calculated: 561.6; observed: 562.2 (M+1). 1H-NMR (400 MHz, DMSO-d6): δ 8.30 (s, 2H), 7.86 (s, 1H), 7.23 (t, J=11.44 Hz, 1H), 7.05 (d, J=2.48 Hz, 1H), 6.84 (t, J=8.40 Hz, 1H), 6.67-6.68 (m, 1H), 4.33-4.43 (m, 2H), 3.74 (d, J=4.96 Hz, 2H), 3.32 (s, 1H), 3.18 (t, J=19.44 Hz, 3H), 2.97-3.06 (m, 5H), and 2.63 (s, 10H).

Example 3: 5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluoro-N-methylbenzamide

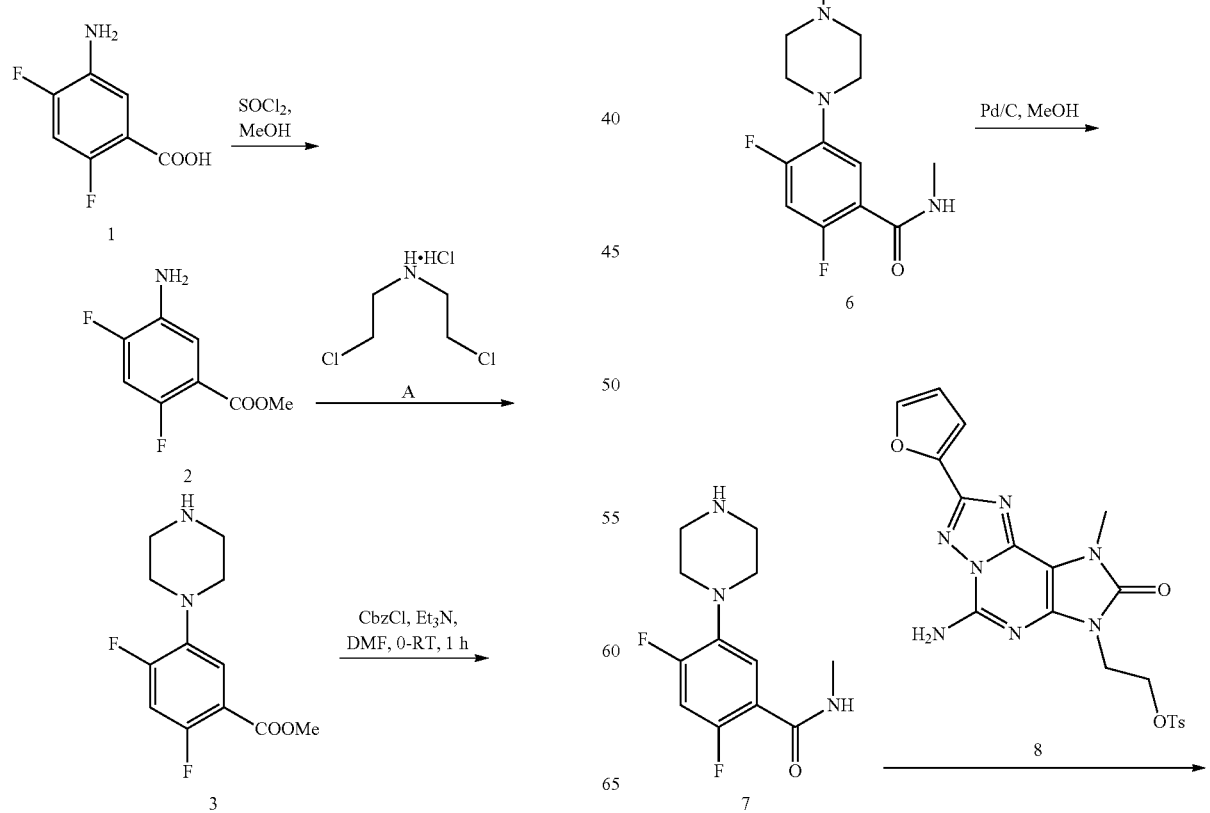

-continued

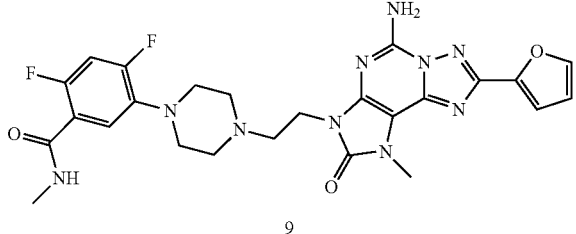

9

Step 1: Preparation of methyl 5-amino-2,4-difluorobenzoate (2)

To a stirred solution of 5-amino-2,4-difluorobenzoic acid (1) (15.0 g, 0.087 mol), in MeOH, thionyl chloride (9.5 mL, 0.130 mol) was added slowly and heated to reflux for 5 h. Progress of the reaction mixture was monitored by TLC. After completion, the reaction mixture was concentrated under reduced pressure. The residue obtained was taken in ethyl acetate and washed with a solution of saturated sodium bicarbonate. The organic layer was dried over anhydrous Na2SO4, filtered and concentrated under reduced pressure. The crude was purified by column chromatography (230-400 silica gel, 5% methanol in dichloromethane as an eluent) to afford the title product as an off white solid. Yield (16.22 g, 83%). LCMS (ESI positive ion) m/z: calculated: 187.15; observed: 188.0 (M+1).

Step 2: Preparation of methyl 2,4-difluoro-5-(piperazin-1-yl)benzoate (3)

To a solution of methyl 5-amino-2,4-difluorobenzoate (2) (700 mg, 3.74 mmol) in diethylene glycol monoethyl ether (10 mL), bis(2-chloroethyl)amine hydrochloride (A) (868 mg, 4.86 mmol) was added and heated to 170° C. for 1 h. The reaction progress was monitored by TLC. After completion, the reaction mixture was evaporated under reduced pressure. The residue was taken to next step without further purification. Yield (500 mg, 43%). LCMS (ESI positive ion) m/z: calculated: 256.1; observed: 257.1 (M+1).

Step 3: Preparation of Benzyl 4-(2,4-difluoro-5-(methoxycarbonyl)phenyl)piperazine-1-carboxylate (4)

To an ice cold solution of methyl 2,4-difluoro-5-(piperazin-1-yl)benzoate hydrochloride (3) (1.0 g, 0.003 mol) in dichloromethane, triethylamine (1.2 mL, 0.009 mol) and benzyl chloroformate (0.641 g, 0.004 mol) were added. The resulting mixture was stirred at RT for 16 h. After completion, the reaction mixture was diluted with dichloromethane and washed with water. The organic layer was separated, dried over anhydrous Na2SO4, filtered and concentrated under reduced pressure. The crude obtained was purified by column chromatography (230-400 silica gel, 5% methanol in dichloromethane as an eluent) to afford the title product as an off white solid. Yield (16.22 g, 83%). LCMS (ESI positive ion) m/z: calculated: 390.4; observed: 391.1 (M+1). 1H NMR (400 MHz, DMSO-d6) δ 7.44-7.50 (m, 2H), 7.39 (q, J=7.60 Hz, 4H), 7.34 (q, J=4.40 Hz, 1H), 5.12 (s, 2H), 3.85 (s, 3H), 3.57 (s, 4H), 2.99 (d, J=4.00 Hz, 4H).

Step 4: Preparation of 5-(4-((benzyloxy)carbonyl)piperazin-1-yl)-2,4-difluorobenzoic acid (5)

To a solution of benzyl 4-(2,4-difluoro-5-(methoxycarbonyl)-phenyl)-piperazine-1-carboxylate (4) (0.6 g, 1.537 mmol) in THF:MeOH:H2O (4:4:2), lithium hydroxide monohydrate (0.516 g, 12.30 mmol) was added and stirred at RT for 6 h. After the completion, the reaction mixture was evaporated under reduced pressure. The residue was taken in water and the pH was adjusted to 2 with a solution of hydrochloric acid (1.5 N). The solid formed was filtered, washed with ether to afford the title product as an off white solid. Yield (450 mg, 77%). LCMS (ESI positive ion) m/z: calculated: 376.3; observed: 377.0 (M+1). 1H NMR (400 MHz, DMSO-d6) δ 7.45 (q, J=7.64 Hz, 1H), 7.34-7.38 (m, 5H), 7.32 (q, J=2.84 Hz, 1H), 5.10 (s, 2H), 3.55 (s, 4H), 2.97 (t, J=4.56 Hz, 4H).

Step 5: Preparation of Benzyl 4-(2,4-difluoro-5-(methylcarbamoyl)phenyl)piperazine-1-carboxylate (6)

To an ice cold stirred solution of 5-(4-((benzyloxy)carbonyl)piperazin-1-yl)-2,4-difluoro-benzoic acid (5) (800 mg, 2.12 mmol) in dichloromethane, DMF (catalytic amount) and oxalyl chloride (0.270 mL, 3.19 mmol) were added. The resulting mixture was stirred at RT for 2 h. After completion of the reaction, the volatiles were evaporated under reduced pressure. The residue was dissolved in dichloromethane under nitrogen atmosphere. To the resulting solution, methyl amine 2M in THF (0.162 mL, 10.63 mmol) was added at 0° C. The resulting mixture was stirred at RT for 2 h. After completion of the reaction, the organic layer was separated and concentrated under reduced pressure. The crude obtained was purified by column chromatography (230-400 silica gel, 50% ethyl acetate in petroleum ether as an eluent) to afford the title product as an off white solid. Yield (650 mg, 78.5%). LCMS (ESI positive ion) m/z: calculated: 389.41; observed: 390.1 (M+1).

Step 6: Preparation of 2,4-difluoro-N-methyl-5-(piperazin-1-yl)benzamide (7)

To a stirred solution of benzyl 4-(2,4-difluoro-5-(methylcarbamoyl)phenyl)piperazine-1-carboxylate (6) (430 mg, 1.104 mmol), in methanol, palladium on carbon 10% (100 mg) was added. The resulting mixture was stirred RT under hydrogen atmosphere (balloon pressure) for 16 h. After completion the reaction mixture was filtered through celite pad and washed with methanol. The filtrate was concentrated under reduced pressure to afford the title product as a white solid. Yield (260 mg, 92.5%). LCMS (ESI positive ion) m/z: calculated: 255; observed: 256.1 (M+1).

Step 7: Preparation of 5-(4-(2-(5-amino-8-(furan-2-yl)-1-methyl-2-oxo-1,2-dihydro-3H-[1,2,4]triazolo[5,1-i]purin-3-yl)ethyl)piperazin-1-yl)-2,4-difluoro-N-methylbenzamide (9)

To an ice cold stirred solution of 2-(5-amino-2-(furan-2-yl)-7H-pyrazolo[4,3-e][1,2,4]-triazolo[1,5-c]pyrimidin-7-yl)ethyl methane sulfonate (8) (prepared as described in WO 2012038980, 100 mg, 0.2131 mmol), DIPEA (74 μL, 0.426 mmol) in DMF (3 mL), 2,4-difluoro-N-methyl-5-(piperazin-1-yl)benzamide (7) (59.85 mg, 0.234 mmol) was added. After addition, the reaction was allowed to reach RT before heating at 100° C. under stirring for 16 h. The reaction mixture was cooled to RT and quenched by addition of water. The slurry was extracted with ethyl acetate. Combined organic layers were washed with saturated brine solution, dried over anhydrous Na2SO4, filtered and concentrated under reduced pressure. The crude was purified by RP preparative HPLC to afford the title product as an off white solid. Yield (11.20 mg, 9%). LCMS (ESI positive ion) m/z: calculated: 552; observed: 553.1 (M+1). 1H-NMR (400 MHz, DMSO-d6): δ 8.18 (s, 1H), 7.93 (s, 1H), 7.77 (s, 2H), 7.19-7.30 (m, 3H), 6.72 (s, 1H), 3.95 (t, J=6.00 Hz, 2H), 3.57 (s, 3H), 2.94 (s, 4H), 2.63-2.75 (m, 9H).

Example 4: 5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluoro-N-methylbenzamide

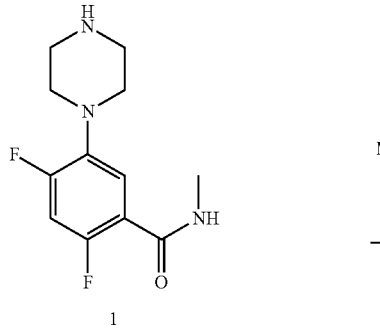

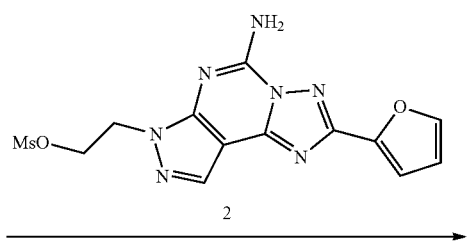

To an ice cold stirred solution of 2-(5-amino-2-(furan-2-yl)-7H-pyrazolo[4,3-e][1,2,4]triazolo-[1,5-c]pyrimidin-7-yl)ethyl methanesulfonate (2) (prepared as described in Example 12, 100 mg, 0.275 mmol), DIPEA (95 µL, 0.550 mmol) in DMF (3 mL) was added 2,4-difluoro-N-methyl-5-(piperazin-1-yl)benzamide (1) (77 mg, 0.303 mol). After addition, the reaction was allowed to reach RT before heating at 100° C. under stirring for 16 h. The reaction mixture was cooled to RT, quenched by addition of water and extracted with ethyl acetate. The organic layer was washed with saturated brine solution, dried over anhydrous Na2SO4, filtered and concentrated under reduced pressure. The crude was purified by prep HPLC to afford the title product as an off white solid. Yield (31.64 mg, 22%). LCMS (ESI positive ion) m/z: calculated: 522; observed: 523.1 (M+1). 1H-NMR (400 MHz, DMSO-d6): δ 8.08 (brs, 2H), 7.94 (brs, 3H), 7.19-7.28 (m, 3H), 6.73 (d, J=3.20 Hz, 1H), 4.42 (t, J=6.80 Hz, 2H), 2.93 (m, 4H), 2.84 (s, 2H), 2.73-2.75 (m, 3H), and 2.63-2.67 (m, 4H).

Example 5: N5-(2-(4-(2,4-difluoro-5-(2-(methylsulfonyl)ethoxy)phenyl)piperazin-1-yl)ethyl)-2-(furan-2-yl)-N5-methyl-[1,2,4]triazolo[1,5-a][1,3,5]triazine-5,7-diamine

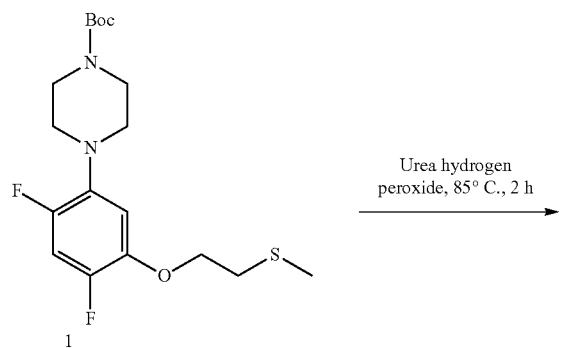

Urea hydrogen peroxide, 85° C., 2 h

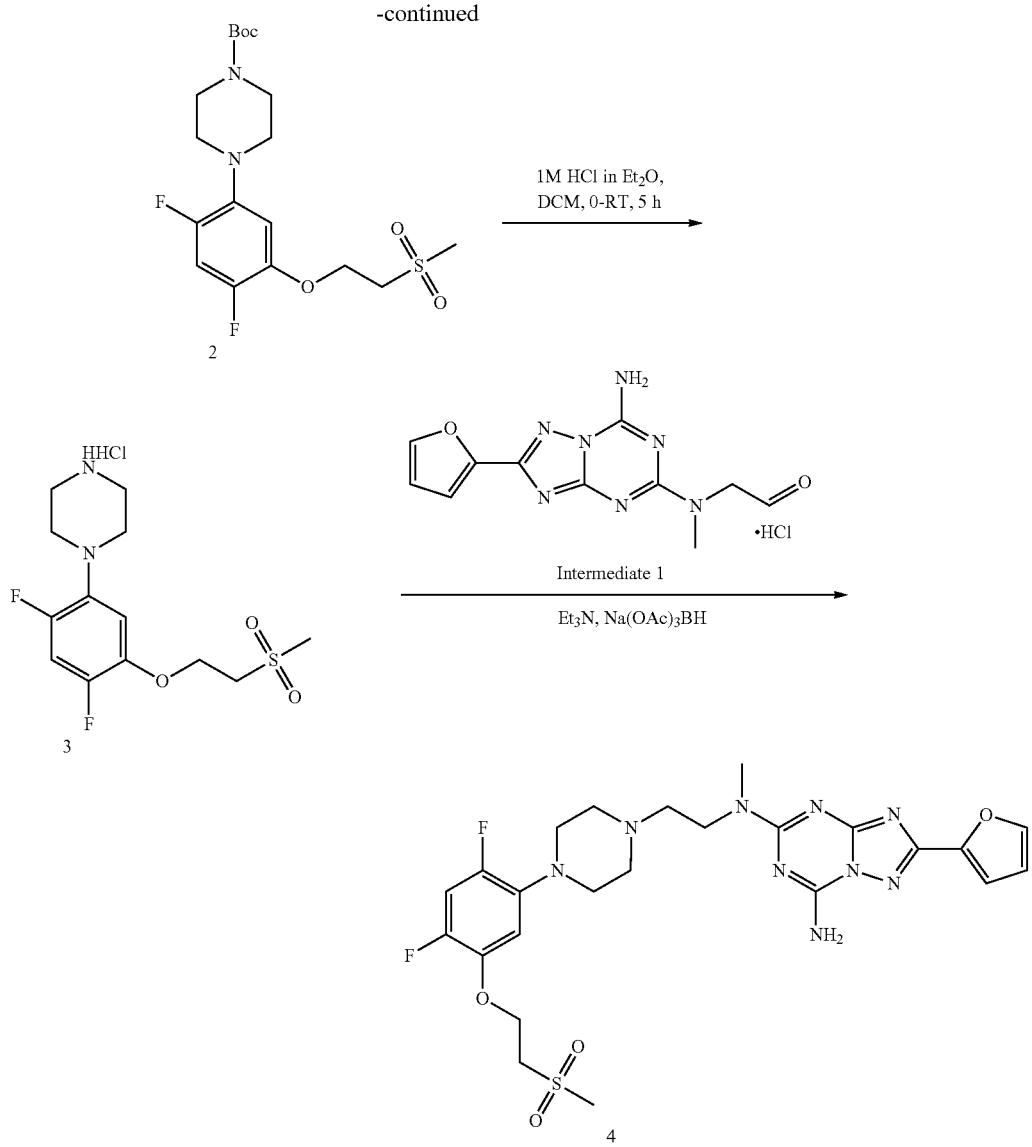

Step 1: Preparation of tert-butyl 4-(2,4-difluoro-5-(2-(methylsulfonyl)ethoxy)phenyl)piperazine-1-carboxylate (2)

In a vial, tert-butyl 4-(2,4-difluoro-5-(2-(methylthio)ethoxy)phenyl)-piperazine-1-carboxylate (1) (0.8 g, 0.002 mol) and urea hydrogen peroxide (0.774 g, 0.008 mol, 4. eq) were mixed and heated to 90° C. After 0.5 h, the solids will melt, the heating was continued at the same temperature for another 0.5 h. After the reaction completion (monitored by TLC), the reaction mixture was chilled to RT. Ethyl acetate (500 mL) was added and stirred for 0.5 h. The slurry was filtered, and the filtrate was evaporated under reduced pressure. The crude was purified by column chromatography (50% ethyl acetate in petroleum ether as eluent) to afford the title product as an off-white solid. Yield (0.35 g, 34%). LCMS (ESI positive ion) m/z: calculated: 420.5; observed: 421.0 (M+1).

Step 2: Preparation of 1-(2,4-difluoro-5-(2-(methylsulfonyl)ethoxy)phenyl)piperazine Hydrochloride (3)

To an ice cold solution of tert-butyl 4-(2,4-difluoro-5-(2-(methylsulfonyl)ethoxy)phenyl)-piperazine-1-carboxylate (2) (0.35 g, 0.714 mmol) in dichloromethane (2 mL), 2M hydrochloric acid in diethyl ether (1 mL) was added. The reaction mixture was stirred at 0° C. for 0.5 h and 16 h at RT. After reaction completion (monitored by TLC), the reaction mixture was concentrated under reduced pressure at RT. The residue was triturated with diethyl ether to afford the crude product. Yield (0.270 g). 1H-NMR (400 MHz, DMSO-d6): δ 7.26 (d, 1H), 6.84 (d, 1H), 4.42 (t, J=5.60 Hz, 2H), 3.64 (t, J=5.20 Hz, 2H), 3.17 (t, J=3.60 Hz, 1H), 3.09 (s, 3H), 2.91 (d, J=4.00 Hz, 4H), and 2.84 (d, J=4.00 Hz, 4H).

Step 3: Preparation of N5-(2-(4-(2,4-difluoro-5-(2-(methylsulfonyl)ethoxy)phenyl)piperazin-1-yl)ethyl)-2-(furan-2-yl)-N5-methyl-[1,2,4]triazolo[1,5-a][1,3,5]triazine-5,7-diamine (4)

To a stirred suspension of 1-(2,4-difluoro-5-(2-(methylsulfonyl)ethoxy)phenyl)piperazine hydrochloride (3) (0.150 g, 0.468 mmol) in dry dichloromethane (5 mL), triethyl amine (130 µL, 0.936 mmol) and 2-[[7-amino-2-(2-furyl)-[1,2,4]triazolo[1,5-a][1,3,5]triazin-5-yl]-methyl-amino]acetaldehyde hydrochloride (Intermediate 1, 0.145 g, 0.468 mmol) were added. After stirring at RT for 3 h, sodium triacetoxyborohydride (198 mg, 0.936 mmol) was added. The resulting mixture was stirred at RT for 24 h. After reaction completion, the reaction mixture was diluted with dichloromethane and was washed successively with a saturated bicarbonate solution and saturated brine solution, dried over anhydrous Na2SO4, filtered and concentrated under reduced pressure. The crude was purified by column chromatography (230-400 silica gel, 5% methanol in dichloromethane as eluent) to afford the title product as an off white solid. Yield (40 mg, 15%). LCMS (ESI positive ion) m/z: calculated: 577.6; observed: 578.1 (M+1). 1H-NMR (400 MHz, DMSO-d6): δ 8.37 (b, s, 2H), 7.88 (s, 1H), 7.27 (t, J=11.60 Hz, 1H), 7.06 (d, J=2.40 Hz, 1H), 6.85 (t, J=6.40 Hz, 1H), 6.68-6.69 (m, 1H), 4.42 (t, J=5.20 Hz, 2H), 3.76 (s, 2H), 3.63 (t, J=5.20 Hz, 2H), 3.28 (d, 3H), 3.18 (s, 3H), 3.03-3.13 (m, 4H), 2.56-2.63 (m, 6H).

Example 6: Preparation of N5-(2-(4-(2,4-difluoro-5-(2-(methylsulfonyl)ethoxy)phenyl)piperazin-1-yl)ethyl)-2-(furan-2-yl)-[1,2,4]triazolo[1,5-a][1,3,5]triazine-5,7-diamine Step 1: 2-(5-amino-8-(furan-2-yl)-2-oxothiazolo[5,4-e][1,2,4]triazolo[1,5-c]pyrimidin-3(2H)-yl)acetaldehyde (2)

To a stirred solution of 5-amino-8-(furan-2-yl)-3-(2-hydroxyethyl)thiazolo[5,4-e][1,2,4]triazolo-[1,5-c]pyrimidin-2(3H)-one (1) (3.6 g, 10.74 mmol, 1.0 eq) in THF (150 mL) was added a solution of IBX (15.04 g, 53.72 mmol, 5.0 eq) in DMSO (35 mL). The resulting mixture was stirred at RT for 6 h. The reaction mixture was diluted with DCM and the layers were separated. The organic layer was washed successively with saturated NaHCO3 solution and saturated brine solution. Then it was dried over anhydrous Na2SO4, filtered and concentrated under reduced pressure. The crude residue obtained was used for next step without further purification. Yield: 75% (3 g).

Step 2: Preparation of N5-(2-(4-(2,4-difluoro-5-(2-(methylsulfonyl)ethoxy)phenyl)piperazin-1-yl)ethyl)-2-(furan-2-yl)-[1,2,4]triazolo[1,5-a][1,3,5]triazine-5,7-diamine (4)

To a stirred suspension of 1-(2,4-difluoro-5-(2-(methylsulfonyl)ethoxy)phenyl)piperazine hydrochloride (3) (0.120 g, 0.374 mmol, 1 eq) in dry dichloromethane (5 mL), triethyl amine (157.91 mg, 0.748 mmol, 2 eq) and 2-[[7-amino-2-(2-furyl)-[1,2,4]triazolo[1,5-a][1,3,5]-triazin-5-yl]amino]

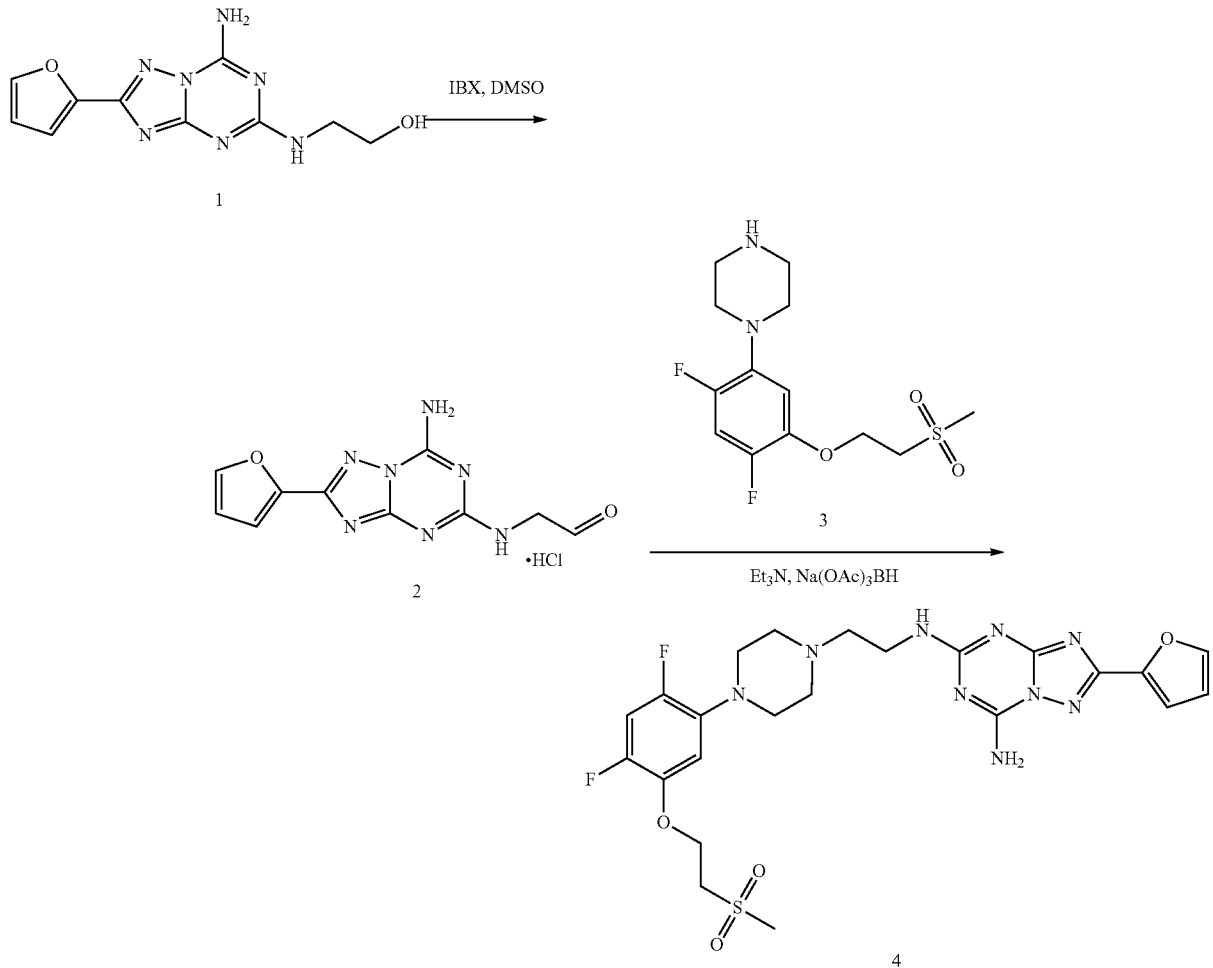

acetaldehyde (2) (0.097 g, 0.374 mmol, 1 eq) (crude aldehyde freshly prepared from oxidation of 1 g of alcohol) were added. After stirring at room temperature for 3 h, sodium triacetoxy borohydride (75.59 mg, 0.748 mmol, 2.0 eq) was added. The resulting mixture was stirred at room temperature for 24 h. After completion, the reaction mixture was diluted with dichloromethane. The organic layer separated was washed successively with saturated bicarbonate solution and saturated brine solution. Then it was dried over anhydrous Na2SO4, filtered and concentrated under reduced pressure. The crude obtained was purified by column chromatography (230-400 silica gel, 5% methanol/dichloromethane as an eluent) to afford the product as off white solid. Yield (30 mg, 13.0%). LCMS (ESI positive ion) m/z: calculated: 563.5; observed: 564.1 (M+1). 1H-NMR (400 MHz, DMSO-d6): δ 8.14 (s, 2H), 7.86 (s, 1H), 7.27 (d, J=11.32 Hz, 2H), 7.05 (s, 1H), 6.85 (s, 1H), 6.67 (s, 1H), 4.41 (s, 2H), 3.63 (s, 2H), 3.43 (s, 2H), 3.07 (s, 3H), 3.00 (s, 4H), and 2.66 (s, 6H).

Example 7: (S)-5-amino-3-(2-(4-(2,4-difluoro-5-(2-(methylsulfinyl)ethoxy)phenyl)piperazin-1-yl)ethyl)-8-(furan-2-yl)-1-methyl-1H-[1,2,4]triazolo[5,1-i]purin-2-one

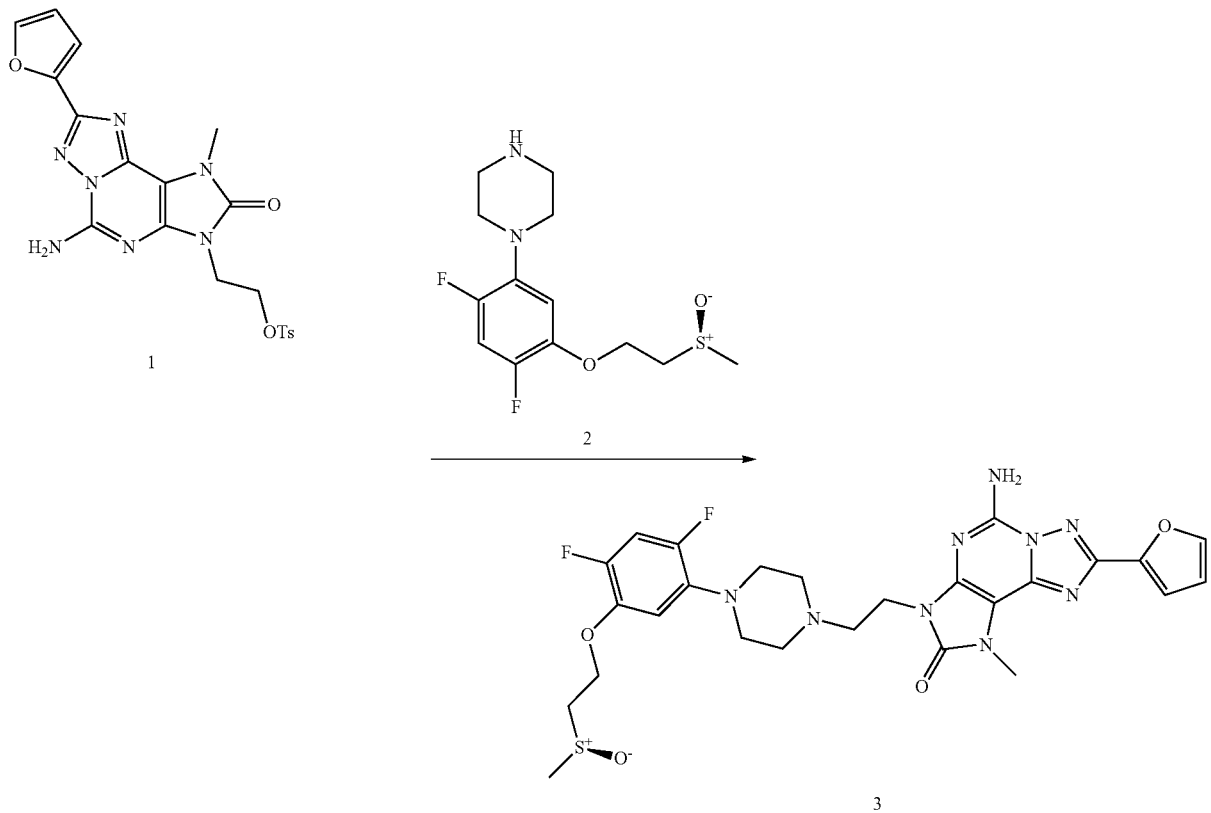

To a stirred mixture of 2-(5-amino-8-(furan-2-yl)-1-methyl-2-oxo-1,2-dihydro-3H-[1,2,4]triazolo[5,1-i]purin-3-yl)ethyl 4-methylbenzenesulfonate (1) (prepared as described in WO 2012038980, 100 mg, 0.213 mmol) and (S)-1-(2,4-difluoro-5-(2-(methylsulfinyl)ethoxy)phenyl) piperazine (2) (77.79 mg, 0.256 mmol) in benzonitrile (0.05 mL), DIPEA (46 µL, 0.266 mmol) was added. The resulting mixture was stirred at 80° C. for 48 h. After completion of the reaction, the reaction mixture was cooled to RT. The precipitate was filtered and washed with acetonitrile, MTBE and dried under vacuum to afford the title product as an off white solid. Yield (50 mg, 39%). LCMS (ESI positive ion) m/z: calculated: 601.6; observed: 602.2 (M+1). 1H-NMR (400 MHz, DMSO-d6): δ 7.94 (s, 1H), 7.80 (s, 2H), 7.21-7.27 (m, 2H), 6.83 (t, J=7.72 Hz, 1H), 6.73 (d, J=1.60 Hz, 1H), 4.36-4.43 (m, 2H), 3.96 (s, 2H), 3.58 (s, 3H), 3.34 (s, 1H), 3.03 (m, 1H), 2.95 (brs, 4H), 2.63-2.70 (m, 8H), and 2.51 (brs, 1H).

Example 8: (R)-5-amino-3-(2-(4-(2,4-difluoro-5-(2-(methylsulfinyl)ethoxy)-phenyl)piperazin-1-yl)ethyl)-8-(furan-2-yl)-1-methyl-1H-[1,2,4]triazolo[5,1-i]purin-2-one

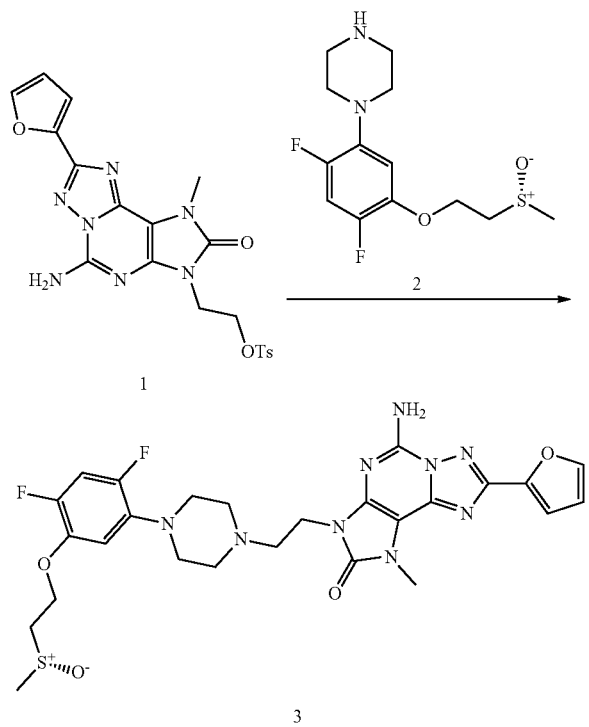

To a stirred solution of 2-[5-amino-8-(2-furyl)-1-methyl-2-oxo-[1,2,4]triazolo[5,1-f]purin-3-yl]ethyl 4-methylbenzenesulfonate (1) (prepared as described in WO 2012038980, 50 mg, 0.107 mmol) and (R)-1-(2,4-difluoro-5-(2-(methylsulfinyl)ethoxy)phenyl)piperazine (2) (38.90 mg, 0.128 mmol) in benzonitrile (0.05 mL), DIPEA (24 μL, 0.133 mmol) was added. The resulting mixture was stirred at 80° C. for 48 h. After completion of the reaction, the reaction mixture was cool to RT. The precipitate was filtered and washed with acetonitrile, MTBE and dried under vacuum to obtain the title compound as an off whited solid. Yield (21.9 mg, 31%). LCMS (ESI positive ion) m/z: calculated: 601.6; observed: 602.2 (M+1). 1H-NMR (400 MHz, DMSO-d6): δ 7.94 (s, 1H), 7.80 (s, 2H), 7.21-7.27 (m, 2H), 6.83 (t, J=7.72 Hz, 1H), 6.73 (d, J=1.60 Hz, 1H), 4.36-4.43 (m, 2H), 3.96 (s, 2H), 3.58 (s, 3H), 3.34 (s, 1H), 3.03 (m, 1H), 2.95 (brs, 4H), 2.63-2.70 (m, 8H), and 2.51 (brs, 1H).

Example 9: 5-amino-3-(2-(4-(2,4-difluoro-5-(2-(methylsulfonyl)ethoxy)phenyl)piperazin-1-yl)ethyl)-8-(furan-2-yl)-1-methyl-1H-[1,2,4]triazolo[5,1-i]purin-2(3H)-one

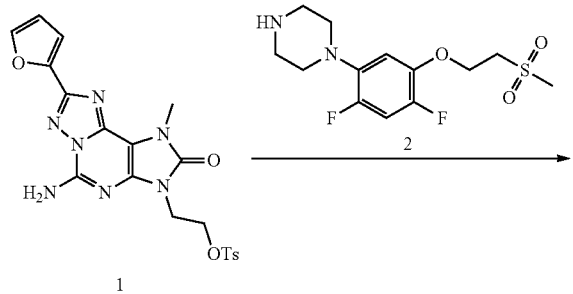

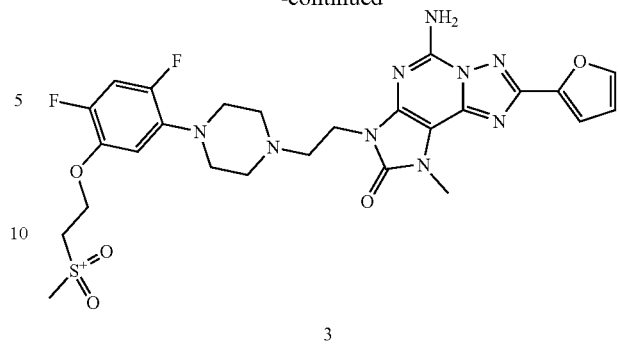

To a stirred solution of 2-(5-amino-8-(furan-2-yl)-1-methyl-2-oxo-1,2-dihydro-3H-[1,2,4]-triazolo[5,1-i]purin-3-yl)ethyl 4-methylbenzenesulfonate (1) (prepared as described in WO 2012038980, 150 mg, 0.320 mmol), 1-(2,4-difluoro-5-(2-(methyl sulfonyl)ethoxy)phenyl)piperazine (2) (122.83 mg, 0.383 mmol) in DMF (3 mL), DIPEA (114 μL, 0.639 mmol) was added. The resulting mixture was stirred at 100° C. for 18 h. After completion of reaction, the reaction mixture was concentrated and the residue was purified by preparative TLC (5% MeOH in dichloromethane as an eluent) to afford the title product as an off-white solid. Yield (21 mg, 10%). LCMS (ESI positive ion) m/z: calculated: 617.63; observed: 618.2 (M+1). 1H-NMR (400 MHz, DMSO-d6): δ 7.94 (d, J=0.80 Hz, 1H), 7.79 (s, 2H), 7.20-7.29 (m, 2H), 6.82 (t, J=8.60 Hz, 1H), 6.72-6.74 (m, 1H), 4.40 (t, J=5.64 Hz, 2H), 3.96 (brs, 2H), 3.62 (t, J=5.40 Hz, 2H), 3.58 (brs, 3H), 3.07 (brs, 3H), 2.95 (s, 4H), and 2.68-2.71 (m, 6H).

Example 10: (S)—N5-(2-(4-(2,4-difluoro-5-(2-(methylsulfinyl)ethoxy)phenyl)piperazin-1-yl)ethyl)-2-(furan-2-yl)-[1,2,4]triazolo[1,5-a][1,3,5]triazine-5,7-diamine

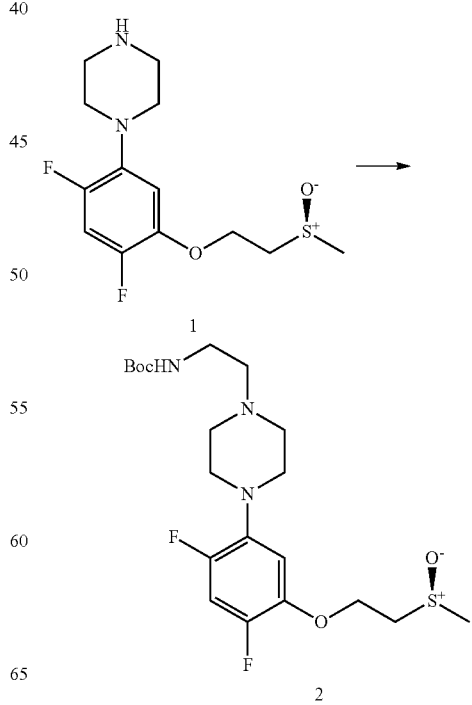

-continued

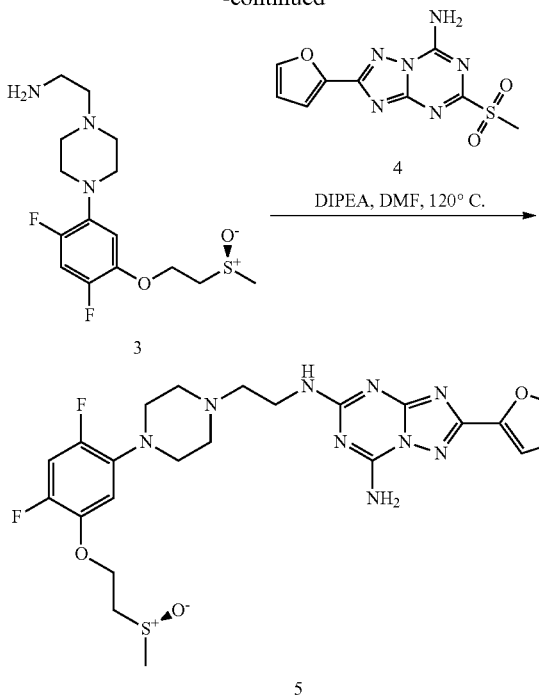

Step 1: Preparation of tert-butyl (S)-(2-(4-(2,4-difluoro-5-(2-(methylsulfinyl)ethoxy)-phenyl)piperazin-1-yl)ethyl)carbamate (2)

To a stirred solution of (S)-1-(2,4-difluoro-5-(2-(methylsulfinyl)ethoxy)phenyl)piperazine (2) (0.2 g, 0.657 mmol, 1 eq) in acetonitrile (2 mL), DIPEA (230 µL, 1.314 mmol, 2 eq) and tert-butyl N-(2-bromoethyl)carbamate (0.162 g, 0.723 mmol, 1.1 eq) were added. The resulting mixture was heated at 50° C. for 5 h. After completion of reaction, reaction mixture was poured into ice water and extracted with ethyl acetate. Combined organic layers were washed with brine, dried over Na2SO4, and evaporated under reduced pressure. The crude was purified by column chromatography with 50% ethylacetate in petroleum ether, to afford the pure product as an off white solid. Yield (140 mg, 43%). LCMS (ESI positive ion) m/z: calculated: 447.58; observed: 448.5 (M+1).

Step 2: Preparation of (S)-2-(4-(2,4-difluoro-5-(2-(methylsulfinyl)ethoxy)phenyl)-piperazin-1-yl)ethan-1-amine hydro chloride (3)

To an ice cold solution of tert-butyl (S)-(2-(4-(2,4-difluoro-5-(2-(methylsulfinyl)ethoxy)-phenyl)piperazin-1-yl)ethyl)carbamate (2) (0.14 g, 0.313 mmol, 1 eq) in dichloromethane (2 mL), 2M HCl in ether (0.5 mL) was added and the reaction mixture was stirred at 0° C. for 1 h. After reaction completion (monitored by TLC), the reaction mixture was concentrated under reduced pressure at RT. The residue obtained was triturated in diethyl ether to afford the pure product as an hydrochloride salt. Then it was dissolved in methanol, passed through Si-Carbonate resin to release the free base. The crude product was directly used for next step. Yield (110 mg, 88%).

Step 3: Preparation of (S)—N5-(2-(4-(2,4-difluoro-5-(2-(methylsulfinyl)ethoxy)phenyl)piperazin-1-yl)ethyl)-2-(furan-2-yl)-[1,2,4]triazolo[1,5-a][1,3,5]triazine-5,7-diamine (5)

To a stirred solution of 2-((7-amino-2-(furan-2-yl)-[1,2,4]triazolo[1,5-a][1,3,5]triazin-5-yl)amino)ethyl methane sulfonate (4) (prepared according to the procedure described in EP459702, 0.150 g, 0.442 mmol) in DMF (5 mL), (S)-1-(2,4-difluoro-5-(2-(methylsulfinyl)ethoxy)phenyl)piperazine (0.186 g, 0.612 mmol), DIPEA (280 µL, 1.6 mmol) were added. The resultant mixture was heated to 120° C. for 16 h. After completion of the reaction, the reaction mixture was concentrated under reduced pressure. The crude was purified by column chromatography to afford the pure compound as an off white solid. Yield (25 mg, 8%). LCMS (ESI positive ion) m/z: calculated: 547.5; observed: 548.2 (M+1). 1H-NMR (400 MHz, DMSO-d6): δ 8.35 (m, 2H), 7.89 (s, 1H), 7.67 (s, 1H), 7.35 (t, J=11.60 Hz, 1H), 7.06-7.10 (m, 1H), 6.92-6.97 (m, 1H), 6.69 (t, J=2.00 Hz, 1H), 4.37-4.42 (m, 2H), 3.67-3.83 (m, 4H), 3.45 (m, 2H), 3.26-3.32 (m, 4H), 3.03-3.07 (m, 4H), and 2.65 (s, 3H).

Example 11: (R)—N5-(2-(4-(2,4-difluoro-5-(2-(methylsulfinyl)ethoxy)phenyl)piperazin-1-yl)ethyl)-2-(furan-2-yl)-[1,2,4]triazolo[1,5-a][1,3,5]triazine-5,7-diamine

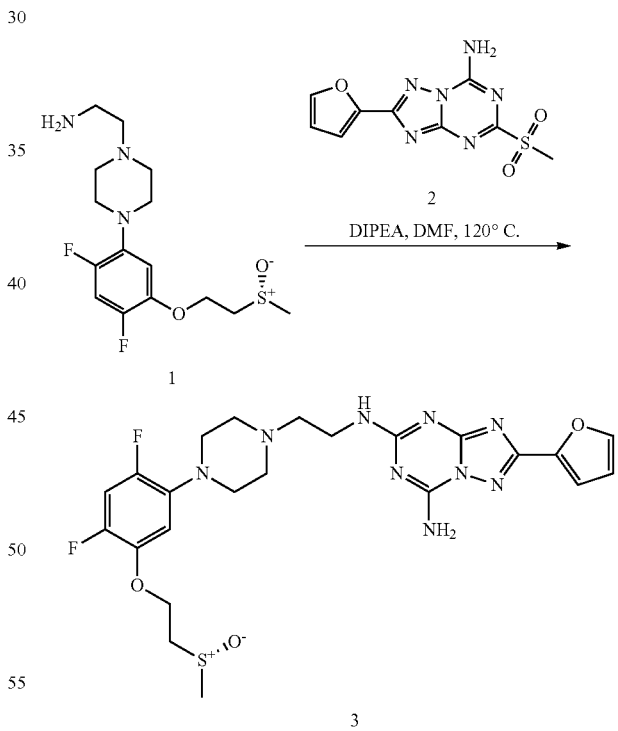

To a stirred solution of 2-((7-amino-2-(furan-2-yl)-[1,2,4]triazolo[1,5-a][1,3,5]triazin-5-yl)amino)ethyl methane sulfonate (1) (0.100 g, 0.357 mmol) in DMF (5 mL), (R)-1-(2,4-difluoro-5-(2-(methylsulfinyl)ethoxy)phenyl)piperazine (0.136 g, 0.392 mmol), DIPEA (310 µL, 1.8 mmol) were added. The resultant mixture was heated to 120° C. for 16 h. After completion of the reaction, the reaction mixture was concentrated under reduced pressure and purified by column chromatography to afford the pure compound as an off white solid. Yield (17 mg, 7%). LCMS (ESI positive ion) m/z: calculated: 547.5; observed: 548.2 (M+1). 1H-NMR (400 MHz, DMSO-d6): δ 8.35 (m, 2H), 7.89 (s, 1H), 7.67 (s, 1H), 7.35 (t, J=11.60 Hz, 1H), 7.06-7.10 (m, 1H), 6.92-6.97 (m, 1H), 6.69 (t, J=2.00 Hz, 1H), 4.37-4.42 (m, 2H), 3.67-3.83 (m, 4H), 3.45 (m, 2H), 3.26-3.32 (m, 4H), 3.03-3.07 (m, 4H), and 2.65 (s, 3H).

Example 12: (S)-7-(2-(4-(2,4-difluoro-5-(2-(methyl-sulfinyl)ethoxy)phenyl)piperazin-1-yl)ethyl)-2-(furan-2-yl)-7H-pyrazolo[4,3-e][1,2,4]triazolo[1,5-c]pyrimidin-5-amine

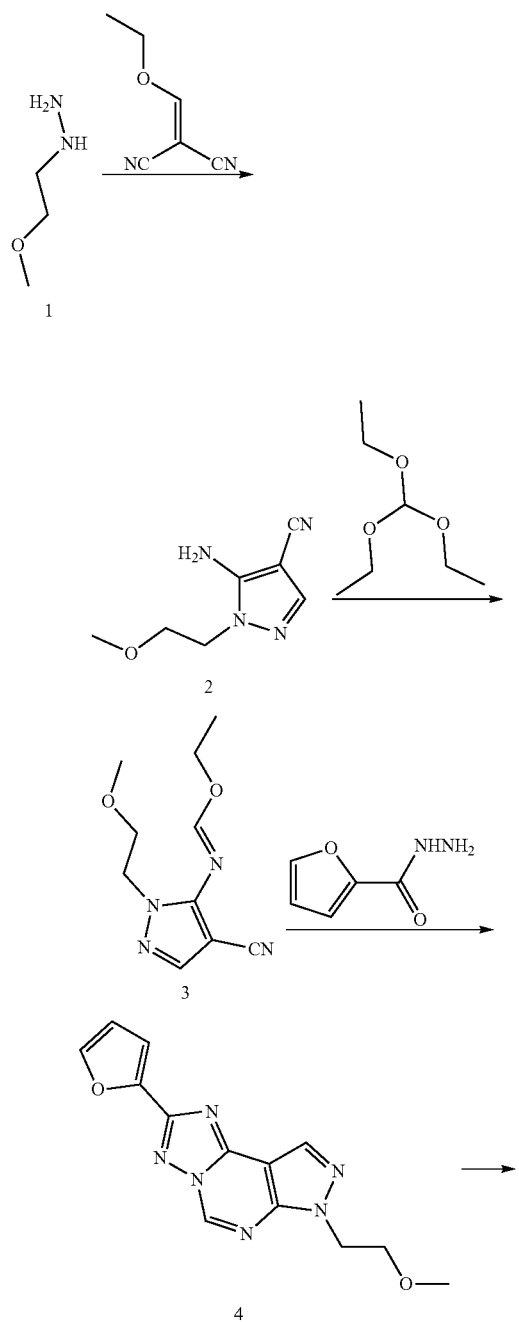

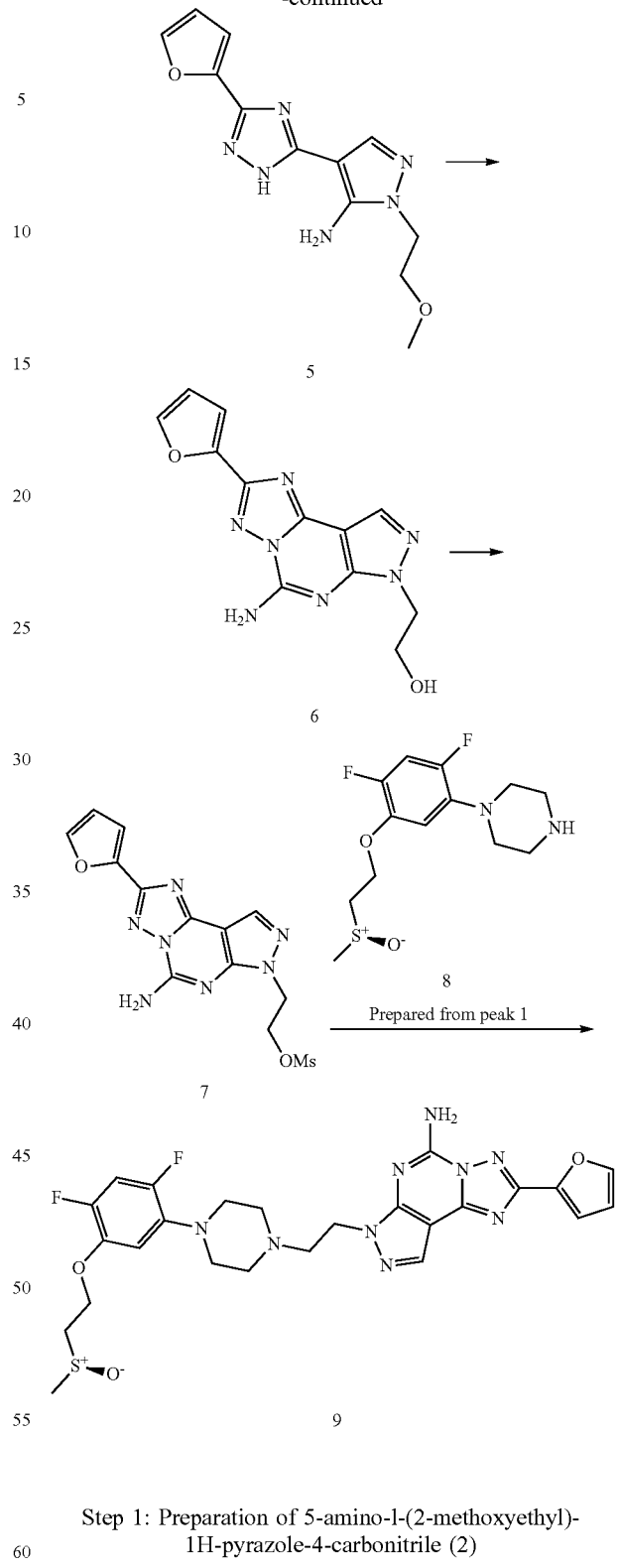

Step 1: Preparation of 5-amino-1-(2-methoxyethyl)-1H-pyrazole-4-carbonitrile (2)

A solution of (2-methoxyethyl)hydrazine (1) (15 g, 166.43 mmol) and 2-(ethoxymethylene) malononitrile (30.49 g, 249.65 mmol) in ethanol (150 mL) was heated at 95° C. for 16 h. After the reaction completion (monitored by TLC), the reaction mixture was concentrated under reduced pressure. The residue was taken up in water and extracted with dichloromethane. The organic layer was washed with saturated brine solution, dried over anhydrous Na2SO4, filtered and concentrated under reduced pressure to afford a brown liquid. Yield: (12 g, 26%). LCMS (ESI positive ion) m/z: calculated: 166.18; observed: 167.0 (M+1).

Step 2: Preparation of ethyl (E)-N-(4-cyano-1-(2-methoxyethyl)-1H-pyrazol-5-yl)-formimidate (3)

To a solution of 5-amino-1-(2-methoxyethyl)-1H-pyrazole-4-carbonitrile (2) (12 g, 72.21 mmol) and triethoxymethane (53.51 g, 361.05 mmol) in toluene (120 mL), was added pTSA (0.12 g, 0.63 mmol). The reaction mixture was heated at 110° C. for 16 h. After the reaction completion (monitored by TLC), the reaction mixture was concentrated and the residue was taken up in water and extracted with ethyl acetate. The organic layer was washed with saturated brine solution, dried over anhydrous Na2SO4, filtered and concentrated under reduced pressure. The crude was purified by column chromatography (50% EtOAc in Hexane as eluent) to afford the title compound as a brown solid. Yield: (9.5 g, 55%). LCMS (ESI positive ion) m/z: calculated: 222.2; observed: 223.1 (M+1); 1H-NMR (400 MHz, DMSO-d6): δ 8.45 (s, 1H), 7.92 (s, 1H), 4.40-4.35 (m, 2H), 4.17 (t, J=10.8 Hz, 2H), 3.67 (t, J=9.2 Hz, 2H), 3.19 (s, 3H), and 1.36 (t, J=14 Hz, 3H).

Step 3: Preparation of 2-(furan-2-yl)-7-(2-methoxyethyl)-7H-pyrazolo[4,3-e][1,2,4]-triazolo[1,5-c]pyrimidine (4)

To a solution of ethyl (E)-N-(4-cyano-1-(2-methoxyethyl)-1H-pyrazol-5-yl)formimidate (3) (9.5 g, 42.75 mmol) and furan-2-carbohydrazide (6.47 g, 51.29 mmol) in toluene (95 mL), was added isobutyric acid (3.76 g, 42.75 mmol). The reaction mixture was heated at 110° C. for 16 h. After the reaction completion (monitored by TLC), reaction mixture was concentrated and the residue was taken up in water and extracted with ethyl acetate. The organic layer was washed with saturated brine solution, dried over anhydrous Na2SO4, filtered and concentrated under reduced pressure. The crude was triturated with acetonitrile to afford the title product as a white solid. Yield: (8 g, 54%). LCMS (ESI positive ion) m/z: calculated: 284.2; observed: 285.2 (M+1).

Step 4: Preparation of 4-(3-(furan-2-yl)-1H-1,2,4-triazol-5-yl)-1-(2-methoxyethyl)-1H-pyrazol-5-amine (5)

To 2-(furan-2-yl)-7-(2-methoxyethyl)-7H-pyrazolo[4,3-e][1,2,4]triazolo[1,5-c]-pyrimidine (4) (8 g, 28.14 mmol), 1.5N HCl (80 mL) was added and the resulting reaction mixture was heated at 100° C. for 16 h. After the reaction completion (monitored by TLC), reaction mixture was cooled to 0° C. and basified with aqueous ammonia solution (pH-8) and concentrated. The resulting solid was filtered, washed with 10% MeOH in dichloromethane. The filtrate was dried over anhydrous Na2SO4, concentrated under reduced pressure to afford the title product as an off white solid. Yield: (4.5 g, 57%). LCMS (ESI positive ion) m/z: calculated: 274.2; observed: 275.2 (M+1). 1H-NMR (400 MHz, DMSO-d6): δ 13.80 (s, 1H), 7.77 (d, J=0.8 Hz, 1H), 7.68 (s, 1H), 6.96 (d, J=3.2 Hz, 1H), 6.62-6.61 (m, 1H), 5.82 (s, 2H), 4.12-4.11 (m, 2H), 3.67 (t, J=11.6 Hz, 2H), and 3.25 (s, 3H).

Step 5: Preparation of 2-(5-amino-2-(furan-2-yl)-7H-pyrazolo[4,3-e][1,2,4]triazolo[1,5-c]pyrimidin-7-yl)ethan-1-ol (6)

A solution of 2-(furan-2-yl)-7-(2-methoxyethyl)-7H-pyrazolo[4,3-e][1,2,4]-triazolo[1,5-c]-pyrimidin-5-amine (5) (0.7 g, 2.33 mmol) in dichloromethane (70 mL) was cooled to −60° C. Boron tribromide (1.75 g, 7.01 mmol) was added drop wise and the resulting mixture was stirred at RT for 2 h. After the reaction completion (monitored by TLC), the reaction mixture was diluted with cold water, neutralised with NaHCO3 and extracted by dichloromethane. The organic layer was washed with water and dried over Na2SO4 and concentrated under reduced pressure to afford the title product as an off white solid. Yield: (0.5 g, 72%). LCMS (ESI positive ion) m/z: calculated: 285; observed: 286.2 (M+1); 1H-NMR (400 MHz, DMSO-d6): δ 8.16 (s, 1H), 8.07 (brs, 2H), 7.95 (s, 1H), 7.24 (d, J=3.2 Hz, 1H), 6.74-6.73 (m, 1H), 4.32 (t, J=14.4 Hz, 2H), and 3.84 (t, J=12.4 Hz, 2H).

Step 6: Preparation of 2-(5-amino-2-(furan-2-yl)-7H-pyrazolo[4,3-e][1,2,4]triazolo[1,5-c]pyrimidin-7-yl)ethyl methane sulfonate (7)

To an ice cold solution of 2-(5-amino-2-(furan-2-yl)-7H-pyrazolo[4,3-e][1,2,4]triazolo[1,5-c]pyrimidin-7-yl)ethan-1-ol (6) (0.5 g, 1.75 mmol) in DMF (5 mL), triethylamine (480 μL, 3.50 mmol) and methane sulphonyl chloride (0.24 g, 2.10 mmol) were successively added. After stirring at RT for 1 h, the reaction mixture was diluted with cold water and extracted with ethyl acetate. The organic layer was washed with brine, dried over Na2SO4, filtered and concentrated under reduced pressure. The residue was triturated with dichloromethane to afford the title compound as an off white solid. Yield: (0.3 g, 45%). LCMS (ESI positive ion) m/z: calculated: 363.3 observed: 363.9 (M+1); 1H-NMR (400 MHz, DMSO-d6): δ8.23-8.15 (m, 3H), 7.94 (s, 1H), 7.23 (d, J=4.4 Hz, 1H), 6.74-6.72 (m, 1H), 4.66-4.59 (m, J=29.6 Hz, 4H), and 3.08 (s, 3H).

Step 7: Preparation of (S)-7-(2-(4-(2,4-difluoro-5-(2-(methylsulfinyl)ethoxy)phenyl)-piperazin-1-yl)ethyl)-2-(furan-2-yl)-7H-pyrazolo[4,3-e][1,2,4]triazolo[1,5-c]pyrimidin-5-amine (9)

To a mixture of 2-(5-amino-2-(furan-2-yl)-7H-pyrazolo[4,3-e][1,2,4]triazolo[1,5-c]pyrimidin-7-yl)ethyl methane sulfonate (7) (0.039 g, 0.108 mmol) and (S)-1-(2,4-difluoro-5-(2-(methylsulfinyl)ethoxy)phenyl)piperazine (8) (0.03 g, 0.099 mmol) in benzonitrile (0.2 mL), DIPEA (26 μL, 0.148 mmol) was added. The reaction mixture was heated at 110° C. for 16 h. After the reaction completion (monitored by TLC), the reaction mixture was concentrated, the residue was purified by column chromatography (5% MeOH in dichloromethane as eluent) to afford the title product as an off white solid. Yield (0.02 g, 35%). LCMS (ESI positive ion) m/z: calculated: 571.6 observed: 572.2 (M+1); 1H-NMR (400 MHz, DMSO-d6): δ 8.16 (s, 1H), 8.07 (s, 1H), 7.94 (s, 1H), 7.25-7.19 (m, 2H), 6.83 (t, J=17.2 Hz, 1H), 6.73 (t, J=3.2 Hz, 1H), 4.42-4.33 (m, 4H), 3.21-3.15 (m, 2H), 3.04-2.98 (m, 1H), 2.92 (s, 4H), 2.85 (t, J=12.8 Hz, 2H), and 2.62 (s, 6H).

Example 13: (R)-7-(2-(4-(2,4-difluoro-5-(2-(methyl-sulfinyl)ethoxy)phenyl)piperazin-1-yl)ethyl)-2-(furan-2-yl)-7H-pyrazolo[4,3-e][1,2,4]triazolo[1,5-c]pyrimidin-5-amine Example 14: (1s,4s)-4-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)tetrahydro-2H-thiopyran 1-oxide

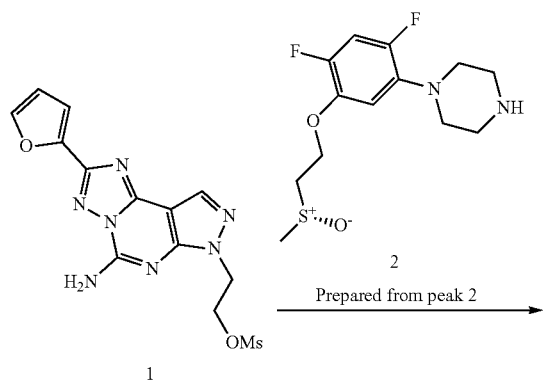

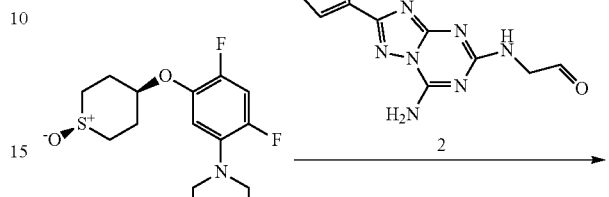

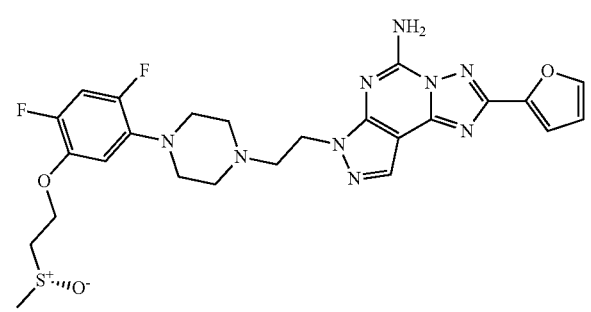

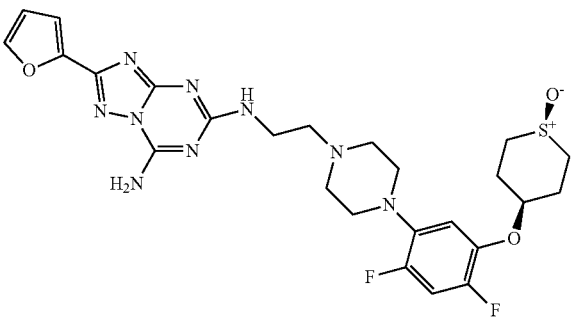

To a mixture of 2-(5-amino-2-(furan-2-yl)-7H-pyrazolo[4,3-e][1,2,4]triazolo[1,5-c]pyrimidin-7-yl)ethyl methanesulfonate (1) (prepared according to the protocol described in Example 12, steps 1-6, 0.033 g, 0.090 mmol) and (R)-1-(2,4-difluoro-5-(2-(methyl-sulfinyl)ethoxy)phenyl)piperazine (2) (0.025 g, 0.082 mmol) in benzonitrile (0.13 mL), DIPEA (22 µL, 0.123 mmol) was added. The reaction mixture was heated at 110° C. for 16 h. After the reaction completion (monitored by TLC), the reaction mixture was concentrated, the residue was purified by column chromatography (5% MeOH in dichloromethane as eluent) to afford the title product as an off white solid. Yield (0.012 g, 24%). LCMS (ESI positive ion) m/z: calculated: 571.6 observed: 572.2 (M+1). 1H-NMR (400 MHz, DMSO-d6): δ 8.17 (s, 1H), 8.08 (s, 1H), 7.95 (s, 1H), 7.26-7.20 (m, 2H), 6.84-6.3 (m, 2H), 4.43-4.35 (m, 4H), 3.25-3.16 (m, 2H), 3.04-3.01 (m, 1H), 2.93 (s, 4H), 2.86 (t, J=13.2 Hz, 2H), and 2.67 (s, 6H).

To a solution of 2-((7-amino-2-(furan-2-yl)-[1,2,4]triazolo[1,5-a][1,3,5]triazin-5-yl)amino)acetaldehyde (2) (0.264 g, 1.017 mmol) and (cis)-4-(2,4-difluoro-5-(piperazin-1-yl)-phenoxy)-tetrahydro-2H-thiopyran 1-oxide (1) (0.280 g, 0.847 mmol) in methanol (3 mL) was added MP-CNBH3 (0.28 g) followed by a drop of acetic acid. The reaction mixture was stirred at RT for 16 h. After completion of the reaction (TLC), reaction mass was filtered, concentrated and purified by preparative HPLC to afford the title compound as an off white solid. Yield: (0.06 g; 12%); LCMS (ESI positive ion) m/z: calculated: 573.6; observed: 574.2 (M+1); 1H-NMR (400 MHz, DMSO-d6): δ 8.16 (brs, 2H), 7.87 (s, 1H), 7.31-7.22 (m, 2H), 7.05 (d, J=3.2 Hz, 1H), 6.88-6.84 (m, 1H), 6.67 (m, 1H), 4.42-4.37 (m, 1H), 3.44-3.42 (m, 2H), 2.98-2.92 (m, 6H), 2.83-2.77 (m, 2H), 2.67-2.50 (m, 6H), 2.33-2.21 (m, 2H), 2.20-2.12 (m, 2H).

Example 15: 4-(5-(4-(2-((7-amino-2-(furan-2-yl)-[1,2,4]triazolo[1,5-a][1,3,5]triazin-5-yl)amino)ethyl)piperazin-1-yl)-2,4-difluorophenyl)thiomorpholine 1-oxide

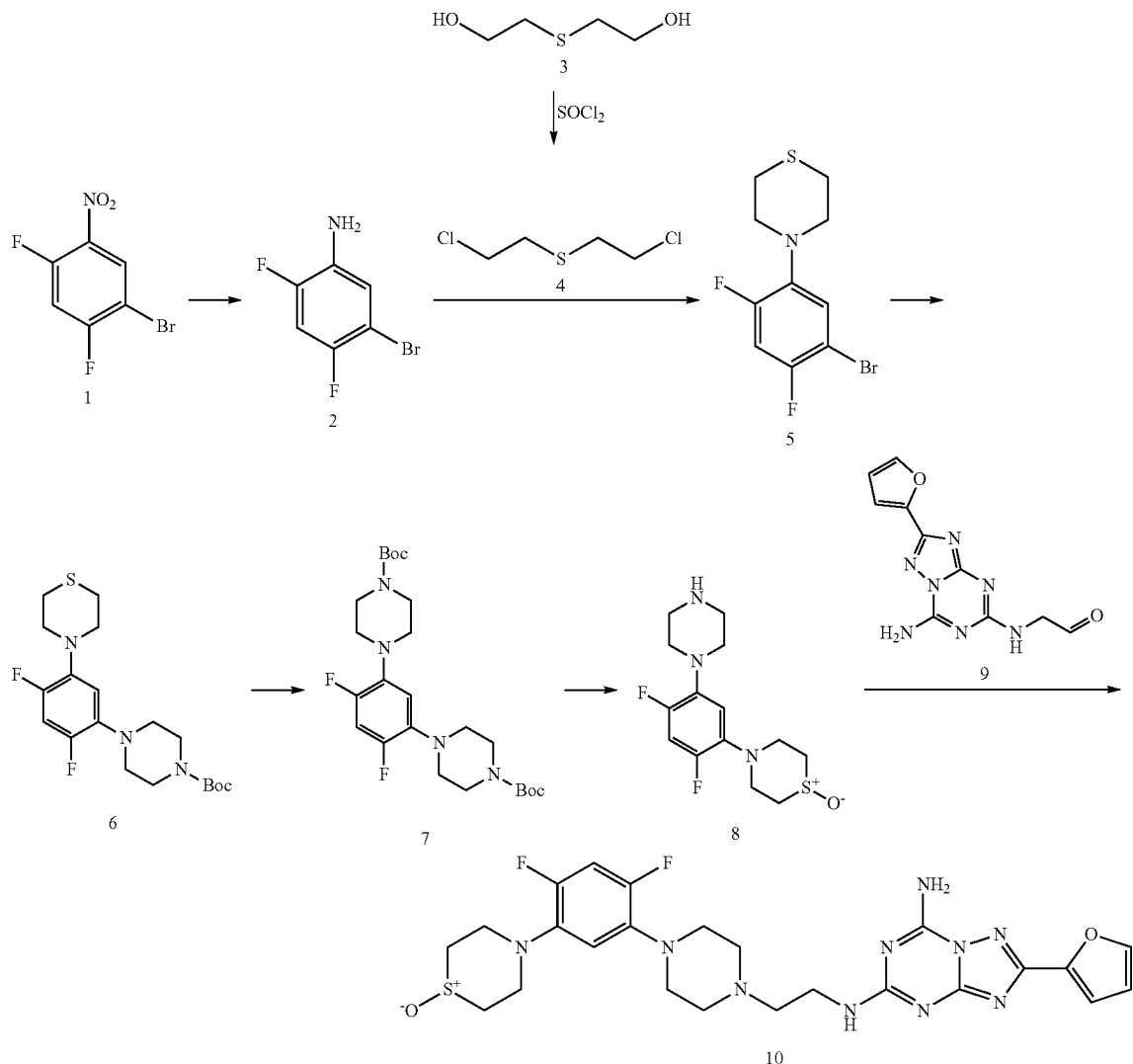

Step 1: Preparation of 5-bromo-2,4-difluoroaniline (2)

To a stirred solution of 1-bromo-2,4-difluoro-5-nitrobenzene (1) (3.0 g, 0.013 mol) in ethanol (40 mL), iron powder (4.928 g, 0.088 mol) and acetic acid (10.60 mL, 0.176 mol) were added and the reaction mixture was stirred at 80° C. for 2 h. The progress of the reaction was monitored by TLC. The reaction mixture was filtered through a celite bed and the filtrate was concentrated under reduced pressure. The residue was dissolved in water and extracted with ethyl acetate. Combined organic layers were concentrated under reduced pressure to afford the title compound as an off white solid. Yield (2.0 g, 90%). LCMS (ESI positive ion) m/z: calculated: 208.1; observed: 210.1 (M+2).

Step 2: Preparation of bis(2-chloroethyl)sulfane (4)

Thionyl chloride (1.781 mL) was added to 2,2'-thiobis(ethan-1-ol) (3) (2.0 g, 0.041 mol) under ice cold condition. The resulting mixture was stirred at 80° C. for 2 h. The progress of the reaction was monitored by TLC. The crude was concentrated under reduced pressure to afford the title compound as brown colour liquid. Yield (1.5 g, 51%). 1H-NMR (400 MHz, DMSO-d6): δ 3.77 (t, J=7.44 Hz, 4H), and 2.94 (t, J=7.32 Hz, 4H).

Step 3: Preparation of 4-(5-bromo-2,4-difluorophenyl)thiomorpholine (5)

A solution of 5-bromo-2,4-difluoroaniline (2) (1.4 g, 0.007 mol) and bis(2-chloroethyl)sulfane (4) (1.392 g, 0.009 mol) in sulfolane (6 mL) was heated to 150° C. 16 h. Progress of the reaction was monitored by TLC. After completion, the crude sample obtained was purified by column chromatography (10% EtOAc/Hexane as eluent) to afford the title compound as brown solid. Yield (1.3 g, 57.5%). LCMS (ESI positive ion) m/z: calculated: 294.1; observed: 295 (M+1).

Step 4: Preparation of tert-butyl 4-(2,4-difluoro-5-thiomorpholinophenyl)piperazine-1-carboxylate (6)

To a stirred solution of 4-(5-bromo-2,4-difluorophenyl) thiomorpholine (5) (0.750 g, 0.003 mol) and tert-butyl piperazine-1-carboxylate (0.617 g, 0.003 mol) in dioxane (15 mL), NaOtBu (0.490 g, 0.005 mol) was added. The reaction mixture was purged with nitrogen. Then Pd2(dba)3 (0.117 g, 0.00012 mol) and BINAP (0.048 g, 0.00007 mol) were added. The resulting mixture was stirred at 120° C. for 16 h. After completion, the reaction mixture was concentrated under reduced pressure. The crude residue obtained was purified by column chromatography (20% EtOAc/ Hexane as eluent) to afford the title compound as brown solid. Yield (150 mg, 13.5%). LCMS (ESI positive ion) m/z: calculated: 399.5; observed: 401.1 (M+1).

Step 5: Preparation of tert-butyl 4-(2,4-difluoro-5-(1-oxidothiomorpholino)phenyl)-piperazine-1-carboxylate (7)

To an ice cold solution of tert-butyl 4-(2,4-difluoro-5-thiomorpholinophenyl)piperazine-1-carboxylate (6) (0.150 g, 0.0003 mol) in acetic acid (2.0 mL), hydrogen peroxide (0.018 mL, 0.0007 mol) was added. The reaction mixture was stirred at 0° C. for 3 h. After the completion, the reaction mixture was concentrated under reduced pressure. The residue was purified by column chromatography (2% methanol/ dichloromethane as eluent) to afford the title compound as an off white solid. Yield (100 mg, 52%). LCMS (ESI positive ion) m/z: calculated: 415.5; observed: 360.0 (M–56).

Step 6: Preparation of 4-(2,4-difluoro-5-(piperazin-1-yl)phenyl)thiomorpholine 1-oxide (8)

To an ice cold solution of tert-butyl 4-(2,4-difluoro-5-(1-oxidothiomorpholino)phenyl) piperazine-1-carboxylate (7) (0.090 g, 0.0002 mol) in dichloromethane, TFA (0.05 mL) was added. The reaction mixture was stirred at RT for 1 h. Progress of the reaction was monitored by LCMS. The reaction mixture was concentrated under reduced pressure. The crude residue was dissolved in methanol and treated with tosic acid resin, to afford the title compound as an off white solid. Yield (60 mg, 79%). LCMS (ESI positive ion) m/z: calculated: 315.3; observed: 316.3 (M+1).

Step 7: Preparation of 4-(5-(4-(2-((7-amino-2-(furan-2-yl)-[1,2,4]triazolo[1,5-a][1,3,5]-triazin-5-yl) amino)ethyl)piperazin-1-yl)-2,4-difluorophenyl) thiomorpholine 1-oxide (10)

To a stirred solution of 2-((7-amino-2-(furan-2-yl)-[1,2,4]triazolo[1,5-a][1,3,5]triazin-5-yl)-amino)acetaldehyde (9) (55 mg, 0.00022 mol) and 4-(2,4-difluoro-5-(piperazin-1-yl)phenyl)thiomorpholine 1-oxide (8) (80 mg, 0.00025 mole) in methanol, MP-CNBH3 (0.200 g) was added. The resulting mixture was stirred at RT for 16 h. After completion of the reaction (TLC), reaction mixture was filtered, and the filtrate was concentrated under reduced pressure. The crude residue was purified by preparative HPLC to afford the title compound as a light brown colour solid. Yield: (16 mg; 13%); LCMS (ESI positive ion) m/z: calculated: 558.6; observed: 559.2 (M+1); 1H-NMR (400 MHz, DMSO-d6): δ 8.06-8.21 (bs, 2H), 7.88 (s, 1H), 7.39 (s, 2H), 7.14 (s, 1H), 6.80 (s, 2H), 4.30 (d, J=Hz, 2H), 3.42-3.56 (m, 5H), 3.18 (d, J=2.80 Hz, 3H), 3.01-3.04 (m, 6H), 2.59-2.87 (m, 2H), and 2.51-2.51 (m, 2H).

Example 16: (R)—N5-(2-(4-(2,4-difluoro-5-(methylsulfinyl)phenyl)piperazin-1-yl)ethyl)-2-(furan-2-yl)-[1,2,4]triazolo[1,5-a][1,3,5]triazine-5,7-diamine

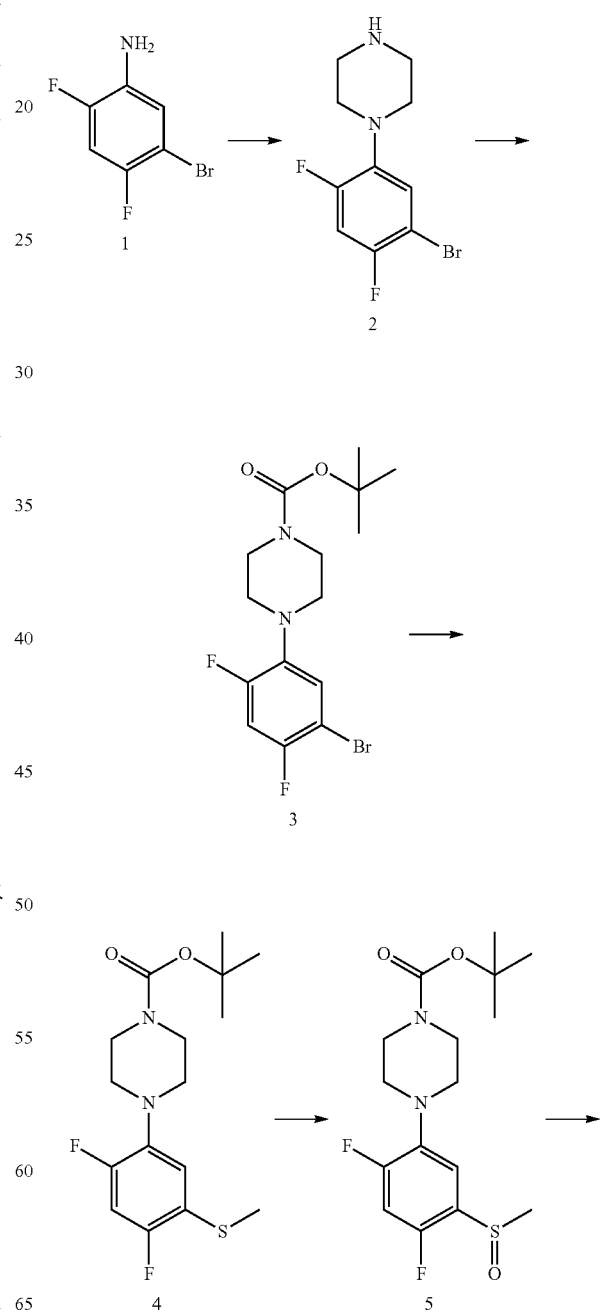

-continued

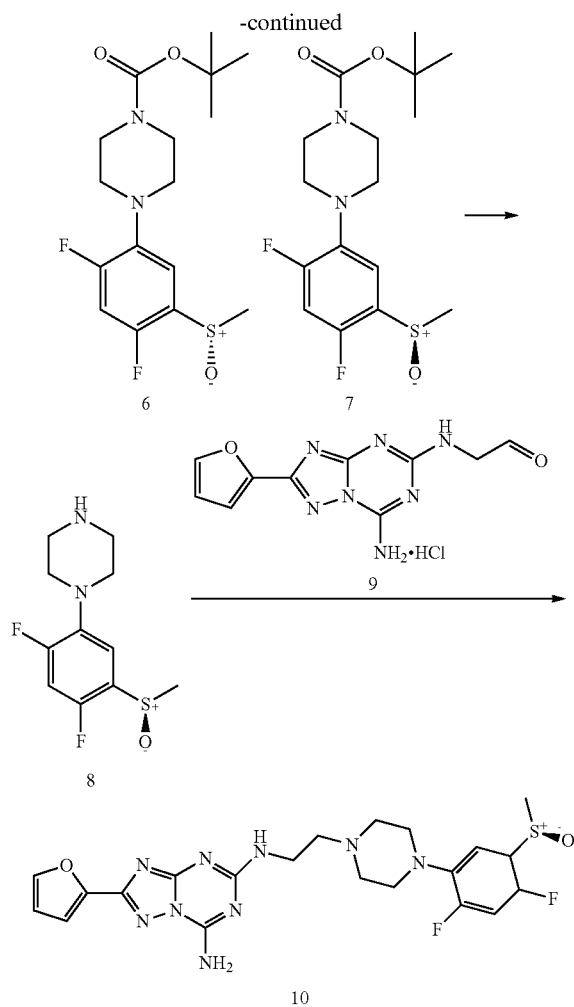

Step 1: Preparation of 1-(5-bromo-2,4-difluorophenyl)piperazine (2)

To a stirred solution of 5-bromo-2,4-difluoroaniline (1) (2.0 g, 0.01 mol) in sulfolane was added bis(2-chloroethyl) amine hydrochloride (2.23 g, 0.012 mol). The resulting mixture was stirred at 150° C. under nitrogen atmosphere for 16 h. At RT, acetone (10 mL) was added to the reaction mixture and stirred at 0° C. After 1 h, the precipitated solid was filtered and washed with cold acetone (5 mL) under nitrogen atmosphere. The solid was dried under vacuum to afford the title compound as off a white solid. Yield: (1.6 g; 59%); LCMS (ESI positive ion) m/z: calculated: 277.1; observed: 279.5 (M+2).

Step 2: Preparation of tert-butyl 4-(5-bromo-2,4-difluorophenyl)piperazine-1-carboxylate (3)

To an ice cold solution of 1-(5-bromo-2,4-difluorophenyl) piperazine hydrochloride (2) (1 g, 0.003 mol) in DCM (15 mL), triethylamine (1.02 mL, 0.008 mol) and di-tert-butyl dicarbonate (1.04 mL, 0.005 mol) were added. The resulting mixture was stirred at RT for 16 h. After completion, the reaction mixture was diluted with water and extracted with ethyl acetate. Combined organic layers were washed with saturated brine solution, dried over anhydrous Sodium sulphate, filtered and concentrated under reduced pressure to afford a brown colour solid, which was taken into next step without further purification. Yield: (0.9 g, 74%). LCMS (ESI positive ion) m/z: calculated: 377.2; observed: 323 (M−54).

Step 3: Preparation of tert-butyl 4-(2,4-difluoro-5-(methylthio)phenyl)piperazine-1-carboxylate (4)

To a stirred solution of tert-butyl 4-(5-bromo-2,4-difluorophenyl)piperazine-1-carboxylate (3) (50 mg, 0.13 mmol) in DMSO (2 mL) was added CuI (25 mg, 0.13 mmol) and DABCO (29 mg, 0.26 mmol). The resulting reaction mixture was stirred at 150° C. in sealed tube for 48 h. After completion, the reaction mixture was quenched with water and extracted with ethyl acetate. Combined organic layers were washed with saturated brine solution, dried over anhydrous sodium sulphate, filtered and concentrated under reduced pressure to afford a brown gum, which was taken into next step without further purification. Yield: (30 mg, 66%). LCMS (ESI positive ion) m/z: calculated: 344.3; observed: 345.2 (M+1).

Step 4: Preparation of tert-butyl (S)-4-(2,4-difluoro-5-(methylsulfinyl)phenyl)piperazine-1-carboxylate (6), tert-butyl (R)-4-(2,4-difluoro-5-(methylsulfinyl) phenyl)piperazine-1-carboxylate (7)

To an ice cold stirred solution of tert-butyl 4-(2,4-difluoro-5-(methylthio)phenyl)piperazine-1-carboxylate (4) (2.7 g, 7.8 mmol) in DCM (30 mL), was added m-CPBA (1.93 g, 7.8 mmol). The resulting reaction mixture was stirred at RT for 8 h. After completion, the reaction mixture was neutralized with saturated NaHCO3 solution and extracted with DCM. Combined organic layers were dried over sodium sulphate, and concentrated under reduced pressure. The residue was purified by column chromatography (80% EtOAc/Hexane as eluent) to afford the title compound as an off white solid. Yield: (2.2 g, 71%).

The enantiomers were separated through chiral SFC purification. The first peak eluted (fraction 1) was collected and concentrated to afford tert-butyl (R)-4-(2,4-difluoro-5-(methylsulfinyl)-phenyl)-piperazine-1-carboxylate (7); Yield (0.6 g). The second peak eluted out (fraction 2) was collected and concentrated to afford tert-butyl (S)-4-(2,4-difluoro-5-(methylsulfinyl)phenyl)piperazine-1-carboxylate (6); Yield (0.7 g). LCMS (ESI positive ion) m/z: calculated: 360.10; observed: 261.1 (M−100).

Step 5: Preparation of (R)-1-(2,4-difluoro-5-(methylsulfinyl)phenyl)piperazine (8)

To an ice cold stirred solution of tert-butyl (R)-4-(2,4-difluoro-5-(methylsulfinyl)phenyl) piperazine-1-carboxylate (7) (0.54 g, 1.52 mmol) in DCM (10 mL) was added TFA (1.3 g, 12.1 mmol). The resulting reaction mixture was stirred at RT for 2 h. After completion, the reaction mixture was concentrated under reduced pressure and neutralized by treating with tosic acid resin to afford the title compound as a colourless gum. Yield (0.32 g, 88%). LCMS (ESI positive ion) m/z: calculated: 260.3; observed: 261.1 (M+1).

Step 6: Preparation of (R)—N5-(2-(4-(2,4-difluoro-5-(methylsulfinyl)phenyl)piperazin-1-yl)ethyl)-2-(furan-2-yl)-[1,2,4]triazolo[1,5-a][1,3,5]triazine-5,7-diamine (10)

To a solution of 2-((7-amino-2-(furan-2-yl)-[1,2,4]triazolo[1,5-a][1,3,5]triazin-5-yl)amino)-acetaldehyde (9)

(120 mg, 0.463 mmol) and (R)-1-(2,4-difluoro-5-(methylsulfinyl)phenyl)-piperazine (8) (144.35 mg, 0.555 mmol) in methanol was added MP-CNBH4 resin (140 mg). The reaction mixture was stirred at RT for 16 h. After completion, the reaction mixture was filtered and filtrate was concentrated under reduced pressure. The residue was purified by column chromatography (2% methanol/dichloromethane as eluent) to afford the title compound as an off white solid. Yield (40 mg, 17%). LCMS (ESI positive ion) m/z: calculated: 503.5; observed: 504.1 (M+1). 1H-NMR (400 MHz, DMSO-36): δ 8.19 (brs, 2H), 7.87 (s, 1H), 7.46 (t, J=12 Hz, 1H), 7.36-7.28 (m, 2H), 7.06 (d, J=3.20 Hz, 1H), 6.68 (m, 1H), 3.45 (m, 2H), 3.05 (m, 4H), 2.82 (s, 3H), and 2.67-2.62 (m, 6H).

Example 17: (S)—N5-(2-(4-(2,4-difluoro-5-(methylsulfinyl)phenyl)piperazin-1-yl)ethyl)-2-(furan-2-yl)-[1,2,4]triazolo[1,5-a][1,3,5]triazine-5,7-diamine

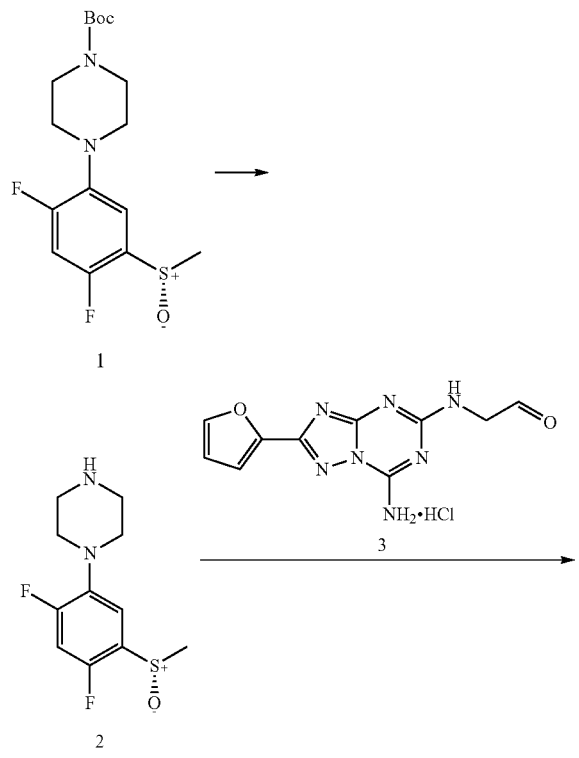

Step 1: Preparation of (S)-1-(2,4-difluoro-5-(methylsulfinyl)phenyl)piperazine (2)

To a stirred solution of tert-butyl (S)-4-(2,4-difluoro-5-(methylsulfinyl)phenyl)piperazine-1-carboxylate (1) (0.67 g, 1.85 mmol) in DCM (10 mL) was added TFA (1.6 g, 14.87 mmol) at 0° C. and stirred at RT for 2 h. After completion, the reaction mixture was concentrated under reduced pressure and the residue was neutralized by treating with tosic acid resin to afford the title compound as a pale brown gum. Yield (0.42 g, 86%). LCMS (ESI positive ion) m/z: calculated: 260.3; observed: 261.1 (M+1).

Step 2: Preparation of (S)—N5-(2-(4-(2,4-difluoro-5-(methylsulfinyl)phenyl)piperazin-1-yl)ethyl)-2-(furan-2-yl)-[1,2,4]triazolo[1,5-a][1,3,5]triazine-5,7-diamine To a solution of 2-((7-amino-2-(furan-2-yl)-[1,2,4]triazolo[1,5-a][1,3,5]triazin-5-yl)amino)-acetaldehyde (3) (200 mg, 0.772 mmol) and (S)-1-(2,4-difluoro-5-(methylsulfinyl)phenyl)-piperazine (2) (261 mg, 1.003 mmol) in methanol, MP-CNBH3 resin (260 mg) was added. The reaction mixture was stirred at RT for 16 h. The reaction mixture was filtered and the filtrate was concentrated under reduced pressure. The residue was purified by column chromatography (2% methanol/dichloromethane as eluent) to afford the title compound as an off white solid. Yield (50 mg, 13%). LCMS (ESI positive ion) m/z: calculated: 503.5; observed: 504.2 (M+1). 1H-NMR (400 MHz, DMSO-d6): δ 8.19 (brs, 2H), 7.87 (s, 1H), 7.49-7.46 (m, 1H), 7.37-7.28 (m, 2H), 7.05 (d, J=3.20 Hz, 1H), 6.67 (m, 1H), 3.43-3.39 (m, 2H), 3.05 (m, 4H), 2.82 (s, 3H), and 2.68-2.67 (m, 6H).

Example 18: (4-(4-(2-((7-amino-2-(furan-2-yl)-[1,2,4]triazolo[1,5-a][1,3,5]triazin-5-yl)amino)ethyl)piperazin-1-yl)-3-fluorophenyl)(1-oxidothiomorpholino)methanone

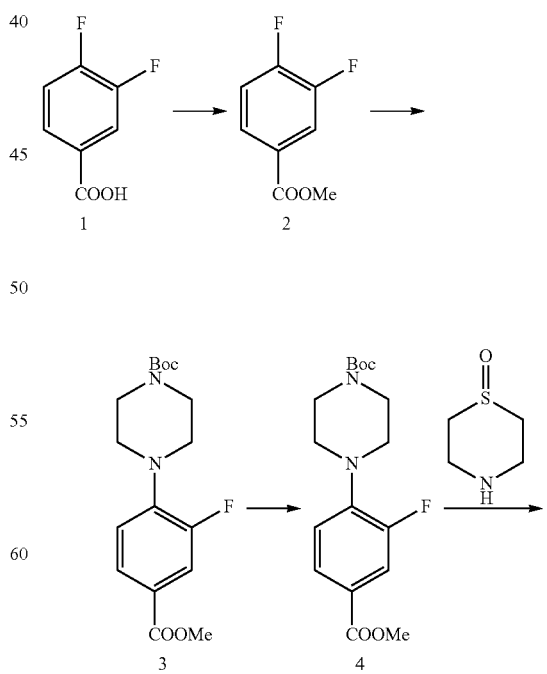

-continued

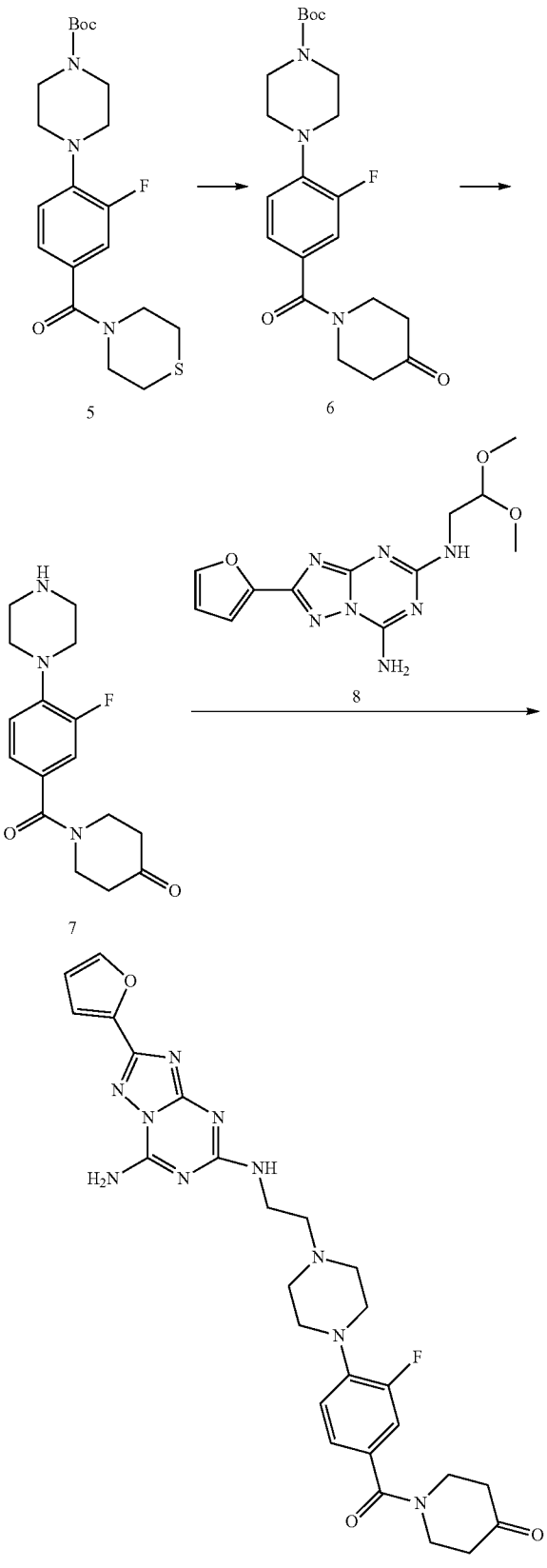

Step 1: Preparation of methyl 3,4-difluorobenzoate (2)

To a stirred solution of 3,4-difluorobenzoic acid (1) (25 g, 0.158 mol) in methanol (50 mL), thionyl chloride (22.57 g, 0.190 mol) was added. The resulting mixture was stirred at 60° C. for 2 h. The reaction mixture was concentrated under reduced pressure. The residue was taken in water and extracted with ethyl acetate. Combined organic layers were washed successively with saturated NaHCO$_3$ solution, brine solution and dried over anhydrous sodium sulphate, filtered and concentrated under reduced pressure to afford the title compound as a white gummy solid. Yield (20 g, 73%). 1H-NMR (400 MHz, DMZO-d6): δ 8.01-7.95 (m, 1H), 7.45-7.40 (m, 1H), 7.26-7.21 (m, 1H), and 3.85 (s, 3H).

Step 2: Preparation of tert-butyl 4-(2-fluoro-4-(methoxycarbonyl)phenyl)piperazine-1-carboxylate (3)

Potassium carbonate (8.029 g, 0.058 mol) was added to a mixture of methyl 3,4-difluorobenzoate (2) (5 g, 0.029 mol) and tert-butyl piperazine-1-carboxylate (7.0330 g, 0.038 mmol) in DMSO. The reaction mixture was stirred at 100° C. for 16 h. After completion, the reaction mixture was poured into ice cold water. The solid formed was filtered and dried under vacuum to afford the title compound as an off white solid, which was used without further purification. Yield (12 g, crude). LCMS (ESI positive ion) m/z: calculated: 338.1; observed: 339.0 (M+1).

Step 3: Preparation of 4-(4-(tert-butoxycarbonyl)piperazin-1-yl)-3-fluorobenzoic acid (4)

To a stirred solution of tert-butyl 4-(2-fluoro-4-(methoxycarbonyl)phenyl)piperazine-1-carboxylate (3) (10 g, 0.030 mol) in THF (80 mL), 2N NaOH (1.18 g, 0.030 mol) was added and resulting mixture was heated to 75° C. for 3 h. The reaction mixture was concentrated under reduced pressure, neutralized with 1.5 N HCl, and extracted with ethyl acetate. Combined organic layers were washed successively with NaHCO$_3$ solution, brine solution, dried over anhydrous sodium sulphate, filtered and concentrated under reduced pressure to afford the title compound as an off white solid. Yield (8.5 g, 85%). LCMS (ESI positive ion) m/z: calculated: 324.3; observed: 325.1 (M+1).

Step 4: Preparation of tert-butyl 4-(2-fluoro-4-(thiomorpholine-4-carbonyl)phenyl)-piperazine-1-carboxylate (5)

To a stirred solution of 4-(4-(tert-butoxycarbonyl)piperazin-1-yl)-3-fluorobenzoic acid (4) (4 g, 12.3 mmol) in N,N-dimethylformamide were added thiomorpholine (2 mL, 19 mmol), DIPEA (11 mL, 61 mmol), EDC.HCl (7.07 g, 36 mmol) and HOBt (4.98 g, 36 mmol). The resulting reaction mixture was stirred at RT for 4 h. The reaction progress was monitored by TLC. After completion, the reaction mixture was poured into crushed ice. The solid precipitated was filtered and washed well with cold water and dried under vacuum to afford the product as an off white solid. Yield (3 g, 47.5%). LCMS (ESI positive ion) m/z: calculated: 409.5; observed: 410.1 (M+1).

Step 5: Preparation of tert-butyl 4-(2-fluoro-4-(1-oxidothiomorpholine-4-carbonyl)phenyl)piperazine-1-carboxylate (6)

To a stirred solution of tert-butyl 4-(2-fluoro-4-(thiomorpholine-4-carbonyl)phenyl) piperazine-1-carboxylate (5) (3.1 g, 7.5 mmol) in acetic acid (30 mL) was added H₂O₂ (2.5 mL, 22.7 mmol) at 0° C. After stirring at 0° C. for 0.5 h, the reaction mixture was poured into cold 10% NaOH solution and extracted with dichloromethane. Combined organic layers were concentrated under reduced pressure. The residue was purified by column chromatography (2% methanol/dichloromethane as eluent) to afford the title compound as an off white solid. Yield (2.8 g, 69.5%). LCMS (ESI positive ion) m/z: calculated: 425.5; observed: 426.2 (M+1).

Step 6: Preparation of (3-fluoro-4-(piperazin-1-yl)phenyl)(1-oxidothiomorpholino)-methanone (7)

To an ice cold stirred solution of tert-butyl tert-butyl 4-(2-fluoro-4-(1-oxidothiomorpholine-4-carbonyl)phenyl) piperazine-1-carboxylate (6) (1.2 g, 2.82 mmol) in DCM (25 mL) was added TFA (2.5 g, 22.5 mmol). The resulting reaction mixture was stirred at RT for 2 h. After completion, the reaction mixture was concentrated under reduced pressure and neutralized by treating with tosic acid resin to afford the title compound as a pale brown gum. Yield (0.8 g, 61%). LCMS (ESI positive ion) m/z: calculated: 325.4; observed: 326.0 (M+1).

Step 7: Preparation of (4-(4-(2-((7-amino-2-(furan-2-yl)-[1,2,4]triazolo[1,5-a][1,3,5]triazin-5-yl)amino)ethyl)piperazin-1-yl)-3-fluorophenyl) (1-oxidothiomorpholino) methanone (9)

To a solution of N5-(2,2-dimethoxyethyl)-2-(furan-2-yl)-N5-methyl-[1,2,4]triazolo[1,5-a]-[1,3,5]triazine-5,7-diamine (8) (225 mg, 0.705 mmol) in dichloromethane, TFA and water mixture (9 mL, 2:1) was added drop wise. The resulting reaction mixture was stirred at RT for 2 h. After completion, the reaction mixture was neutralized with triethylamine at 0° C. Then (3-fluoro-4-(piperazin-1-yl)phenyl)(1-oxidothiomorpholino)methanone (7) (200 mg, 0.615 mmol) and sodium triacetoxyborohydride (300 mg, 1.4 mmol) were added at 0° C. The reaction mixture was stirred at RT for 16 h. After completion, the reaction mixture was quenched with saturated NaHCO₃ solution and extracted with dichloromethane. Combined organic layers were concentrated under reduced pressure. The residue was purified by preparative HPLC purification to afford the title compound as an off white solid. Yield (40 mg, 10%). LCMS (ESI positive ion) m/z: calculated: 568.6; observed: 569.2 (M+1). 1H-NMR (400 MHz, DMSO-d6): δ 8.17 (brs, 2H), 7.87 (s, 1H), 7.30-7.24 (m, 2H), 7.05 (d, J=3.00 Hz, 1H), 6.83-6.78 (m, 2H), 6.68 (s, 1H), 4.34 (m, 1H), 3.79-3.66 (m, 4H), 3.51-3.43 (m, 4H), 3.26 (m, 5H), and 2.89-2.78 (m, 6H).

Example 19: (1s,4s)-4-(4-(4-(2-((7-amino-2-(furan-2-yl))-[1,2,4]triazolo[1,5-a][1,3,5]triazin-5-yl)amino)ethyl)piperazin-1-yl)-3-fluorophenoxy)tetrahydro-2H-thiopyran 1-oxide

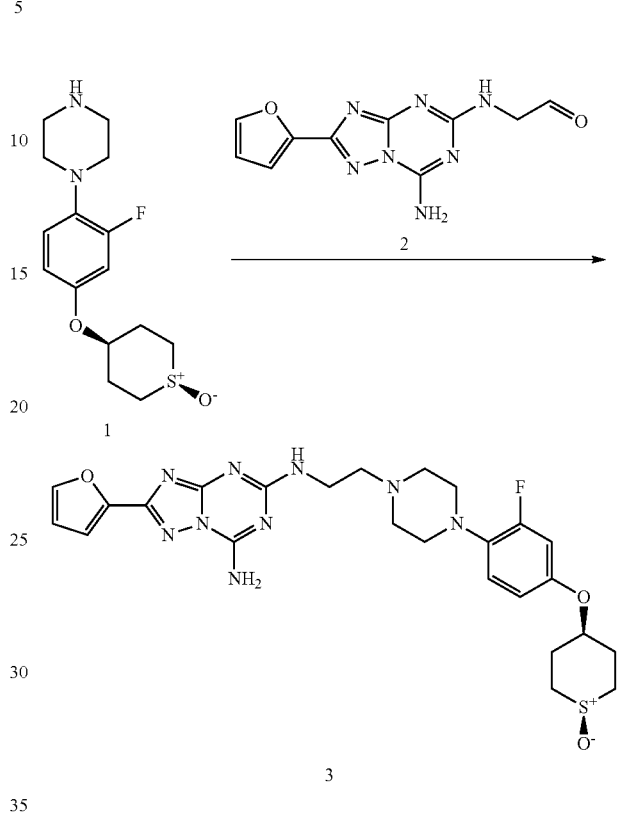

Step 1: Preparation of (1s,4s)-4-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)tetrahydro-2H-thiopyran 1-oxide To a stirred suspension of (cis)-4-(3-fluoro-4-(piperazin-1-yl)phenoxy)tetrahydro-2H-thiopyran 1-oxide (1) (0.150 g, 0.479 mmol, 1.1 eq) in dry dichloromethane (5 mL), triethyl amine (88.05 mg, 0.872 mmol, 2 eq) and 2-[[7-amino-2-(2-furyl)-[1,2,4]triazolo[1,5-a][1,3,5]triazin-5-yl]amino]acetaldehyde (2) (0.113 g, 0.436 mmol, 1 eq) (crude aldehyde freshly prepared from oxidation of 1 g of alcohol) were added. After stirring at RT for 3 h, sodium triacetoxy borohydride (183.95 mg, 0.872 mmol, 2.0 eq) was added. The resulting mixture was stirred at RT for 24 h. After completion, the reaction mixture was diluted with dichloromethane. The organic layer was separated, washed successively with saturated bicarbonate solution and saturated brine solution, dried over anhydrous sodium sulphate, filtered and concentrated under reduced pressure. The residue was purified by column chromatography (230-400 silica gel, 5% methanol/dichloromethane as an eluent) to afford the title compound as an off white solid. Yield (40 mg, 16%). LCMS (ESI positive ion) m/z: calculated: 555.6; observed: 556 (M+1). 1H-NMR (400 MHz, DMSO-d6): δ 8.20 (b, s, 2H), 7.88 (s, 1H), 7.28 (b, s, 1H), 7.06 (s, 1H), 6.90-7.00 (m, 2H), 6.78 (d, J=8.80 Hz, 1H), 6.68 (s, 1H), 4.61 (s, 1H), 3.43 (s, 2H), 2.92 (m, 7H), 2.68-2.72 (m, 2H), 2.59 (m, 3H), 2.28-2.35 (m, 3H), and 1.83 (t, J=5.60 Hz, 2H).

Example 20: 5-amino-3-(2-(4-(2-fluoro-4-(2-(methylsulfinyl)ethoxy)phenyl)piperazin-1-yl)ethyl)-8-(furan-2-yl)-1-methyl-1H-[1,2,4]triazolo[5,1-i]purin-2(3H)-one

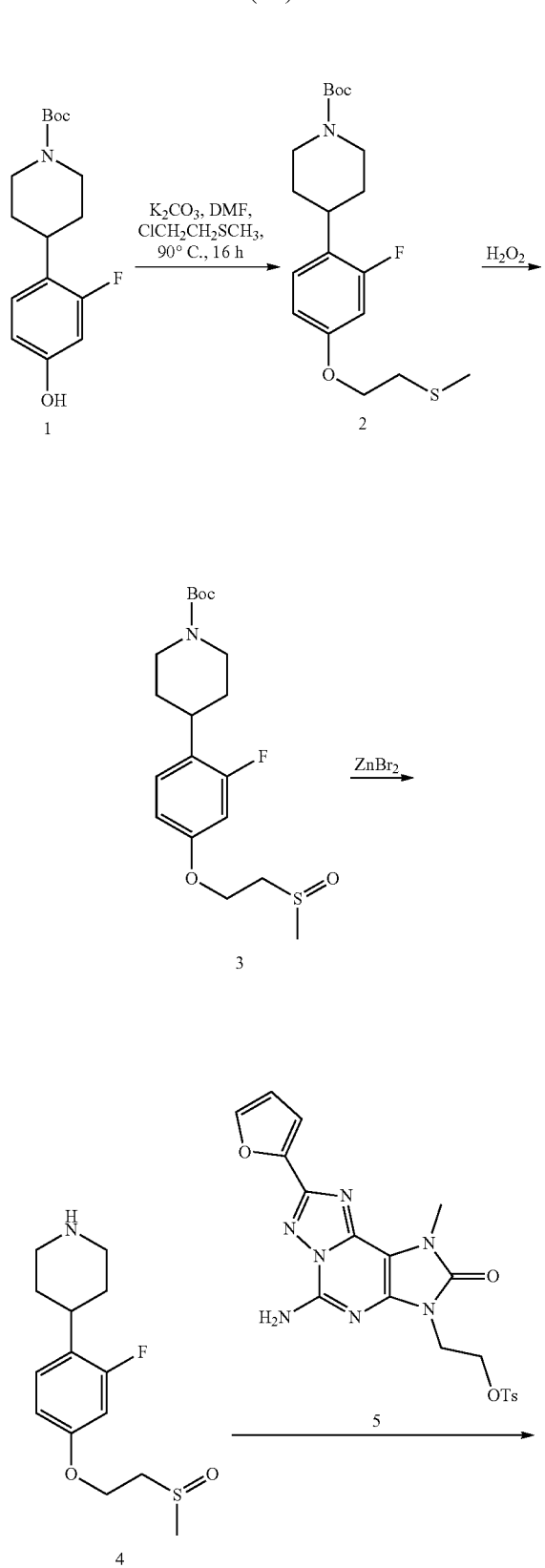

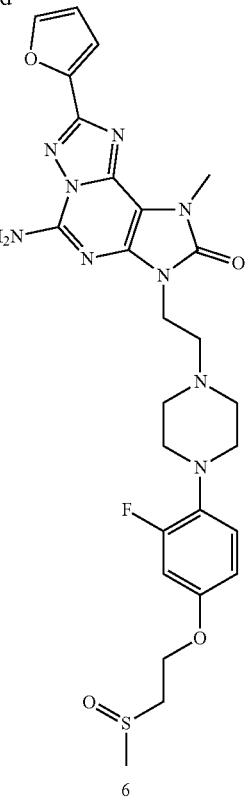

Step 1: Preparation of tert-butyl 4-(2-fluoro-4-(2-(methylthio)ethoxy)phenyl)piperazine-1-carboxylate (2)

To a stirred mixture of tert-butyl 4-(2-fluoro-4-hydroxyphenyl)piperazine-1-carboxylate (1) (1.2 g, 0.004 mol) and 1-chloro-2-methylsulfanyl-ethane (0.582 mL, 0.005 mol) in N,N-dimethylformamide (13 mL), potassium carbonate (1.118 g, 0.008 mol) was added and the resulting mixture was heated to 80° C. for 16 h. After completion, the reaction mixture was diluted with water (20 mL) and extracted with ethyl acetate (2×20 mL). Combined organic layers were dried over anhydrous sodium sulphate and concentrated under reduced pressure. The residue was purified by column chromatography (230-400 silica gel, 20% ethyl acetate/petroleum ether as eluent) to afford the title compound as an off white solid. Yield (1 g, 63%). LCMS (ESI positive ion) m/z: calculated: 370.48; observed: 371.1 (M+1).

Step 2: Preparation of tert-butyl 4-(2-fluoro-4-(2-(methylsulfinyl)ethoxy)phenyl)-piperazine-1-carboxylate (3)

To an ice cold stirred solution of tert-butyl 4-(2-fluoro-4-(2-(methylthio)ethoxy)phenyl)-piperazine-1-carboxylate (2) (400 mg, 0.001 mol) in acetic acid (1.0 mL), hydrogen peroxide (0.278 mL, 0.003 mol) was added. The resulting mixture was stirred at 0° C. for 3 h. After completion, the reaction mixture was poured into cold 10% NaOH solution and extracted with dichloromethane. The combined organic layers were concentrated under reduced pressure. The residue was purified by column chromatography (230-400 silica gel, 40% ethyl acetate/petroleum ether as eluent) to afford the title compound as an off white solid. Yield (300 mg, 71%). LCMS (ESI positive ion) m/z: calculated: 386.4; observed: 387.1 (M+1).

Step 3: Preparation of 1-(2-fluoro-4-(2-(methylsulfonyl)ethoxy)phenyl)piperazine (4)

To a stirred solution of tert-butyl 4-[2-fluoro-4-(2-methylsulfinylethoxy)phenyl]piperazine-1-carboxylate (3) (100 mg, 0.0002 mol) in ethyl acetate (5 mL), zinc bromide (146 mg, 0.0006 mol) was added. The resulting mixture was stirred at 70° C. for 6 h. The reaction mixture cooled to RT and washed with water. The aqueous layer was basified with solid NaHCO₃ and extracted with dichloromethane. The combined organic layers were washed with saturated brine solution, dried over anhydrous sodium sulphate, filtered and concentrated under reduced pressure to afford the title compound as an off white solid. Yield (70 mg, 92%). LCMS (ESI positive ion) m/z: calculated: 286.3; observed: 287.2 (M+1).

Step 4: Preparation of 5-amino-3-(2-(4-(2-fluoro-4-(2-(methylsulfinyl)ethoxy)phenyl)-piperazin-1-yl) ethyl)-8-(furan-2-yl)-1-methyl-1H-[1,2,4]triazolo[5,1-i]purin-2(3H)-one (6)

To a mixture of 2-(5-amino-8-(furan-2-yl)-1-methyl-2-oxo-1,2-dihydro-3H-[1,2,4]triazolo-[5,1-i]purin-3-yl)ethyl 4-methylbenzenesulfonate (5) (50 mg, 0.0001 mol) and 1-[2-fluoro-4-(2-methylsulfinylethoxy)phenyl]piperazine (4) (34 mg, 0.00017 mol) in N,N-dimethylformamide (0.8 mL), was added DIPEA (0.037 mL, 0.00021 mol) and the reaction mixture was stirred at 100° C. for 16 h. After completion (TLC & LCMS), the reaction mixture was concentrated under reduced pressure. The residue was purified by preparative HPLC to afford the title compound as an off white solid. Yield (20 mg, 31%). LCMS (ESI positive ion) m/z: calculated: 583.6; observed: 584.2 (M+1). 1H-NMR (400 MHz, DMSO-d6): δ 7.90-7.95 (m, 3H), 7.22 (d, J=3.36 Hz, 1H), 7.06 (s, 1H), 6.92-6.96 (m, 1H), 6.73-6.79 (m, 2H), 4.26-4.32 (m, 6H), 3.91 (d, J=11.24 Hz, 3H), 3.43 (d, J=11.96 Hz, 2H), 3.23-3.32 (m, 4H), 2.93-3.04 (m, 4H), and 2.62 (s, 3H).

Example 21: 5-amino-3-(2-(4-(2,4-difluoro-5-((2-oxopyrrolidin-3-yl)oxy)phenyl)piperazin-1-yl)ethyl)-8-(furan-2-yl)-1-methyl-1H-[1,2,4]triazolo[5,1-i]purin-2(3H)-one

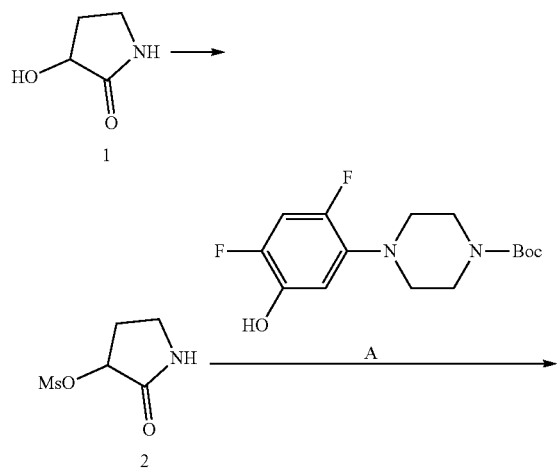

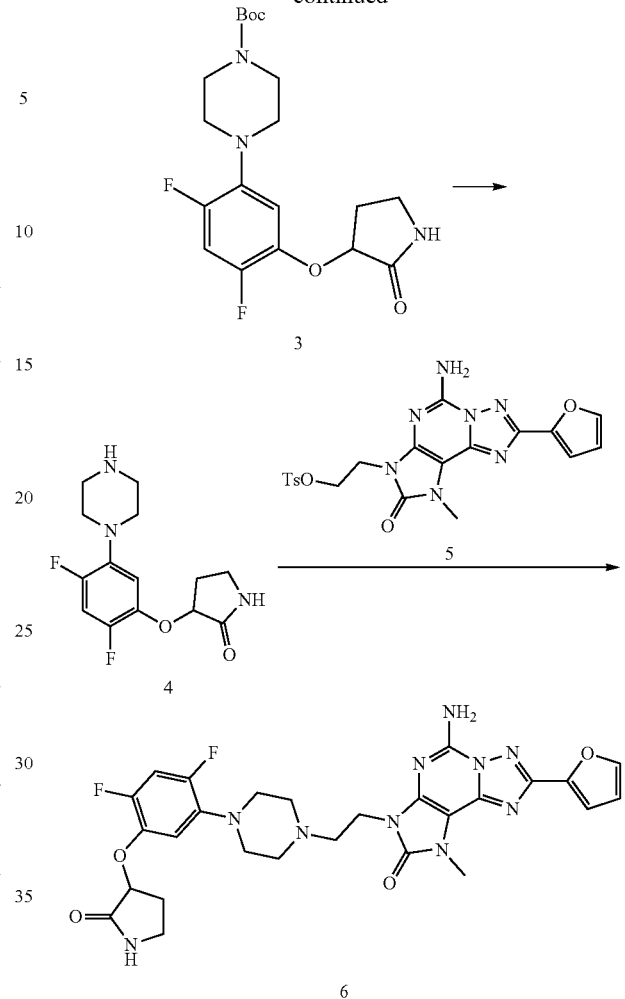

Step 1: Preparation of 2-oxopyrrolidin-3-yl Methanesulfonate (2)

To a stirred mixture of 3-hydroxypyrrolidin-2-one (1) (1 g, 0.010 mol), triethylamine (1.199 g, 0.012 mol) in DCM (5 mL), mesyl chloride (1.24 g, 0.011 mol) was added at 0° C. The resulting mixture was stirred at RT for 2 h. After completion of the reaction, reaction mixture was quenched with ice and extracted with DCM. Combined organic part was concentrated under reduced pressure. The crude product obtained was taken to next step without further purification. Yield (1.1 g, 62.07%). LCMS (ESI positive ion) m/z: calculated: 179.19; observed: 179.9 (M+1).

Step 2: Preparation of tert-butyl 4-(2,4-difluoro-5-((2-oxopyrrolidin-3-yl)oxy)phenyl)-piperazine-1-carboxylate (3)

To a solution of tert-butyl 4-(2,4-difluoro-5-hydroxyphenyl)piperazine-1-carboxylate (A) (1 g, 0.003 mol) in N,N-dimethylformamide (10 mL) was added 2-oxopyrrolidin-3-yl methane sulfonate (2) (1.140 g, 0.006 mol) and K₂CO₃ (0.878 g, 0.006 mol). The resulting mixture was heated to 90° C. for 16 h. After completion, reaction mixture was diluted with water and extracted with ethyl acetate. The combined organic layers were dried over sodium sulphate and concentrated under reduced pressure. The residue was purified by column chromatography (1% Methanol/DCM as eluent) to afford the title compound as an off white solid. Yield (1 g, 75%). LCMS (ESI positive ion) m/z: calculated: 397.42; observed: 398.2 (M+1).

Step 3: Preparation of 3-(2,4-difluoro-5-(piperazin-1-yl)phenoxy)pyrrolidin-2-one (4)

To an ice cold solution of tert-butyl 4-[2,4-difluoro-5-[2-oxopyrrolidin-3-yl]oxy-phenyl]piperazine-1-carboxylate (3) (1 g, 0.003 mol) in DCM (1 mL), was added HCl in dioxane (4M) (0.551 g, 0.015 mol). The resulting mixture was stirred at RT for 2 h. After completion, the reaction mixture was concentrated under reduced pressure. The crude HCl salt obtained was neutralized by treating with tosic acid resin to afford the title compound as a gummy liquid. Yield (0.5 g, 65%). LCMS (ESI positive ion) m/z: calculated: 297.31; observed: 298.2 (M+1).

Step 4: Preparation of 5-amino-3-(2-(4-(2,4-difluoro-5-((2-oxopyrrolidin-3-yl)oxy)-phenyl)piperazin-1-yl)ethyl)-8-(furan-2-yl)-1-methyl-1,3-dihydro-2H-[1,2,4]triazolo[5,1-i]purin-2-one (6)

To a stirred solution of 2-[5-amino-8-(2-furyl)-1-methyl-2-oxo-[1,2,4]triazolo[5,1-f]purin-3-yl]ethyl 4-methylbenzenesulfonate (5) (150 mg, 0.320 mmol), 3-(2,4-difluoro-5-(piperazin-1-yl)-phenoxy)pyrrolidin-2-one (4) (113.91 mg, 0.383 mmol) in N,N-dimethylformamide (1 mL), DIPEA (51.52 mg, 0.399 mmol) was added. The resulting mixture was stirred at 100° C. for 16 h. After completion, the reaction mixture was concentrated under reduced pressure. The residue was purified by preparative HPLC to afford the title compound as an off white solid. Yield (50 mg, 25%). LCMS (ESI positive ion) m/z: calculated: 594.58; observed: 595.2 (M+1). 1H-NMR (400 MHz, DMSO-d6): δ 8.08 (s, 1H), 7.94 (s, 1H), 7.79 (s, 2H), 7.18-7.24 (m, 2H), 6.97 (t, J=8.80 Hz, 1H), 6.73 (s, 1H), 4.92 (t, J=7.40 Hz, 1H), 3.96 (t, J=6.08 Hz, 2H), 3.57 (s, 3H), 3.18-3.28 (m, 2H), 2.92 (brs, 4H), 2.63-2.72 (m, 7H), 1.98-2.03 (m, 1H).

II. Biology Examples

II.1. Assays for A2A Functional Activities

The two following assays aim at showing that the compounds of the invention effectively inhibit A2A receptor by showing that they inhibit its functional activities.

II.1.A. Inhibition of cAMP Production in HEK Cells

Purpose.

When the A2A receptor is activated, is induces the production of cAMP. The present assay thus aims at showing that cAMP production is inhibited in HEK cells in response to their exposure to the compounds of the invention.

Method.

HEK-293 cells with a stable transfection of A2A receptor were bought from PerkinElmer® (#ES-011-C). Cells were cultured in EMEM medium (Lonza, #BE12-611F) supplemented with 10% FBS (Lonza, #DE14-801F) and 200 µg/mL of G418 (Tocris, #4131) at 37° C. and 5% $CO_2$. Fresh media without the selection marker was added on the day immediately before the experiment to stop selection pressure.

cAMP inhibition and antagonist $IC_{50}$ determination were accessed using the LANCE® Ultra cAMP Kit from PerkinElmer® (#TRF0262) on white half area 96 well plates (PerkinElmer®, #6005560). The assays were conducted in two different stimulation buffers:

a) normal with 1×HBSS (Gibco®, #141750-95), 5 mM HEPES (Lonza, #BE17-737E), 0.1% BSA and 25 µM Rolipram and b) HSA with 1×HBSS (Gibco®, #141750-95), 5 mM HEPES (Lonza, #BE17-737E), 2% Human Serum Albumin (Sigma-Aldrich®—A1653), 30 µM of EHNA (Tocris—#1261) and 100 µM Rolipram. Stimulation buffer b) mimics the human situation by increasing the amount of albumin present in the assay.

Compounds of the present invention were diluted 100× in either of the buffers depending on the assay performed. A total of 1000 cells per well were pre-incubated for 10 minutes with the compounds of the present invention before adding the corresponded EC80 of A2A agonist (3 nM of NECA in normal buffer) or 5 µM of Adenosine (in HAS buffer) for a total reaction time of 30 minutes. The total volume of the reaction was 20 µl (10 µl of cells, 5 µl of antagonist and 5 µl of agonist). The reaction was finalized by adding 10 µl of 4×EU-cAMP tracer working solution and 10 µl of 4× ULight-anti-cAMP working solution. The TR-FRET signal was measured after 1 hour using a Spectramax Paradigm (Molecular Devices).

Results.

As evidenced in Table 2 below, the compounds of the present invention inhibit the production of cAMP in response to the stimulation of A2A-overexpressing HEK cells with an A2A agonist or with Adenosine, in different conditions.

TABLE 2

| Compound | $IC_{50}$ (nM) (3 nM NECA as agonist, 0.1% BSA) | $IC_{50}$ (nM) (5 µM Adenosine as agonist, 2.0% HSA) |
|---|---|---|
| 1 | 0.4 | 33 |
| 2 | 0.6 | 28 |
| 3 | 0.1 | 176 |
| 4 | 0.3 | 150 |
| 5 | 0.6 | 41 |
| 6 | 0.9 | 63 |
| 7 | 0.3 | 64 |
| 8 | 0.3 | 70 |
| 9 | 0.5 | 104 |
| 10 | 0.2 | 25 |
| 11 | 0.4 | 41 |
| 12 | 0.4 | 162 |
| 13 | 0.5 | 131 |
| 14 | 0.7 | 71 |
| 15 | 1.7 | 81 |
| 16 | 7.4 | 73 |
| 17 | 1.8 | 201 |
| 18 | 0.5 | 632 |
| 19 | 0.8 | 106 |
| 20 | 0.4 | 72 |
| 21 | 0.4 | 178 |

II.1.B. Restoration of the Production of Pro-Inflammatory Cytokines by Human T-Cells Purpose.

When T-cells are activated, they produce pro-inflammatory cytokines. When the A2A receptor is activated in T cells, the amount of cytokines produced in response to stimulation of T-cells is reduced. The present assay thus aims at showing that the production of pro-inflammatory cytokines by T-cells may be restored by exposure to the compounds of the invention.

PBMC and CD3+ T cell isolation. Venous blood from healthy volunteers, all of whom signed an informed consent approved by the Ethics Committee (FOR-UIC-BV-050-01-01 ICF_HBS_HD Version 5.0), was obtained via Immune-Health (Centre Hospitalier Universitaire Tivoli, La Louviere, Belgium). Mononuclear cells were collected by density gradient centrifugation, using SepMate-50 tubes (StemCell Technologies, Grenoble, France) and Lymphoprep (Axis-shield, Oslo, Norway) according to the manufacturer's instructions. CD3+ T cells were isolated by immunomagnetic negative selection, using the EasySep Human T Cell Isolation Kit (StemCell Technologies) as per manufacturer's instructions. CD3+ T cells were stored in heat inactivated foetal bovine serum (hiFBS; Gibco, ThermoFisher Scientific, Merelbeke, Belgium) containing 10% DMSO in liquid nitrogen.

Human IL-2 T Cell Assay.

Human purified CD3+ T cells were thawed and washed twice with RPMI1640 medium (with UltraGlutamine; Lonza, Verviers, Belgium) supplemented with 1× non-essential amino acids (Lonza), 2% Pen/Strep (Lonza) and 1 mM Sodium Pyruvate (Gibco) (complete media), containing 10% hiFBS. The cells were suspended either in complete media containing 20% hiFBS or in 100% heat inactivated human serum (hiHS; Sigma-Aldrich, Diegem, Belgium). Cells were activated by adding anti-CD3 and anti-CD28 coated microbeads (Dynabeads human T-activator CD3/CD28; Life Technologies, Paisley, UK), suspended either in complete media containing 20% hiFBS or in 100% hiHS. Selective A2A R agonist CGS-21680 (Sigma-Aldrich; stock solution of 10 mM in DMSO) was added at a final assay concentration of 0.5 or 5 µM. Serial dilutions of the compounds of the present invention were prepared and added to the wells. The cells were placed in a 37° C. humidified tissue culture incubator with 5% $CO_2$ for 72 hours. After 72 hours, supernatants were sampled and IL-2 was quantified using the IL-2 (human) AlphaLISA Biotin-Free Detection Kit (AL333F; Perkin-Elmer, Zaventem, Belgium), according to the manufacturer's instructions.

II.1.C. Restoration of the Production of Pro-Inflammatory Cytokines in Human Whole Blood Preparation of Test Tubes.

Tubes containing selected stimulants (SEB, LPS, zymosan, anti-CD3/CD28) and TruCulture medium were purchased from Myriad RBM (catalogue numbers respectively 782-001124, 782-001087, 782-001259 and 782-001125) and A2a agonists (CGS-21680 and NECA) and were added and the tubes directly frozen at −20° C. until use in the cell culture experiments.

Compounds of the present invention were dissolved in DMSO at 10 mM and then dilutions were made with TC medium. Solutions were microscopically inspected to rule out the presence of particles. Freshly-prepared compound-containing solutions were added to thawed TC tubes containing stimulants and 1 µM CGS-21680, where appropriate.

Cell Culture.

Blood was drawn from healthy donors from the pre-tested donor pool of HOT Screen GmbH (age: 20-65 years, both sexes). Heparinized fresh peripheral whole blood (1 mL) from 3 healthy donors was added to thawed TC tubes and incubated in a heating block at 37° C. for 24 hours (LPS and zymosan stimulations), or 48 hours (SEB and anti-CD3/CD28 stimulation). At the end of the culture period, seraplas filters were inserted for harvesting of the supernatants. Supernatants were carefully collected, mixed, aliquoted and frozen at −20° C.

Mediators quantification. Cytokines and chemokines released in TC supernatants were measured using Human Cytokine MAP A panel for Luminex assays. The following mediators were analysed: GM-CSF, IFNg, IL-2, IL-3, IL-4, IL-5, IL-6, IL-7, IL-8, IL-10, IL-18, MCP-1, MIP-1a, MIP-1b, TNF-a, TNF-b.

Data analysis. To assess the biological activity of CGS-21680 and NECA, alterations of cytokine and chemokine secretion in TC supernatants induced by increasing doses of A2A agonists were analyzed. The percentage change of the concentrations of soluble mediators (SM) was calculated for each stimulation condition as follows:

% change=100×[SMTC+$A2A$ agonist]/[SMTC−$A2A$ agonist].

To assess the biological activity of the compounds of the present invention, the compound-induced restoration of cytokine and chemokine secretion in CGS-21680-supplemented TC to baseline levels (i.e. TC stimulation without supplementation of CGS-21680) was analyzed.

The rescue of cytokine secretion was estimated by calculating the percentage control for each stimulation condition of whole blood TC as follows:

% control=100×[SMTC+CGS+ compound]/[SMTC−CGS− compound].

II.2. Modulation of pCREB

II.2.A. Modulation of pCREB in Human Immune Cells

Purpose.

The A2A receptor is known to mediate CREB phosphorylation. The present assay aims at showing that the compounds of the invention effectively inhibit A2A receptor by showing that CREB phosphorylation may be inhibited by exposing human immune cells to compounds of the invention.

Method.

Venous blood from healthy volunteers, all of whom signed an informed consent approved by the Ethics Committee (FOR-UIC-BV-050-01-01 ICF_HBS_HD Version 5.0), was obtained via ImmuneHealth (Centre Hospitalier Universitaire Tivoli, La Louviere, Belgium). Peripheral blood cells were treated with A2AR agonists CGS-21680 or NECA (Sigma-Aldrich, Diegem, Belgium), and a serial dilution of compounds of the present invention (all used stock solutions at 10 mM in DMSO). All dilutions were prepared in RPMI1640 medium (with UltraGlutamine; Lonza, Verviers, Belgium), and cells were incubated with compounds in a 37° C. humidified tissue culture incubator with 5% $CO_2$. After stimulation, cells were fixed and permeabilized, followed by intracellular staining using mouse anti-human pCREB antibodies (Clone J151-21; BD Biosciences) at room temperature. Data were acquired using an LSRFortessa flow cytometer (BD Biosciences) and analyzed using FlowJo software (FlowJo, LLC, Ashland, Oreg.).

II.2.B. Modulation of pCREB Ex Vivo in Mice

Purpose.

The A2A receptor is known to mediate CREB phosphorylation. The present assay aims at showing that the compounds of the invention effectively inhibit A2A receptor by showing that CREB phosphorylation may be inhibited in mice by dosing compounds of the invention to mice.

Method.

Compounds of the present invention were formulated in 10% DMSO, 10% solutol, 80% water, pH 3 to obtain a homogeneous solution. Volume was calculated in order to administer the final dose in 100 µl per oral (PO). BALB/cAnNCrl female mice were purchased from Charles River Laboratories. Mice were orally treated with a single dose of A2A receptor antagonist. At the specific time point, animals were anesthetized with IP injection of 200 µl of ketamine 10%/xylazine 0.1% in PBS and blood was collected via retro-orbital bleeding in EDTA tubes. 45 µl of blood/well was dispensed in a master block. A2A receptor agonist NECA (Tocris) was prepared at concentration of 3 µM in RPMI 1640 (Lonza) supplemented with medium 2% Penicillin/Streptomycin (Lonza) and 50 µM 2-Mercaptoethanol (Sigma), and 50 µl was added to the wells and incubated for 45 minutes in a 37° C. humidified cell culture incubator with 5% $CO_2$. The final concentration of DMSO in the assay was 0.125%. Cells were fixed by adding 1 ml of pre-warmed Lyse/Fix buffer (BD Biosciences) in each well, carefully mixed and incubated for 10 minutes in a 37° C. humidified cell culture incubator with 5% $CO_2$. Cells were pelleted by centrifugation at 600×g for 5 minutes. After a wash with 1 ml of DPBS with $Ca^{2+}Mg^{2+}$ (Lonza), cells were permeabilized with 200 µl of ice-cold Perm Buffer II (BD Biosciences) and incubated for 30 minutes on ice. During permeabilization, cells were transferred to a 96-well U-bottom plate. Cells were pelleted and washed twice with FACS buffer composed by PBS (Lonza), 0.1% BSA (VWR), 2 mM EDTA (Ambion). The FACS staining was performed resuspending the cells in FACS buffer containing Fc block (CD16/CD32 Monoclonal Antibody (93), eBioscience); after 5 min incubation at room temperature the antibody mix was added and cells incubated for 1 hour at room temperature. Cells were washed with FACS buffer and resuepended in the same for acquisition at BD Fortessa (BD Biosciences).

Data obtained with flow cytometry were analyzed with FlowJo 10.4 software. MFI (median fluorescence intensity) of our marker of interest, pCREB, was evaluated, normalized by the respective DMSO control (ratio) and reported in graph. Dose-response data were analyzed with GraphPad Prism 7.0 software using nonlinear regression applied to a sigmoidal dose-response model. Data were acquired using an LSRFortessa flow cytometer (BD Biosciences) and analyzed using FlowJo software (FlowJo, LLC, Ashland, Oreg.).

II.3. Cytotoxicity Assay

Purpose.

The activation of the A2A receptor provides an immunosuppressive signal that inhibit cytotoxicity. The present assay aims at showing that the compounds of the invention effectively inhibit A2A receptor by showing that cytotoxicity may be increased by exposure to compounds of the invention.

Method.

A cytotoxicity assay was conducted to assess the antigen-specific cytotoxic activity of OT-I CD8 cells towards OVA-pulsed target cells and the effect of the compounds of the present invention to alleviate A2AR mediated inhibition of Cytotoxicity: OT1 cells were isolated from the spleens of C57BL/6-Tg(TcraTcrb)1100Mjb/Crl mice (Charles River). OT1 cells were primed with 1 ug/ml OVA peptide (Ovalbumin (257-264) chicken (S7951-1MG), Sigma Aldrich), in the presence of 5 µM CGS-21680 (Sigma-Aldrich) and increasing concentrations of compounds of the present invention, for 3 days in a 37° C. humidified tissue culture incubator with 5% $CO_2$. On day 3 all the cells were pooled and counted. For the cytotoxicity assay on day 3, Panc02 (target cells) were pulsed with 1 µg/ml OVA. Target cells and non-pulsed Panc02 cells (non-target bystander) were labelled with CFSE (C1157 (ThermoFisher)) and CellTrace™ Far Red Cell Proliferation Kit (C34564, ThermoFisher) respectively, according to manufacturer instructions. The stimulated OT-1 cells were added as effector cells in a 10:1 effector to target ratio. The co-culture reaction was incubated at 37° C. humidified tissue culture incubator with 5% $CO_2$. After 24 hrs cells were washed and stained with Live/dead fixable violet dead cell staining kit (Molecular Probes, L34955). Cytotoxic-killing of target cells was then measured by monitoring the change in the ratio of living target cells to non-target cells by flow-cytometry (MACSQuant® Analyzer 10—Miltenyi Biotec).

The % cytotoxicity is calculated as follows:

$$\% \text{ Cytotoxicity} = (1 - R1/R2)*100$$

wherein R1=(% of Target cells)/(% non-target cells)*100 in presence of effector cells and R2=(% of Target cells)/(% non-target cells)*100 in absence of effector cells.

III. Pharmacokinetic Examples

III.1. Determination of Permeability and Efflux in Caco-2 Cells

Purpose.

As mentioned in the introduction, the compounds of the invention have to exhibit a limited, if any, CNS penetrance, in order to avoid deleterious side effects that can occur if these compounds penetrate significantly into the brain.

The present assay aims at showing that the compounds of the invention do not have any significant CNS penetrance by showing that they are substrates of transporters that efflux them from brain.

Indeed, it is well known in the art that xenobiotics that are substrates of transporters such as P-Glycoprotein are not efficient in penetrating the Blood-Brain Barrier, and are thus less effective in the Central Nervous System (Alfred H. Schinkel, "P-Glycoprotein, a gatekeeper in the blood-brain barrier", Advanced Drug Delivery Reviews 36 (1999) 179-194).

The present assay thus aims at showing that the compounds of the present invention are substrates to such transporters present in the Caco-2 cell line and thus do not cross the Blood-Brain Barrier.

Material.

The transport buffer (TB, pH 7.4) used in the study is Hank's Buffered Saline Solution (HBSS, Gibco, Cat #14025-076) with 10 mM HEPES at pH 7.4. Fetal bovine serum (FBS) (Corning, Cat #Corning-35-076-CV, or other vendors), Minimum Essential Media (MEM) (Gibco, Cat #41500-034) as well as its supplements are purchased from Invitrogen (Carlsbad, Calif., USA). Caco-2 cell line (Cat #HTB-37) is purchased from the ATCC (Rockville, Md., USA). The organic solvents used in the study are purchased from Sigma Aldrich (St. Louis, Mo., USA).

Preparation of Working Solutions.

For reference compounds (fenoterol, propranolol and digoxin) and test compounds, 0.4 mM intermediate solutions are prepared by diluting 10 mM or other appropriate concentrations of DMSO stock solutions with DMSO. 2 µM dosing solutions for reference compounds and test compounds are prepared by spiking the appropriate volume of intermediate solution to TB with and without 1 µM Zosuquidar. The final concentration of DMSO is no more than 1% (v/v).

Caco-2 Cell Culture.

Caco-2 cells are grown in MEM supplemented with 2 mM L-glutamine, 10% FBS, 100 U/mL penicillin-G and 100 µg/mL streptomycin. The cells are incubated at 37° C., 5% $CO_2$ and relatively saturated humidity. After reaching 80-90% confluency, the cells are gently detached with 0.05% trypsin-EDTA solution. Cells at passage 30-50 are seeded on the 96-well BD insert system (Cat #359274) at the density of 1×105 cells/cm2 and cultured for 21-28 days with medium changed every 4-5 days.

Transport Procedures.

TB and dosing solutions were pre-warmed to 37° C. before transport assay. The cell monolayer was washed twice with HBSS containing 10 mM HEPES. For A-B (apical to basolateral) directional transport assay, 75 µL dosing solution is added to the apical well. Fill each basolateral well with 250 µL TB. For B-A (basolateral to apical) directional transport assay, 250 µL of dosing solution is added to the basolateral well after filling each apical well with 75 µL TB. Test compound(s) and digoxin are tested at 2 µM in the presence or absence of 1 µM zosuquidar bidirectionally in duplicate. Atenolol and propranolol are tested at 2 µM in the absence of zosuquidar in A to B direction in duplicate. The plates are incubated for 120 minutes at 37° C. with 5% C02 and saturated humidity. The time zero samples are generated by mixing 50 µL initial dosing solution of test compound or reference compound with 100 µL TB and 250 µL quench solution (acetonitrile (ACN) or other appropriate solvent with internal standard (s), based on the bioanalytical method development). At 120 minutes, 150 µL of solution is collected from each A-B receiver well followed by addition of 250 µL quench solution to get A-B receiver sample. And for other samples (A-B donor, B-A donor and receiver), 50 µL of solution is collected from each corresponding well followed by addition of 250 µL quench solution and 100 µL TB. All samples are vortex-mixed and centrifuged at 3220 g for 20 minutes. Subsequently, supernatant is diluted with ultra pure water for LC-MS/MS analysis. The concentrations of test compound in all samples are determined by LC-MS/MS and expressed as peak area ratio of analyte to internal standard.

The concentration of samples is expressed using the peak area ratio of Analyte to Internal Standard (Analyte/IS).

The apparent permeability coefficient (Papp) is calculated using the following equation:

$$P_{app}=V_R/(Area*Time)*(C_R/C_0)$$

wherein $V_R$ is the solution volume in the receiver chamber (0.075 mL on the apical side, 0.25 mL on the basolateral side); Area is the surface area for the transport, i.e. 0.0804 cm2 for the area of the monolayer; Time is incubation time, expressed in seconds, 2 h=2×3600 s; $C_0$ is the initial concentration in the donor chamber; $C_R$ is the final concentrations in receiver chamber.

The efflux ratio is calculated using the following equation:

$$\text{Efflux ratio}=Papp(A-B)/Papp(B-A)$$

where Papp (A-B) and Papp (B-A) are the Papp values of compound in Apical to Basolateral and Basolateral to Apical directional transport, respectively.

Results.

Compounds are generally considered to be P-Glycoprotein substrates when the value of efflux ratio is >3. Compounds of the present invention typically have efflux ratios >3, as evidenced in Table 3 below.

TABLE 3

| Compounds | Efflux ratio |
|---|---|
| 3 | 53 |
| 4 | 8 |
| 5 | >340 |
| 7 | >500 |
| 8 | >400 |
| 9 | >300 |

TABLE 3-continued

| Compounds | Efflux ratio |
|---|---|
| 10 | >900 |
| 11 | >600 |
| 12 | >140 |
| 13 | >100 |
| 14 | >900 |
| 18 | >80 |
| 19 | >110 |
| 20 | >300 |
| 21 | >150 |

III.2. Determination of the Concentration A2A Antagonists in Brain and Cerebrospinal Fluid Compared to Plasma Purpose.

The present assay aims at showing that the compounds of the invention do not have any significant CNS penetrance by determining the concentration of these compounds in brain and cerebrospinal fluid (CSF) compared to plasma.

Method.

7-9 weeks old female Balb-c mice (obtained from SLAC Laboratory Animal Co. Ltd., Shanghai, China or SIPPR-B&K Laboratory Animal Co. Ltd., Shanghai, China) were dosed orally at a dose of 10 mg/kg, as a 1.00 mg/mL suspension in 10% DMSO+10% solutol+80% water, adjusted to pH 3-4 (homogenous opaque suspension).

Animals were fasted at least 12 hours prior to the administration. All animals had access to Certified Rodent Diet (Catalog #M01-F, SLAC Laboratory Animal Cl. Ltd., Shanghai, China) ad libitum 4 hours post dosing. Serial bleeding (about 30 µL blood per time point) were performed from submadibular or saphenous vein. Those samples were transferred into prechilled microcentrifuge tubes containing 2 µL of K2EDTA (0.5M) as anti-coagulant and placed on wet ice for further treatment. Immediately after blood collection, the whole brain was harvested immediately at the designed time points. At selected timepoints post-dose, CSF was collected from cisterna magna.

Blood samples were processed for plasma by centrifugation at approximately 4° C., 3000 g 15 min within half an hour of collection. Plasma samples were stored in polypropylene tubes, quick frozen over dry ice and kept at −70° C. until LC/MS/MS analysis. Brain samples were weighed, rinsed in cold distilled water to remove blood, and homogenized using pre-cooled water at the ratio of 1:4 (1 g brain used 4 mL water). And the brain homogenization was kept at −70° C. until LC/MSMS analysis. CSF was quick frozen over dry ice and kept at −70° C. until LC/MS/MS analysis.

III.3. Determination of the CNS Activity by a Locomotion Assay

Purpose.

In addition to adenosines immune-suppressive effects, it has also been established that adenosine modulates neuronal functions via its interaction with A2AR in the central nervous system. This interaction mediates part of the dopamine pathway which is involved in movement. Prevention of this signalling in the brain, by highly brain penetrant A2AR antagonist compounds such as Preladenant (originally synthesised for prevention of Parkinson's disease), have been shown to induce hyper locomotion in animals. This could potentially pose a problem with compounds that were purposed for Parkisons's therapy (like Prelandenant) that are being repurposed for cancer immunotherapy.

The present assay aims at showing that the compounds of the invention do not have any significant CNS activity by using a method published by Hodgson et al. (J. Pharma. And Exp. Thera. 2009). The principle of this assay is that CGS21680, a brain penetrant A2AR specific adenosine analogue, induces immobility (hypolocomotion) within minutes after subcutaneous (s.c.) injection in mice. Therefore a mouse treated with a brain penetrant A2AR antagonist prior to treatment with CGS21680 will prevent hypolocomotion.

Preladenant, a reference brain penetrant compound, was compared to the compounds of the present invention at various concentrations per os (PO) for their effect on CGS21680 induced immobility.

Methods.

Compounds were administered 30 min prior to CGS21680 and locomotion was monitored over a 30 min period. Mice were scored for immobility, using a range of scores described in Table 4.

TABLE 4

Locomotion scoring

| Score | Description |
| --- | --- |
| 0 | Fully active - alert, running cage perimeter, rearing up, stretch, climbing, digging, gnawing, feeding |
| + | Active - alert, localized running, digging, rear up, stretching, gnawing |
| ++ | Activity limited - intermittent localized walking, gnawing, lethargic, some hunching |
| +++ | Activity severely abrogated/sleep - intermittent rearing up and gnawing, no walking, lethargic, eyes partly closed, hunched |
| ++++ | No activity/deep sleep - no movement, eyes closed, shivering |

The invention claimed is:

1. A method of treating cancer, comprising administering to a patient in need thereof a therapeutically acceptable effective amount of compound selected from the group consisting of
(S)—N5-(2-(4-(2,4-difluoro-5-(2-(methylsulfinyl) ethoxy)phenyl)piperazin-1-yl)ethyl)-2-(furan-2-yl)-N5-methyl-[1,2,4]triazolo[1,5-a][1,3,5]triazine-5,7-diamine;
(R)—N5-(2-(4-(2,4-difluoro-5-(2-(methylsulfinyl) ethoxy)phenyl)piperazin-1-yl)ethyl)-2-(furan-2-yl)-N5-methyl-[1,2,4]triazolo[1,5-a][1,3,5]triazine-5,7-diamine;
5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluoro-N-methylbenzamide;
5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluoro-N-methylbenzamide;
N5-(2-(4-(2,4-difluoro-5-(2-(methylsulfonyl)ethoxy)phenyl)piperazin-1-yl)ethyl)-2-(furan-2-yl)-N5-methyl-[1,2,4]triazolo[1,5-a][1,3,5]triazine-5,7-diamine;
N5-(2-(4-(2,4-difluoro-5-(2-(methylsulfonyl)ethoxy)phenyl)piperazin-1-yl)ethyl)-2-(furan-2-yl)-[1,2,4]triazolo[1,5-a][1,3,5]triazine-5,7-diamine;
(S)-5-amino-3-(2-(4-(2,4-difluoro-5-(2-(methylsulfinyl) ethoxy)phenyl)piperazin-1-yl)ethyl)-8-(furan-2-yl)-1-methyl-1H-[1,2,4]triazolo[5,1-i]purin-2(3H)-one;
(R)-5-amino-3-(2-(4-(2,4-difluoro-5-(2-(methylsulfinyl) ethoxy)phenyl)piperazin-1-yl)ethyl)-8-(furan-2-yl)-1-methyl-1H-[1,2,4]triazolo[5,1-i]purin-2(3H)-one;
5-amino-3-(2-(4-(2,4-difluoro-5-(2-(methylsulfonyl) ethoxy)phenyl)piperazin-1-yl)ethyl)-8-(furan-2-yl)-1-methyl-1H-[1,2,4]triazolo[5,1-i]purin-2(3H)-one;
(S)—N5-(2-(4-(2,4-difluoro-5-(2-(methylsulfinyl) ethoxy)phenyl)piperazin-1-yl)ethyl)-2-(furan-2-yl)-[1,2,4]triazolo[1,5-a][1,3,5]triazine-5,7-diamine;
(R)—N5-(2-(4-(2,4-difluoro-5-(2-(methylsulfinyl) ethoxy)phenyl)piperazin-1-yl)ethyl)-2-(furan-2-yl)-[1,2,4]triazolo[1,5-a][1,3,5]triazine-5,7-diamine;
(S)-7-(2-(4-(2,4-difluoro-5-(2-(methylsulfinyl)ethoxy) phenyl)piperazin-1-yl)ethyl)-2-(furan-2-yl)-7H-pyrazolo[4,3-e][1,2,4]triazolo[1,5-c]pyrimidin-5-amine;
(R)-7-(2-(4-(2,4-difluoro-5-(2-(methylsulfinyl)ethoxy) phenyl)piperazin-1-yl)ethyl)-2-(furan-2-yl)-7H-pyrazolo[4,3-e][1,2,4]triazolo[1,5-c]pyrimidin-5-amine;
(1s,4s)-4-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)tetrahydro-2H-thiopyran 1-oxide;
4-(5-(4-(2-((7-amino-2-(furan-2-yl)-[1,2,4]triazolo[1,5-a][1,3,5]triazin-5-yl)amino)ethyl)piperazin-1-yl)-2,4-difluorophenyl)thiomorpholine 1-oxide;
(R)—N5-(2-(4-(2,4-difluoro-5-(methylsulfinyl)phenyl) piperazin-1-yl)ethyl)-2-(furan-2-yl)-[1,2,4]triazolo[1,5-a][1,3,5]triazine-5,7-diamine;
(S)—N5-(2-(4-(2,4-difluoro-5-(methylsulfinyl)phenyl) piperazin-1-yl)ethyl)-2-(furan-2-yl)-[1,2,4]triazolo[1,5-a][1,3,5]triazine-5,7-diamine;
(4-(4-(2-((7-amino-2-(furan-2-yl)-[1,2,4]triazolo[1,5-a][1,3,5]triazin-5-yl)amino)ethyl)piperazin-1-yl)-3-fluorophenyl)(1-oxidothiomorpholino)methanone;
(1s,4s)-4-(4-(4-(2-((7-amino-2-(furan-2-yl)-[1,2,4]triazolo[1,5-a][1,3,5]triazin-5-yl)amino)ethyl)piperazin-1-yl)-3-fluorophenoxy)tetrahydro-2H-thiopyran 1-oxide;
5-amino-3-(2-(4-(2-fluoro-4-(2-(methylsulfinyl)ethoxy) phenyl)piperazin-1-yl)ethyl)-8-(furan-2-yl)-1-methyl-1H-[1,2,4]triazolo[5,1-i]purin-2(3H)-one; and
5-amino-3-(2-(4-(2,4-difluoro-5-((2-oxopyrrolidin-3-yl) oxy)phenyl)piperazin-1-yl)ethyl)-8-(furan-2-yl)-1-methyl-1H-[1,2,4]triazolo[5,1-i]purin-2(3H)-one;
or a pharmaceutically acceptable salt thereof.

2. A method of modulating A2A activity in a patient in need thereof, comprising administering to said patient a therapeutically acceptable effective amount of compound selected from the group consisting of
(S)—N5-(2-(4-(2,4-difluoro-5-(2-(methylsulfinyl) ethoxy)phenyl)piperazin-1-yl)ethyl)-2-(furan-2-yl)-N5-methyl-[1,2,4]triazolo[1,5-a][1,3,5]triazine-5,7-diamine;
(R)—N5-(2-(4-(2,4-difluoro-5-(2-(methylsulfinyl) ethoxy)phenyl)piperazin-1-yl)ethyl)-2-(furan-2-yl)-N5-methyl-[1,2,4]triazolo[1,5-a][1,3,5]triazine-5,7-diamine;
5-(4-(2-(5-amino-8-(furan-2-yl)-1-methyl-2-oxo-1H-[1,2,4]triazolo[5,1-i]purin-3(2H)-yl)ethyl)piperazin-1-yl)-2,4-difluoro-N-methylbenzamide;
5-(4-(2-(5-amino-2-(furan-2-yl)-7H-pyrazolo[4,3-e][1,2,4]triazolo[1,5-c]pyrimidin-7-yl)ethyl)piperazin-1-yl)-2,4-difluoro-N-methylbenzamide;
N5-(2-(4-(2,4-difluoro-5-(2-(methylsulfonyl)ethoxy)phenyl)piperazin-1-yl)ethyl)-2-(furan-2-yl)-N5-methyl-[1,2,4]triazolo[1,5-a][1,3,5]triazine-5,7-diamine;
N5-(2-(4-(2,4-difluoro-5-(2-(methylsulfonyl)ethoxy)phenyl)piperazin-1-yl)ethyl)-2-(furan-2-yl)-[1,2,4]triazolo[1,5-a][1,3,5]triazine-5,7-diamine;
(S)-5-amino-3-(2-(4-(2,4-difluoro-5-(2-(methylsulfinyl) ethoxy)phenyl)piperazin-1-yl)ethyl)-8-(furan-2-yl)-1-methyl-1H-[1,2,4]triazolo[5,1-i]purin-2(3H)-one;

(R)-5-amino-3-(2-(4-(2,4-difluoro-5-(2-(methylsulfinyl)ethoxy)phenyl)piperazin-1-yl)ethyl)-8-(furan-2-yl)-1-methyl-1H-[1,2,4]triazolo[5,1-i]purin-2(3H)-one;

5-amino-3-(2-(4-(2,4-difluoro-5-(2-(methylsulfonyl)ethoxy)phenyl)piperazin-1-yl)ethyl)-8-(furan-2-yl)-1-methyl-1H-[1,2,4]triazolo[5,1-i]purin-2(3H)-one;

(S)—N5-(2-(4-(2,4-difluoro-5-(2-(methylsulfinyl)ethoxy)phenyl)piperazin-1-yl)ethyl)-2-(furan-2-yl)-[1,2,4]triazolo[1,5-a][1,3,5]triazine-5,7-diamine;

(R)—N5-(2-(4-(2,4-difluoro-5-(2-(methylsulfinyl)ethoxy)phenyl)piperazin-1-yl)ethyl)-2-(furan-2-yl)-[1,2,4]triazolo[1,5-a][1,3,5]triazine-5,7-diamine;

(S)-7-(2-(4-(2,4-difluoro-5-(2-(methylsulfinyl)ethoxy)phenyl)piperazin-1-yl)ethyl)-2-(furan-2-yl)-7H-pyrazolo[4,3-e][1,2,4]triazolo[1,5-c]pyrimidin-5-amine;

(R)-7-(2-(4-(2,4-difluoro-5-(2-(methylsulfinyl)ethoxy)phenyl)piperazin-1-yl)ethyl)-2-(furan-2-yl)-7H-pyrazolo[4,3-e][1,2,4]triazolo[1,5-c]pyrimidin-5-amine;

(1s,4s)-4-(5-(4-(2-((7-amino-2-(furan-2-yl)-[1,2,4]triazolo[1,5-a][1,3,5]triazin-5-yl)amino)ethyl)piperazin-1-yl)-2,4-difluorophenoxy)tetrahydro-2H-thiopyran 1-oxide;

4-(5-(4-(2-((7-amino-2-(furan-2-yl)-[1,2,4]triazolo[1,5-a][1,3,5]triazin-5-yl)amino)ethyl)piperazin-1-yl)-2,4-difluorophenyl)thiomorpholine 1-oxide;

(R)—N5-(2-(4-(2,4-difluoro-5-(methylsulfinyl)phenyl)piperazin-1-yl)ethyl)-2-(furan-2-yl)-[1,2,4]triazolo[1,5-a][1,3,5]triazine-5,7-diamine;

(S)—N5-(2-(4-(2,4-difluoro-5-(methylsulfinyl)phenyl)piperazin-1-yl)ethyl)-2-(furan-2-yl)-[1,2,4]triazolo[1,5-a][1,3,5]triazine-5,7-diamine;

(4-(4-(2-((7-amino-2-(furan-2-yl)-[1,2,4]triazolo[1,5-a][1,3,5]triazin-5-yl)amino)ethyl)piperazin-1-yl)-3-fluorophenyl)(1-oxidothiomorpholino)methanone;

(1s,4s)-4-(4-(2-((7-amino-2-(furan-2-yl)-[1,2,4]triazolo[1,5-a][1,3,5]triazin-5-yl)amino)ethyl)piperazin-1-yl)-3-fluorophenoxy)tetrahydro-2H-thiopyran 1-oxide;

5-amino-3-(2-(4-(2-fluoro-4-(2-(methylsulfinyl)ethoxy)phenyl)piperazin-1-yl)ethyl)-8-(furan-2-yl)-1-methyl-1H-[1,2,4]triazolo[5,1-i]purin-2(3H)-one; and 5-amino-3-(2-(4-(2,4-difluoro-5-((2-oxopyrrolidin-3-yl)oxy)phenyl)piperazin-1-yl)ethyl)-8-(furan-2-yl)-1-methyl-1H-[1,2,4]triazolo[5,1-i]purin-2(3H)-one;

or a pharmaceutically acceptable salt thereof.

\* \* \* \* \*